US009963710B2

(12) United States Patent
Chen et al.

(10) Patent No.: US 9,963,710 B2
(45) Date of Patent: May 8, 2018

(54) METHODS AND COMPOSITIONS FOR IDENTIFYING AND ENRICHING FOR CELLS COMPRISING SITE SPECIFIC GENOMIC MODIFICATIONS

(71) Applicant: SYNGENTA PARTICIPATIONS AG, Basel (CH)

(72) Inventors: Zhongying Chen, Durham, NC (US); Myoung Kim, Durham, NC (US); Mary-Dell Chilton, Durham, NC (US); Heng Zhong, Durham, NC (US); Weining Gu, Durham, NC (US); Yaping Jiang, Durham, NC (US); Qiudeng Que, Durham, NC (US)

(73) Assignee: Syngenta Participations AG, Basel (CH)

(*) Notice: Subject to any disclaimer, the term of this patent is extended or adjusted under 35 U.S.C. 154(b) by 21 days.

(21) Appl. No.: 14/974,247

(22) Filed: Dec. 18, 2015

(65) Prior Publication Data
US 2017/0016010 A1 Jan. 19, 2017

Related U.S. Application Data

(60) Provisional application No. 62/096,442, filed on Dec. 23, 2014.

(51) Int. Cl.
*C12N 15/82* (2006.01)
*C12N 15/10* (2006.01)

(52) U.S. Cl.
CPC ..... *C12N 15/8213* (2013.01); *C12N 15/1058* (2013.01); *C12N 15/8205* (2013.01); *C12N 15/8207* (2013.01)

(58) Field of Classification Search
None
See application file for complete search history.

(56) References Cited

U.S. PATENT DOCUMENTS

| | | | |
|---|---|---|---|
| 6,455,315 B1 | 9/2002 | Baszczynski et al. | |
| 7,935,862 B2 | 5/2011 | Que | |
| 8,329,986 B2 | 12/2012 | Butler et al. | |
| 8,354,519 B2 | 1/2013 | Steiner et al. | |
| 8,399,254 B2 | 3/2013 | Que | |
| 8,470,973 B2 | 6/2013 | Bonas et al. | |
| 8,586,363 B2 | 11/2013 | Voytas et al. | |
| 8,586,526 B2 | 11/2013 | Gregory et al. | |
| 8,697,359 B1 | 4/2014 | Zhang et al. | |
| 8,697,853 B2 | 4/2014 | Voytas et al. | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 2005/0216970 A1 | 9/2005 | Steiner et al. | |
| 2006/0253918 A1 | 11/2006 | Que | |
| 2009/0133152 A1 | 5/2009 | Lyznik et al. | |
| 2011/0191899 A1 | 8/2011 | Ainley et al. | |
| 2011/0201055 A1 | 8/2011 | Doyon et al. | |
| 2011/0201118 A1 | 8/2011 | Yang et al. | |
| 2014/0068797 A1 | 3/2014 | Doudna et al. | |
| 2014/0090113 A1 | 3/2014 | Cogan et al. | |
| 2014/0298547 A1 | 10/2014 | Sastry-Dent et al. | |
| 2015/0128309 A1* | 5/2015 | Sastry-Dent | A01H 5/10 800/320.1 |

FOREIGN PATENT DOCUMENTS

| | | |
|---|---|---|
| WO | 2007142840 A2 | 12/2007 |
| WO | 2011154158 A1 | 12/2011 |
| WO | 2011154159 A1 | 12/2011 |
| WO | 2012129373 A2 | 9/2012 |
| WO | 2013019411 A1 | 2/2013 |
| WO | 2013026740 A2 | 2/2013 |
| WO | 2013066423 A2 | 5/2013 |
| WO | 2013112686 A1 | 8/2013 |
| WO | 2013141680 A1 | 9/2013 |
| WO | 2013160230 A1 | 10/2013 |
| WO | 2013169802 A1 | 11/2013 |
| WO | 2014161821 A1 | 10/2014 |
| WO | 2014199358 A1 | 12/2014 |

OTHER PUBLICATIONS

Ainley et al, 2013 Plant Biotechnology Journal 11:1126-1134.*
Ayar et al., Plant Biotechnology Journal, 2013, 11, 305-314.
Belhaj et al., Plant Methods, 2013, 9, 39.
Bortesi and Fischer, Biotechnology Advances, 33, 2015, 41-52.
Cai et al., Plant Mol Biol, 2009, 69, 699-709.
Cermak et al., Nucleic Acids Research, 2011, 39, 12, e82.
Chen and Gao, Plant Cell Rep, 2014, 33, 575-583.
Christian et al., Genetics, 186, 757-761 (Oct. 2010).
Cibulskis et al., Nature Biotechnology, vol. 31, No. 3, Mar. 2013, 213-221.
Curtin et al., The Plant Genome, Jul. 2012, vol. 5, No. 2, 42-50.
Dahlem et al., PLOS Genetics, Aug. 2012, vol. 8, Issue 8, e1002861.
D'Halluin et al., Plant Biotechnology Journal, 2008, 6, 93-102.
D'Halluin et al., Plant Biotechnology Journal, 2013, 11, 933-941.
Djukanovic et al., The Plant Journal, 2013, 76, 888-899.
Doudna and Charpentier, Science, Nov. 28, 2014, vol. 346, Issue 6213, 1077-1086.
Grove, Journal of Biomolecular Techniques, vol. 10, Issue 1, Mar. 1999, 11-16.
Ishida et al., Nature Protocols, vol. 2, No. 7, 2007, 1614-1621.
Jiang et al., Nucleic Acids Research, 2013, 1-12.
Li et al., Nucleic Acids Research, 2011, vol. 39, No. 14, 6315-6325.
Liang et al., Journal of Genetics and Genomics, 41, 2014, 63-68.
Malnoy et al., Tree Genetics and Genomes, 2010, 6, 423-433.
Marton et al., Plant Physiology, Nov. 2010, vol. 154, 1079-1087.
Negrotto et al., Plant Cell Reports, 2000, 19, 798-803.
Nekrasov et al., Nature Biotechnology, vol. 31, No. 8, Aug. 2013, 691-693.
Papapetrou et al., Nature Biotechnology, vol. 29, No. 1, Jan. 2011, 73-81.
Permingeat et al., Plant Molecular Biology, 52, 415-419, 2003.
Puchta and Fauser, The Plant Journal, 2014, 78, 727-741.
Qi et al., Genome Research, 2013, 1-8.
Qiu et al., BioTechniques, 2004, 36, 4, 702-707.
Que et al., Frontiers in Plant Science, Aug. 2014, 6, 379, 1-19.

(Continued)

*Primary Examiner* — Brent T Page
(74) *Attorney, Agent, or Firm* — Yoshimi D. Barron

(57) ABSTRACT

The present invention relates to methods and compositions for modifying a target site in the genome of a plant cell. Such modifications include integration of a transgene and mutations. The present invention also relates to methods and compositions for identifying and enriching for cells which comprise a modified target site.

11 Claims, 13 Drawing Sheets

(56) References Cited

OTHER PUBLICATIONS

Sadelain et al., Nature Reviews, Jan. 2012, 12, 51-58.
Saika et al., Plant Physiology, Jul. 2011, 156, 1269-1277.
Shukla et al., Nature, May 21, 2009, 459, 437-443.
Townsend et al., Nature, May 21, 2009, 459, 442-446.
Tzfira et al., Plant Biotechnology Journal, 2012, 10, 373-389.
Voytas, Annu. Rev. Plant Biol., 2013, 64, 327-50.
Voytas and Gao, PLOS Biology, Jun. 2014, 12, 6, e1001877.
Voytas and Joung, Science, Dec. 11, 2009, 326, 1491-1492.
Yang et al., Plant Mol Biol, 2009, 70, 669-679.
Version et al., Jun. 1, 2014, Retrieved from the Internet: URL:http://www.bc-diagnostics.com/downloads/products/bpz/Z_720_06_20_foodproof_SL_GM0_MIR604_Maize_Detection_Kit_V1-1.pfd [retrieved on Mar. 7, 2016].
International Search Report for International Application No. PCT/US2015/066619 dated Mar. 29, 2016.

\* cited by examiner

Detecting targeted mutagenesis: Taqman assay design

```
          Taqman Fw primer                         MGB Probe
                              TALEN 1 binding site                              TALEN 2 binding site
CGGTGCGGGA CACACCTGGT TGCCAAGCT GCATCGGTGC AGTGCAGTGC AGGACTTCCT TTGTTTAGGA CGCGATGCTG
GCCACGCCCT GTGTGGAGCA ACGGTTTCGA CGTAGCCACG TCACGTCACG TCCTGAAGGA AACAAATCCT GCGCTACGAC
                                                                              Taqman Rv Primer
```

Interpretation of Taqman results

| Taqman Readings | Target Site Modification Status |
|---|---|
| 2 | both copies aren't modified |
| 1 | one copy is modified, one copy isn't |
| 0 | both copies are modified |

FIG. 7

(B) Copy number call of different types of events

| Event type | T assay copy number call | M assay copy number call | G assay copy number call |
|---|---|---|---|
| Event with no targeted insertion | | | |
| a) WT, no mutation in both alleles | 2 | 2 | 0 |
| b) Small indel in one allele | 2 | 1 | 0 |
| c) Small indel in both alleles | 2 | 0 | 0 |
| d) Small indel in one allele and large deletion in another allele | 1 | 0 | 0 |
| e) Large insertion in both alleles | 0 | 0 | 0 |
| Event with targeted insertion | | | |
| f) No mutation in one allele, targeted insertion in another allele | 1 | 1 | 1 |
| g) Small indel in each allele, targeted insertion in another allele | 1 | 0 | 1 |
| h) Large deletion in in each allele, targeted insertion in another allele | 0 | 0 | 1 |
| i) Targeted insertion in both alleles | 0 | 0 | 2 |

FIG. 8B (cont'd.)

Note: Drawing not to scale

SEQUENCE LISTING

<160> NUMBER OF SEQ ID NOS: 140

<210> SEQ ID NO 1
<211> LENGTH: 1582
<212> TYPE: DNA
<213> ORGANISM: Zea mays

<400> SEQUENCE: 1

```
cgagcagtag aaaaaaaaaa caacgccaag agatggcaga gtcaacaacc gatcacagta      60
cgtatcgcat tcacatcaag attttaagaa cgaccccccg gctggccaat ggccactttc     120
ttgcccgtgc ccgacagcgg acacggcgcc atgccctccg cgccgcacga gcgaggtgtc     180
gtgagaaccg gcaaaaaaaa aaaaaaaaat catcccaagt gcgctgaagt gaagtgcctt     240 ccccgcgtt  tccttgcccc tggccggtac ccatttggcg ccgattcttt tcttgccccc     300
ccggccggcc gctcgctcgc ctttggattc ttccaaagcc gctgatggga tcgtggcgaa     360
cacacccacc acccgtcttt gcccaaagcg acccggcaca ggccgcgccg gcttcactaa     420
ccactagcgc ttgtactaat aaaatggttt ctagcgtttg ttgctctcct ttttcctttt     480
ttcgccggtt cttcggagcc gtgtggacag cgtccagtcc agcaggcata gggtggtctc     540
ggcggcggcc gtccgacgac gatcgatctc catgagattc cgcgacaggc caggacggaa     600
agctgggccc ttctcaccaa ttcgcgtcgg agccggaaca agattccctc ccccaatcat     660
ttcgacgcgc cctttcttcg ccaccctcg  tggccgtgtt tcgcggccct tatctctttc     720
ccgtgacgcg ttcttttgta gcttagcggc cggcacgttg ctaaccaggc tagcttcgtt     780
cgtttttaat ctgcctatcg agaagagaag aaaaattcgt ccatggggcc acggcctctt     840
ctgcaggcat ttggcagaac cagtgaatgg agatggacgg atgctgctca gatacgcagt     900
caaacctgcc ggcgaaatta cgggggagc  tggctggctg gctggacgcc agagcacaca     960
tggatgacgc ggcacggcag ctagccgagc aggcgctctg cgcacgcaag tgtcgtgccg    1020
atctcgcacc agcagcatcg cgtcctaaac aaaggaggtc ctgtcctgca ctgcactgca    1080
```

| | |
|---|---:|
| cggatgcagc tttggcaacg aggtgtgtcg cgcagcgctc ctgcacggat gtagctttgg | 1140 |
| attgctggat aatatctcgc gcaagcatcg tatttattta tttaatttat tatttattta | 1200 |
| tttattacga cgtccaccgc tgtgcgtgct ccgtttcgga ttataataaa actaatatta | 1260 |
| aataaaaaaa tcggattaaa ggatgtttcc gaaataaaga tctccaccac aggagcgaaa | 1320 |
| gaaaagagaa acgaaatggt gttgcgatta tacggcggct ccgtcgtcgt cggatcgaca | 1380 |
| tgtaaaaagt acgtgcacaa aaggcaaagc aaaatcacct catcaaagac caaaagcgga | 1440 |
| gcaaagaata gatactaaat ccacatattt tttttgttc ctgtctacta tgtgctgtgc | 1500 |
| ctgtgcgtga agcacgatta gtacgtgtag tcacttgtca tattctttt agtgtcttgt | 1560 |
| cactagtcac atggagtagc aa | 1582 |

```
<210> SEQ ID NO 2
<211> LENGTH: 17176
<212> TYPE: DNA
<213> ORGANISM: Zea mays

<400> SEQUENCE: 2
```

| | |
|---|---:|
| ccattaaatc gacgaaagca actagatcct gattttgatt acgattacga ttgacgagta | 60 |
| tggatcatga ttttattgca tattttatga ttttattgca tattttatta ttttattgtc | 120 |
| gatttatgta ctaacttgtt tttgttaaaa taggatgtca agaaaatga agtctttagc | 180 |
| tcgtagtttg cttgggtcga ggaggagctc gaggagcagc tcgaggggtg aggattcagt | 240 |
| ttttcagggc acaggttcta ccatgagcag acggagagcg ctggcagaac atttgcctcc | 300 |
| acaagatgta agttagttgt taaattacat tatttgagtt acttaatatt gtatgatgta | 360 |
| agttatttgt ttcataggat gctgaaattg aggaaccagt ggtagaggat catgcaagag | 420 |
| atgatgttga agatgatggt ggagataatg tgggagatga tgctggagac gacgctggtg | 480 |
| gggattctgg ggctggggat tctggggctg gtggagattc tgcagctggg tctggaactt | 540 |
| ctcgagttaa gagaacgagg aagctgcatt ttgttggacc cctccagag cttccacccg | 600 |
| aatctcgggt tgtaataaag cctagtggaa agtgagtgac atatctttgc ttaaatgtta | 660 |
| ttgaaagtta tgttttaatt tctacattga tttctgtttg caggacttgg atcgacgact | 720 |
| cgttcacagg cacaggacac tacaggcagg tgaacatggt tcttggtaat cttgttcgtc | 780 |
| tgcactggcc tggtcttgtg actttgccta ctggcgagtc tgtccccgcc accacttggg | 840 |
| agcattatcg ctatggtgtc tgtagaacgt ttggcaacac acaggcacta gtttgggatg | 900 |
| cattctgggt atgacttgtt tatactattt tagttattcc atatatgttt gcttttatga | 960 |
| taacactatg gttttgcag aaacggtaca agttgccgga cgatggatca tatgatatga | 1020 |
| acgctcgtta cgtgtttgag tttaacgcga acgatgtcgt tgcagatgca atgtactatg | 1080 |
| cacgaattca ggctataaag gcatggtaca gagcaaatgc tgatgatcga ccgatgccaa | 1140 |
| atacaaaggc cgagtggtca tcaatttact tgacggagga gcaataccta gaggtaaaca | 1200 |
| ggttgttgcc tctcatatcg cacaaagcca tgtatttgct tgctttattt aaaaattttg | 1260 |
| atgtaggtgt cggtgccgtg gatggccacc cgaccagacg gttatcgggc attgtgcaga | 1320 |
| tggtgggctt cccctgactt tcgtgccatt tccgaaagga acaggggaaa ccgtgggact | 1380 |
| gagtcgttcc acaactacgg cggtgatggt catgtgcgct tggctaagcg aatggtaagt | 1440 |
| cacagtttgt cgtaactttg aatcacatag caaatgtgtc attataactt ttatgtacag | 1500 |
| gaagtcaaat ccggccgtac gcccacggat gtggaggtgt atatgcaagg gcatagggcc | 1560 |

```
ataggggttc tgatcctcag aatcctgatg tgttatgcac tcagacggcc accgaccgtc   1620
tagtgagttt ttgatactct attatgtgtg ttgatattgt ttgcaagggc atagggggtta   1680 tgcacttata tttgatattg tttgcctcca ggcttcgtat gggcaggaga tggttcaacg   1740
ccatggggag gagtacgatt ggaggagcca gccaatcgac cctcagacag catatgctag   1800
cgcaggagga caagctcatg gacggtgaga ttatttgatt tggttttcaa aattgtcatc   1860
atatgcttgc gattcaactg agccatgagt tactatacta agtgcatggt tcactcttgt   1920
aggttgggta tttttgattc tacgattgat tccagagagc tgagacgccg tggacgacaa   1980
tccacatcgt cgtcttcaca gtcgtcccgt tcacgatcag cagcccatga gatagagctt   2040
gcagtgttgc gtcaacaggc agagtaccat caatcagtct tgagggaaca attggagtac   2100
cagaggcaac aatctgaata ccagagacaa caagccgagt accagaagaa gagggacgag   2160
tattatgcaa gcctccaggc ccaaaatcaa gctcttctct cggtaagttg aagtaacatt   2220
ttgtagctta ttttgcaaaa cacttgatgt gtatcttgtt tgttcaacaa tgacttgtat   2280
ataatttgta gcaactagcc caacaagcgg gcgtcccgat gccgacatat gggatgccgc   2340
ctccggactt tgcactgcca atgccaatgt tggcgcctcc acctccacct ccgcctccgc   2400
ctacgtcaca attccctatg gtatgtacac atatgcgtgt gtgacatgtt catagatgtc   2460
ttatgtgttt aaatgaacaa ctgagtggtt actatttcat gtgcttgtgt tatagggatt   2520
tcagacacca cccgcttcag ttgccgcacc tggagatggg tctgggcaag acgacacaac   2580
acattcgtgg gtcaacaacc tattcaacac gcagagtcca gccggaggag gtggctactt   2640
gaaccatcca gacgatggat atgattgatg tgtcgtgatg tttatttatg aaacactttg   2700
caacacttgt ttgtgagaca caatttcagt ttgcaacaac cgtcgaacct atatgttgat   2760
gttaaatttg tgaatgttat tatttatgtg agaatatttg tgattgtgaa tacttattag   2820
aatgtgtata tttgtgattg tgaatgtgaa tgtgtatatg tgcatgaatc tgttttcgtt   2880
ttgtaaatgt cagattttt aaaaaacaga attttgtgta aattctgtaa tttgttatgt   2940
ccgacggcct agtggtagcc gtcggacata acacatggtt atgtccgacg cattaacta   3000 ccgtcggaca taagggatgc ttatgtccga cggcctagtg gtagccgtcg gacttaatcc   3060
tgtggggccc acattccgac cggtaaaacg gttgggattt gttatctccg acgggcacac   3120
gcagccgtcg gagatagctt atgtccgacg gctgccgtcg gacattgcac tatttccgac   3180
gagttatctc cgacggctta agccgtcgg agataaggct ttgccgtcgg aaataatcta   3240
tttccgacgg tttattcctt atgtccgacg gttttggcca tcggacgttt ctccgtttac   3300
tgtagtggaa gggagtgcag tagaagtgca atggcctaat gtccttcacc ataaaaaaaa   3360
caaagttcaa atctttcaga tttatttact cttggagtag catagcatag gtgtacaagg   3420
gaagtgctta taataatggt aacaagatac tcatcctctc atacctgccg tctcactgac   3480
aggaaacggt aggtggcaag ttggtaagct tttcggtttt agccatgtcc gatcccatgt   3540
gtggatcctg tactgtacat cgacatgcga catcttggtt ggcctatctg atctttaatg   3600
tcgccgcgca cagagaggag atccggtctc atgaagtggc tccgcagatt cctcaagggg   3660
ccgaagcccg gcgaaccgag ccgccggcgg cccaggtgg cggccgggga agaggaggac   3720
gcgctttggc accaacgacc agctagacca aaggtactac tactaccact gtactagtga   3780
ctgagttcct cccttcttct tctacagttc gtctctgtct ctccaaatgg ctctttgatc   3840
tatccaaaca tgccgtttca cagcttcaca tccgattcaa ctcgcatcca ttgcagtgcc   3900
atcttaaact cttagctccg aaaaaggaag ttgctaaaga ctagtacaat atctttcttc   3960
```

```
gctgtttcca gatcgatcca cctaggaacg agaatgagga actagtggac cgtgccattg   4020
ccgagcctct tgcagaggct gtcaaaccgc ccagaggtag taccgtagat ggacgaatcc   4080
agatacacat tccatgtcag catggtataa atttctctga aaccgtttca tccctgcatc   4140
ccgttgctgt aaattgctgc gccagagaaa acccataggg gagaagacag caacgacgac   4200
gaagatctgg caagagccgt acaggacagt ctgaatatga acccttacac gccttacaac   4260
ccctatccac cctctcaggc ccaacctaga gggcacaggt caaccgctat cacaatcacc   4320
atttactggc accctaagat attctctaac gcgccaaagc agctcaatgc cgtcagtgtc   4380
cgtgctgcag ggtatgcgga ggctgcaagc atgagatagg gcgtggccat tacttgagct   4440
gcatgggcat ttactggcac cctcagtgct tccgctgcag gtcctgcggt caccttatcc   4500
gtgagaccga ggtaattaag ctcttgcatt ttctttcacc gtggaagtgt gttacagtgt   4560
taccagagat gagatcatat ccgttattct tttcgtcgtg ccttccagtt caccttgctg   4620
ggtgcggatt cgtaccacaa gctgtgctac aaggagctgc atcatccaaa atgcgacgtc   4680
tgccttcagt ttgtaaggcc tcgtgtcctc ggaaaacctg agcgatctgc actacagact   4740
gataaactgc gtacgcgtta gcatttctac accgtgccgt ctcgtcagtg taatgagagg   4800
ctcattcttt gtagatgtgt ttctgcagat cccaacgaac gggagtggct tgatagagta   4860
cagagcccac ccgttctggg gccagaagta ttgcccttcg catgagcgcg acaggacgcc   4920
acgttgctgc agctgtgaga aaatggaggt acaggtacag atactagata gaaaatgtgg   4980
tcgcagtccg atcactcgtt ttcaaactag gttgtacatt gcctgatcat attcaagggc   5040 atcactttc ggttgtgatt gtgcagccaa ggaacacgaa gtacatgtcg ctgggagacg   5100
gacgcggcct gtgcatggaa tgcctgggat ctgcagtgat ggacgcgagc gagtgccagc   5160
ctctgtacca ttctatcaga gactactacg aggggatgga catgagactg gaccagcaga   5220
tacccgtgct cttggttgag cggcaagcgc tcaacgaagc catggaaggg gagagtaaag   5280
tgagtgtttc ttctggttct gccccttttt tttgtgtgtg tttctgcaaa acgtacagcc   5340
ttcggaaaca ctaacgctga ccgcatctgc gaaatccagg gcccacgcca catgcctgag   5400 actagggcc tatgtctgtc cgaggagcgg actgtgagca gtgtaagtgt tcaacaactc   5460
aagctgtggc ggttactgct gggatgctta gcccacaatg cgacagtttc tgctcttctg   5520
actgtgtgtt acttctgcag atacttagga ggcccagaat tggtggaaac aaccggttac   5580
tagacatgag aactcggcca cagaagctga ctaggagatg tgaagttact gcaatacttg   5640
tcctgtatgc cctccccagg tctggcaatt ttttttttat ctctggagtc tggaggacat   5700 cactttttg tacctaccgg attcaaatac tgcggttctt ctcacgttct gtgaccggtg   5760
gtgtcgtcgt ttgtgtcaca acgctattgc aggctactga caggttccat cctcgcccat   5820
gagctgatgc acgggtggct gcgtctcaaa ggtacatccg tatatggatg gatggacaaa   5880
acatttcata cacccattta tcatctttat ttatgaattt tcttggaaag ctctaccgga   5940
tcgtactttt cattcaggtt accgaaacct aaacgcggag gtggaagaag gcatatgcca   6000
ggtcatgtct tacttgtggc tggaatcaga gattcttccg tcatcctcga ggcacgcgca   6060
gccttcatca tcctatccag caacatcatc cgagaaaggt ggaatatctc ataccgggaa   6120
gaagctgggc gagttcttca tgcaccagat tgccaatgac acgtcgacgg cctatggtga   6180
cgggttcaga actgcgtacg ctgccgtcaa caagtatggc cttcgcccaaa cactgagcca   6240 tatacgccta acaggaggtt tccctgtata ataagagtga aaaaaacata aaatgtccat   6300
```

```
gcatgatcat atcgatatca aaaggttata tacatattgg gatgaagttg gctatggaac    6360
actggatgca tagtgattca atttcggtga cctttgagtt ttcaaagagg taatgtcgga    6420
gtaaatcaga aagtaaaccc gtataaagca tggttgagac gattgtttac tctatagtga    6480
tgcatgctac atgcatggcc aagaagagag caacgggcca taggaccatc gttattaccc    6540
atcgttgtta atcaaattta gggctagata aatagtaaac catctatagg aacatccaga    6600
gtcaatctac tctatgtatc ataccgacca ggggcggatc taggtaaaat aaccattgat    6660
gtcatctcca ttaaattata gtatcatcaa cctatttaag tgctaacaat catacatttt    6720
aatgaagatt attaaaatcc attggtgtca catgacacca caaaaatggc ctagatccgc    6780
ccctgatacc gacaaaccta gaaaaatttg taactgagaa ctgatgacca tacacatgaa    6840
catgaattag acttttcaaa gagtccaatc aaagtaaaca attagactaa gcatgtaaga    6900
tagggtgcca gatgttgtat caggcttttg agcacatgtg caacttgtat gtcgtggaac    6960
gtgacaaccg tcaaggaat gcgcatgtga cggtgtaaaa tcaatataac aacatgaaga    7020
acaatcataa gtataggttg aaactacaca tgataactag tatatctttc taacaacaat    7080
gattagtaca atatgtaccg tggtaaagtg gtgacaccat tagagatcgc attagaacgg    7140
catggcgctt actttaaaaa atgttagaga agcggttatg gtcaaacaga atattatgtg    7200
aatatgcggg aagatgaaca aatctataac acagaaacga aggaaccaaa taggatcagc    7260
ggagagtaca gtgccaacgc gcgacgaaac gaggaagcca gaaaggcacc gccgcatgcc    7320
cgcaccgcgt gactgtcgaa ggcggccgtg agcgctccga catcgaagga gtttatttca    7380
aaaatgggac gaccaacatt gcgcttttca catttgtttc ctaacgttgc actctttcac    7440
atatggcacc gagacacgca atcttgttga caccgctcgt agtccggtcc gggcagtgag    7500
gtcttacctg tcgtggtttc agaaaccggg gataataaga tttgtgttcg gtaaggacgc    7560
agcgcggact cactctgaat ggtcagagga ctcaatgatg gatctgagac aagggggttat    7620 actggtttag gcttgcgccc tagtccaatg ttgatcatag tattgcttag agcgtgttac    7680
agttgagtgc tcgtatctag aagatggggg ttgtcttgct cttttatagc tcaaggatag    7740
atcttacaat gagacttgta ttctgttggg gtcgagctca gcttcctact tctgggtgac    7800
gtagctcctc cggtatcgtc tgctgggtcg tgcgccatcg tatccctggt atggcgtcgc    7860
gtcttatccg ttcgccgtat gagttcttgt agctattctg atgcaaacgt agtggtgcct    7920
ggtgggtctc gcagagtcgg tttgtggtga ggtttagggg cgtctttagt acaacttcat    7980
cttccatcat tccctatgcg tcaccttcca gcatgcgtag gcgtacgctt cgtacagcgt    8040
attaccgcgt cccttctgga cttctggtat gtaggtcact gtagagaccc aatgctgggt    8100
tgattggtcc caccggtcag cgaggatgct ctctagaatg tatctggcgt cgtgattggc    8160
agaggccttc ggtactgctc ccatggttca gacgtggctt ggtggtgatc tgtctcatcg    8220
tgctgacgtg acttgatagt actaggtcgg ctcttacctc ctatagatgt gctcgctaga    8280
aagtccattg tcatcttgct gggttgctcg gcatgtaggt tgatcggtaa atccgcctcg    8340
tcgagttgct cgataatgtt gctcggcggg cgggtatgta ggtagtccga cctcaccggg    8400
ttgttcggca atcccgcctc gccgagttgc tcggtgaacg ggttggtcgg cagccccacc    8460
tcgccaggtt gtttggcaca cgtgttggtc tgttggtggg tcgtcgagag cccttttggg    8520
cttttttggg cacccggttt ctggtacccc acaatacccg agctagagtt ccacatttgc    8580
ccctaccttc cttcccggct ccggcgacaa gcccaggatc ctggtgtaat ggggcgagga    8640
gaagcagttc ttgacggagg agaccagctc catgatcccc aacaaaatga aggagacaac    8700
```

```
cgaggcctac ctcggcgtca ccatcaataa cactgttgtc accgtcccag tctatttcaa    8760
tgagtcccag cgccagacta ccaaaaacgt cgccgtcatc tccggccttc accgtcatgc    8820
gcatcatcaa cgagcccacc actgtcgcca tcacctacgg gctcgacaag aaatcgagca    8880
gcaacaacga gaataatgtc gtcatcttcg acctcgacgg cggtaccttt gacgtcgcgc    8940
tccggcggct aaggaccgca ctgccgacga gggcatgagt ggcgccgaga tggaagagaa    9000
gaggagcaca aatggcggtc gtcggcaaag acaaagagaa ctcgagcgtg agtggaggaa    9060
ggggcaaatg tgtaactcca gcttggatat gactccactg accagattac gagcgacatc    9120
aactagattg tgtgtctcag tggctcagtg ccattttttg aggtttgggt gccaatattt    9180
tttcgtagtg gaaggcaccg cgcccatcgg gttttgggag ccaaacgcca aacccgctcg    9240
cctcatattc cgcaacgtac agcggtttca tgggctggtt gaaggcccgg gccgcaaacc    9300
aaccgagtcg ggccgacgcc ctgggagatc cgcacggctg gtctggccca agcaacctgg    9360
tgggttggtg ccaggttaca gcctgggctg atctgtggac ggtggaccat gcaaggttgt    9420
actgggcttg caaggttgta ctgggcctac tggaacagtc atagcccgtg ccgtcgtggt    9480
gaccgtcgta cgcggccgat ctggcagact gggcaggtcg ctgctccgtg ctgtttgtgg    9540
atgcaatgca actatgcaag agtgatcacg gaaaacggac ggagcctgtc tgtcctgttg    9600
cgacgtagta caagcgcctg aacagtgacg ctacgctatg ccacgagcct acgagtggta    9660
ggtagtagta cactggtcag aatccagcag tgcacccacg ccgctgctga ctttgctgat    9720
gagagggagg ggtcgagcga gtctgtgtga aaccgtgaac cccgccgggg ccttcagtac    9780
gtacgatacc acgagcagta gaaaaaacaa cgccaagatg gcagagtcaa caaccgatca    9840
cagtacgtat cgcattcaca tcaagatttt aagaacgacc cccggctggc caatggcagg    9900
ccacttggtt gcccgtgccc gacagaggga cacggcgcca tgccctccgc gccgcacgga    9960
cgaggtgtcg tgagaaccgg caaaaaaaaa aatcatcgca agtgcgctga agtgaagtgc   10020 cttccccgc gtttccttgc ccctggccgg tacccatttg gcgccgattc ttttcttgcc   10080 cccggccgg ccgctcgctc gccttttggat tcttccaaag ccgctgatgg gatggtggcg   10140
aacacaccca ccacccgtct ttgcccaaag cgacccggca caggccgcgc cggcttcact   10200
aaccactagc gcttgtacta ataaaatggt ttctagcgtt tgttgctctc cttttttctt   10260
tttcgccggt tcttcggagc cgtgtggaca ctggacagcg tccagtccag caggcatagg   10320
gtggtctcgg cggcggtcgt ccgacgacga tcgatctcca tgagattccg cgacaggcca   10380
ggacggaaag ctgggcccct tctcaccaat cgcgtcggag ccggaacaag attccctccc   10440
ccaatcattt cgacgcgccc tttcttcgcc accccctcgtg gccgtgtttc gcggccggcc   10500
cttatctcct tcccgtgacg cgttcttttg tagcttagcg gccggcacgt tgctaaccag   10560
gctagcttcg ttcgttttta atctgcctat cgagaagaga agaaaaattc gtccatgggg   10620
ccacggcctc ttctgcaggc atttggcatg tgaaggaacc cgaaccagtg aatggagatg   10680
gacggatgct gctcagatac gcagtcaaac ctgccggcga aattacgggg ggagctggct   10740
ggctggctgg ctggacgcca gatcacacat ggatgacgcg gcacggcagc tagccgagca   10800
ggcgctctgc gcacgcaagt gtcgtgccga tctcgcacca gcagcatcgc gtcctaaaca   10860
aaggaggtcc tgtcctgcac tgcactgcac tgcacggatg cagctttggc aacgaggtgt   10920
gtcgcgcagc gctcctgcac ggatgtagct ttggattgct ggataatgtc tcgcgcaagc   10980
gtcgtattta tttatttatt tattacagcc tccaccgccg tgcgtgctcc gtttcggatt   11040
```

```
ataataaaac taatattaaa taaaaaaatc ggattaaagg atgtttccga aataaagatc   11100
tccaccacag gagcgaaaga aaaaaaaaga gaaacgggct atggagaaat ggtgttgcga   11160
gtatacggcg gctccgtcgt cgtcggatcg acatgtacaa agtaggtgca caaaaggcaa   11220
agcaaaatca cctcatcaaa gaccaaaagc ggagcaaaga atcgatacta aatccacatg   11280
ttttttttgt tcctgtctac tacgtgctgt gcctgtgcgt gaagcacgat tagtacgtgt   11340
actcactctt gtcatattct ttttagtgtc ttgtcactag tcacatggag tagcaaccat   11400
ggctggcgat acccgcgata aataaaaaaa agagagaggg agtaatatat tagatactca   11460
cccattataa attataaaat attttagagt ttgaataggt agttcttgta tatttattta   11520
tagaccttca agtttgtccg cctctcgaga gccgaacttt gttgcccatg cttccccggc   11580
tcaggtcatg ccacctcctt caccaagggc acacggaaga tctggtggag cttgtcatca   11640
ccccgcgccc ttcaaacatg tgaggatgcg tcgtcgctgg cactagtagc actcattgta   11700
ggcactacat tgacagtttc ctccagatat gtagtgagga aacacttgaa caacacgttt   11760
gggattacat atgatgtttt gtttgttcat caatgataat tccttcttct tgcttaatga   11820
ttggctctag aaccgataca tggcacattt catcaggaag ggcgcatgca cgaaattaaa   11880
ctgttatcga tgtttcggtt tctaagttga agaaaacaat ggctaacaac tagcccatgt   11940
gagcataacg acaaggccta caaacaaaac ccaagaaata gctaaatcat ggtctggatc   12000
cactctgcta tgatagatca ccttttctaa catagttcat cctcccattt gctctcgctc   12060
acctagtgcc tccatcgctg agatcaatga taagtaccaa gtgtacgatg aatcccattt   12120
gtcatgcgtc ttgcaagaat ggttggtccg cttgcagtgc cggtccagct atggacccag   12180
gggcctatgt cataactcaa gcaagaccat accccccatat gctaccaaga tgcctttttaa   12240 gaatcctggt aaaagaaatc ggtggaagac gactcaacga ctatcaggcc ccatttttttg   12300 ggaccatgct caaggatttg gctttagcaa aagtagataa cactattttg gggagcttga   12360
tctcaaggac acatgaagga ataaagctat tttagtcaag acgtccttaa ggaacacaat   12420
aagaccctag gtccctaatg actagtgtgt tatatgtttc gagacgctcc tacacctaag   12480 ttctttttagc tatttccatt cacaatgatg gtatatgacc taggtaccaa tgccccacgg   12540
agtttctaac attaagaatg atctaaaaca taaggaccct agagccaggg cactcctggt   12600
attaaaacat ttaaaccecta ttgccttagt gctgatttttt gttttttgtt tgtaggagga   12660
gaaacgagca cttgttgcct ctcgcgacaa tcttgatagg ctgtaccgtg atgccagtaa   12720
ctccttgacc atcctagaga ggagccaccg cttcaccatg tctgacctag atcatccacca   12780 ccatgagctg caggcgtctc aagatgaagt cttgcaactt ggacgattgt tgtcgactaa   12840
ggattccacc atcaaggatc tgcgcttcta aaaagctcgt cccgcaggag ctagaggcgg   12900
cccagcttgc tattaagact ctaaaggaca actgcaccgt cctgaagacc cagcgcgata   12960
aagctatgga taaagttgtt cgcgctggac ggatcctgat gaggaggcac ggcgttgtgg   13020
tgcctgacga tattgttgtc gatgtcaagg ccgcgcctga tgctacaagt cgtccctctt   13080
tttctgttgc tcctgcgaag gataccgtct gcaaggatgt ttcgatgcag tgatgtcctg   13140
taaaacactt tacttattga gttagtatct ccttggagga tggatgtaat atggattcaa   13200
tgtgcatgcg acaattgtgt tagaactcga atattctacg aacagggtgc cggaaaacgg   13260
ccctagcact ggcaagtaag atgttctctt ttcctgaagt gttttcaatt ttagccggtt   13320
gttatgctat tagggtatag tggtcaccct aaacagcgca aatgcaagta taccgcgttg   13380
gcttaaggtg tgttccgact taagtcagtt gccttgctgg tagggcatag tggtcaccct   13440
```

```
gagtaaagta agtcagagta tattgcaccg acctaagtcg attgcactac tagcagggta    13500
tagtgatcac cctaagtcaa gtaagcatga gcatatcgca ccgacttagg tcatcaccga    13560
cttaagccga ttgttctgtt agcagggtat aatggtcacc ctaagtcaga taagcatgag    13620
catgtcacac cggcttaagt cgttgccgac ttaagccgat tgctccgtca gcagggtata    13680
gtggtcaccc taataagtca ggtaagcatg agcatatcgc actggcttaa gtcgttgccg    13740
acttaagccg attgctccgt cagtagggta tagtggtcac cctaagtcaa gtaagcgtga    13800
gcatgtcgca ctggcttaag tcgattgctc cgtcagcagg gtataatggt cactttaagt    13860
caagtaagtg tgagcatgtc gcaccagctt aagtcatcgc cgacttaagc tgattgctcc    13920
attagcaggg tatagtggtc accctaagtt aggtaatcgt gctgatttca agtctagccc    13980
aatcaaagtc agttgtaagt caagagtatg aatgcctttg gagaatgaaa actttattga    14040
tgatgaaatt ctcggattta cagagtacaa tgttccttca agaatttga ggccttgcta    14100 aggatagaat tttctgaggt gttctatgtt ccatgagttc ccttctgtgc cgtccatttg    14160
agtaagccgg tatggtcccg gccgagtgac cgcctctaat atgatgaacg atccttccca    14220
cagtggtgat agcttgtgcc gcccttcccc cgttagaatt cggcgaagga ccaagtctcc    14280
cactgcaaag gatcggtgcc gcatagcttt atcatggtag cacctcaagg tctgctggta    14340
cctagccgac tgaattactg tgttcaatag ttcttcttcc agtacatcaa tatcttccag    14400
tctggtcgct tctgcttcag ctatgctttc gaaagttaat cttggtgccc tgaagattag    14460
gtcagcgggc agcactgcct ctaacccata aaccatgaaa aacggggtat ttctatgcag    14520
agctcgactg ggttgagttc tcaggctcta gaccacgtat ggcagctctc tgatccattt    14580
tcctgcaagc ttttcactct tgtcaaatat tttcttcctg agtgcttcta gtatcattcc    14640
gttggttctt tctacctggc cattggctct tgggtgtgct actgatgcat acttaacctg    14700
gaagctccgt tgctcgcaga aatcgagttc agagctggtg aagttggatc ccagatcggt    14760
gatgatgttg tttggtatcc caaacctgaa tattatgtct tgtataaact ccaccacttt    14820
ggctgaggtc aaggaagcaa ttggcttgta ctttatccat tttgtgaatt tgttaatggc    14880
aaccagtaca tgagtatagc ctccctgagc cttcttaaaa ggtccgatca tgtccagccc    14940
acagcatgcg aacggccatg ttacaggaat ggtctgcagc tgctgcgcgg gtaagtgttg    15000 ttgcttttgat aggaattggc atgcttcaca cttctggact aactcggcaa catcgttctt    15060
tattgttggc aatagaaac cggatctaaa agccttcccg accagagtcc ttgacgctgc    15120
atgtattcca cactgcccgg cgtggatttc atccaacaat tgtttctcgg tagtcgagtg    15180
aatacatttc atgaggactc ttgctgcacc tctcctgtac agtaagcccc atatgatggt    15240
gtagtgggcc aactgcctcg cgatgcattc cactgcagcc ttgtcatctg gctcttcttc    15300 attttatat acctgatgat aggctctctc cagtcgttgg ggtccgactc tggttggctc    15360
aaggtattgc acacttccac ctgatccaag atgatgcttg gttgtgatat ttcttggacg    15420
aagatcccag gtggagcctg ggcccgactg gatcccagct tcgacaacgc gtctgctgct    15480
gcgttgcggt ctcgttccac atgatggaac tctaatcctt caaatttgtc ctctagtttt    15540
cgcacaaccg cgcagtattt gcccatggag tcagtcgagc agtcctagtc tttgcttatc    15600
tggattatga ccactagcga atcaccatat accatcagtt tcttgatgcc gagtgataca    15660
acaatgctta aacctggat cagttcttca tactttgctg cattatttga cgctggaaat    15720
agtagctgga gtgcataatt gtgttgctca cctccaggag caataaagag aatccctgca    15780
```

-continued

```
cccgctccct atagtttcaa cgagccatca aagtacattt tccacacctc gataacctct    15840
gggctatctg ggacctgatg ttcagtccac tctgatacga agtcaaccag cgcctgagtc    15900
ttgattgccg tgcggggcca gaactctatg ttgtgagctc caagctcaca cgcccacttg    15960
gcgatccttc caatagcttc tttgttgtgg agaatgtccc ctattgggaa tcctatgacc    16020
actatgactt tgtggtcgtc aaagtagtgt cggagtttgc gtgcggttag aagtactgca    16080
tacaacaact tctgtacttg aggatacctt atctttgagg gcccgaggac ttcactgatg    16140
aagtagactg gatgttgcac cgggtacaca tgtccttcct ccacccgctt gactactaac    16200
gtggtgctta ccacgtgagt cgtgctggag atgtataaca tcaaatcttc caccaactga    16260
ttcagcgtag ctcgtcgtgg cggcttgagc actggtggtg tagtcaaaaa attttagttc    16320
ctctagagct tcctgcgcct ctgtggtcca ctgaaacttg tccaccttt tgagcaattt     16380 gtagaaggcc atgccttgct cccctagtct tgatatgaac ctgctcaggg ctgccatgca    16440
tccagtaagc ctctgtacct ttttctatga tcgcaacact tccattctca tgatggcctt    16500 gacctttcc gggttagctt caatcccttg gtgactgaca atgaatctga gtaacttccc     16560
tgcctgtact ctgaaaacac acttttctgg gttgagcttc caccggtaat gcctcaggct    16620
attgaagact agctgcaaat cttcaatgaa gttttctgtt ttgatcacca catcatcaac    16680
ataggcttcc acccgcttgc cccagtggtc ggctaagcat gtctgaatgg ctctctggta    16740
agttgctccc gtgttcttga ggtcgaatga catgaaggtg taatagaaag ctccaaatgg    16800
ggtgatgaaa gcattcttct cctcatcttc ttttgctaag cagatatgat ggtatctaga    16860
atagcagtct aggaaggaca acatagaaca gccagcggtc gaatcaacca cctgatctat    16920
tctagggagc ccgaagggat ctttggtgtc tcagacctgg gggaccctca accaaatcga    16980
caagtgaatt ttgtgtcgcg tgtccctgcc cagatggatt agtgcaagat gaaacacaag    17040
aggaggggtg aggtttatat tatcttgcac caggtgtt gcagtagggg atacaatctt      17100
tgcgagagag ggaacggatc ccaggtctct tgagagatct agtgttgtga aggggagttc    17160
gatgtttgag caagcc                                                   17176
```

```
<210> SEQ ID NO 3
<211> LENGTH: 23
<212> TYPE: DNA
<213> ORGANISM: Zea mays

<400> SEQUENCE: 3
agtgcagtgc agtgcaggac agg                                               23

<210> SEQ ID NO 4
<211> LENGTH: 23
<212> TYPE: DNA
<213> ORGANISM: Zea mays

<400> SEQUENCE: 4
actaatcgtg cttcacgcac agg                                               23

<210> SEQ ID NO 5
<211> LENGTH: 23
<212> TYPE: DNA
<213> ORGANISM: Zea mays

<400> SEQUENCE: 5
aggcacagca cgtagtagac agg                                               23
```

```
<210> SEQ ID NO 6
<211> LENGTH: 23
<212> TYPE: DNA
<213> ORGANISM: Zea mays

<400> SEQUENCE: 6
acatgtcgat ccgacgacga cgg                                              23

<210> SEQ ID NO 7
<211> LENGTH: 23
<212> TYPE: DNA
<213> ORGANISM: Zea mays

<400> SEQUENCE: 7
agttttatta taatccgaaa cgg                                              23

<210> SEQ ID NO 8
<211> LENGTH: 23
<212> TYPE: DNA
<213> ORGANISM: Zea mays

<400> SEQUENCE: 8
aatccgaaac ggagcacgca cgg                                              23

<210> SEQ ID NO 9
<211> LENGTH: 23
<212> TYPE: DNA
<213> ORGANISM: Zea mays

<400> SEQUENCE: 9
aaacggagca cgcacggcgg tgg                                              23

<210> SEQ ID NO 10
<211> LENGTH: 22
<212> TYPE: DNA
<213> ORGANISM: Zea mays

<400> SEQUENCE: 10
ggagcacgca cggcggtgga gg                                               22

<210> SEQ ID NO 11
<211> LENGTH: 23
<212> TYPE: DNA
<213> ORGANISM: Zea mays

<400> SEQUENCE: 11
atccaaagct acatccgtgc agg                                              23

<210> SEQ ID NO 12
<211> LENGTH: 22
<212> TYPE: DNA
<213> ORGANISM: Zea mays

<400> SEQUENCE: 12
gtgcagtgca gtgcagtgca gg                                               22

<210> SEQ ID NO 13
<211> LENGTH: 23
<212> TYPE: DNA
<213> ORGANISM: Zea mays

<400> SEQUENCE: 13
ggacaggacc tcctttgttt agg                                              23
```

```
<210> SEQ ID NO 14
<211> LENGTH: 23
<212> TYPE: DNA
<213> ORGANISM: Zea mays

<400> SEQUENCE: 14
gcgtgcgcag agcgcctgct cgg                                              23

<210> SEQ ID NO 15
<211> LENGTH: 22
<212> TYPE: DNA
<213> ORGANISM: Zea mays

<400> SEQUENCE: 15
gcgtcatcca tgtgtgatct gg                                               22

<210> SEQ ID NO 16
<211> LENGTH: 24
<212> TYPE: DNA
<213> ORGANISM: Zea mays

<400> SEQUENCE: 16
gtccatctcc attcactggt tcgg                                             24

<210> SEQ ID NO 17
<211> LENGTH: 23
<212> TYPE: DNA
<213> ORGANISM: Zea mays

<400> SEQUENCE: 17
aatgcctgca gaagaggccg tgg                                              23

<210> SEQ ID NO 18
<211> LENGTH: 24
<212> TYPE: DNA
<213> ORGANISM: Zea mays

<400> SEQUENCE: 18
gcggccggca cgttgctaac cagg                                             24

<210> SEQ ID NO 19
<211> LENGTH: 23
<212> TYPE: DNA
<213> ORGANISM: Zea mays

<400> SEQUENCE: 19
agagaagaaa aattcgtcca tgg                                              23

<210> SEQ ID NO 20
<211> LENGTH: 22
<212> TYPE: DNA
<213> ORGANISM: Zea mays

<400> SEQUENCE: 20
ggcctcttct gcaggcattt gg                                               22

<210> SEQ ID NO 21
<211> LENGTH: 23
<212> TYPE: DNA
<213> ORGANISM: Zea mays

<400> SEQUENCE: 21
aaggaacccg aaccagtgaa tgg                                              23
```

```
<210> SEQ ID NO 22
<211> LENGTH: 21
<212> TYPE: DNA
<213> ORGANISM: Zea mays

<400> SEQUENCE: 22
atcggtccta aacaaaggag g                                              21

<210> SEQ ID NO 23
<211> LENGTH: 22
<212> TYPE: DNA
<213> ORGANISM: Zea mays

<400> SEQUENCE: 23
ggatgcagct ttggcaacga gg                                             22

<210> SEQ ID NO 24
<211> LENGTH: 22
<212> TYPE: DNA
<213> ORGANISM: Zea mays

<400> SEQUENCE: 24
gtcgcgcagc gctcctgcac gg                                             22

<210> SEQ ID NO 25
<211> LENGTH: 24
<212> TYPE: DNA
<213> ORGANISM: Zea mays

<400> SEQUENCE: 25
gctcctgcac ggatgtagct ttgg                                           24

<210> SEQ ID NO 26
<211> LENGTH: 22
<212> TYPE: DNA
<213> ORGANISM: Zea mays

<400> SEQUENCE: 26
ggatgtagct ttggattgct gg                                             22

<210> SEQ ID NO 27
<211> LENGTH: 23
<212> TYPE: DNA
<213> ORGANISM: Zea mays

<400> SEQUENCE: 27
aaataaaaaa atcggattaa agg                                            23

<210> SEQ ID NO 28
<211> LENGTH: 20
<212> TYPE: DNA
<213> ORGANISM: Zea mays

<400> SEQUENCE: 28
agtgcagtgc agtgcaggac                                                20

<210> SEQ ID NO 29
<211> LENGTH: 4170
<212> TYPE: DNA
<213> ORGANISM: Artificial Sequence
<220> FEATURE:
<223> OTHER INFORMATION: Streptococcus pyogenes, Zea mays
```

<400> SEQUENCE: 29

```
atggacaaga agtacagcat cggcctggac atcggcacca acagcgtggg ctgggccgtg      60
atcaccgacg agtacaaggt gccgagcaag aagttcaagg tgctgggcaa caccgacagg     120
cacagcatca agaagaacct gatcggcgcc ctgctgttcg acagcggcga gaccgccgag     180
gccaccaggc tgaagaggac cgccaggagg aggtacacca ggaggaagaa caggatctgc     240
tacctgcagg agatcttcag caacgagatg gccaaggtgg acgacagctt cttccacagg     300
ctggaggaga gcttcctggt ggaggaggac aagaagcacg agaggcaccc gatcttcggc     360
aacatcgtgg acgaggtggc ctaccacgag aagtacccga ccatctacca cctgaggaag     420
aagctggtgg acagcaccga caaggccgac ctgaggctga tctacctggc cctggcccac     480
atgatcaagt tcaggggcca cttcctgatc gagggcgacc tgaacccgga caacagcgac     540
gtggacaagc tgttcatcca gctggtgcag acctacaacc agctgttcga ggagaacccg     600
atcaacgcca gcggcgtgga cgccaaggcc atcctgagcg ccaggctgag caagagcagg     660
aggctggaga acctgatcgc ccagctgccg ggcgagaaga gaacggcct gttcggcaac     720
ctgatcgccc tgagcctggg cctgaccccg aacttcaaga gcaacttcga cctggccgag     780
gacgccaagc tgcagctgag caaggacacc tacgacgacg acctggacaa cctgctggcc     840
cagatcggcg accagtacgc cgacctgttc ctggccgcca gaaacctgag cgacgccatc     900
ctgctgagcg acatcctgag ggtgaacacc gagatcacca aggcccgct gagcgccagc     960
atgatcaaga ggtacgacga gcaccaccag gacctgaccc tgctgaaggc cctggtgagg    1020
cagcagctgc cggagaagta caaggagatc ttcttcgacc agagcaagaa cggctacgcc    1080
ggctacatcg acggcggcgc cagccaggag gagttctaca agttcatcaa gccgatcctg    1140
gagaagatga cgcaccga ggagctgctg gtgaagctga acaggagga cctgctgagg    1200
aagcagagga ccttcgacaa cggcagcatc ccgcaccaga tccacctggg cgagctgcac    1260
gccatcctga ggaggcagga ggacttctac ccgttcctga aggacaacag ggagaagatc    1320
gagaagatcc tgaccttccg catcccgtac tacgtgggcc cgctggccag gggcaacagc    1380
aggttcgcct ggatgaccag gaagagcgag gagaccatca ccccgtggaa cttcgaggag    1440
gtggtggaca agggcgccag cgcccagagc ttcatcgaga ggatgaccaa cttcgacaag    1500
aacctgccga cgagaaggt gctgccgaag cacagcctgc tgtacgagta cttcaccgtg    1560
tacaacgagc tgaccaaggt gaagtacgtg accgagggca tgaggaagcc ggccttcctg    1620
agcggcgagc agaagaaggc catcgtggac ctgctgttca gaccaacag gaaggtgacc    1680
gtgaagcagc tgaaggagga ctacttcaag aagatcgagt gcttcgacag cgtggagatc    1740
agcggcgtgg aggacaggtt caacgccagc ctgggcacct accacgacct gctgaagatc    1800
atcaaggaca aggacttcct ggacaacgag gagaacgagg acatcctgga ggacatcgtg    1860
ctgaccctga cctgttcga ggacagggag atgatcgagg agaggctgaa gacctacgcc    1920
cacctgttcg acgacaaggt gatgaagcag ctgaagagga gaggtacac cggctggggc    1980
aggctgagca ggaagctgat caacggcatc agggacaagc agagcggcaa gaccatcctg    2040
gacttcctga gagcgacgg cttcgccaac aggaacttca tgcagctgat ccacgacgac    2100
agcctgacct tcaaggagga catccagaag gcccaggtga gcggccaggg cgacagcctg    2160
cacgagcaca tcgccaacct ggccggcagc ccggccatca gaagggcat cctgcagacc    2220
gtgaaggtgg tggacgagct ggtgaaggtg atggcaggc acaagccgga gaacatcgtg    2280
atcgagatgg ccagggagaa ccagaccacc cagaagggcc agaagaacag cagggagagg    2340
```

```
atgaagagga tcgaggaggg catcaaggag ctgggcagcc agatcctgaa ggagcacccg    2400
gtggagaaca cccagctgca gaacgagaag ctgtacctgt actacctgca gaacggcagg    2460
gacatgtacg tggaccagga gctggacatc aacaggctga gcgactacga cgtggaccac    2520
atcgtgccgc agagcttcct gaaggacgac agcatcgaca caaggtgctg accaggagc    2580 gacaagaaca gggcaagag cgacaacgtg ccgagcgagg aggtggtgaa gaagatgaaa    2640
aactactgga ggcagctgct gaacgccaag ctgatcaccc agaggaagtt cgacaacctg    2700
accaaggccg agaggggcgg cctgagcgag ctggacaagg ccggcttcat taaaaggcag    2760
ctggtggaga ccaggcagat caccaagcac gtggcccaga tcctggacag caggatgaac    2820
accaagtacg acgagaacga caagctgatc agggaggtga aggtgatcac cctgaagagc    2880
aagctggtga gcgacttcag gaaggacttc cagttctaca aggtgaggga gatcaataat    2940
taccaccacg cccacgacgc ctacctgaac gccgtggtgg gcaccgccct gattaaaaag    3000
tacccgaagc tggagagcga gttcgtgtac ggcgactaca aggtgtacga cgtgaggaag    3060
atgatcgcca agagcgagca ggagatcggc aaggccaccg ccaagtactt cttctacagc    3120
aacatcatga acttcttcaa gaccgagatc accctggcca acggcgagat caggaagagg    3180
ccgctgatcg agaccaacgg cgagaccggc gagatcgtgt gggacaaggg cagggacttc    3240
gccaccgtga ggaaggtgct gtccatgccg caggtgaaca tcgtgaagaa gaccgaggtg    3300
cagaccggcg gcttcagcaa ggagagcatc ctgccgaaga ggaacagcga caagctgatc    3360
gccaggaaga aggactggga cccgaagaag tacggcggct cgacagccc gaccgtggcc    3420 tacagcgtgc tggtggtggc caaggtggag aagggcaaga gcaagaagct gaagagcgtg    3480
aaggagctgg tgggcatcac catcatggag aggagcagct tcgagaagaa cccagtggac    3540
ttcctggagg ccaagggcta caaggaggtg aagaaggacc tgatcattaa actgccgaag    3600
tacagcctgt tcgagctgga gaacggcagg aagaggatgc tggccagcgc cggcgagctg    3660
cagaagggca acgagctggc cctgccgagc aagtacgtga acttcctgta cctggccagc    3720
cactacgaga gctgaagggg cagcccggag gacaacgagc gaagcagct gttcgtggag    3780 cagcacaagc actacctgga cgagatcatc gagcagatca gcgagttcag caagagggtg    3840
atcctggccg acgccaacct ggacaaggtg ctgagcgcct acaacaagca cagggacaag    3900
ccgatcaggg agcaggccga gaacatcatc cacctgttca cccctgaccaa cctgggcgcc    3960 ccggccgcct tcaagtactt cgacaccacc atcgacagga gaggtacac cagcaccaag    4020 gaggtgctgg acgccaccct gatccaccag agcatcaccg cctgtacga gaccaggatc    4080 gacctgagcc agctgggcgg cgacagcagc ccgccgaaga gaagaggaa ggtgagctgg    4140 aaggacgcca gcggctggag caggatgtga                                      4170
```

<210> SEQ ID NO 30
<211> LENGTH: 1389
<212> TYPE: PRT
<213> ORGANISM: Artificial Sequence
<220> FEATURE:
<223> OTHER INFORMATION: Streptococcus pyogenes, Zea mays

<400> SEQUENCE: 30

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

-continued

```
Lys Val Leu Gly Asn Thr Asp Arg His Ser Ile Lys Lys Asn Leu Ile
            35                  40                  45

Gly Ala Leu Leu Phe Asp Ser Gly Thr Ala Glu Ala Thr Arg Leu
 50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
    195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
```

```
            450                 455                 460
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880
```

-continued

```
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Val Gly Ile Thr Ile Met Glu Arg Ser Ser
    1160                1165                1170
Phe Glu Lys Asn Pro Val Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
```

```
Arg Val Ile Leu Ala Asp Ala Asn Leu Asp Lys Val Leu Ser Ala
    1280             1285                 1290

Tyr Asn Lys His Arg Asp Lys Pro Ile Arg Glu Gln Ala Glu Asn
    1295             1300                 1305

Ile Ile His Leu Phe Thr Leu Thr Asn Leu Gly Ala Pro Ala Ala
    1310             1315                 1320

Phe Lys Tyr Phe Asp Thr Thr Ile Asp Arg Lys Arg Tyr Thr Ser
    1325             1330                 1335

Thr Lys Glu Val Leu Asp Ala Thr Leu Ile His Gln Ser Ile Thr
    1340             1345                 1350

Gly Leu Tyr Glu Thr Arg Ile Asp Leu Ser Gln Leu Gly Gly Asp
    1355             1360                 1365

Ser Ser Pro Pro Lys Lys Lys Arg Lys Val Ser Trp Lys Asp Ala
    1370             1375                 1380

Ser Gly Trp Ser Arg Met
    1385
```

<210> SEQ ID NO 31
<211> LENGTH: 17
<212> TYPE: DNA
<213> ORGANISM: Zea mays

<400> SEQUENCE: 31
gcagtgcagt gcaggac                                                17

<210> SEQ ID NO 32
<211> LENGTH: 18
<212> TYPE: DNA
<213> ORGANISM: Zea mays

<400> SEQUENCE: 32
tgcagtgcag tgcaggac                                               18

<210> SEQ ID NO 33
<211> LENGTH: 19
<212> TYPE: DNA
<213> ORGANISM: Zea mays

<400> SEQUENCE: 33
gtgcagtgca gtgcaggac                                              19

<210> SEQ ID NO 34
<211> LENGTH: 21
<212> TYPE: DNA
<213> ORGANISM: Zea mays

<400> SEQUENCE: 34
cagtgcagtg cagtgcagga c                                           21

<210> SEQ ID NO 35
<211> LENGTH: 85
<212> TYPE: DNA
<213> ORGANISM: Artificial Sequence
<220> FEATURE:
<223> OTHER INFORMATION: Streptococcus pyogenes, Oryzae sativa

<400> SEQUENCE: 35
gttttagagc tagaaatagc aagttaaaat aaggctagtc cgttatcaac ttgaaaaagt    60
ggcaccgagt cggtgctttt ttttt                                          85

-continued

```
<210> SEQ ID NO 36
<211> LENGTH: 105
<212> TYPE: DNA
<213> ORGANISM: Artificial Sequence
<220> FEATURE:
<223> OTHER INFORMATION: Streptococcus pyogenes, Zea mays, Oryza sativa

<400> SEQUENCE: 36
agtgcagtgc agtgcaggac gttttagagc tagaaatagc aagttaaaat aaggctagtc      60
cgttatcaac ttgaaaaagt ggcaccgagt cggtgctttt ttttt                     105

<210> SEQ ID NO 37
<211> LENGTH: 480
<212> TYPE: DNA
<213> ORGANISM: Artificial Sequence
<220> FEATURE:
<223> OTHER INFORMATION: Streptococcus pyogenes, Zea mays, Oryza sativa

<400> SEQUENCE: 37
gggatcttta acatacgaa cagatcactt aaagttcttc tgaagcaact taaagttatc       60
aggcatgcat ggatcttgga ggaatcagat gtgcagtcag ggaccatagc acaggacagg     120
cgtcttctac tggtgctacc agcaaatgct ggaagccggg aacactgggt acgttggaaa     180
ccacgtgatg tggagtaaga taaactgtag gagaaaagca tttcgtagtg ggccatgaag     240
cctttcagga catgtattgc agtatgggcc ggcccattac gcaattggac gacaacaaag     300
actagtatta gtaccacctc ggctatccac atagatcaaa gctggtttaa aagagttgtg     360
cagatgatcc gtggcagtgc agtgcagtgc aggacgtttt agagctagaa atagcaagtt     420
aaaataaggc tagtccgtta tcaacttgaa aaagtggcac cgagtcggtg cttttttttt     480

<210> SEQ ID NO 38
<211> LENGTH: 1995
<212> TYPE: DNA
<213> ORGANISM: Zea mays

<400> SEQUENCE: 38
aacgagaata atgtcgtcat cttcgacctc gacggcggta cctttgacgt cgcgctccgg      60
cggctaagga ccgcactgcc gacgagggca tgagtggcgc cgagatggaa gagaagagga     120
gcacaaatgg cggtcgtcgg caaagacaaa gagaactcga gcgtgagtgg aggaaggggc     180
aaatgtgtaa ctccagcttg gatatgactc cactgaccag attacgagcg acatcaacta     240
gattgtgtgt ctcagtggct cagtgccatt ttttgaggtt tgggtgccaa tattttttcg     300
tagtggaagg caccgcgccc atcgggtttt gggagccaaa cgccaaaccc gctcgcctca     360
tattccgcaa cgtacagcgg tttcatgggc tggttgaagg cccgggccgc aaaccaaccg     420
agtcgggccg acgccctggg agatccgcac ggctggtctg gccaagcaa cctggtgggt     480 tggtgccagg ttacagcctg ggctgatctg tggacggtgg accatgcaag gttgtactgg     540
gcttgcaagg ttgtactggg cctactgaa cagtcatagc ccgtgccgtc gtggtgaccg     600
tcgtacgcgg ccgatctggc agactgggca ggtcgctgct ccgtgctgtt tgtggatgca     660
atgcaactat gcaagagtga tcacggaaaa cggacggagc ctgtctgtcc tgttgcgacg     720
tagtacaagc gcctgaacag tgacgctacg ctatgccacg agcctacgag tggtaggtag     780
tagtacactg gtcagaatcc agcagtgcac ccacgccgct gctgactttg ctgatgagag     840
ggaggggtcg agcgagtctg tgtgaaaccg tgaaccccgc cggggccttc agtacgtacg     900
ataccacgag cagtagaaaa acaacgccac agatggcaga gtcaacaacc gatcacagta     960
```

| | |
|---|---|
| cgtatcgcat tcacatcaag attttaagaa cgaccccccgg ctggccaatg gcaggccact | 1020 |
| tggttgcccg tgcccgacag agggacacgg cgccatgccc tccgcgccgc acggacgagg | 1080 |
| tgtcgtgaga accggcaaaa aaaaaaatca tcgcaagtgc gctgaagtga agtgccttcc | 1140 |
| cccgcgtttc cttgcccctg gccggtaccc atttggcgcc gattcttttc ttgcccccg | 1200 |
| gccggccgct cgctcgcctt tggattcttc caaagccgct gatgggatgg tggcgaacac | 1260 |
| acccaccacc cgtctttgcc caaagcgacc cggcacaggc cgcgccggct tcactaacca | 1320 |
| ctagcgcttg tactaataaa atggtttcta gcgtttgttg ctctccttttt tcttttttcg | 1380 |
| ccggttcttc ggagccgtgt ggacactgga cagcgtccag tccagcaggc ataggtggt | 1440 |
| ctcggcggcg gtcgtccgac gacgatcgat ctccatgaga ttccgcgaca ggccaggacg | 1500 |
| gaaagctggg cccttctcac caattcgcgt cggagccgga acaagattcc ctcccccaat | 1560 |
| catttcgacg cgccctttct tcgccacccc tcgtggccgt gtttcgcggc cggcccttat | 1620 |
| ctccttcccg tgacgcgttc ttttgtagct tagcggccgg cacgttgcta accaggctag | 1680 |
| cttcgttcgt ttttaatctg cctatcgaga agagaagaaa aattcgtcca tggggccacg | 1740 |
| gcctcttctg caggcatttg gcatgtgaag gaacccgaac cagtgaatgg agatggacgg | 1800 |
| atgctgctca gatacgcagt caaacctgcc ggcgaaatta cggggggagc tggctggctg | 1860 |
| gctggctgga cgccagatca cacatggatg acgcggcacg gcagctagcc gagcaggcgc | 1920 |
| tctgcgcacg caagtgtcgt gccgatctcg caccagcagc atcgcgtcct aaacaaagga | 1980 |
| ggtcctgtcc tgcac | 1995 |

<210> SEQ ID NO 39
<211> LENGTH: 942
<212> TYPE: DNA
<213> ORGANISM: Zea mays

<400> SEQUENCE: 39

| | |
|---|---|
| gcactgcact gcactgcacg gatgcagctt tggcaacgag gtgtgtcgcg cagcgctcct | 60 |
| gcacggatgt agctttggat tgctggataa tgtctcgcgc aagcgtcgta tttatttatt | 120 |
| tatttattac agcctccacc gccgtgcgtg ctccgtttcg gattataata aaactaatat | 180 |
| taaataaaaa aatcggatta aaggatgttt ccgaaataaa gatctccacc acaggagcga | 240 |
| aagaaaaaaa aagagaaacg ggctatggag aaatggtgtt gcgagtatac ggcggctccg | 300 |
| tcgtcgtcgg atcgacatgt acaaagtagg tgcacaaaag gcaaagcaaa atcacctcat | 360 |
| caaagaccaa aagcggagca aagaatcgat actaaatcca catgtttttt ttgttcctgt | 420 |
| ctactacgtg ctgtgcctgt gcgtgaagca cgattagtac gtgtactcac tcttgtcata | 480 |
| ttcttttag tgtcttgtca ctagtcacat ggagtagcaa ccatggctgg cgataccgc | 540 |
| gataaataaa aaaagagag agggagtaat atattagata ctcacccatt ataaattata | 600 |
| aaatatttta gagtttgaat aggtagttct tgtatattta tttatagacc ttcaagtttg | 660 |
| tccgcctctc gagagccgaa ctttgttgcc catgcttccc cggctcaggt catgccacct | 720 |
| ccttcaccaa gggcacacgg aagatctggt ggagcttgtc atcaccccgc gcccttcaaa | 780 |
| catgtgagga tgcgtcgtcg ctggcactag tagcactcat tgtaggcact acattgacag | 840 |
| tttcctccag atatgtagtg aggaaacact tgaacaacac gtttgggatt acatatgatg | 900 |
| ttttgtttgt tcatcaatga taattccttc ttcttgctta at | 942 |

<210> SEQ ID NO 40
<211> LENGTH: 18

```
<212> TYPE: DNA
<213> ORGANISM: Zea mays

<400> SEQUENCE: 40
ttgctactcc atgtgact                                                    18

<210> SEQ ID NO 41
<211> LENGTH: 16
<212> TYPE: DNA
<213> ORGANISM: Zea mays

<400> SEQUENCE: 41
ttgtcatatt cttttt                                                      16

<210> SEQ ID NO 42
<211> LENGTH: 19
<212> TYPE: DNA
<213> ORGANISM: Zea mays

<400> SEQUENCE: 42
tacacgtact aatcgtgct                                                   19

<210> SEQ ID NO 43
<211> LENGTH: 18
<212> TYPE: DNA
<213> ORGANISM: Zea mays

<400> SEQUENCE: 43
tcctgtctac tacgtgct                                                    18

<210> SEQ ID NO 44
<211> LENGTH: 19
<212> TYPE: DNA
<213> ORGANISM: Zea mays

<400> SEQUENCE: 44
ttgttcctgt ctactacgt                                                   19

<210> SEQ ID NO 45
<211> LENGTH: 20
<212> TYPE: DNA
<213> ORGANISM: Zea mays

<400> SEQUENCE: 45
ttggtctttg atgaggtgat                                                  20

<210> SEQ ID NO 46
<211> LENGTH: 20
<212> TYPE: DNA
<213> ORGANISM: Zea mays

<400> SEQUENCE: 46
tcgacatgta caaagtaggt                                                  20

<210> SEQ ID NO 47
<211> LENGTH: 19
<212> TYPE: DNA
<213> ORGANISM: Zea mays

<400> SEQUENCE: 47
ttcggaaaca tcctttaat                                                   19

<210> SEQ ID NO 48
```

```
<211> LENGTH: 19
<212> TYPE: DNA
<213> ORGANISM: Zea mays

<400> SEQUENCE: 48
ttataataaa actaatatt                                                    19

<210> SEQ ID NO 49
<211> LENGTH: 20
<212> TYPE: DNA
<213> ORGANISM: Zea mays

<400> SEQUENCE: 49
taataaataa ataaataaat                                                   20

<210> SEQ ID NO 50
<211> LENGTH: 19
<212> TYPE: DNA
<213> ORGANISM: Zea mays

<400> SEQUENCE: 50
ttggattgct ggataatgt                                                    19

<210> SEQ ID NO 51
<211> LENGTH: 18
<212> TYPE: DNA
<213> ORGANISM: Zea mays

<400> SEQUENCE: 51
tcgttgccaa agctgcat                                                     18

<210> SEQ ID NO 52
<211> LENGTH: 19
<212> TYPE: DNA
<213> ORGANISM: Zea mays

<400> SEQUENCE: 52
tcctgtcctg cactgcact                                                    19

<210> SEQ ID NO 53
<211> LENGTH: 19
<212> TYPE: DNA
<213> ORGANISM: Zea mays

<400> SEQUENCE: 53
tgcatccgtg cagtgcagt                                                    19

<210> SEQ ID NO 54
<211> LENGTH: 17
<212> TYPE: DNA
<213> ORGANISM: Zea mays

<400> SEQUENCE: 54
tcctaaacaa aggaggt                                                      17

<210> SEQ ID NO 55
<211> LENGTH: 17
<212> TYPE: DNA
<213> ORGANISM: Zea mays

<400> SEQUENCE: 55
taggacgcga tgctgct                                                      17
```

```
<210> SEQ ID NO 56
<211> LENGTH: 18
<212> TYPE: DNA
<213> ORGANISM: Zea mays

<400> SEQUENCE: 56
tgcgcacgca agtgtcgt                                                 18

<210> SEQ ID NO 57
<211> LENGTH: 19
<212> TYPE: DNA
<213> ORGANISM: Zea mays

<400> SEQUENCE: 57
tccatctcca ttcactggt                                                19

<210> SEQ ID NO 58
<211> LENGTH: 19
<212> TYPE: DNA
<213> ORGANISM: Zea mays

<400> SEQUENCE: 58
ttctgcaggc atttggcat                                                19

<210> SEQ ID NO 59
<211> LENGTH: 18
<212> TYPE: DNA
<213> ORGANISM: Zea mays

<400> SEQUENCE: 59
ttttcttctc ttctcgat                                                 18

<210> SEQ ID NO 60
<211> LENGTH: 19
<212> TYPE: DNA
<213> ORGANISM: Zea mays

<400> SEQUENCE: 60
taaccaggct agcttcgtt                                                19

<210> SEQ ID NO 61
<211> LENGTH: 18
<212> TYPE: DNA
<213> ORGANISM: Zea mays

<400> SEQUENCE: 61
taagctacaa aagaacgc                                                 18

<210> SEQ ID NO 62
<211> LENGTH: 18
<212> TYPE: DNA
<213> ORGANISM: Zea mays

<400> SEQUENCE: 62
tgtttcgcgg ccggccct                                                 18

<210> SEQ ID NO 63
<211> LENGTH: 18
<212> TYPE: DNA
<213> ORGANISM: Zea mays

<400> SEQUENCE: 63
tttccgtcct ggcctgtc                                                 18
```

-continued

<210> SEQ ID NO 64
<211> LENGTH: 19
<212> TYPE: DNA
<213> ORGANISM: Zea mays

<400> SEQUENCE: 64
tcgtccgacg acgatcgat                                               19

<210> SEQ ID NO 65
<211> LENGTH: 19
<212> TYPE: DNA
<213> ORGANISM: Zea mays

<400> SEQUENCE: 65
tcctaaacaa aggaggtcc                                               19

<210> SEQ ID NO 66
<211> LENGTH: 51
<212> TYPE: DNA
<213> ORGANISM: Zea mays

<400> SEQUENCE: 66
tacacgtact aatcgtgctt cacgcacagg cacagcacgt agtagacagg a            51

<210> SEQ ID NO 67
<211> LENGTH: 51
<212> TYPE: DNA
<213> ORGANISM: Zea mays

<400> SEQUENCE: 67
tgcatccgtg cagtgcagtg cagtgcagga caggacctcc tttgtttagg a            51

<210> SEQ ID NO 68
<211> LENGTH: 1343
<212> TYPE: PRT
<213> ORGANISM: Artificial Sequence
<220> FEATURE:
<223> OTHER INFORMATION: Xanthomonas spp, Zea mays

<400> SEQUENCE: 68

Met Ala Ser Ser Pro Lys Lys Lys Arg Lys Val Ser Trp Lys Asp
1               5                   10                  15

Ala Ser Gly Trp Ser Arg Met His Ala Asp Pro Ile Arg Pro Arg
            20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
            115                 120                 125

Asp Glu Met Gln Ser Ala Leu Arg Ala Ala Asp Asp Pro Pro Thr
    130                 135                 140

Val Arg Val Ala Val Thr Ala Ala Arg Pro Pro Arg Ala Lys Pro Ala
145                 150                 155                 160

```
Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Glu Lys Ile
            180                 185                 190

Lys Pro Lys Val Arg Ser Thr Val Ala Gln His His Glu Ala Leu Val
                195                 200                 205

Gly His Gly Phe Thr His Ala His Ile Val Ala Leu Ser Gln His Pro
210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
                260                 265                 270

Arg Gly Pro Pro Leu Gln Leu Asp Thr Gly Gln Leu Val Lys Ile Ala
                275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Asp Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Ala His Gly Leu Thr Pro Asp Gln Val
                340                 345                 350

Val Ala Ile Ala Ser His Asp Gly Gly Lys Gln Ala Leu Glu Thr Val
                355                 360                 365

Gln Arg Leu Leu Pro Val Leu Cys Gln Asp His Gly Leu Thr Pro Glu
    370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser His Asp Gly Gly Lys Gln Ala
                420                 425                 430

Leu Glu Thr Val Gln Arg Leu Leu Pro Val Leu Cys Gln Ala His Gly
                435                 440                 445

Leu Thr Pro Asp Gln Val Val Ala Ile Ala Ser Asn Asn Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Asp Gln Val Val Ala Ile Ala Ser Asn Gly Gly
                485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser Asn
    515                 520                 525

Ile Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
                565                 570                 575
```

```
Pro Val Leu Cys Gln Asp His Gly Leu Thr Pro Glu Gln Val Val Ala
            580                 585                 590

Ile Ala Ser Asn Gly Gly Gly Lys Gln Ala Leu Glu Thr Val Gln Arg
        595                 600                 605

Leu Leu Pro Val Leu Cys Gln Ala His Gly Leu Thr Pro Asp Gln Val
    610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Ser Asn Ile Gly Gly Lys Gln Ala Leu Glu
            660                 665                 670

Thr Val Gln Arg Leu Leu Pro Val Leu Cys Gln Asp His Gly Leu Thr
        675                 680                 685

Pro Glu Gln Val Val Ala Ile Ala Ser Asn Gly Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser His Asp Gly Gly Lys
                725                 730                 735

Gln Ala Leu Glu Thr Val Gln Arg Leu Leu Pro Val Leu Cys Gln Ala
            740                 745                 750

His Gly Leu Thr Pro Asp Gln Val Val Ala Ile Ala Ser Asn Asn Gly
        755                 760                 765

Gly Lys Gln Ala Leu Glu Thr Val Gln Arg Leu Leu Pro Val Leu Cys
    770                 775                 780

Gln Ala His Gly Leu Thr Pro Asp Gln Val Val Ala Ile Ala Ser Asn
785                 790                 795                 800

Gly Gly Gly Lys Gln Ala Leu Glu Thr Val Gln Arg Leu Leu Pro Val
                805                 810                 815

Leu Cys Gln Ala His Gly Leu Thr Pro Glu Gln Val Val Ala Ile Ala
            820                 825                 830

Ser Asn Asn Gly Gly Lys Gln Ala Leu Glu Thr Val Gln Arg Leu Leu
        835                 840                 845

Pro Val Leu Cys Gln Ala His Gly Leu Thr Pro Glu Gln Val Val Ala
    850                 855                 860

Ile Ala Ser His Asp Gly Gly Lys Gln Ala Leu Glu Thr Val Gln Arg
865                 870                 875                 880

Leu Leu Pro Val Leu Cys Gln Asp His Gly Leu Thr Pro Asp Gln Val
                885                 890                 895

Val Ala Ile Ala Ser Asn Gly Gly Lys Gln Ala Leu Glu Ser Ile Val
            900                 905                 910

Ala Gln Leu Ser Arg Pro Asp Pro Ala Leu Ala Ala Leu Thr Asn Asp
        915                 920                 925

His Leu Val Ala Leu Ala Cys Leu Gly Gly Arg Pro Ala Met Asp Ala
    930                 935                 940

Val Lys Lys Gly Leu Pro His Ala Pro Glu Leu Ile Arg Arg Val Asn
945                 950                 955                 960

Arg Arg Ile Gly Glu Arg Thr Ser His Arg Val Ala Asp Tyr Ala Gln
                965                 970                 975

Val Val Arg Val Leu Glu Phe Phe Gln Cys His Ser His Pro Ala Tyr
            980                 985                 990

Ala Phe Asp Glu Ala Met Thr Gln  Phe Gly Met Ser Arg  Asn Gly Leu
```

```
                995                 1000                1005
Val Gln Leu Phe Arg Arg Val Gly Val Thr Glu Leu Glu Ala Arg
    1010                1015                1020

Gly Gly Thr Leu Pro Pro Ala Ser Gln Arg Trp Asp Arg Ile Leu
    1025                1030                1035

Gln Ala Ser Gly Met Lys Arg Ala Lys Pro Ser Pro Thr Ser Ala
    1040                1045                1050

Gln Thr Pro Asp Gln Ala Ser Leu His Ala Phe Ala Asp Ser Leu
    1055                1060                1065

Glu Arg Asp Leu Asp Ala Pro Ser Pro Met His Glu Gly Asp Gln
    1070                1075                1080

Thr Arg Ala Ser Ser Arg Lys Arg Ser Arg Ser Asp Arg Ala Val
    1085                1090                1095

Thr Gly Pro Ser Ala Gln Gln Ala Val Glu Val Arg Val Pro Glu
    1100                1105                1110

Gln Arg Asp Ala Leu His Leu Pro Leu Ser Trp Arg Val Lys Arg
    1115                1120                1125

Pro Arg Thr Arg Ile Trp Gly Gly Leu Pro Asp Pro Gly Thr Pro
    1130                1135                1140

Thr Ala Ala Asp Gln Leu Val Lys Ser Glu Leu Glu Glu Lys Lys
    1145                1150                1155

Ser Glu Leu Arg His Lys Leu Lys Tyr Val Pro His Glu Tyr Ile
    1160                1165                1170

Glu Leu Ile Glu Ile Ala Arg Asn Ser Thr Gln Asp Arg Ile Leu
    1175                1180                1185

Glu Met Lys Val Met Glu Phe Phe Met Lys Val Tyr Gly Tyr Arg
    1190                1195                1200

Gly Lys His Leu Gly Gly Ser Arg Lys Pro Asp Gly Ala Ile Tyr
    1205                1210                1215

Thr Val Gly Ser Pro Ile Asp Tyr Gly Val Ile Val Asp Thr Lys
    1220                1225                1230

Ala Tyr Ser Gly Gly Tyr Asn Leu Pro Ile Gly Gln Ala Asp Glu
    1235                1240                1245

Met Gln Arg Tyr Val Glu Glu Asn Gln Thr Arg Asn Lys His Ile
    1250                1255                1260

Asn Pro Asn Glu Trp Trp Lys Val Tyr Pro Ser Ser Val Thr Glu
    1265                1270                1275

Phe Lys Phe Leu Phe Val Ser Gly His Phe Lys Gly Asn Tyr Lys
    1280                1285                1290

Ala Gln Leu Thr Arg Leu Asn His Ile Thr Asn Cys Asn Gly Ala
    1295                1300                1305

Val Leu Ser Val Glu Glu Leu Leu Ile Gly Gly Glu Met Ile Lys
    1310                1315                1320

Ala Gly Thr Leu Thr Leu Glu Glu Val Arg Arg Lys Phe Asn Asn
    1325                1330                1335

Gly Glu Ile Asn Phe
    1340

<210> SEQ ID NO 69
<211> LENGTH: 1211
<212> TYPE: PRT
<213> ORGANISM: Artificial Sequence
<220> FEATURE:
<223> OTHER INFORMATION: Xanthomonas spp, Zea mays
```

<400> SEQUENCE: 69

```
Met Ala Ser Ser Pro Lys Lys Arg Lys Val Ser Trp Lys Asp
1               5                   10                  15

Ala Ser Gly Trp Ser Arg Met His Ala Asp Pro Trp Pro Arg Arg
            20                  25                  30

Ala Ala Gln Pro Ser Asp Ala Ser Pro Ala Ala Gln Val Asp Leu Arg
        35                  40                  45

Thr Leu Gly Tyr Ser Gln Gln Gln Glu Lys Ile Lys Pro Lys Val
        50                  55                  60

Arg Ser Thr Val Ala Gln His His Glu Ala Leu Val Gly His Gly Phe
65                  70                  75                  80

Thr His Ala His Ile Val Ala Leu Ser Gln His Pro Ala Ala Leu Gly
                85                  90                  95

Thr Val Ala Val Thr Tyr Gln His Ile Ile Thr Ala Leu Pro Glu Ala
                100                 105                 110

Thr His Glu Asp Ile Val Gly Val Gly Lys Gln Trp Ser Gly Ala Arg
            115                 120                 125

Ala Leu Glu Ala Leu Leu Thr Asp Ala Gly Glu Leu Arg Gly Pro Pro
    130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser Asn
            180                 185                 190

Ile Gly Gly Lys Gln Ala Leu Glu Thr Val Gln Arg Leu Leu Pro Val
        195                 200                 205

Leu Cys Gln Ala His Gly Leu Thr Pro Asp Gln Val Val Ala Ile Ala
    210                 215                 220

Ser His Asp Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
                245                 250                 255

Ile Ala Ser Asn Ile Gly Gly Lys Gln Ala Leu Glu Thr Val Gln Arg
            260                 265                 270

Leu Leu Pro Val Leu Cys Gln Asp His Gly Leu Thr Pro Asp Gln Val
        275                 280                 285

Val Ala Ile Ala Ser His Asp Gly Gly Lys Gln Ala Leu Glu Thr Val
    290                 295                 300

Gln Arg Leu Leu Pro Val Leu Cys Gln Ala His Gly Leu Thr Pro Asp
305                 310                 315                 320

Gln Val Val Ala Ile Ala Ser Asn Asn Gly Gly Lys Gln Ala Leu Glu
                325                 330                 335

Thr Val Gln Arg Leu Leu Pro Val Leu Cys Gln Ala His Gly Leu Thr
            340                 345                 350

Pro Asp Gln Val Val Ala Ile Ala Ser Asn Gly Gly Lys Gln Ala
        355                 360                 365

Leu Glu Thr Val Gln Arg Leu Leu Pro Val Leu Cys Gln Ala His Gly
    370                 375                 380

Leu Thr Pro Glu Gln Val Val Ala Ile Ala Ser Asn Ile Gly Gly Lys
385                 390                 395                 400

Gln Ala Leu Glu Thr Val Gln Arg Leu Leu Pro Val Leu Cys Gln Ala
                405                 410                 415
```

```
His Gly Leu Thr Pro Glu Gln Val Val Ala Ile Ala Ser His Asp Gly
            420                 425                 430

Gly Lys Gln Ala Leu Glu Thr Val Gln Arg Leu Leu Pro Val Leu Cys
        435                 440                 445

Gln Asp His Gly Leu Thr Pro Glu Gln Val Val Ala Ile Ala Ser Asn
    450                 455                 460

Gly Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
            485                 490                 495

Ser Asn Ile Gly Gly Lys Gln Ala Leu Glu Thr Val Gln Arg Leu Leu
            500                 505                 510

Pro Val Leu Cys Gln Ala His Gly Leu Thr Pro Asp Gln Val Val Ala
            515                 520                 525

Ile Ala Ser Asn Ile Gly Gly Lys Gln Ala Leu Glu Thr Val Gln Arg
    530                 535                 540

Leu Leu Pro Val Leu Cys Gln Asp His Gly Leu Thr Pro Glu Gln Val
545                 550                 555                 560

Val Ala Ile Ala Ser Asn Gly Gly Gly Lys Gln Ala Leu Glu Thr Val
                565                 570                 575

Gln Arg Leu Leu Pro Val Leu Cys Gln Asp His Gly Leu Thr Pro Asp
            580                 585                 590

Gln Val Val Ala Ile Ala Ser His Asp Gly Gly Lys Gln Ala Leu Glu
        595                 600                 605

Thr Val Gln Arg Leu Leu Pro Val Leu Cys Gln Ala His Gly Leu Thr
    610                 615                 620

Pro Asp Gln Val Val Ala Ile Ala Ser Asn Asn Gly Gly Lys Gln Ala
625                 630                 635                 640

Leu Glu Thr Val Gln Arg Leu Leu Pro Val Leu Cys Gln Ala His Gly
                645                 650                 655

Leu Thr Pro Asp Gln Val Val Ala Ile Ala Ser Asn Gly Gly Gly Lys
            660                 665                 670

Gln Ala Leu Glu Thr Val Gln Arg Leu Leu Pro Val Leu Cys Gln Ala
        675                 680                 685

His Gly Leu Thr Pro Glu Gln Val Val Ala Ile Ala Ser Asn Asn Gly
    690                 695                 700

Gly Lys Gln Ala Leu Glu Thr Val Gln Arg Leu Leu Pro Val Leu Cys
705                 710                 715                 720

Gln Ala His Gly Leu Thr Pro Glu Gln Val Val Ala Ile Ala Ser His
                725                 730                 735

Asp Gly Gly Lys Gln Ala Leu Glu Thr Val Gln Arg Leu Leu Pro Val
            740                 745                 750

Leu Cys Gln Asp His Gly Leu Thr Pro Asp Gln Val Val Ala Ile Ala
    755                 760                 765

Ser Asn Gly Gly Lys Gln Ala Leu Glu Ser Ile Val Ala Gln Leu Ser
    770                 775                 780

Arg Pro Asp Pro Ala Leu Ala Ala Leu Thr Asn Asp His Leu Val Ala
785                 790                 795                 800

Leu Ala Cys Leu Gly Gly Arg Pro Ala Met Asp Ala Val Lys Lys Gly
                805                 810                 815

Leu Pro His Ala Pro Glu Leu Ile Arg Arg Val Asn Arg Arg Ile Gly
            820                 825                 830
```

-continued

```
Glu Arg Thr Ser His Arg Val Ala Asp Tyr Ala Gln Val Arg Val
            835                 840                 845

Leu Glu Phe Phe Gln Cys His Ser His Pro Ala Tyr Ala Phe Asp Glu
850                 855                 860

Ala Met Thr Gln Phe Gly Met Ser Arg Asn Gly Leu Val Gln Leu Phe
865                 870                 875                 880

Arg Arg Val Gly Val Thr Glu Leu Glu Ala Arg Gly Gly Thr Leu Pro
                885                 890                 895

Pro Ala Ser Gln Arg Trp Asp Arg Ile Leu Gln Ala Ser Gly Met Lys
            900                 905                 910

Arg Ala Lys Pro Ser Pro Thr Ser Ala Gln Thr Pro Asp Gln Ala Ser
        915                 920                 925

Leu His Ala Phe Ala Asp Ser Leu Glu Arg Asp Leu Asp Ala Pro Ser
    930                 935                 940

Pro Met His Glu Gly Asp Gln Thr Arg Ala Ser Ser Arg Lys Arg Ser
945                 950                 955                 960

Arg Ser Asp Arg Ala Val Thr Gly Pro Ser Ala Gln Gln Ala Val Glu
                965                 970                 975

Val Arg Val Pro Glu Gln Arg Asp Ala Leu His Leu Pro Leu Ser Trp
            980                 985                 990

Arg Val Lys Arg Pro Arg Thr Arg Ile Trp Gly Gly Leu Pro Asp Pro
        995                 1000                1005

Gly Thr Pro Thr Ala Ala Asp Gln Leu Val Lys Ser Glu Leu Glu
    1010                1015                1020

Glu Lys Lys Ser Glu Leu Arg His Lys Leu Lys Tyr Val Pro His
    1025                1030                1035

Glu Tyr Ile Glu Leu Ile Glu Ile Ala Arg Asn Ser Thr Gln Asp
    1040                1045                1050

Arg Ile Leu Glu Met Lys Val Met Glu Phe Phe Met Lys Val Tyr
    1055                1060                1065

Gly Tyr Arg Gly Lys His Leu Gly Gly Ser Arg Lys Pro Asp Gly
    1070                1075                1080

Ala Ile Tyr Thr Val Gly Ser Pro Ile Asp Tyr Gly Val Ile Val
    1085                1090                1095

Asp Thr Lys Ala Tyr Ser Gly Gly Tyr Asn Leu Pro Ile Gly Gln
    1100                1105                1110

Ala Asp Glu Met Gln Arg Tyr Val Glu Glu Asn Gln Thr Arg Asn
    1115                1120                1125

Lys His Ile Asn Pro Asn Glu Trp Trp Lys Val Tyr Pro Ser Ser
    1130                1135                1140

Val Thr Glu Phe Lys Phe Leu Phe Val Ser Gly His Phe Lys Gly
    1145                1150                1155

Asn Tyr Lys Ala Gln Leu Thr Arg Leu Asn His Ile Thr Asn Cys
    1160                1165                1170

Asn Gly Ala Val Leu Ser Val Glu Glu Leu Leu Ile Gly Gly Glu
    1175                1180                1185

Met Ile Lys Ala Gly Thr Leu Thr Leu Glu Glu Val Arg Arg Lys
    1190                1195                1200

Phe Asn Asn Gly Glu Ile Asn Phe
    1205                1210

<210> SEQ ID NO 70
<211> LENGTH: 1037
<212> TYPE: PRT
```

<213> ORGANISM: Artificial Sequence
<220> FEATURE:
<223> OTHER INFORMATION: Xanthomonas spp, Zea mays

<400> SEQUENCE: 70

```
Met Ala Ser Ser Pro Pro Lys Lys Lys Arg Lys Val Ser Trp Lys Asp
1               5                   10                  15

Ala Ser Gly Trp Ser Arg Met His Ala Asp Pro Trp Pro Arg Arg Arg
            20                  25                  30

Ala Ala Gln Pro Ser Asp Ala Ser Pro Ala Ala Gln Val Asp Leu Arg
        35                  40                  45

Thr Leu Gly Tyr Ser Gln Gln Gln Gln Glu Lys Ile Lys Pro Lys Val
    50                  55                  60

Arg Ser Thr Val Ala Gln His His Glu Ala Leu Val Gly His Gly Phe
65                  70                  75                  80

Thr His Ala His Ile Val Ala Leu Ser Gln His Pro Ala Ala Leu Gly
                85                  90                  95

Thr Val Ala Val Thr Tyr Gln His Ile Ile Thr Ala Leu Pro Glu Ala
            100                 105                 110

Thr His Glu Asp Ile Val Gly Val Gly Lys Gln Trp Ser Gly Ala Arg
        115                 120                 125

Ala Leu Glu Ala Leu Leu Thr Asp Ala Gly Glu Leu Arg Gly Pro Pro
    130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser Asn
            180                 185                 190

Ile Gly Gly Lys Gln Ala Leu Glu Thr Val Gln Arg Leu Leu Pro Val
        195                 200                 205

Leu Cys Gln Ala His Gly Leu Thr Pro Asp Gln Val Val Ala Ile Ala
    210                 215                 220

Ser His Asp Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
                245                 250                 255

Ile Ala Ser Asn Ile Gly Gly Lys Gln Ala Leu Glu Thr Val Gln Arg
            260                 265                 270

Leu Leu Pro Val Leu Cys Gln Asp His Gly Leu Thr Pro Asp Gln Val
        275                 280                 285

Val Ala Ile Ala Ser His Asp Gly Gly Lys Gln Ala Leu Glu Thr Val
    290                 295                 300

Gln Arg Leu Leu Pro Val Leu Cys Gln Ala His Gly Leu Thr Pro Asp
305                 310                 315                 320

Gln Val Val Ala Ile Ala Ser Asn Asn Gly Gly Lys Gln Ala Leu Glu
                325                 330                 335

Thr Val Gln Arg Leu Leu Pro Val Leu Cys Gln Ala His Gly Leu Thr
            340                 345                 350

Pro Asp Gln Val Val Ala Ile Ala Ser Asn Gly Gly Gly Lys Gln Ala
        355                 360                 365

Leu Glu Thr Val Gln Arg Leu Leu Pro Val Leu Cys Gln Ala His Gly
    370                 375                 380

Leu Thr Pro Glu Gln Val Val Ala Ile Ala Ser Asn Ile Gly Gly Lys
```

```
385                 390                 395                 400
Gln Ala Leu Glu Thr Val Gln Arg Leu Leu Pro Val Leu Cys Gln Ala
                405                 410                 415

His Gly Leu Thr Pro Glu Gln Val Val Ala Ile Ala Ser His Asp Gly
                420                 425                 430

Gly Lys Gln Ala Leu Glu Thr Val Gln Arg Leu Leu Pro Val Leu Cys
                435                 440                 445

Gln Asp His Gly Leu Thr Pro Glu Gln Val Val Ala Ile Ala Ser Asn
450                 455                 460

Gly Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
                485                 490                 495

Ser Asn Ile Gly Gly Lys Gln Ala Leu Glu Thr Val Gln Arg Leu Leu
                500                 505                 510

Pro Val Leu Cys Gln Ala His Gly Leu Thr Pro Asp Gln Val Val Ala
                515                 520                 525

Ile Ala Ser Asn Ile Gly Gly Lys Gln Ala Leu Glu Thr Val Gln Arg
                530                 535                 540

Leu Leu Pro Val Leu Cys Gln Asp His Gly Leu Thr Pro Glu Gln Val
545                 550                 555                 560

Val Ala Ile Ala Ser Asn Gly Gly Gly Lys Gln Ala Leu Glu Thr Val
                565                 570                 575

Gln Arg Leu Leu Pro Val Leu Cys Gln Asp His Gly Leu Thr Pro Asp
                580                 585                 590

Gln Val Val Ala Ile Ala Ser His Asp Gly Gly Lys Gln Ala Leu Glu
                595                 600                 605

Thr Val Gln Arg Leu Leu Pro Val Leu Cys Gln Ala His Gly Leu Thr
                610                 615                 620

Pro Asp Gln Val Val Ala Ile Ala Ser Asn Asn Gly Gly Lys Gln Ala
625                 630                 635                 640

Leu Glu Thr Val Gln Arg Leu Leu Pro Val Leu Cys Gln Ala His Gly
                645                 650                 655

Leu Thr Pro Asp Gln Val Val Ala Ile Ala Ser Asn Gly Gly Gly Lys
                660                 665                 670

Gln Ala Leu Glu Thr Val Gln Arg Leu Leu Pro Val Leu Cys Gln Ala
                675                 680                 685

His Gly Leu Thr Pro Glu Gln Val Val Ala Ile Ala Ser Asn Asn Gly
                690                 695                 700

Gly Lys Gln Ala Leu Glu Thr Val Gln Arg Leu Leu Pro Val Leu Cys
705                 710                 715                 720

Gln Ala His Gly Leu Thr Pro Glu Gln Val Val Ala Ile Ala Ser His
                725                 730                 735

Asp Gly Gly Lys Gln Ala Leu Glu Thr Val Gln Arg Leu Leu Pro Val
                740                 745                 750

Leu Cys Gln Asp His Gly Leu Thr Pro Asp Gln Val Val Ala Ile Ala
                755                 760                 765

Ser Asn Gly Gly Lys Gln Ala Leu Glu Ser Ile Val Ala Gln Leu Ser
                770                 775                 780

Arg Pro Asp Pro Ala Leu Ala Ala Leu Thr Asn Asp His Leu Val Ala
785                 790                 795                 800

Leu Ala Cys Leu Gly Gly Arg Pro Ala Met Asp Ala Val Lys Lys Gly
                805                 810                 815
```

```
Leu Pro His Ala Pro Glu Leu Ile Arg Arg Val Asn Arg Arg Ile Gly
            820                 825                 830

Glu Arg Thr Ser His Arg Val Ala Leu Gln Leu Val Lys Ser Glu Leu
            835                 840                 845

Glu Glu Lys Lys Ser Glu Leu Arg His Lys Leu Lys Tyr Val Pro His
850                 855                 860

Glu Tyr Ile Glu Leu Ile Glu Ile Ala Arg Asn Ser Thr Gln Asp Arg
865                 870                 875                 880

Ile Leu Glu Met Lys Val Met Glu Phe Phe Met Lys Val Tyr Gly Tyr
            885                 890                 895

Arg Gly Lys His Leu Gly Gly Ser Arg Lys Pro Asp Gly Ala Ile Tyr
            900                 905                 910

Thr Val Gly Ser Pro Ile Asp Tyr Gly Val Ile Val Asp Thr Lys Ala
            915                 920                 925

Tyr Ser Gly Gly Tyr Asn Leu Pro Ile Gly Gln Ala Asp Glu Met Gln
930                 935                 940

Arg Tyr Val Glu Glu Asn Gln Thr Arg Asn Lys His Ile Asn Pro Asn
945                 950                 955                 960

Glu Trp Trp Lys Val Tyr Pro Ser Ser Val Thr Glu Phe Lys Phe Leu
            965                 970                 975

Phe Val Ser Gly His Phe Lys Gly Asn Tyr Lys Ala Gln Leu Thr Arg
            980                 985                 990

Leu Asn His Ile Thr Asn Cys Asn Gly Ala Val Leu Ser Val Glu Glu
            995                1000                1005

Leu Leu Ile Gly Gly Glu Met Ile Lys Ala Gly Thr Leu Thr Leu
            1010                1015                1020

Glu Glu Val Arg Arg Lys Phe Asn Asn Gly Glu Ile Asn Phe
            1025                1030                1035

<210> SEQ ID NO 71
<211> LENGTH: 1309
<212> TYPE: PRT
<213> ORGANISM: Artificial Sequence
<220> FEATURE:
<223> OTHER INFORMATION: Xanthomonas spp, Zea mays

<400> SEQUENCE: 71

Met Ala Ser Ser Pro Lys Lys Lys Arg Lys Val Ser Trp Lys Asp
1               5                   10                  15

Ala Ser Gly Trp Ser Arg Met His Ala Asp Pro Ile Arg Pro Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Met Gln Ser Ala Leu Arg Ala Ala Asp Asp Pro Pro Pro Thr
    130                 135                 140
```

```
Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Asp Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Asp Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Asp His Gly Leu Thr Pro Glu
    370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Asp Gln Val Val Ala Ile Ala Ser Asn Gly Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560
```

-continued

```
Ser Asn Ile Gly Gly Lys Gln Ala Leu Glu Thr Val Gln Arg Leu Leu
                565                 570                 575

Pro Val Leu Cys Gln Asp His Gly Leu Thr Pro Glu Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Ala His Gly Leu Thr Pro Asp Gln Val
    610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Asp
            645                 650                 655

Gln Val Val Ala Ile Ala Ser Asn Ile Gly Gly Lys Gln Ala Leu Glu
        660                 665                 670

Thr Val Gln Arg Leu Leu Pro Val Leu Cys Gln Asp His Gly Leu Thr
    675                 680                 685

Pro Glu Gln Val Val Ala Ile Ala Ser His Asp Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Gly Gly Lys
            725                 730                 735

Gln Ala Leu Glu Thr Val Gln Arg Leu Leu Pro Val Leu Cys Gln Ala
        740                 745                 750

His Gly Leu Thr Pro Asp Gln Val Val Ala Ile Ala Ser Asn Gly Gly
    755                 760                 765

Gly Lys Gln Ala Leu Glu Thr Val Gln Arg Leu Leu Pro Val Leu Cys
770                 775                 780

Gln Ala His Gly Leu Thr Pro Asp Gln Val Val Ala Ile Ala Ser Asn
785                 790                 795                 800

Asn Gly Gly Lys Gln Ala Leu Glu Thr Val Gln Arg Leu Leu Pro Val
            805                 810                 815

Leu Cys Gln Ala His Gly Leu Thr Pro Glu Gln Val Val Ala Ile Ala
        820                 825                 830

Ser His Asp Gly Gly Lys Gln Ala Leu Glu Thr Val Gln Arg Leu Leu
    835                 840                 845

Pro Val Leu Cys Gln Asp His Gly Leu Thr Pro Asp Gln Val Val Ala
    850                 855                 860

Ile Ala Ser Asn Gly Gly Lys Gln Ala Leu Glu Ser Ile Val Ala Gln
865                 870                 875                 880

Leu Ser Arg Pro Asp Pro Ala Leu Ala Ala Leu Thr Asn Asp His Leu
            885                 890                 895

Val Ala Leu Ala Cys Leu Gly Gly Arg Pro Ala Met Asp Ala Val Lys
        900                 905                 910

Lys Gly Leu Pro His Ala Pro Glu Leu Ile Arg Arg Val Asn Arg Arg
    915                 920                 925

Ile Gly Glu Arg Thr Ser His Arg Val Ala Asp Tyr Ala Gln Val Val
    930                 935                 940

Arg Val Leu Glu Phe Phe Gln Cys His Ser His Pro Ala Tyr Ala Phe
945                 950                 955                 960

Asp Glu Ala Met Thr Gln Phe Gly Met Ser Arg Asn Gly Leu Val Gln
            965                 970                 975

Leu Phe Arg Arg Val Gly Val Thr Glu Leu Glu Ala Arg Gly Gly Thr
```

```
                980             985             990
Leu Pro Pro Ala Ser Gln Arg Trp Asp Arg Ile Leu Gln Ala Ser Gly
            995             1000            1005

Met Lys Arg Ala Lys Pro Ser Pro Thr Ser Ala Gln Thr Pro Asp
    1010            1015            1020

Gln Ala Ser Leu His Ala Phe Ala Asp Ser Leu Glu Arg Asp Leu
    1025            1030            1035

Asp Ala Pro Ser Pro Met His Glu Gly Asp Gln Thr Arg Ala Ser
    1040            1045            1050

Ser Arg Lys Arg Ser Arg Ser Asp Arg Ala Val Thr Gly Pro Ser
    1055            1060            1065

Ala Gln Gln Ala Val Glu Val Arg Val Pro Glu Gln Arg Asp Ala
    1070            1075            1080

Leu His Leu Pro Leu Ser Trp Arg Val Lys Arg Pro Arg Thr Arg
    1085            1090            1095

Ile Trp Gly Gly Leu Pro Asp Pro Gly Thr Pro Thr Ala Ala Asp
    1100            1105            1110

Gln Leu Val Lys Ser Glu Leu Glu Glu Lys Ser Glu Leu Arg
    1115            1120            1125

His Lys Leu Lys Tyr Val Pro His Glu Tyr Ile Glu Leu Ile Glu
    1130            1135            1140

Ile Ala Arg Asn Ser Thr Gln Asp Arg Ile Leu Glu Met Lys Val
    1145            1150            1155

Met Glu Phe Phe Met Lys Val Tyr Gly Tyr Arg Gly Lys His Leu
    1160            1165            1170

Gly Gly Ser Arg Lys Pro Asp Gly Ala Ile Tyr Thr Val Gly Ser
    1175            1180            1185

Pro Ile Asp Tyr Gly Val Ile Val Asp Thr Lys Ala Tyr Ser Gly
    1190            1195            1200

Gly Tyr Asn Leu Pro Ile Gly Gln Ala Asp Glu Met Gln Arg Tyr
    1205            1210            1215

Val Glu Glu Asn Gln Thr Arg Asn Lys His Ile Asn Pro Asn Glu
    1220            1225            1230

Trp Trp Lys Val Tyr Pro Ser Ser Val Thr Glu Phe Lys Phe Leu
    1235            1240            1245

Phe Val Ser Gly His Phe Lys Gly Asn Tyr Lys Ala Gln Leu Thr
    1250            1255            1260

Arg Leu Asn His Ile Thr Asn Cys Asn Gly Ala Val Leu Ser Val
    1265            1270            1275

Glu Glu Leu Leu Ile Gly Gly Glu Met Ile Lys Ala Gly Thr Leu
    1280            1285            1290

Thr Leu Glu Glu Val Arg Arg Lys Phe Asn Asn Gly Glu Ile Asn
    1295            1300            1305

Phe

<210> SEQ ID NO 72
<211> LENGTH: 1177
<212> TYPE: PRT
<213> ORGANISM: Artificial Sequence
<220> FEATURE:
<223> OTHER INFORMATION: Xanthomonas spp, Zea mays

<400> SEQUENCE: 72

Met Ala Ser Ser Pro Pro Lys Lys Lys Arg Lys Val Ser Trp Lys Asp
1               5                   10                  15
```

```
Ala Ser Gly Trp Ser Arg Met His Ala Asp Pro Trp Pro Arg Arg
            20                  25                  30

Ala Ala Gln Pro Ser Asp Ala Ser Pro Ala Ala Gln Val Asp Leu Arg
        35                  40                  45

Thr Leu Gly Tyr Ser Gln Gln Gln Glu Lys Ile Lys Pro Lys Val
50                  55                  60

Arg Ser Thr Val Ala Gln His His Glu Ala Leu Val Gly His Gly Phe
65                  70                  75                  80

Thr His Ala His Ile Val Ala Leu Ser Gln His Pro Ala Ala Leu Gly
                85                  90                  95

Thr Val Ala Val Thr Tyr Gln His Ile Ile Thr Ala Leu Pro Glu Ala
                100                 105                 110

Thr His Glu Asp Ile Val Gly Val Gly Lys Gln Trp Ser Gly Ala Arg
                115                 120                 125

Ala Leu Glu Ala Leu Leu Thr Asp Ala Gly Glu Leu Arg Gly Pro Pro
130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser His
                180                 185                 190

Asp Gly Gly Lys Gln Ala Leu Glu Thr Val Gln Arg Leu Leu Pro Val
                195                 200                 205

Leu Cys Gln Ala His Gly Leu Thr Pro Asp Gln Val Val Ala Ile Ala
                210                 215                 220

Ser His Asp Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
                245                 250                 255

Ile Ala Ser Asn Gly Gly Gly Lys Gln Ala Leu Glu Thr Val Gln Arg
                260                 265                 270

Leu Leu Pro Val Leu Cys Gln Asp His Gly Leu Thr Pro Asp Gln Val
                275                 280                 285

Val Ala Ile Ala Ser Asn Asn Gly Gly Lys Gln Ala Leu Glu Thr Val
                290                 295                 300

Gln Arg Leu Leu Pro Val Leu Cys Gln Ala His Gly Leu Thr Pro Asp
305                 310                 315                 320

Gln Val Val Ala Ile Ala Ser Asn Gly Gly Lys Gln Ala Leu Glu
                325                 330                 335

Thr Val Gln Arg Leu Leu Pro Val Leu Cys Gln Ala His Gly Leu Thr
                340                 345                 350

Pro Asp Gln Val Val Ala Ile Ala Ser His Asp Gly Gly Lys Gln Ala
                355                 360                 365

Leu Glu Thr Val Gln Arg Leu Leu Pro Val Leu Cys Gln Ala His Gly
                370                 375                 380

Leu Thr Pro Glu Gln Val Val Ala Ile Ala Ser Asn Gly Gly Gly Lys
385                 390                 395                 400

Gln Ala Leu Glu Thr Val Gln Arg Leu Leu Pro Val Leu Cys Gln Ala
                405                 410                 415

His Gly Leu Thr Pro Glu Gln Val Val Ala Ile Ala Ser Asn Ile Gly
                420                 425                 430
```

```
Gly Lys Gln Ala Leu Glu Thr Val Gln Arg Leu Leu Pro Val Leu Cys
            435                 440                 445

Gln Asp His Gly Leu Thr Pro Glu Gln Val Val Ala Ile Ala Ser His
        450                 455                 460

Asp Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
                485                 490                 495

Ser Asn Gly Gly Lys Gln Ala Leu Glu Thr Val Gln Arg Leu Leu
            500                 505                 510

Pro Val Leu Cys Gln Ala His Gly Leu Thr Pro Asp Gln Val Val Ala
        515                 520                 525

Ile Ala Ser Asn Ile Gly Gly Lys Gln Ala Leu Glu Thr Val Gln Arg
530                 535                 540

Leu Leu Pro Val Leu Cys Gln Asp His Gly Leu Thr Pro Glu Gln Val
545                 550                 555                 560

Val Ala Ile Ala Ser His Asp Gly Gly Lys Gln Ala Leu Glu Thr Val
                565                 570                 575

Gln Arg Leu Leu Pro Val Leu Cys Gln Asp His Gly Leu Thr Pro Asp
            580                 585                 590

Gln Val Val Ala Ile Ala Ser Asn Gly Gly Lys Gln Ala Leu Glu
        595                 600                 605

Thr Val Gln Arg Leu Leu Pro Val Leu Cys Gln Ala His Gly Leu Thr
        610                 615                 620

Pro Asp Gln Val Val Ala Ile Ala Ser Asn Gly Gly Lys Gln Ala
625                 630                 635                 640

Leu Glu Thr Val Gln Arg Leu Leu Pro Val Leu Cys Gln Ala His Gly
                645                 650                 655

Leu Thr Pro Asp Gln Val Val Ala Ile Ala Ser Asn Asn Gly Gly Lys
            660                 665                 670

Gln Ala Leu Glu Thr Val Gln Arg Leu Leu Pro Val Leu Cys Gln Ala
        675                 680                 685

His Gly Leu Thr Pro Glu Gln Val Val Ala Ile Ala Ser His Asp Gly
        690                 695                 700

Gly Lys Gln Ala Leu Glu Thr Val Gln Arg Leu Leu Pro Val Leu Cys
705                 710                 715                 720

Gln Asp His Gly Leu Thr Pro Asp Gln Val Val Ala Ile Ala Ser Asn
                725                 730                 735

Gly Gly Lys Gln Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
        755                 760                 765

Cys Leu Gly Gly Arg Pro Ala Met Asp Ala Val Lys Lys Gly Leu Pro
770                 775                 780

His Ala Pro Glu Leu Ile Arg Arg Val Asn Arg Arg Ile Gly Glu Arg
785                 790                 795                 800

Thr Ser His Arg Val Ala Asp Tyr Ala Gln Val Val Arg Val Leu Glu
                805                 810                 815

Phe Phe Gln Cys His Ser His Pro Ala Tyr Ala Phe Asp Glu Ala Met
            820                 825                 830

Thr Gln Phe Gly Met Ser Arg Asn Gly Leu Val Gln Leu Phe Arg Arg
        835                 840                 845

Val Gly Val Thr Glu Leu Glu Ala Arg Gly Gly Thr Leu Pro Pro Ala
```

```
                    850                 855                 860
Ser Gln Arg Trp Asp Arg Ile Leu Gln Ala Ser Gly Met Lys Arg Ala
865                 870                 875                 880

Lys Pro Ser Pro Thr Ser Ala Gln Thr Pro Asp Gln Ala Ser Leu His
                885                 890                 895

Ala Phe Ala Asp Ser Leu Glu Arg Asp Leu Asp Ala Pro Ser Pro Met
            900                 905                 910

His Glu Gly Asp Gln Thr Arg Ala Ser Arg Lys Arg Ser Arg Ser
        915                 920                 925

Asp Arg Ala Val Thr Gly Pro Ser Ala Gln Gln Ala Val Glu Val Arg
930                 935                 940

Val Pro Glu Gln Arg Asp Ala Leu His Leu Pro Leu Ser Trp Arg Val
945                 950                 955                 960

Lys Arg Pro Arg Thr Arg Ile Trp Gly Gly Leu Pro Asp Pro Gly Thr
                965                 970                 975

Pro Thr Ala Ala Asp Gln Leu Val Lys Ser Glu Leu Glu Glu Lys Lys
            980                 985                 990

Ser Glu Leu Arg His Lys Leu Lys Tyr Val Pro His Glu Tyr Ile Glu
        995                 1000                1005

Leu Ile Glu Ile Ala Arg Asn Ser Thr Gln Asp Arg Ile Leu Glu
    1010                1015                1020

Met Lys Val Met Glu Phe Phe Met Lys Val Tyr Gly Tyr Arg Gly
    1025                1030                1035

Lys His Leu Gly Gly Ser Arg Lys Pro Asp Gly Ala Ile Tyr Thr
    1040                1045                1050

Val Gly Ser Pro Ile Asp Tyr Gly Val Ile Val Asp Thr Lys Ala
    1055                1060                1065

Tyr Ser Gly Gly Tyr Asn Leu Pro Ile Gly Gln Ala Asp Glu Met
    1070                1075                1080

Gln Arg Tyr Val Glu Glu Asn Gln Thr Arg Asn Lys His Ile Asn
    1085                1090                1095

Pro Asn Glu Trp Trp Lys Val Tyr Pro Ser Ser Val Thr Glu Phe
    1100                1105                1110

Lys Phe Leu Phe Val Ser Gly His Phe Lys Gly Asn Tyr Lys Ala
    1115                1120                1125

Gln Leu Thr Arg Leu Asn His Ile Thr Asn Cys Asn Gly Ala Val
    1130                1135                1140

Leu Ser Val Glu Glu Leu Leu Ile Gly Gly Glu Met Ile Lys Ala
    1145                1150                1155

Gly Thr Leu Thr Leu Glu Glu Val Arg Arg Lys Phe Asn Asn Gly
    1160                1165                1170

Glu Ile Asn Phe
    1175

<210> SEQ ID NO 73
<211> LENGTH: 1003
<212> TYPE: PRT
<213> ORGANISM: Artificial Sequence
<220> FEATURE:
<223> OTHER INFORMATION: Xanthomonas spp, Zea mays

<400> SEQUENCE: 73

Met Ala Ser Ser Pro Lys Lys Lys Arg Lys Val Ser Trp Lys Asp
1               5                   10                  15

Ala Ser Gly Trp Ser Arg Met His Ala Asp Pro Trp Pro Arg Arg Arg
```

-continued

```
                20                  25                  30
Ala Ala Gln Pro Ser Asp Ala Ser Pro Ala Ala Gln Val Asp Leu Arg
            35                  40                  45
Thr Leu Gly Tyr Ser Gln Gln Gln Glu Lys Ile Lys Pro Lys Val
 50                  55                  60
Arg Ser Thr Val Ala Gln His His Glu Ala Leu Val Gly His Gly Phe
 65                  70                  75                  80
Thr His Ala His Ile Val Ala Leu Ser Gln His Pro Ala Ala Leu Gly
                85                  90                  95
Thr Val Ala Val Thr Tyr Gln His Ile Ile Thr Ala Leu Pro Glu Ala
                100                 105                 110
Thr His Glu Asp Ile Val Gly Val Gly Lys Gln Trp Ser Gly Ala Arg
            115                 120                 125
Ala Leu Glu Ala Leu Leu Thr Asp Ala Gly Leu Arg Gly Pro Pro
        130                 135                 140
Leu Gln Leu Asp Thr Gly Gln Leu Val Lys Ile Ala Lys Arg Gly Gly
145                 150                 155                 160
Val Thr Ala Met Glu Ala Val His Ala Ser Arg Asn Ala Leu Thr Gly
                165                 170                 175
Ala Pro Leu Asn Leu Thr Pro Asp Gln Val Val Ala Ile Ala Ser His
            180                 185                 190
Asp Gly Gly Lys Gln Ala Leu Glu Thr Val Gln Arg Leu Leu Pro Val
            195                 200                 205
Leu Cys Gln Ala His Gly Leu Thr Pro Asp Gln Val Val Ala Ile Ala
        210                 215                 220
Ser His Asp Gly Gly Lys Gln Ala Leu Glu Thr Val Gln Arg Leu Leu
225                 230                 235                 240
Pro Val Leu Cys Gln Asp His Gly Leu Thr Pro Glu Gln Val Val Ala
                245                 250                 255
Ile Ala Ser Asn Gly Gly Gly Lys Gln Ala Leu Glu Thr Val Gln Arg
            260                 265                 270
Leu Leu Pro Val Leu Cys Gln Asp His Gly Leu Thr Pro Asp Gln Val
        275                 280                 285
Val Ala Ile Ala Ser Asn Asn Gly Gly Lys Gln Ala Leu Glu Thr Val
        290                 295                 300
Gln Arg Leu Leu Pro Val Leu Cys Gln Ala His Gly Leu Thr Pro Asp
305                 310                 315                 320
Gln Val Val Ala Ile Ala Ser Asn Gly Gly Lys Gln Ala Leu Glu
                325                 330                 335
Thr Val Gln Arg Leu Leu Pro Val Leu Cys Gln Ala His Gly Leu Thr
            340                 345                 350
Pro Asp Gln Val Val Ala Ile Ala Ser His Asp Gly Gly Lys Gln Ala
        355                 360                 365
Leu Glu Thr Val Gln Arg Leu Leu Pro Val Leu Cys Gln Ala His Gly
    370                 375                 380
Leu Thr Pro Glu Gln Val Val Ala Ile Ala Ser Asn Gly Gly Gly Lys
385                 390                 395                 400
Gln Ala Leu Glu Thr Val Gln Arg Leu Leu Pro Val Leu Cys Gln Ala
                405                 410                 415
His Gly Leu Thr Pro Glu Gln Val Val Ala Ile Ala Ser Asn Ile Gly
            420                 425                 430
Gly Lys Gln Ala Leu Glu Thr Val Gln Arg Leu Leu Pro Val Leu Cys
        435                 440                 445
```

```
Gln Asp His Gly Leu Thr Pro Glu Gln Val Val Ala Ile Ala Ser His
    450                 455                 460

Asp Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
                    485                 490                 495

Ser Asn Gly Gly Lys Gln Ala Leu Glu Thr Val Gln Arg Leu Leu
            500                 505                 510

Pro Val Leu Cys Gln Ala His Gly Leu Thr Pro Asp Gln Val Val Ala
            515                 520                 525

Ile Ala Ser Asn Ile Gly Gly Lys Gln Ala Leu Glu Thr Val Gln Arg
530                 535                 540

Leu Leu Pro Val Leu Cys Gln Asp His Gly Leu Thr Pro Glu Gln Val
545                 550                 555                 560

Val Ala Ile Ala Ser His Asp Gly Gly Lys Gln Ala Leu Glu Thr Val
                565                 570                 575

Gln Arg Leu Leu Pro Val Leu Cys Gln Asp His Gly Leu Thr Pro Asp
            580                 585                 590

Gln Val Val Ala Ile Ala Ser Asn Asn Gly Gly Lys Gln Ala Leu Glu
            595                 600                 605

Thr Val Gln Arg Leu Leu Pro Val Leu Cys Gln Ala His Gly Leu Thr
    610                 615                 620

Pro Asp Gln Val Val Ala Ile Ala Ser Asn Gly Gly Gly Lys Gln Ala
625                 630                 635                 640

Leu Glu Thr Val Gln Arg Leu Leu Pro Val Leu Cys Gln Ala His Gly
                645                 650                 655

Leu Thr Pro Asp Gln Val Val Ala Ile Ala Ser Asn Asn Gly Gly Lys
            660                 665                 670

Gln Ala Leu Glu Thr Val Gln Arg Leu Leu Pro Val Leu Cys Gln Ala
            675                 680                 685

His Gly Leu Thr Pro Glu Gln Val Val Ala Ile Ala Ser His Asp Gly
    690                 695                 700

Gly Lys Gln Ala Leu Glu Thr Val Gln Arg Leu Leu Pro Val Leu Cys
705                 710                 715                 720

Gln Asp His Gly Leu Thr Pro Asp Gln Val Val Ala Ile Ala Ser Asn
                725                 730                 735

Gly Gly Lys Gln Ala Leu Glu Ser Ile Val Ala Gln Leu Ser Arg Pro
            740                 745                 750

Asp Pro Ala Leu Ala Ala Leu Thr Asn Asp His Leu Val Ala Leu Ala
            755                 760                 765

Cys Leu Gly Gly Arg Pro Ala Met Asp Ala Val Lys Lys Gly Leu Pro
770                 775                 780

His Ala Pro Glu Leu Ile Arg Arg Val Asn Arg Arg Ile Gly Glu Arg
785                 790                 795                 800

Thr Ser His Arg Val Ala Leu Gln Leu Val Lys Ser Glu Leu Glu Glu
                805                 810                 815

Lys Lys Ser Glu Leu Arg His Lys Leu Lys Tyr Val Pro His Glu Tyr
            820                 825                 830

Ile Glu Leu Ile Glu Ile Ala Arg Asn Ser Thr Gln Asp Arg Ile Leu
            835                 840                 845

Glu Met Lys Val Met Glu Phe Phe Met Lys Val Tyr Gly Tyr Arg Gly
850                 855                 860
```

```
Lys His Leu Gly Gly Ser Arg Lys Pro Asp Gly Ala Ile Tyr Thr Val
865                 870                 875                 880

Gly Ser Pro Ile Asp Tyr Gly Val Ile Val Asp Thr Lys Ala Tyr Ser
            885                 890                 895

Gly Gly Tyr Asn Leu Pro Ile Gly Gln Ala Asp Glu Met Gln Arg Tyr
        900                 905                 910

Val Glu Glu Asn Gln Thr Arg Asn Lys His Ile Asn Pro Asn Glu Trp
        915                 920                 925

Trp Lys Val Tyr Pro Ser Ser Val Thr Glu Phe Lys Phe Leu Phe Val
        930                 935                 940

Ser Gly His Phe Lys Gly Asn Tyr Lys Ala Gln Leu Thr Arg Leu Asn
945                 950                 955                 960

His Ile Thr Asn Cys Asn Gly Ala Val Leu Ser Val Glu Leu Leu
                965                 970                 975

Ile Gly Gly Glu Met Ile Lys Ala Gly Thr Leu Thr Leu Glu Glu Val
            980                 985                 990

Arg Arg Lys Phe Asn Asn Gly Glu  Ile Asn Phe
            995                 1000

<210> SEQ ID NO 74
<211> LENGTH: 1343
<212> TYPE: PRT
<213> ORGANISM: Artificial Sequence
<220> FEATURE:
<223> OTHER INFORMATION: Xanthomonas spp, Zea mays

<400> SEQUENCE: 74

Met Ala Ser Ser Pro Pro Lys Lys Arg Lys Val Ser Trp Lys Asp
1               5                   10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
    50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Met Gln Ser Ala Leu Arg Ala Ala Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220
```

```
Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
            245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Asp Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Asp Gln Val
            340                 345                 350

Val Ala Ile Ala Ser His Asp Gly Gly Lys Gln Ala Leu Glu Thr Val
            355                 360                 365

Gln Arg Leu Leu Pro Val Leu Cys Gln Asp His Gly Leu Thr Pro Glu
370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Gly Gly Lys Gln Ala
        420                 425                 430

Leu Glu Thr Val Gln Arg Leu Leu Pro Val Leu Cys Gln Ala His Gly
            435                 440                 445

Leu Thr Pro Asp Gln Val Val Ala Ile Ala Ser His Asp Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Asp Gln Val Val Ala Ile Ala Ser His Asp Gly
                485                 490                 495

Gly Lys Gln Ala Leu Glu Thr Val Gln Arg Leu Leu Pro Val Leu Cys
        500                 505                 510

Gln Ala His Gly Leu Thr Pro Glu Gln Val Val Ala Ile Ala Ser Asn
    515                 520                 525

Asn Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Glu Gln Val Val Ala
            580                 585                 590

Ile Ala Ser Asn Asn Gly Gly Lys Gln Ala Leu Glu Thr Val Gln Arg
        595                 600                 605

Leu Leu Pro Val Leu Cys Gln Ala His Gly Leu Thr Pro Asp Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Asp
```

```
                645                 650                 655
Gln Val Val Ala Ile Ala Ser Asn Ile Gly Gly Lys Gln Ala Leu Glu
                660                 665                 670

Thr Val Gln Arg Leu Leu Pro Val Leu Cys Gln Asp His Gly Leu Thr
                675                 680                 685

Pro Glu Gln Val Val Ala Ile Ala Ser Asn Asn Gly Gly Lys Gln Ala
    690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Gly Gly Gly Lys
                725                 730                 735

Gln Ala Leu Glu Thr Val Gln Arg Leu Leu Pro Val Leu Cys Gln Ala
                740                 745                 750

His Gly Leu Thr Pro Asp Gln Val Val Ala Ile Ala Ser Asn Asn Gly
                755                 760                 765

Gly Lys Gln Ala Leu Glu Thr Val Gln Arg Leu Leu Pro Val Leu Cys
                770                 775                 780

Gln Ala His Gly Leu Thr Pro Asp Gln Val Val Ala Ile Ala Ser His
785                 790                 795                 800

Asp Gly Gly Lys Gln Ala Leu Glu Thr Val Gln Arg Leu Leu Pro Val
                805                 810                 815

Leu Cys Gln Ala His Gly Leu Thr Pro Glu Gln Val Val Ala Ile Ala
                820                 825                 830

Ser Asn Ile Gly Gly Lys Gln Ala Leu Glu Thr Val Gln Arg Leu Leu
                835                 840                 845

Pro Val Leu Cys Gln Ala His Gly Leu Thr Pro Glu Gln Val Val Ala
    850                 855                 860

Ile Ala Ser Asn Asn Gly Gly Lys Gln Ala Leu Glu Thr Val Gln Arg
865                 870                 875                 880

Leu Leu Pro Val Leu Cys Gln Asp His Gly Leu Thr Pro Asp Gln Val
                885                 890                 895

Val Ala Ile Ala Ser Asn Gly Gly Lys Gln Ala Leu Glu Ser Ile Val
                900                 905                 910

Ala Gln Leu Ser Arg Pro Asp Pro Ala Leu Ala Ala Leu Thr Asn Asp
                915                 920                 925

His Leu Val Ala Leu Ala Cys Leu Gly Gly Arg Pro Ala Met Asp Ala
                930                 935                 940

Val Lys Lys Gly Leu Pro His Ala Pro Glu Leu Ile Arg Arg Val Asn
945                 950                 955                 960

Arg Arg Ile Gly Glu Arg Thr Ser His Arg Val Ala Asp Tyr Ala Gln
                965                 970                 975

Val Val Arg Val Leu Glu Phe Phe Gln Cys His Ser His Pro Ala Tyr
                980                 985                 990

Ala Phe Asp Glu Ala Met Thr Gln Phe Gly Met Ser Arg Asn Gly Leu
    995                 1000                1005

Val Gln Leu Phe Arg Arg Val Gly Val Thr Glu Leu Glu Ala Arg
    1010                1015                1020

Gly Gly Thr Leu Pro Pro Ala Ser Gln Arg Trp Asp Arg Ile Leu
    1025                1030                1035

Gln Ala Ser Gly Met Lys Arg Ala Lys Pro Ser Pro Thr Ser Ala
    1040                1045                1050

Gln Thr Pro Asp Gln Ala Ser Leu His Ala Phe Ala Asp Ser Leu
    1055                1060                1065
```

```
Glu Arg Asp Leu Asp Ala Pro Ser Pro Met His Glu Gly Asp Gln
    1070                1075                1080

Thr Arg Ala Ser Ser Arg Lys Arg Ser Arg Ser Asp Arg Ala Val
    1085                1090                1095

Thr Gly Pro Ser Ala Gln Gln Ala Val Glu Val Arg Val Pro Glu
    1100                1105                1110

Gln Arg Asp Ala Leu His Leu Pro Leu Ser Trp Arg Val Lys Arg
    1115                1120                1125

Pro Arg Thr Arg Ile Trp Gly Gly Leu Pro Asp Pro Gly Thr Pro
    1130                1135                1140

Thr Ala Ala Asp Gln Leu Val Lys Ser Glu Leu Glu Glu Lys Lys
    1145                1150                1155

Ser Glu Leu Arg His Lys Leu Lys Tyr Val Pro His Glu Tyr Ile
    1160                1165                1170

Glu Leu Ile Glu Ile Ala Arg Asn Ser Thr Gln Asp Arg Ile Leu
    1175                1180                1185

Glu Met Lys Val Met Glu Phe Phe Met Lys Val Tyr Gly Tyr Arg
    1190                1195                1200

Gly Lys His Leu Gly Gly Ser Arg Lys Pro Asp Gly Ala Ile Tyr
    1205                1210                1215

Thr Val Gly Ser Pro Ile Asp Tyr Gly Val Ile Val Asp Thr Lys
    1220                1225                1230

Ala Tyr Ser Gly Gly Tyr Asn Leu Pro Ile Gly Gln Ala Asp Glu
    1235                1240                1245

Met Gln Arg Tyr Val Glu Glu Asn Gln Thr Arg Asn Lys His Ile
    1250                1255                1260

Asn Pro Asn Glu Trp Trp Lys Val Tyr Pro Ser Ser Val Thr Glu
    1265                1270                1275

Phe Lys Phe Leu Phe Val Ser Gly His Phe Lys Gly Asn Tyr Lys
    1280                1285                1290

Ala Gln Leu Thr Arg Leu Asn His Ile Thr Asn Cys Asn Gly Ala
    1295                1300                1305

Val Leu Ser Val Glu Glu Leu Leu Ile Gly Gly Glu Met Ile Lys
    1310                1315                1320

Ala Gly Thr Leu Thr Leu Glu Glu Val Arg Arg Lys Phe Asn Asn
    1325                1330                1335

Gly Glu Ile Asn Phe
    1340

<210> SEQ ID NO 75
<211> LENGTH: 1211
<212> TYPE: PRT
<213> ORGANISM: Artificial Sequence
<220> FEATURE:
<223> OTHER INFORMATION: Xanthomonas spp, Zea mays

<400> SEQUENCE: 75

Met Ala Ser Ser Pro Lys Lys Arg Lys Val Ser Trp Lys Asp
1               5                   10                  15

Ala Ser Gly Trp Ser Arg Met His Ala Asp Pro Trp Pro Arg Arg
                20                  25                  30

Ala Ala Gln Pro Ser Asp Ala Ser Pro Ala Ala Gln Val Asp Leu Arg
        35                  40                  45

Thr Leu Gly Tyr Ser Gln Gln Gln Gln Glu Lys Ile Lys Pro Lys Val
        50                  55                  60
```

-continued

```
Arg Ser Thr Val Ala Gln His His Glu Ala Leu Val Gly His Gly Phe
 65                  70                  75                  80

Thr His Ala His Ile Val Ala Leu Ser Gln His Pro Ala Ala Leu Gly
                 85                  90                  95

Thr Val Ala Val Thr Tyr Gln His Ile Ile Thr Ala Leu Pro Glu Ala
            100                 105                 110

Thr His Glu Asp Ile Val Gly Val Gly Lys Gln Trp Ser Gly Ala Arg
            115                 120                 125

Ala Leu Glu Ala Leu Leu Thr Asp Ala Gly Glu Leu Arg Gly Pro Pro
130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser Asn
            180                 185                 190

Asn Gly Gly Lys Gln Ala Leu Glu Thr Val Gln Arg Leu Leu Pro Val
            195                 200                 205

Leu Cys Gln Ala His Gly Leu Thr Pro Asp Gln Val Val Ala Ile Ala
210                 215                 220

Ser His Asp Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
                245                 250                 255

Ile Ala Ser Asn Ile Gly Gly Lys Gln Ala Leu Glu Thr Val Gln Arg
            260                 265                 270

Leu Leu Pro Val Leu Cys Gln Asp His Gly Leu Thr Pro Asp Gln Val
            275                 280                 285

Val Ala Ile Ala Ser Asn Gly Gly Lys Gln Ala Leu Glu Thr Val
290                 295                 300

Gln Arg Leu Leu Pro Val Leu Cys Gln Ala His Gly Leu Thr Pro Asp
305                 310                 315                 320

Gln Val Val Ala Ile Ala Ser His Asp Gly Gly Lys Gln Ala Leu Glu
                325                 330                 335

Thr Val Gln Arg Leu Leu Pro Val Leu Cys Gln Ala His Gly Leu Thr
            340                 345                 350

Pro Asp Gln Val Val Ala Ile Ala Ser His Asp Gly Gly Lys Gln Ala
            355                 360                 365

Leu Glu Thr Val Gln Arg Leu Leu Pro Val Leu Cys Gln Ala His Gly
370                 375                 380

Leu Thr Pro Glu Gln Val Val Ala Ile Ala Ser Asn Asn Gly Gly Lys
385                 390                 395                 400

Gln Ala Leu Glu Thr Val Gln Arg Leu Leu Pro Val Leu Cys Gln Ala
                405                 410                 415

His Gly Leu Thr Pro Glu Gln Val Val Ala Ile Ala Ser Asn Gly Gly
            420                 425                 430

Gly Lys Gln Ala Leu Glu Thr Val Gln Arg Leu Leu Pro Val Leu Cys
            435                 440                 445

Gln Asp His Gly Leu Thr Pro Glu Gln Val Val Ala Ile Ala Ser Asn
            450                 455                 460

Asn Gly Gly Lys Gln Ala Leu Glu Thr Val Gln Arg Leu Leu Pro Val
465                 470                 475                 480
```

```
Leu Cys Gln Ala His Gly Leu Thr Pro Asp Gln Val Val Ala Ile Ala
            485                 490                 495
Ser His Asp Gly Gly Lys Gln Ala Leu Glu Thr Val Gln Arg Leu Leu
        500                 505                 510
Pro Val Leu Cys Gln Ala His Gly Leu Thr Pro Asp Gln Val Val Ala
            515                 520                 525
Ile Ala Ser Asn Ile Gly Gly Lys Gln Ala Leu Glu Thr Val Gln Arg
        530                 535                 540
Leu Leu Pro Val Leu Cys Gln Asp His Gly Leu Thr Pro Glu Gln Val
545                 550                 555                 560
Val Ala Ile Ala Ser Asn Asn Gly Gly Lys Gln Ala Leu Glu Thr Val
            565                 570                 575
Gln Arg Leu Leu Pro Val Leu Cys Gln Asp His Gly Leu Thr Pro Asp
        580                 585                 590
Gln Val Val Ala Ile Ala Ser Asn Gly Gly Gly Lys Gln Ala Leu Glu
    595                 600                 605
Thr Val Gln Arg Leu Leu Pro Val Leu Cys Gln Ala His Gly Leu Thr
    610                 615                 620
Pro Asp Gln Val Val Ala Ile Ala Ser Asn Asn Gly Gly Lys Gln Ala
625                 630                 635                 640
Leu Glu Thr Val Gln Arg Leu Leu Pro Val Leu Cys Gln Ala His Gly
            645                 650                 655
Leu Thr Pro Asp Gln Val Val Ala Ile Ala Ser His Asp Gly Gly Lys
        660                 665                 670
Gln Ala Leu Glu Thr Val Gln Arg Leu Leu Pro Val Leu Cys Gln Ala
    675                 680                 685
His Gly Leu Thr Pro Glu Gln Val Val Ala Ile Ala Ser Asn Ile Gly
    690                 695                 700
Gly Lys Gln Ala Leu Glu Thr Val Gln Arg Leu Leu Pro Val Leu Cys
705                 710                 715                 720
Gln Ala His Gly Leu Thr Pro Glu Gln Val Val Ala Ile Ala Ser Asn
            725                 730                 735
Asn Gly Gly Lys Gln Ala Leu Glu Thr Val Gln Arg Leu Leu Pro Val
        740                 745                 750
Leu Cys Gln Asp His Gly Leu Thr Pro Asp Gln Val Val Ala Ile Ala
        755                 760                 765
Ser Asn Gly Gly Lys Gln Ala Leu Glu Ser Ile Val Ala Gln Leu Ser
        770                 775                 780
Arg Pro Asp Pro Ala Leu Ala Ala Leu Thr Asn Asp His Leu Val Ala
785                 790                 795                 800
Leu Ala Cys Leu Gly Gly Arg Pro Ala Met Asp Ala Val Lys Lys Gly
            805                 810                 815
Leu Pro His Ala Pro Glu Leu Ile Arg Arg Val Asn Arg Arg Ile Gly
        820                 825                 830
Glu Arg Thr Ser His Arg Val Ala Asp Tyr Ala Gln Val Val Arg Val
        835                 840                 845
Leu Glu Phe Phe Gln Cys His Ser His Pro Ala Tyr Ala Phe Asp Glu
    850                 855                 860
Ala Met Thr Gln Phe Gly Met Ser Arg Asn Gly Leu Val Gln Leu Phe
865                 870                 875                 880
Arg Arg Val Gly Val Thr Glu Leu Glu Ala Arg Gly Gly Thr Leu Pro
            885                 890                 895
Pro Ala Ser Gln Arg Trp Asp Arg Ile Leu Gln Ala Ser Gly Met Lys
```

900 905 910

Arg Ala Lys Pro Ser Pro Thr Ser Ala Gln Thr Pro Asp Gln Ala Ser
915 920 925

Leu His Ala Phe Ala Asp Ser Leu Glu Arg Asp Leu Asp Ala Pro Ser
930 935 940

Pro Met His Glu Gly Asp Gln Thr Arg Ala Ser Ser Arg Lys Arg Ser
945 950 955 960

Arg Ser Asp Arg Ala Val Thr Gly Pro Ser Ala Gln Gln Ala Val Glu
965 970 975

Val Arg Val Pro Glu Gln Arg Asp Ala Leu His Leu Pro Leu Ser Trp
980 985 990

Arg Val Lys Arg Pro Arg Thr Arg Ile Trp Gly Gly Leu Pro Asp Pro
995 1000 1005

Gly Thr Pro Thr Ala Ala Asp Gln Leu Val Lys Ser Glu Leu Glu
1010 1015 1020

Glu Lys Lys Ser Glu Leu Arg His Lys Leu Lys Tyr Val Pro His
1025 1030 1035

Glu Tyr Ile Glu Leu Ile Glu Ile Ala Arg Asn Ser Thr Gln Asp
1040 1045 1050

Arg Ile Leu Glu Met Lys Val Met Glu Phe Phe Met Lys Val Tyr
1055 1060 1065

Gly Tyr Arg Gly Lys His Leu Gly Gly Ser Arg Lys Pro Asp Gly
1070 1075 1080

Ala Ile Tyr Thr Val Gly Ser Pro Ile Asp Tyr Gly Val Ile Val
1085 1090 1095

Asp Thr Lys Ala Tyr Ser Gly Gly Tyr Asn Leu Pro Ile Gly Gln
1100 1105 1110

Ala Asp Glu Met Gln Arg Tyr Val Glu Glu Asn Gln Thr Arg Asn
1115 1120 1125

Lys His Ile Asn Pro Asn Glu Trp Trp Lys Val Tyr Pro Ser Ser
1130 1135 1140

Val Thr Glu Phe Lys Phe Leu Phe Val Ser Gly His Phe Lys Gly
1145 1150 1155

Asn Tyr Lys Ala Gln Leu Thr Arg Leu Asn His Ile Thr Asn Cys
1160 1165 1170

Asn Gly Ala Val Leu Ser Val Glu Glu Leu Leu Ile Gly Gly Glu
1175 1180 1185

Met Ile Lys Ala Gly Thr Leu Thr Leu Glu Glu Val Arg Arg Lys
1190 1195 1200

Phe Asn Asn Gly Glu Ile Asn Phe
1205 1210

<210> SEQ ID NO 76
<211> LENGTH: 1037
<212> TYPE: PRT
<213> ORGANISM: Artificial Sequence
<220> FEATURE:
<223> OTHER INFORMATION: Xanthomonas spp, Zea mays

<400> SEQUENCE: 76

Met Ala Ser Ser Pro Pro Lys Lys Lys Arg Lys Val Ser Trp Lys Asp
1 5 10 15

Ala Ser Gly Trp Ser Arg Met His Ala Asp Pro Trp Pro Arg Arg Arg
20 25 30

Ala Ala Gln Pro Ser Asp Ala Ser Pro Ala Ala Gln Val Asp Leu Arg

```
                35                  40                  45
Thr Leu Gly Tyr Ser Gln Gln Gln Glu Lys Ile Lys Pro Lys Val
        50                  55                  60
Arg Ser Thr Val Ala Gln His His Glu Ala Leu Val Gly His Gly Phe
65                  70                  75                  80
Thr His Ala His Ile Val Ala Leu Ser Gln His Pro Ala Ala Leu Gly
                85                  90                  95
Thr Val Ala Val Thr Tyr Gln His Ile Ile Thr Ala Leu Pro Glu Ala
                100                 105                 110
Thr His Glu Asp Ile Val Gly Val Gly Lys Gln Trp Ser Gly Ala Arg
                115                 120                 125
Ala Leu Glu Ala Leu Leu Thr Asp Ala Gly Glu Leu Arg Gly Pro Pro
            130                 135                 140
Leu Gln Leu Asp Thr Gly Gln Leu Val Lys Ile Ala Lys Arg Gly Gly
145                 150                 155                 160
Val Thr Ala Met Glu Ala Val His Ala Ser Arg Asn Ala Leu Thr Gly
                165                 170                 175
Ala Pro Leu Asn Leu Thr Pro Asp Gln Val Val Ala Ile Ala Ser Asn
                180                 185                 190
Asn Gly Gly Lys Gln Ala Leu Glu Thr Val Gln Arg Leu Leu Pro Val
            195                 200                 205
Leu Cys Gln Ala His Gly Leu Thr Pro Asp Gln Val Val Ala Ile Ala
    210                 215                 220
Ser His Asp Gly Gly Lys Gln Ala Leu Glu Thr Val Gln Arg Leu Leu
225                 230                 235                 240
Pro Val Leu Cys Gln Asp His Gly Leu Thr Pro Glu Gln Val Val Ala
                245                 250                 255
Ile Ala Ser Asn Ile Gly Gly Lys Gln Ala Leu Glu Thr Val Gln Arg
                260                 265                 270
Leu Leu Pro Val Leu Cys Gln Asp His Gly Leu Thr Pro Asp Gln Val
            275                 280                 285
Val Ala Ile Ala Ser Asn Gly Gly Lys Gln Ala Leu Glu Thr Val
    290                 295                 300
Gln Arg Leu Leu Pro Val Leu Cys Gln Ala His Gly Leu Thr Pro Asp
305                 310                 315                 320
Gln Val Val Ala Ile Ala Ser His Asp Gly Gly Lys Gln Ala Leu Glu
                325                 330                 335
Thr Val Gln Arg Leu Leu Pro Val Leu Cys Gln Ala His Gly Leu Thr
                340                 345                 350
Pro Asp Gln Val Val Ala Ile Ala Ser His Asp Gly Gly Lys Gln Ala
            355                 360                 365
Leu Glu Thr Val Gln Arg Leu Leu Pro Val Leu Cys Gln Ala His Gly
        370                 375                 380
Leu Thr Pro Glu Gln Val Val Ala Ile Ala Ser Asn Gly Gly Lys
385                 390                 395                 400
Gln Ala Leu Glu Thr Val Gln Arg Leu Leu Pro Val Leu Cys Gln Ala
                405                 410                 415
His Gly Leu Thr Pro Glu Gln Val Val Ala Ile Ala Ser Asn Gly Gly
                420                 425                 430
Gly Lys Gln Ala Leu Glu Thr Val Gln Arg Leu Leu Pro Val Leu Cys
            435                 440                 445
Gln Asp His Gly Leu Thr Pro Glu Gln Val Val Ala Ile Ala Ser Asn
        450                 455                 460
```

-continued

```
Asn Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
            485                 490                 495

Ser His Asp Gly Gly Lys Gln Ala Leu Glu Thr Val Gln Arg Leu Leu
        500                 505                 510

Pro Val Leu Cys Gln Ala His Gly Leu Thr Pro Asp Gln Val Val Ala
    515                 520                 525

Ile Ala Ser Asn Ile Gly Gly Lys Gln Ala Leu Glu Thr Val Gln Arg
530                 535                 540

Leu Leu Pro Val Leu Cys Gln Asp His Gly Leu Thr Pro Glu Gln Val
545                 550                 555                 560

Val Ala Ile Ala Ser Asn Asn Gly Gly Lys Gln Ala Leu Glu Thr Val
            565                 570                 575

Gln Arg Leu Leu Pro Val Leu Cys Gln Asp His Gly Leu Thr Pro Asp
        580                 585                 590

Gln Val Val Ala Ile Ala Ser Asn Gly Gly Gly Lys Gln Ala Leu Glu
    595                 600                 605

Thr Val Gln Arg Leu Leu Pro Val Leu Cys Gln Ala His Gly Leu Thr
610                 615                 620

Pro Asp Gln Val Val Ala Ile Ala Ser Asn Asn Gly Gly Lys Gln Ala
625                 630                 635                 640

Leu Glu Thr Val Gln Arg Leu Leu Pro Val Leu Cys Gln Ala His Gly
            645                 650                 655

Leu Thr Pro Asp Gln Val Val Ala Ile Ala Ser His Asp Gly Gly Lys
        660                 665                 670

Gln Ala Leu Glu Thr Val Gln Arg Leu Leu Pro Val Leu Cys Gln Ala
    675                 680                 685

His Gly Leu Thr Pro Glu Gln Val Val Ala Ile Ala Ser Asn Ile Gly
    690                 695                 700

Gly Lys Gln Ala Leu Glu Thr Val Gln Arg Leu Leu Pro Val Leu Cys
705                 710                 715                 720

Gln Ala His Gly Leu Thr Pro Glu Gln Val Val Ala Ile Ala Ser Asn
            725                 730                 735

Asn Gly Gly Lys Gln Ala Leu Glu Thr Val Gln Arg Leu Leu Pro Val
        740                 745                 750

Leu Cys Gln Asp His Gly Leu Thr Pro Asp Gln Val Val Ala Ile Ala
    755                 760                 765

Ser Asn Gly Gly Lys Gln Ala Leu Glu Ser Ile Val Ala Gln Leu Ser
    770                 775                 780

Arg Pro Asp Pro Ala Leu Ala Ala Leu Thr Asn Asp His Leu Val Ala
785                 790                 795                 800

Leu Ala Cys Leu Gly Gly Arg Pro Ala Met Asp Ala Val Lys Lys Gly
            805                 810                 815

Leu Pro His Ala Pro Glu Leu Ile Arg Arg Val Asn Arg Arg Ile Gly
        820                 825                 830

Glu Arg Thr Ser His Arg Val Ala Leu Gln Leu Val Lys Ser Glu Leu
    835                 840                 845

Glu Glu Lys Lys Ser Glu Leu Arg His Lys Leu Lys Tyr Val Pro His
    850                 855                 860

Glu Tyr Ile Glu Leu Ile Glu Ile Ala Arg Asn Ser Thr Gln Asp Arg
865                 870                 875                 880
```

-continued

```
Ile Leu Glu Met Lys Val Met Glu Phe Phe Met Lys Val Tyr Gly Tyr
                885                 890                 895

Arg Gly Lys His Leu Gly Gly Ser Arg Lys Pro Asp Gly Ala Ile Tyr
            900                 905                 910

Thr Val Gly Ser Pro Ile Asp Tyr Gly Val Ile Val Asp Thr Lys Ala
            915                 920                 925

Tyr Ser Gly Gly Tyr Asn Leu Pro Ile Gly Gln Ala Asp Glu Met Gln
        930                 935                 940

Arg Tyr Val Glu Glu Asn Gln Thr Arg Asn Lys His Ile Asn Pro Asn
945                 950                 955                 960

Glu Trp Trp Lys Val Tyr Pro Ser Ser Val Thr Glu Phe Lys Phe Leu
                965                 970                 975

Phe Val Ser Gly His Phe Lys Gly Asn Tyr Lys Ala Gln Leu Thr Arg
            980                 985                 990

Leu Asn His Ile Thr Asn Cys Asn Gly Ala Val Leu Ser Val Glu Glu
        995                 1000                1005

Leu Leu Ile Gly Gly Glu Met Ile Lys Ala Gly Thr Leu Thr Leu
    1010                1015                1020

Glu Glu Val Arg Arg Lys Phe Asn Asn Gly Glu Ile Asn Phe
    1025                1030                1035
```

<210> SEQ ID NO 77
<211> LENGTH: 1275
<212> TYPE: PRT
<213> ORGANISM: Artificial Sequence
<220> FEATURE:
<223> OTHER INFORMATION: Xanthomonas ssp, Zea mays

<400> SEQUENCE: 77

```
Met Ala Ser Ser Pro Lys Lys Arg Lys Val Ser Trp Lys Asp
1               5                   10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Met Gln Ser Ala Leu Arg Ala Ala Asp Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205
```

```
Gly His Gly Phe Thr His Ala His Ile Val Ala Leu Ser Gln His Pro
    210                 215                 220
Ala Ala Leu Gly Thr Val Ala Val Thr Tyr Gln His Ile Ile Thr Ala
225                 230                 235                 240
Leu Pro Glu Ala Thr His Glu Asp Ile Val Gly Val Gly Lys Gln Trp
                245                 250                 255
Ser Gly Ala Arg Ala Leu Glu Ala Leu Leu Thr Asp Ala Gly Glu Leu
            260                 265                 270
Arg Gly Pro Pro Leu Gln Leu Asp Thr Gly Gln Leu Val Lys Ile Ala
        275                 280                 285
Lys Arg Gly Gly Val Thr Ala Met Glu Ala Val His Ala Ser Arg Asn
    290                 295                 300
Ala Leu Thr Gly Ala Pro Leu Asn Leu Thr Pro Asp Gln Val Val Ala
305                 310                 315                 320
Ile Ala Ser His Asp Gly Gly Lys Gln Ala Leu Glu Thr Val Gln Arg
                325                 330                 335
Leu Leu Pro Val Leu Cys Gln Ala His Gly Leu Thr Pro Asp Gln Val
            340                 345                 350
Val Ala Ile Ala Ser His Asp Gly Gly Lys Gln Ala Leu Glu Thr Val
        355                 360                 365
Gln Arg Leu Leu Pro Val Leu Cys Gln Asp His Gly Leu Thr Pro Glu
    370                 375                 380
Gln Val Val Ala Ile Ala Ser Asn Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Ile Gly Gly Lys Gln Ala
            420                 425                 430
Leu Glu Thr Val Gln Arg Leu Leu Pro Val Leu Cys Gln Ala His Gly
        435                 440                 445
Leu Thr Pro Asp Gln Val Val Ala Ile Ala Ser Asn Ile Gly Gly Lys
    450                 455                 460
Gln Ala Leu Glu Thr Val Gln Arg Leu Leu Pro Val Leu Cys Gln Ala
465                 470                 475                 480
His Gly Leu Thr Pro Asp Gln Val Val Ala Ile Ala Ser Asn Ile Gly
                485                 490                 495
Gly Lys Gln Ala Leu Glu Thr Val Gln Arg Leu Leu Pro Val Leu Cys
            500                 505                 510
Gln Ala His Gly Leu Thr Pro Glu Gln Val Val Ala Ile Ala Ser His
        515                 520                 525
Asp Gly Gly Lys Gln Ala Leu Glu Thr Val Gln Arg Leu Leu Pro Val
    530                 535                 540
Leu Cys Gln Asp His Gly Leu Thr Pro Glu Gln Val Val Ala Ile Ala
545                 550                 555                 560
Ser Asn Ile Gly Gly Lys Gln Ala Leu Glu Thr Val Gln Arg Leu Leu
                565                 570                 575
Pro Val Leu Cys Gln Ala His Gly Leu Thr Pro Asp Gln Val Val Ala
            580                 585                 590
Ile Ala Ser Asn Ile Gly Gly Lys Gln Ala Leu Glu Thr Val Gln Arg
        595                 600                 605
Leu Leu Pro Val Leu Cys Gln Ala His Gly Leu Thr Pro Asp Gln Val
    610                 615                 620
Val Ala Ile Ala Ser Asn Ile Gly Gly Lys Gln Ala Leu Glu Thr Val
```

```
                625                 630                 635                 640
        Gln Arg Leu Leu Pro Val Leu Cys Gln Asp His Gly Leu Thr Pro Glu
                        645                 650                 655
        Gln Val Val Ala Ile Ala Ser Asn Asn Gly Gly Lys Gln Ala Leu Glu
                        660                 665                 670
        Thr Val Gln Arg Leu Leu Pro Val Leu Cys Gln Asp His Gly Leu Thr
                        675                 680                 685
        Pro Asp Gln Val Val Ala Ile Ala Ser Asn Asn Gly Gly Lys Gln Ala
                690                 695                 700
        Leu Glu Thr Val Gln Arg Leu Leu Pro Val Leu Cys Gln Ala His Gly
        705                 710                 715                 720
        Leu Thr Pro Asp Gln Val Val Ala Ile Ala Ser Asn Ile Gly Gly Lys
                        725                 730                 735
        Gln Ala Leu Glu Thr Val Gln Arg Leu Leu Pro Val Leu Cys Gln Ala
                        740                 745                 750
        His Gly Leu Thr Pro Asp Gln Val Val Ala Ile Ala Ser Asn Asn Gly
                        755                 760                 765
        Gly Lys Gln Ala Leu Glu Thr Val Gln Arg Leu Leu Pro Val Leu Cys
                770                 775                 780
        Gln Ala His Gly Leu Thr Pro Glu Gln Val Val Ala Ile Ala Ser Asn
        785                 790                 795                 800
        Asn Gly Gly Lys Gln Ala Leu Glu Thr Val Gln Arg Leu Leu Pro Val
                        805                 810                 815
        Leu Cys Gln Asp His Gly Leu Thr Pro Asp Gln Val Val Ala Ile Ala
                        820                 825                 830
        Ser Asn Gly Gly Lys Gln Ala Leu Glu Ser Ile Val Ala Gln Leu Ser
                835                 840                 845
        Arg Pro Asp Pro Ala Leu Ala Ala Leu Thr Asn Asp His Leu Val Ala
                850                 855                 860
        Leu Ala Cys Leu Gly Gly Arg Pro Ala Met Asp Ala Val Lys Lys Gly
        865                 870                 875                 880
        Leu Pro His Ala Pro Glu Leu Ile Arg Arg Val Asn Arg Arg Ile Gly
                        885                 890                 895
        Glu Arg Thr Ser His Arg Val Ala Asp Tyr Ala Gln Val Val Arg Val
                        900                 905                 910
        Leu Glu Phe Phe Gln Cys His Ser His Pro Ala Tyr Ala Phe Asp Glu
                        915                 920                 925
        Ala Met Thr Gln Phe Gly Met Ser Arg Asn Gly Leu Val Gln Leu Phe
                930                 935                 940
        Arg Arg Val Gly Val Thr Glu Leu Glu Ala Arg Gly Gly Thr Leu Pro
        945                 950                 955                 960
        Pro Ala Ser Gln Arg Trp Asp Arg Ile Leu Gln Ala Ser Gly Met Lys
                        965                 970                 975
        Arg Ala Lys Pro Ser Pro Thr Ser Ala Gln Thr Pro Asp Gln Ala Ser
                        980                 985                 990
        Leu His Ala Phe Ala Asp Ser Leu  Glu Arg Asp Leu  Asp Ala Pro Ser
                995                 1000                 1005
        Pro Met His Glu Gly Asp Gln  Thr Arg Ala Ser Ser  Arg Lys Arg
                1010                 1015                 1020
        Ser Arg Ser Asp Arg Ala Val  Thr Gly Pro Ser Ala  Gln Gln Ala
                1025                 1030                 1035
        Val Glu Val Arg Val Pro Glu  Gln Arg Asp Ala Leu  His Leu Pro
                1040                 1045                 1050
```

-continued

```
Leu Ser Trp Arg Val Lys Arg Pro Arg Thr Arg Ile Trp Gly Gly
    1055                1060                1065

Leu Pro Asp Pro Gly Thr Pro Thr Ala Ala Asp Gln Leu Val Lys
    1070                1075                1080

Ser Glu Leu Glu Glu Lys Lys Ser Glu Leu Arg His Lys Leu Lys
    1085                1090                1095

Tyr Val Pro His Glu Tyr Ile Glu Leu Ile Glu Ile Ala Arg Asn
    1100                1105                1110

Ser Thr Gln Asp Arg Ile Leu Glu Met Lys Val Met Glu Phe Phe
    1115                1120                1125

Met Lys Val Tyr Gly Tyr Arg Gly Lys His Leu Gly Gly Ser Arg
    1130                1135                1140

Lys Pro Asp Gly Ala Ile Tyr Thr Val Gly Ser Pro Ile Asp Tyr
    1145                1150                1155

Gly Val Ile Val Asp Thr Lys Ala Tyr Ser Gly Gly Tyr Asn Leu
    1160                1165                1170

Pro Ile Gly Gln Ala Asp Glu Met Gln Arg Tyr Val Glu Glu Asn
    1175                1180                1185

Gln Thr Arg Asn Lys His Ile Asn Pro Asn Glu Trp Trp Lys Val
    1190                1195                1200

Tyr Pro Ser Ser Val Thr Glu Phe Lys Phe Leu Phe Val Ser Gly
    1205                1210                1215

His Phe Lys Gly Asn Tyr Lys Ala Gln Leu Thr Arg Leu Asn His
    1220                1225                1230

Ile Thr Asn Cys Asn Gly Ala Val Leu Ser Val Glu Glu Leu Leu
    1235                1240                1245

Ile Gly Gly Glu Met Ile Lys Ala Gly Thr Leu Thr Leu Glu Glu
    1250                1255                1260

Val Arg Arg Lys Phe Asn Asn Gly Glu Ile Asn Phe
    1265                1270                1275

<210> SEQ ID NO 78
<211> LENGTH: 1143
<212> TYPE: PRT
<213> ORGANISM: Artificial Sequence
<220> FEATURE:
<223> OTHER INFORMATION: Xanthomonas ssp, Zea mays

<400> SEQUENCE: 78

Met Ala Ser Ser Pro Lys Lys Arg Lys Val Ser Trp Lys Asp
1               5                   10                  15

Ala Ser Gly Trp Ser Arg Met His Ala Asp Pro Trp Pro Arg Arg Arg
                20                  25                  30

Ala Ala Gln Pro Ser Asp Ala Ser Pro Ala Ala Gln Val Asp Leu Arg
                35                  40                  45

Thr Leu Gly Tyr Ser Gln Gln Gln Gln Glu Lys Ile Lys Pro Lys Val
    50                  55                  60

Arg Ser Thr Val Ala Gln His His Glu Ala Leu Val Gly His Gly Phe
65                  70                  75                  80

Thr His Ala His Ile Val Ala Leu Ser Gln His Pro Ala Ala Leu Gly
                85                  90                  95

Thr Val Ala Val Thr Tyr Gln His Ile Ile Thr Ala Leu Pro Glu Ala
                100                 105                 110

Thr His Glu Asp Ile Val Gly Val Gly Lys Gln Trp Ser Gly Ala Arg
                115                 120                 125
```

```
Ala Leu Glu Ala Leu Leu Thr Asp Ala Gly Glu Leu Arg Gly Pro Pro
130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser His
                180                 185                 190

Asp Gly Gly Lys Gln Ala Leu Glu Thr Val Gln Arg Leu Leu Pro Val
            195                 200                 205

Leu Cys Gln Ala His Gly Leu Thr Pro Asp Gln Val Val Ala Ile Ala
210                 215                 220

Ser His Asp Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
                245                 250                 255

Ile Ala Ser Asn Gly Gly Lys Gln Ala Leu Glu Thr Val Gln Arg
                260                 265                 270

Leu Leu Pro Val Leu Cys Gln Asp His Gly Leu Thr Pro Asp Gln Val
            275                 280                 285

Val Ala Ile Ala Ser Asn Ile Gly Gly Lys Gln Ala Leu Glu Thr Val
290                 295                 300

Gln Arg Leu Leu Pro Val Leu Cys Gln Ala His Gly Leu Thr Pro Asp
305                 310                 315                 320

Gln Val Val Ala Ile Ala Ser Asn Ile Gly Gly Lys Gln Ala Leu Glu
                325                 330                 335

Thr Val Gln Arg Leu Leu Pro Val Leu Cys Gln Ala His Gly Leu Thr
                340                 345                 350

Pro Asp Gln Val Val Ala Ile Ala Ser Asn Ile Gly Gly Lys Gln Ala
            355                 360                 365

Leu Glu Thr Val Gln Arg Leu Leu Pro Val Leu Cys Gln Ala His Gly
370                 375                 380

Leu Thr Pro Glu Gln Val Val Ala Ile Ala Ser His Asp Gly Gly Lys
385                 390                 395                 400

Gln Ala Leu Glu Thr Val Gln Arg Leu Leu Pro Val Leu Cys Gln Asp
                405                 410                 415

His Gly Leu Thr Pro Glu Gln Val Val Ala Ile Ala Ser Asn Ile Gly
                420                 425                 430

Gly Lys Gln Ala Leu Glu Thr Val Gln Arg Leu Leu Pro Val Leu Cys
            435                 440                 445

Gln Ala His Gly Leu Thr Pro Asp Gln Val Val Ala Ile Ala Ser Asn
450                 455                 460

Ile Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
                485                 490                 495

Ser Asn Ile Gly Gly Lys Gln Ala Leu Glu Thr Val Gln Arg Leu Leu
                500                 505                 510

Pro Val Leu Cys Gln Asp His Gly Leu Thr Pro Glu Gln Val Val Ala
            515                 520                 525

Ile Ala Ser Asn Asn Gly Gly Lys Gln Ala Leu Glu Thr Val Gln Arg
530                 535                 540
```

```
Leu Leu Pro Val Leu Cys Gln Asp His Gly Leu Thr Pro Asp Gln Val
545                 550                 555                 560

Val Ala Ile Ala Ser Asn Asn Gly Gly Lys Gln Ala Leu Glu Thr Val
                565                 570                 575

Gln Arg Leu Leu Pro Val Leu Cys Gln Ala His Gly Leu Thr Pro Asp
            580                 585                 590

Gln Val Val Ala Ile Ala Ser Asn Ile Gly Gly Lys Gln Ala Leu Glu
        595                 600                 605

Thr Val Gln Arg Leu Leu Pro Val Leu Cys Gln Ala His Gly Leu Thr
    610                 615                 620

Pro Asp Gln Val Val Ala Ile Ala Ser Asn Asn Gly Gly Lys Gln Ala
625                 630                 635                 640

Leu Glu Thr Val Gln Arg Leu Leu Pro Val Leu Cys Gln Ala His Gly
                645                 650                 655

Leu Thr Pro Glu Gln Val Val Ala Ile Ala Ser Asn Asn Gly Gly Lys
            660                 665                 670

Gln Ala Leu Glu Thr Val Gln Arg Leu Leu Pro Val Leu Cys Gln Asp
        675                 680                 685

His Gly Leu Thr Pro Asp Gln Val Val Ala Ile Ala Ser Asn Gly Gly
    690                 695                 700

Lys Gln Ala Leu Glu Ser Ile Val Ala Gln Leu Ser Arg Pro Asp Pro
705                 710                 715                 720

Ala Leu Ala Ala Leu Thr Asn Asp His Leu Val Ala Leu Ala Cys Leu
                725                 730                 735

Gly Gly Arg Pro Ala Met Asp Ala Val Lys Lys Gly Leu Pro His Ala
            740                 745                 750

Pro Glu Leu Ile Arg Arg Val Asn Arg Arg Ile Gly Glu Arg Thr Ser
        755                 760                 765

His Arg Val Ala Asp Tyr Ala Gln Val Val Arg Val Leu Glu Phe Phe
    770                 775                 780

Gln Cys His Ser His Pro Ala Tyr Ala Phe Asp Glu Ala Met Thr Gln
785                 790                 795                 800

Phe Gly Met Ser Arg Asn Gly Leu Val Gln Leu Phe Arg Arg Val Gly
                805                 810                 815

Val Thr Glu Leu Glu Ala Arg Gly Gly Thr Leu Pro Pro Ala Ser Gln
            820                 825                 830

Arg Trp Asp Arg Ile Leu Gln Ala Ser Gly Met Lys Arg Ala Lys Pro
        835                 840                 845

Ser Pro Thr Ser Ala Gln Thr Pro Asp Gln Ala Ser Leu His Ala Phe
    850                 855                 860

Ala Asp Ser Leu Glu Arg Asp Leu Asp Ala Pro Ser Pro Met His Glu
865                 870                 875                 880

Gly Asp Gln Thr Arg Ala Ser Ser Arg Lys Arg Ser Arg Ser Asp Arg
                885                 890                 895

Ala Val Thr Gly Pro Ser Ala Gln Gln Ala Val Glu Val Arg Val Pro
            900                 905                 910

Glu Gln Arg Asp Ala Leu His Leu Pro Leu Ser Trp Arg Val Lys Arg
        915                 920                 925

Pro Arg Thr Arg Ile Trp Gly Gly Leu Pro Asp Pro Gly Thr Pro Thr
    930                 935                 940

Ala Ala Asp Gln Leu Val Lys Ser Glu Leu Glu Glu Lys Lys Ser Glu
945                 950                 955                 960

Leu Arg His Lys Leu Lys Tyr Val Pro His Glu Tyr Ile Glu Leu Ile
```

```
                    965                 970                 975
Glu Ile Ala Arg Asn Ser Thr Gln Asp Arg Ile Leu Glu Met Lys Val
                980                 985                 990

Met Glu Phe Phe Met Lys Val Tyr Gly Tyr Arg Gly Lys His Leu Gly
            995                 1000                1005

Gly Ser Arg Lys Pro Asp Gly Ala Ile Tyr Thr Val Gly Ser Pro
        1010                1015                1020

Ile Asp Tyr Gly Val Ile Val Asp Thr Lys Ala Tyr Ser Gly Gly
        1025                1030                1035

Tyr Asn Leu Pro Ile Gly Gln Ala Asp Glu Met Gln Arg Tyr Val
        1040                1045                1050

Glu Glu Asn Gln Thr Arg Asn Lys His Ile Asn Pro Asn Glu Trp
        1055                1060                1065

Trp Lys Val Tyr Pro Ser Ser Val Thr Glu Phe Lys Phe Leu Phe
        1070                1075                1080

Val Ser Gly His Phe Lys Gly Asn Tyr Lys Ala Gln Leu Thr Arg
        1085                1090                1095

Leu Asn His Ile Thr Asn Cys Asn Gly Ala Val Leu Ser Val Glu
        1100                1105                1110

Glu Leu Leu Ile Gly Gly Glu Met Ile Lys Ala Gly Thr Leu Thr
        1115                1120                1125

Leu Glu Glu Val Arg Arg Lys Phe Asn Asn Gly Glu Ile Asn Phe
        1130                1135                1140

<210> SEQ ID NO 79
<211> LENGTH: 969
<212> TYPE: PRT
<213> ORGANISM: Artificial Sequence
<220> FEATURE:
<223> OTHER INFORMATION: Xanthomonas ssp, Zea mays

<400> SEQUENCE: 79

Met Ala Ser Ser Pro Pro Lys Lys Lys Arg Lys Val Ser Trp Lys Asp
1               5                   10                  15

Ala Ser Gly Trp Ser Arg Met His Ala Asp Pro Trp Pro Arg Arg Arg
            20                  25                  30

Ala Ala Gln Pro Ser Asp Ala Ser Pro Ala Ala Gln Val Asp Leu Arg
        35                  40                  45

Thr Leu Gly Tyr Ser Gln Gln Gln Gln Glu Lys Ile Lys Pro Lys Val
    50                  55                  60

Arg Ser Thr Val Ala Gln His His Glu Ala Leu Val Gly His Gly Phe
65                  70                  75                  80

Thr His Ala His Ile Val Ala Leu Ser Gln His Pro Ala Ala Leu Gly
                85                  90                  95

Thr Val Ala Val Thr Tyr Gln His Ile Ile Thr Ala Leu Pro Glu Ala
            100                 105                 110

Thr His Glu Asp Ile Val Gly Val Gly Lys Gln Trp Ser Gly Ala Arg
        115                 120                 125

Ala Leu Glu Ala Leu Leu Thr Asp Ala Gly Glu Leu Arg Gly Pro Pro
    130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser His
```

-continued

```
            180                 185                 190
Asp Gly Gly Lys Gln Ala Leu Glu Thr Val Gln Arg Leu Leu Pro Val
            195                 200                 205

Leu Cys Gln Ala His Gly Leu Thr Pro Asp Gln Val Val Ala Ile Ala
            210                 215                 220

Ser His Asp Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
            245                 250                 255

Ile Ala Ser Asn Gly Gly Lys Gln Ala Leu Glu Thr Val Gln Arg
            260                 265                 270

Leu Leu Pro Val Leu Cys Gln Asp His Gly Leu Thr Pro Asp Gln Val
            275                 280                 285

Val Ala Ile Ala Ser Asn Ile Gly Gly Lys Gln Ala Leu Glu Thr Val
            290                 295                 300

Gln Arg Leu Leu Pro Val Leu Cys Gln Ala His Gly Leu Thr Pro Asp
305                 310                 315                 320

Gln Val Val Ala Ile Ala Ser Asn Ile Gly Gly Lys Gln Ala Leu Glu
            325                 330                 335

Thr Val Gln Arg Leu Leu Pro Val Leu Cys Gln Ala His Gly Leu Thr
            340                 345                 350

Pro Asp Gln Val Val Ala Ile Ala Ser Asn Ile Gly Gly Lys Gln Ala
            355                 360                 365

Leu Glu Thr Val Gln Arg Leu Leu Pro Val Leu Cys Gln Ala His Gly
            370                 375                 380

Leu Thr Pro Glu Gln Val Val Ala Ile Ala Ser His Asp Gly Gly Lys
385                 390                 395                 400

Gln Ala Leu Glu Thr Val Gln Arg Leu Leu Pro Val Leu Cys Gln Asp
            405                 410                 415

His Gly Leu Thr Pro Glu Gln Val Val Ala Ile Ala Ser Asn Ile Gly
            420                 425                 430

Gly Lys Gln Ala Leu Glu Thr Val Gln Arg Leu Leu Pro Val Leu Cys
            435                 440                 445

Gln Ala His Gly Leu Thr Pro Asp Gln Val Val Ala Ile Ala Ser Asn
            450                 455                 460

Ile Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
            485                 490                 495

Ser Asn Ile Gly Gly Lys Gln Ala Leu Glu Thr Val Gln Arg Leu Leu
            500                 505                 510

Pro Val Leu Cys Gln Asp His Gly Leu Thr Pro Glu Gln Val Val Ala
            515                 520                 525

Ile Ala Ser Asn Asn Gly Gly Lys Gln Ala Leu Glu Thr Val Gln Arg
            530                 535                 540

Leu Leu Pro Val Leu Cys Gln Asp His Gly Leu Thr Pro Asp Gln Val
545                 550                 555                 560

Val Ala Ile Ala Ser Asn Asn Gly Gly Lys Gln Ala Leu Glu Thr Val
            565                 570                 575

Gln Arg Leu Leu Pro Val Leu Cys Gln Ala His Gly Leu Thr Pro Asp
            580                 585                 590

Gln Val Val Ala Ile Ala Ser Asn Ile Gly Gly Lys Gln Ala Leu Glu
            595                 600                 605
```

Thr Val Gln Arg Leu Leu Pro Val Leu Cys Gln Ala His Gly Leu Thr
            610                 615                 620

Pro Asp Gln Val Val Ala Ile Ala Ser Asn Asn Gly Gly Lys Gln Ala
625                 630                 635                 640

Leu Glu Thr Val Gln Arg Leu Leu Pro Val Leu Cys Gln Ala His Gly
            645                 650                 655

Leu Thr Pro Glu Gln Val Val Ala Ile Ala Ser Asn Asn Gly Gly Lys
            660                 665                 670

Gln Ala Leu Glu Thr Val Gln Arg Leu Leu Pro Val Leu Cys Gln Asp
        675                 680                 685

His Gly Leu Thr Pro Asp Gln Val Val Ala Ile Ala Ser Asn Gly Gly
        690                 695                 700

Lys Gln Ala Leu Glu Ser Ile Val Ala Gln Leu Ser Arg Pro Asp Pro
705                 710                 715                 720

Ala Leu Ala Ala Leu Thr Asn Asp His Leu Val Ala Leu Ala Cys Leu
            725                 730                 735

Gly Gly Arg Pro Ala Met Asp Ala Val Lys Lys Gly Leu Pro His Ala
            740                 745                 750

Pro Glu Leu Ile Arg Arg Val Asn Arg Arg Ile Gly Glu Arg Thr Ser
            755                 760                 765

His Arg Val Ala Leu Gln Leu Val Lys Ser Glu Leu Glu Glu Lys Lys
770                 775                 780

Ser Glu Leu Arg His Lys Leu Lys Tyr Val Pro His Glu Tyr Ile Glu
785                 790                 795                 800

Leu Ile Glu Ile Ala Arg Asn Ser Thr Gln Asp Arg Ile Leu Glu Met
            805                 810                 815

Lys Val Met Glu Phe Phe Met Lys Val Tyr Gly Tyr Arg Gly Lys His
            820                 825                 830

Leu Gly Gly Ser Arg Lys Pro Asp Gly Ala Ile Tyr Thr Val Gly Ser
            835                 840                 845

Pro Ile Asp Tyr Gly Val Ile Val Asp Thr Lys Ala Tyr Ser Gly Gly
850                 855                 860

Tyr Asn Leu Pro Ile Gly Gln Ala Asp Glu Met Gln Arg Tyr Val Glu
865                 870                 875                 880

Glu Asn Gln Thr Arg Asn Lys His Ile Asn Pro Asn Glu Trp Trp Lys
            885                 890                 895

Val Tyr Pro Ser Ser Val Thr Glu Phe Lys Phe Leu Phe Val Ser Gly
            900                 905                 910

His Phe Lys Gly Asn Tyr Lys Ala Gln Leu Thr Arg Leu Asn His Ile
            915                 920                 925

Thr Asn Cys Asn Gly Ala Val Leu Ser Val Glu Glu Leu Leu Ile Gly
            930                 935                 940

Gly Glu Met Ile Lys Ala Gly Thr Leu Thr Leu Glu Glu Val Arg Arg
945                 950                 955                 960

Lys Phe Asn Asn Gly Glu Ile Asn Phe
            965

<210> SEQ ID NO 80
<211> LENGTH: 1024
<212> TYPE: PRT
<213> ORGANISM: Artificial Sequence
<220> FEATURE:
<223> OTHER INFORMATION: Xanthomonas ssp, Zea mays

<400> SEQUENCE: 80

```
Met Gly Lys Pro Ile Pro Asn Pro Leu Leu Gly Leu Asp Ser Thr Gly
1               5                   10                  15
Gly Met Ala Pro Lys Lys Arg Lys Val Asp Gly Val Asp Leu
            20                  25                  30
Arg Thr Leu Gly Tyr Ser Gln Gln Gln Glu Lys Ile Lys Pro Lys
        35                  40                  45
Val Arg Ser Thr Val Ala Gln His His Glu Ala Leu Val Gly His Gly
50                  55                  60
Phe Thr His Ala His Ile Val Ala Leu Ser Gln His Pro Ala Ala Leu
65              70                  75                  80
Gly Thr Val Ala Val Lys Tyr Gln Asp Met Ile Ala Ala Leu Pro Glu
                85                  90                  95
Ala Thr His Glu Ala Ile Val Gly Val Gly Lys Gln Trp Ser Gly Ala
            100                 105                 110
Arg Ala Leu Glu Ala Leu Leu Thr Val Ala Gly Glu Leu Arg Gly Pro
        115                 120                 125
Pro Leu Gln Leu Asp Thr Gly Gln Leu Leu Lys Ile Ala Lys Arg Gly
130                 135                 140
Gly Val Thr Ala Val Glu Ala Val His Ala Trp Arg Asn Ala Leu Thr
145                 150                 155                 160
Gly Ala Pro Leu Asn Leu Thr Pro Glu Gln Val Val Ala Ile Ala Ser
                165                 170                 175
Asn Asn Gly Gly Lys Gln Ala Leu Glu Thr Val Gln Arg Leu Leu Pro
            180                 185                 190
Val Leu Cys Gln Ala His Gly Leu Thr Pro Glu Gln Val Val Ala Ile
        195                 200                 205
Ala Ser His Asp Gly Gly Lys Gln Ala Leu Glu Thr Val Gln Arg Leu
210                 215                 220
Leu Pro Val Leu Cys Gln Ala His Gly Leu Thr Pro Glu Gln Val Val
225                 230                 235                 240
Ala Ile Ala Ser Asn Ile Gly Gly Lys Gln Ala Leu Glu Thr Val Gln
                245                 250                 255
Arg Leu Leu Pro Val Leu Cys Gln Ala His Gly Leu Thr Pro Glu Gln
            260                 265                 270
Val Val Ala Ile Ala Ser Asn Gly Gly Gly Lys Gln Ala Leu Glu Thr
        275                 280                 285
Val Gln Arg Leu Leu Pro Val Leu Cys Gln Ala His Gly Leu Thr Pro
290                 295                 300
Glu Gln Val Val Ala Ile Ala Ser His Asp Gly Gly Lys Gln Ala Leu
305                 310                 315                 320
Glu Thr Val Gln Arg Leu Leu Pro Val Leu Cys Gln Ala His Gly Leu
                325                 330                 335
Thr Pro Glu Gln Val Val Ala Ile Ala Ser His Asp Gly Gly Lys Gln
            340                 345                 350
Ala Leu Glu Thr Val Gln Arg Leu Leu Pro Val Leu Cys Gln Ala His
        355                 360                 365
Gly Leu Thr Pro Glu Gln Val Val Ala Ile Ala Ser Asn Asn Gly Gly
370                 375                 380
Lys Gln Ala Leu Glu Thr Val Gln Arg Leu Leu Pro Val Leu Cys Gln
385                 390                 395                 400
Ala His Gly Leu Thr Pro Glu Gln Val Val Ala Ile Ala Ser Asn Gly
                405                 410                 415
```

```
Gly Gly Lys Gln Ala Leu Glu Thr Val Gln Arg Leu Leu Pro Val Leu
            420                 425                 430

Cys Gln Ala His Gly Leu Thr Pro Glu Gln Val Val Ala Ile Ala Ser
        435                 440                 445

Asn Asn Gly Gly Lys Gln Ala Leu Glu Thr Val Gln Arg Leu Leu Pro
450                     455                 460

Val Leu Cys Gln Ala His Gly Leu Thr Pro Glu Gln Val Val Ala Ile
465                 470                 475                 480

Ala Ser His Asp Gly Gly Lys Gln Ala Leu Glu Thr Val Gln Arg Leu
                485                 490                 495

Leu Pro Val Leu Cys Gln Ala His Gly Leu Thr Pro Glu Gln Val Val
            500                 505                 510

Ala Ile Ala Ser Asn Ile Gly Gly Lys Gln Ala Leu Glu Thr Val Gln
        515                 520                 525

Arg Leu Leu Pro Val Leu Cys Gln Ala His Gly Leu Thr Pro Glu Gln
530                 535                 540

Val Val Ala Ile Ala Ser Asn Asn Gly Gly Lys Gln Ala Leu Glu Thr
545                 550                 555                 560

Val Gln Arg Leu Leu Pro Val Leu Cys Gln Ala His Gly Leu Thr Pro
                565                 570                 575

Glu Gln Val Val Ala Ile Ala Ser Asn Gly Gly Lys Gln Ala Leu
            580                 585                 590

Glu Thr Val Gln Arg Leu Leu Pro Val Leu Cys Gln Ala His Gly Leu
        595                 600                 605

Thr Pro Glu Gln Val Val Ala Ile Ala Ser Asn Asn Gly Gly Lys Gln
610                     615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser His Asp Gly Gly
                645                 650                 655

Lys Gln Ala Leu Glu Thr Val Gln Arg Leu Leu Pro Val Leu Cys Gln
            660                 665                 670

Ala His Gly Leu Thr Pro Glu Gln Val Val Ala Ile Ala Ser Asn Ile
        675                 680                 685

Gly Gly Lys Gln Ala Leu Glu Thr Val Gln Arg Leu Leu Pro Val Leu
690                     695                 700

Cys Gln Ala His Gly Leu Thr Pro Glu Gln Val Val Ala Ile Ala Ser
705                 710                 715                 720

Asn Asn Gly Gly Lys Gln Ala Leu Glu Thr Val Gln Arg Leu Leu Pro
                725                 730                 735

Val Leu Cys Gln Ala His Gly Leu Thr Pro Gln Gln Val Val Ala Ile
            740                 745                 750

Ala Ser Asn Gly Gly Gly Arg Pro Ala Leu Glu Ser Ile Val Ala Gln
        755                 760                 765

Leu Ser Arg Pro Asp Pro Ala Leu Ala Ala Leu Thr Asn Asp His Leu
770                     775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gln Leu Val Lys
            820                 825                 830

Ser Glu Leu Glu Glu Lys Lys Ser Glu Leu Arg His Lys Leu Lys Tyr
```

```
                    835                 840                 845
Val Pro His Glu Tyr Ile Glu Leu Ile Glu Ile Ala Arg Asn Ser Thr
850                 855                 860

Gln Asp Arg Ile Leu Glu Met Lys Val Met Glu Phe Phe Met Lys Val
865                 870                 875                 880

Tyr Gly Tyr Arg Gly Lys His Leu Gly Gly Ser Arg Lys Pro Asp Gly
                    885                 890                 895

Ala Ile Tyr Thr Val Gly Ser Pro Ile Asp Tyr Gly Val Ile Val Asp
                900                 905                 910

Thr Lys Ala Tyr Ser Gly Gly Tyr Asn Leu Pro Ile Gly Gln Ala Asp
            915                 920                 925

Glu Met Gln Arg Tyr Val Glu Glu Asn Gln Thr Arg Asn Lys His Ile
        930                 935                 940

Asn Pro Asn Glu Trp Trp Lys Val Tyr Pro Ser Ser Val Thr Glu Phe
945                 950                 955                 960

Lys Phe Leu Phe Val Ser Gly His Phe Lys Gly Asn Tyr Lys Ala Gln
                    965                 970                 975

Leu Thr Arg Leu Asn His Ile Thr Asn Cys Asn Gly Ala Val Leu Ser
                980                 985                 990

Val Glu Glu Leu Leu Ile Gly Gly Glu Met Ile Lys Ala Gly Thr Leu
            995                 1000                1005

Thr Leu Glu Glu Val Arg Arg Lys Phe Asn Asn Gly Glu Ile Asn
        1010                1015                1020

Phe
```

```
<210> SEQ ID NO 81
<211> LENGTH: 1024
<212> TYPE: PRT
<213> ORGANISM: Artificial Sequence
<220> FEATURE:
<223> OTHER INFORMATION: Xanthomonas ssp, Zea mays

<400> SEQUENCE: 81

Met Gly Lys Pro Ile Pro Asn Pro Leu Leu Gly Leu Asp Ser Thr Gly
1               5                   10                  15

Gly Met Ala Pro Lys Lys Arg Lys Val Asp Gly Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Glu Gln Val Val Ala Ile Ala Ser
                165                 170                 175
```

```
His Asp Gly Gly Lys Gln Ala Leu Glu Thr Val Gln Arg Leu Leu Pro
            180                 185                 190

Val Leu Cys Gln Ala His Gly Leu Thr Pro Glu Gln Val Val Ala Ile
        195                 200                 205

Ala Ser His Asp Gly Gly Lys Gln Ala Leu Glu Thr Val Gln Arg Leu
    210                 215                 220

Leu Pro Val Leu Cys Gln Ala His Gly Leu Thr Pro Glu Gln Val Val
225                 230                 235                 240

Ala Ile Ala Ser Asn Gly Gly Lys Gln Ala Leu Glu Thr Val Gln
                245                 250                 255

Arg Leu Leu Pro Val Leu Cys Gln Ala His Gly Leu Thr Pro Glu Gln
            260                 265                 270

Val Val Ala Ile Ala Ser Asn Ile Gly Gly Lys Gln Ala Leu Glu Thr
        275                 280                 285

Val Gln Arg Leu Leu Pro Val Leu Cys Gln Ala His Gly Leu Thr Pro
    290                 295                 300

Glu Gln Val Val Ala Ile Ala Ser Asn Ile Gly Gly Lys Gln Ala Leu
305                 310                 315                 320

Glu Thr Val Gln Arg Leu Leu Pro Val Leu Cys Gln Ala His Gly Leu
                325                 330                 335

Thr Pro Glu Gln Val Val Ala Ile Ala Ser Asn Ile Gly Gly Lys Gln
            340                 345                 350

Ala Leu Glu Thr Val Gln Arg Leu Leu Pro Val Leu Cys Gln Ala His
        355                 360                 365

Gly Leu Thr Pro Glu Gln Val Val Ala Ile Ala Ser His Asp Gly Gly
    370                 375                 380

Lys Gln Ala Leu Glu Thr Val Gln Arg Leu Leu Pro Val Leu Cys Gln
385                 390                 395                 400

Ala His Gly Leu Thr Pro Glu Gln Val Val Ala Ile Ala Ser Asn Ile
                405                 410                 415

Gly Gly Lys Gln Ala Leu Glu Thr Val Gln Arg Leu Leu Pro Val Leu
            420                 425                 430

Cys Gln Ala His Gly Leu Thr Pro Glu Gln Val Val Ala Ile Ala Ser
        435                 440                 445

Asn Ile Gly Gly Lys Gln Ala Leu Glu Thr Val Gln Arg Leu Leu Pro
    450                 455                 460

Val Leu Cys Gln Ala His Gly Leu Thr Pro Glu Gln Val Val Ala Ile
465                 470                 475                 480

Ala Ser Asn Ile Gly Gly Lys Gln Ala Leu Glu Thr Val Gln Arg Leu
                485                 490                 495

Leu Pro Val Leu Cys Gln Ala His Gly Leu Thr Pro Glu Gln Val Val
            500                 505                 510

Ala Ile Ala Ser Asn Asn Gly Gly Lys Gln Ala Leu Glu Thr Val Gln
        515                 520                 525

Arg Leu Leu Pro Val Leu Cys Gln Ala His Gly Leu Thr Pro Glu Gln
    530                 535                 540

Val Val Ala Ile Ala Ser Asn Asn Gly Gly Lys Gln Ala Leu Glu Thr
545                 550                 555                 560

Val Gln Arg Leu Leu Pro Val Leu Cys Gln Ala His Gly Leu Thr Pro
                565                 570                 575

Glu Gln Val Val Ala Ile Ala Ser Asn Ile Gly Gly Lys Gln Ala Leu
            580                 585                 590
```

```
Glu Thr Val Gln Arg Leu Leu Pro Val Leu Cys Gln Ala His Gly Leu
            595                 600                 605

Thr Pro Glu Gln Val Val Ala Ile Ala Ser Asn Asn Gly Gly Lys Gln
610                 615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser Asn Asn Gly Gly
                645                 650                 655

Lys Gln Ala Leu Glu Thr Val Gln Arg Leu Leu Pro Val Leu Cys Gln
            660                 665                 670

Ala His Gly Leu Thr Pro Glu Gln Val Val Ala Ile Ala Ser Asn Gly
            675                 680                 685

Gly Gly Lys Gln Ala Leu Glu Thr Val Gln Arg Leu Leu Pro Val Leu
690                 695                 700

Cys Gln Ala His Gly Leu Thr Pro Glu Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Ala His Gly Leu Thr Pro Gln Gln Val Val Ala Ile
            740                 745                 750

Ala Ser His Asp Gly Gly Arg Pro Ala Leu Glu Ser Ile Val Ala Gln
            755                 760                 765

Leu Ser Arg Pro Asp Pro Ala Leu Ala Ala Leu Thr Asn Asp His Leu
            770                 775                 780

Val Ala Leu Ala Cys Leu Gly Gly Arg Pro Ala Leu Asp Ala Val Lys
785                 790                 795                 800

Lys Gly Leu Pro His Ala Pro Ala Leu Ile Lys Arg Thr Asn Arg Arg
                805                 810                 815

Ile Pro Glu Arg Thr Ser His Arg Val Ala Gly Ser Gln Leu Val Lys
            820                 825                 830

Ser Glu Leu Glu Glu Lys Lys Ser Glu Leu Arg His Lys Leu Lys Tyr
            835                 840                 845

Val Pro His Glu Tyr Ile Glu Leu Ile Glu Ile Ala Arg Asn Ser Thr
850                 855                 860

Gln Asp Arg Ile Leu Glu Met Lys Val Met Glu Phe Phe Met Lys Val
865                 870                 875                 880

Tyr Gly Tyr Arg Gly Lys His Leu Gly Gly Ser Arg Lys Pro Asp Gly
                885                 890                 895

Ala Ile Tyr Thr Val Gly Ser Pro Ile Asp Tyr Gly Val Ile Val Asp
            900                 905                 910

Thr Lys Ala Tyr Ser Gly Gly Tyr Asn Leu Pro Ile Gly Gln Ala Asp
            915                 920                 925

Glu Met Gln Arg Tyr Val Glu Glu Asn Gln Thr Arg Asn Lys His Ile
            930                 935                 940

Asn Pro Asn Glu Trp Trp Lys Val Tyr Pro Ser Ser Val Thr Glu Phe
945                 950                 955                 960

Lys Phe Leu Phe Val Ser Gly His Phe Lys Gly Asn Tyr Lys Ala Gln
                965                 970                 975

Leu Thr Arg Leu Asn His Ile Thr Asn Cys Asn Gly Ala Val Leu Ser
            980                 985                 990

Val Glu Glu Leu Leu Ile Gly Gly Glu Met Ile Lys Ala Gly Thr Leu
            995                 1000                1005

Thr Leu  Glu Glu Val Arg Arg  Lys Phe Asn Asn Gly  Glu Ile Asn
```

Phe

<210> SEQ ID NO 82
<211> LENGTH: 4032
<212> TYPE: DNA
<213> ORGANISM: Artificial Sequence
<220> FEATURE:
<223> OTHER INFORMATION: Xanthomonas ssp, Zea mays

<400> SEQUENCE: 82

```
atggctagct ccccccgaa gaagaagagg aaggtcagct ggaaggatgc tagcggctgg      60
agcaggatgc acgctgatcc aatcaggccg aggaggccaa gcccagcaag ggagctgctg     120
ccaggcccac agccagatag ggtgcagcca accgccgata ggggcgtgag cgctccagct     180
ggcagcccgc tggatggcct gccagctagg aggaccgtga gcaggaccag gctgccgagc     240
ccaccagctc cgagcccagc cttcagcgct ggcagcttca gcgatctgct gaggccattc     300
gatccgagcc tgctggatac atcgctgctg atagcatgc cagctgtggg caccccacac     360
accgctgctg ctccagctga gtgggatgag atgcagtccg ccctccgcgc cgccgacgac     420
ccgccgccaa ccgtgagggt ggccgtgacc gctgctaggc cgccaagggc taagccagct     480
ccaaggagga gggccgctca gccaagcgat gctagccccg ccgcgcaggt cgacctcagg     540
accctgggct acagccagca gcagcaggag aagatcaagc cgaaggtgag gagcaccgtg     600
gcccagcacc acgaggctct ggtgggccac ggcttcaccc acgctcacat cgtggccctg     660
agccagcacc cagctgctct gggcaccgtg gctgtgacct accagcacat catcaccgcc     720
ctgccagagg ctacccacga ggacatcgtg ggcgtgggca gcagtggag cggcgctagg     780
gccctggagg ctctgctgac cgatgctggc gagctgaggg gccacccgct ccagctggat     840
accggccagc tggtgaagat cgccaagagg ggcggcgtga ccgctatgga ggctgtgcac     900
gccagcagga acgctctgac cggcgctcca ctgaacctga ccccgacca ggtggtggcc     960
atcgcgagca acatcggcgg caagcaggct ctcgaaaccg tgcagaggct gctcccggtg    1020
ctgtgccagg cccacggcct cacccccagac caggtcgtcg cgatcgcctc ccacgatggc    1080
ggcaagcagg ccctggagac tgtgcagcgc ctgctgcccg tcctgtgcca ggaccacggc    1140
ctcaccccgg agcaggtcgt cgctatcgct agcaacatcg gcggcaagca ggcgctcgaa    1200
accgtccaga ggctcctccc agtcctctgc aggatcacg gcctgacccc ggatcaggtg     1260
gtcgccatcg cttcccacga tggcggcaag caggcgctgg agactgtcca gcgcctcctc    1320
ccagtcctct gccaggcgca cggcctcacc ccgatcagg tcgtggcgat cgcgagcaac    1380
aacggcggca gcaggctct cgaaaccgtg cagaggctgc tgccggtgct ctgccaggct    1440
cacggcctga ccccagacca ggtggtggct atcgcctcca acggcggcgg caagcaggcc    1500
ctggagactg tgcagaggct cctcccggtc ctgtgccagg cccacggcct cacccccgag    1560
caggtcgtcg cgatcgctag caacatcggc ggcaagcagg ccctggagac tgtgcagagg    1620
ctgctcccag tcctgtgcca ggcccacggc ctgaccccg agcaggtggt cgcgatcgcg    1680
agccacgacg gcggcaagca ggcgctcgaa accgtccaga ggctcctccc cgtgctctgc    1740
caggatcacg gcctgacccc agagcaggtg gtggctatcg cgagcaacgg cggcggcaag    1800
caggctctcg aaaccgtcca gaggctcctc ccagtgctct gccaggctca cggcctcacc    1860
ccggaccagg tcgtcgccat cgcttccaac atcggcggca gcaggctct gaaaccgtg    1920
cagaggctgc tcccggtgct gtgccaggcc cacgccctca ccccagacca ggtcgtcgcg    1980
```

```
atcgcctcca acatcggcgg caagcaggcc ctggagactg tgcagcgcct gctgcccgtc    2040
ctgtgccagg accacggcct cacccggag caggtcgtcg ctatcgctag caacggcggc    2100
ggcaagcagg cgctcgaaac cgtccagagg ctcctcccag tcctctgcca ggatcacggc    2160 ctgacccga atcaggtggt cgccatcgct tcccacgatg gcggcaagca ggcgctggag    2220
actgtccagc gcctcctccc agtcctctgc caggcgcacg gcctcacccc cgatcaggtc    2280
gtggcgatcg cgagcaacaa cggcggcaag caggctctcg aaaccgtgca gaggctgctg    2340
ccggtgctct gccaggctca cggcctgacc ccagaccagg tggtggctat cgcctccaac    2400
ggcggcggca agcaggccct ggagactgtg cagaggctcc tcccggtcct gtgccaggcc    2460
cacggcctca cccccgagca ggtcgtcgcg atcgctagca acaacggcgg caagcaggcc    2520
ctggagactg tgcagaggct gctcccagtc ctgtgccagg cccacggcct gacccccgag    2580
caggtggtcg cgatcgcgag ccacgacggc ggcaagcagg cgctcgaaac cgtccagagg    2640
ctcctccccg tgctctgcca ggatcacggc ctcacccccg accaggtcgt ggctatcgcg    2700
tccaacggcg gcaagcaggc tctcgagagc atcgtggccc agctgagcag gccggacccg    2760
gccctggccg ccctgaccaa cgatcacctg gtggctctgg cctgcctggg cggcaggcca    2820
gccatggacg ctgtgaagaa gggcctgccg cacgctccag agctgatccg cagggtgaac    2880
aggaggatcg cgagaggac cagccacagg gtggccgact acgctcaggt ggtgaggtg    2940 ctggagttct tccagtgcca cagccacccg gcctacgcct tcgacgaggc tatgacccag    3000
ttcggcatga gcaggaacgg cctggtgcag ctgttcagga gggtgggcgt gaccgagctg    3060
gaggctaggg gcggcaccct gccgccagct agccagaggt gggaccgcat cctccaggcc    3120
agcggcatga aaagggctaa gccaagcccg accagcgctc agaccccaga tcaggctagc    3180
ctgcacgctt tcgccgacag cctggagagg gatctggatg ctccgagccc aatgcacgag    3240
ggcgaccaga ccagggccag cagcaggaag aggagcagga gcgacagggc tgtgaccggc    3300
ccgagcgccc agcaggctgt ggaggtgagg gtgccagagc agagggatgc cctgcacctg    3360
ccgctgagct ggagggtgaa gaggccaagg accaggatct ggggcggcct gccagatccg    3420 ggcacccaa ccgctgctga tcagctcgtg aagagcgagc tggaggagaa gaagagcgag    3480
ctgaggcata aactgaagta cgtgccacac gagtacatcg agctgatcga gatcgccagg    3540
aacagcaccc aggatcgcat cctggagatg aaggtgatgg agttcttcat gaaagtgtac    3600
ggctacaggg gcaagcacct gggcggcagc aggaagccag atggcgccat ctacaccgtg    3660
ggcagcccaa tcgactacgg cgtgatcgtg gataccaagg cttacagcgg cggctacaac    3720
ctgccgatcg gccaggctga tgagatgcag aggtacgtgg aggagaatca aaccaggaac    3780
aagcacatca acccaaacga gtggtggaag gtgtacccga gcagcgtgac cgagttcaag    3840
ttcctgttcg tgagcggcca cttcaagggc aactacaagg ctcagctcac caggctgaac    3900
cacatcacca actgcaacgg cgccgtgctg agcgtggagg agctgctgat cggcggcgag    3960
atgatcaagg ctggcacccc tgaccctgga gaggtgagga ggaagttcaa caacggcgag    4020
atcaacttct ga                                                      4032
```

<210> SEQ ID NO 83
<211> LENGTH: 3114
<212> TYPE: DNA
<213> ORGANISM: Artificial Sequence
<220> FEATURE:
<223> OTHER INFORMATION: Xanthomonas ssp, Zea mays

```
<400> SEQUENCE: 83
atggctagct ccccccgaa gaagaagagg aaggtcagct ggaaggatgc tagcggctgg      60
agcaggatgc acgctgatcc atggccaagg aggagggccg ctcagccaag cgatgctagc     120
cccgccgcgc aggtcgacct caggaccctg ggctacagcc agcagcagca ggagaagatc     180
aagccgaagg tgaggagcac cgtggcccag caccacgagg ctctggtggg ccacggcttc     240
acccacgctc acatcgtggc cctgagccag cacccagctg ctctgggcac cgtggctgtg     300
acctaccagc acatcatcac cgccctgcca gaggctaccc acgaggacat cgtgggcgtg     360
ggcaagcagt ggagcggcgc tagggccctg gaggctctgc tgaccgatgc tggcgagctg     420
aggggcccac cgctccagct ggataccggc cagctggtga agatcgccaa gaggggcggc     480
gtgaccgcta tggaggctgt gcacgccagc aggaacgctc tgaccggcgc tccactgaac     540
ctgaccccg accaggtggt ggccatcgcg agcaacatcg gcggcaagca ggctctcgaa      600
accgtgcaga ggctgctccc ggtgctgtgc caggcccacg gcctcacccc agaccaggtc     660
gtcgcgatcg cctcccacga tggcggcaag caggccctgg agactgtgca gcgcctgctg     720
cccgtcctgt gccaggacca cggcctcacc ccggagcagg tcgtcgctat cgctagcaac     780
atcggcggca gcaggcgct cgaaaccgtc cagaggctcc tcccagtcct ctgccaggat     840
cacggcctga ccccggatca ggtggtcgcc atcgcttccc acgatggcgg caagcaggcg    900
ctggagactg tccagcgcct cctcccagtc tctgccaggc gcacggcct cacccccgat    960
caggtcgtgg cgatcgcgag caacaacggc ggcaagcagg ctctcgaaac cgtgcagagg   1020
ctgctgccgt gctctgcca ggctcacggc ctgaccccag accaggtggt ggctatcgcc    1080
tccaacggcg gcggcaagca ggccctggag actgtgcaga ggctcctccc ggtcctgtgc    1140
caggcccacg gcctcacccc cgagcaggtc gtcgcgatcg ctagcaacat cggcggcaag   1200
caggccctgg agactgtgca gaggctgctc ccagtcctgt gccaggccca cggcctgacc   1260
cccgagcagg tggtcgcgat cgcgagccac gacggcggca agcaggcgct cgaaaccgtc   1320
cagaggctcc tcccgtgct ctgccaggat cacggcctga ccccagagca ggtggtggct    1380
atcgcgagca acggcggcgg caagcaggct ctcgaaaccg tccagaggct cctcccagtg   1440
ctctgccagg ctcacggcct caccccggac caggtcgtcg ccatcgcttc caacatcggc    1500
ggcaagcagg ctctcgaaac cgtgcagagg ctgctcccgg tgctgtgcca ggcccacggc    1560
ctcaccccag accaggtcgt cgcgatcgcc tccaacatcg gcggcaagca ggccctggag    1620
actgtgcagc gcctgctgcc cgtcctgtgc caggaccacg gcctcacccc ggagcaggtc    1680
gtcgctatcg ctagcaacgg cggcggcaag caggcgctcg aaaccgtcca gaggctcctc    1740
ccagtcctct gccaggatca cggcctgacc ccggatcagg tggtcgccat cgcttcccac    1800
gatggcggca agcaggcgct ggagactgtc agcgcctcc tcccagtcct ctgccaggcg    1860
cacggcctca ccccgatca ggtcgtggcg atcgcgagca acaacggcgg caagcaggct    1920
ctcgaaaccg tgcagaggct gctgccggtg ctctgccagg ctcacggcct gaccccagac    1980
caggtggtgg ctatcgcctc caacggcggc ggcaagcagg ccctggagac tgtgcagagg    2040
ctcctcccgg tcctgtgcca ggcccacggc ctcaccccg agcaggtcgt cgcgatcgct     2100
agcaacaacg gcggcaagca ggccctggag actgtgcaga ggctgctccc agtcctgtgc    2160
caggcccacg gcctgacccc cgagcaggtg gtcgcgatcg cgagccacga cggcggcaag    2220
caggcgctcg aaaccgtcca gaggctcctc ccgtgctct gccaggatca cggcctcacc    2280
cccgaccagg tcgtggctat cgcgtccaac ggcggcaagc aggctctcga gagcatcgtg    2340
```

```
gcccagctga gcaggccgga cccggccctg gccgccctga ccaacgatca cctggtggct    2400
ctggcctgcc tgggcggcag gccagccatg gacgctgtga agaagggcct gccgcacgct    2460
ccagagctga tccgcagggt gaacaggagg atcggcgaga ggaccagcca caggtggcc     2520 ctgcagctcg tgaagagcga gctggaggag aagaagagcg agctgaggca taaactgaag    2580
tacgtgccac acgagtacat cgagctgatc gagatcgcca ggaacagcac ccaggatcgc    2640
atcctggaga tgaaggtgat ggagttcttc atgaaagtgt acggctacag gggcaagcac    2700
ctgggcggca gcaggaagcc agatggcgcc atctacaccg tgggcagccc aatcgactac    2760
ggcgtgatcg tggataccaa ggcttacagc ggcggctaca acctgccgat cggccaggct    2820
gatgagatgc agaggtacgt ggaggagaat caaaccagga caagcacat caacccaaac      2880 gagtggtgga aggtgtaccc gagcagcgtg accgagttca agttcctgtt cgtgagcggc    2940
cacttcaagg gcaactacaa ggctcagctc accaggctga accacatcac caactgcaac    3000
ggcgccgtgc tgagcgtgga ggagctgctg atcggcggcg atgatcaa ggctggcacc      3060 ctgaccctgg aggaggtgag gaggaagttc aacaacggcg agatcaactt ctga          3114

<210> SEQ ID NO 84
<211> LENGTH: 3930
<212> TYPE: DNA
<213> ORGANISM: Artificial Sequence
<220> FEATURE:
<223> OTHER INFORMATION: Xanthomonas ssp, Zea mays

<400> SEQUENCE: 84
atggctagct ccccccccgaa gaagaagagg aaggtcagct ggaaggatgc tagcggctgg       60
agcaggatgc acgctgatcc aatcaggccg aggaggccaa gcccagcaag ggagctgctg      120
ccaggcccac agccagatag ggtgcagcca accgccgata ggggcgtgag cgctccagct      180
ggcagcccgc tggatggcct gccagctagg aggaccgtga gcaggaccag gctgccgagc      240
ccaccagctc cgagcccagc cttcagcgct ggcagcttca gcgatctgct gaggccattc      300
gatccgagcc tgctggatac atcgctgctg gatagcatgc cagctgtggg cacccccacac     360 accgctgctg ctccagctga gtgggatgag atgcagtccg ccctccgcgc cgccgacgac     420
ccgccgccaa ccgtgagggt ggccgtgacc gctgctaggc cgccaagggc taagccagct     480
ccaaggagga gggccgctca gccaagcgat gctagccccg ccgcgcaggt cgacctcagg    540
accctgggct acagccagca gcagcaggag aagatcaagc cgaaggtgag gagcaccgtg    600
gcccagcacc acgaggctct ggtgggccac ggcttcaccc acgctcacat cgtggccctg    660
agccagcacc cagctgctct gggcaccgtg gctgtgacct accagcacat catcaccgcc    720
ctgccagagg ctacccacga ggacatcgtg ggcgtgggca gcagtggag cggcgctagg     780 gccctggagg ctctgctgac cgatgctggc gagctgaggg gccaccgct ccagctggat    840 accgccagc tggtgaagat cgccaagagg ggcggcgtga ccgctatgga ggctgtgcac   900
gccagcagga acgctctgac cggcgctcca ctgaacctga ccccgacca ggtggtggcc    960 atcgcgagcc acgacggcgg caagcaggct ctcgaaaccg tgcagaggct gctcccggtg   1020
ctgtgccagg cccacggcct caccccagac caggtcgtcg cgatcgcctc ccacgatggc   1080
ggcaagcagg ccctggagac tgtgcagcgc ctgctgcccg tcctgtgcca ggaccacggc    1140
ctcaccccgg agcaggtcgt cgctatcgct agcaacggcg gcggcaagca ggcgctcgaa    1200
accgtccaga ggctcctccc agtcctctgc caggatcacg gcctgacccc ggatcaggtg    1260
```

```
gtcgccatcg cttccaacaa cggcggcaag caggcgctgg agactgtcca gcgcctcctc    1320
ccagtcctct gccaggcgca cggcctcacc cccgatcagg tcgtggcgat cgcgagcaac    1380
ggcggcggca agcaggctct cgaaaccgtg cagaggctgc tgccggtgct ctgccaggct    1440
cacggcctga ccccagacca ggtggtggct atcgcctccc acgatggcgg caagcaggcc    1500
ctggagactg tgcagaggct cctcccggtc ctgtgccagg cccacggcct caccccgag    1560 caggtcgtcg cgatcgctag caacggcggc ggcaagcagg ccctggagac tgtgcagagg    1620
ctgctcccag tcctgtgcca ggcccacggc ctgaccccg agcaggtggt cgcgatcgcg    1680
agcaacatcg gcggcaagca ggcgctcgaa accgtccaga ggctcctccc cgtgctctgc    1740
caggatcacg gcctgacccc agagcaggtg gtggctatcg cgagccacga cggcggcaag    1800
caggctctcg aaaccgtcca gaggctcctc ccagtgctct gccaggctca cggcctcacc    1860
ccggaccagg tcgtcgccat cgcttccaac ggcggcggca agcaggctct cgaaaccgtg    1920
cagaggctgc tcccggtgct gtgccaggcc cacggcctca ccccagacca ggtcgtcgcg    1980
atcgcctcca acatcggcgg caagcaggcc ctggagactg tgcagcgcct gctgcccgtc    2040
ctgtgccagg accacggcct caccccggag caggtcgtcg ctatcgctag ccacgacggc    2100
ggcaagcagg cgctcgaaac cgtccagagg ctcctcccag tcctctgcca ggatcacggc    2160
ctgaccccgg atcaggtggt cgccatcgct tccaacaacg gcggcaagca ggcgctggag    2220
actgtccagc gcctctcccc agtcctctgc caggcgcacg gcctcacccc cgatcaggtc    2280
gtggcgatcg cgagcaacgg cggcggcaag caggctctcg aaaccgtgca gaggctgctg    2340
ccggtgctct gccaggctca cggcctgacc ccagaccagg tggtggctat cgcctccaac    2400
aacggcggca agcaggccct ggagactgtg cagaggctcc tcccagtcct gtgccaggcc    2460
cacggcctga ccccgagca ggtggtcgcg atcgcgagcc acgacggcgg caagcaggcg    2520
ctcgaaaccg tccagaggct cctcccgtg ctctgccagg atcacggcct cacccccgac    2580
caggtcgtgg ctatcgcgtc caacggcggc aagcaggctc tcgagagcat cgtggcccag    2640
ctgagcaggc cggacccggc cctggccgcc ctgaccaacg atcacctggt ggctctggcc    2700
tgcctgggcg gcaggccagc catggacgct gtgaagaagg cctgccgca cgctccagag    2760 ctgatccgca gggtgaacag gaggatcggc gagaggacca gccacagggt ggccgactac    2820
gctcaggtgg tgagggtgct ggagttcttc cagtgccaca gccacccggc ctacgccttc    2880
gacgaggcta tgacccagtt cggcatgagc aggaacggcc tggtgcagct gttcaggagg    2940
gtgggcgtga ccgagctgga ggctaggggc ggcaccctgc cgccagctag ccagaggtgg    3000
gaccgcatcc tccaggccag cggcatgaaa agggctaagc caagcccgac cagcgctcag    3060
accccagatc aggctagcct gcacgctttc gccgacagcc tggagaggga tctggatgct    3120
ccgagcccaa tgcacgaggg cgaccagacc agggccagca gcaggaagag gagcaggagc    3180
gacagggctg tgaccggccc gagcgcccag caggctgtgg aggtgagggt gccagagcag    3240
agggatgccc tgcacctgcc gctgagctgg agggtgaaga ggccaaggac caggatctgg    3300
ggcggcctgc cagatccggg caccccaacc gctgctgatc agctcgtgaa gagcgagctg    3360
gaggagaaga gagcgagct gaggcataaa ctgaagtacg tgccacacga gtacatcgag    3420
ctgatcgaga tcgccaggaa cagcacccag gatcgcatcc tggagatgaa ggtgatggag    3480
ttcttcatga agtgtacgg ctacagggc aagcacctgg cggcagcag gaagccagat    3540 ggcgccatct acaccgtggg cagcccaatc gactacggcg tgatcgtgga taccaaggct    3600
tacagcggcg gctacaacct gccgatcggc caggctgatg agatgcagag gtacgtggag    3660
```

```
gagaatcaaa ccaggaacaa gcacatcaac ccaaacgagt ggtggaaggt gtacccgagc    3720
agcgtgaccg agttcaagtt cctgttcgtg agcggccact tcaagggcaa ctacaaggct    3780
cagctcacca ggctgaacca catcaccaac tgcaacggcg ccgtgctgag cgtggaggag    3840
ctgctgatcg gcggcgagat gatcaaggct ggcaccctga ccctggagga ggtgaggagg    3900
aagttcaaca acggcgagat caacttctga                                     3930
```

<210> SEQ ID NO 85
<211> LENGTH: 3012
<212> TYPE: DNA
<213> ORGANISM: Artificial Sequence
<220> FEATURE:
<223> OTHER INFORMATION: Xanthomonas ssp, Zea mays

<400> SEQUENCE: 85

```
atggctagct cccccccgaa gaagaagagg aaggtcagct ggaaggatgc tagcggctgg      60
agcaggatgc acgctgatcc atggccaagg aggagggccg ctcagccaag cgatgctagc     120
cccgccgcgc aggtcgacct caggaccctg gctacagcc agcagcagca ggagaagatc      180
aagccgaagg tgaggagcac cgtggcccag caccacgagg ctctggtggg ccacggcttc     240
acccacgctc acatcgtggc cctgagccag cacccagctg ctctgggcac cgtggctgtg     300
acctaccagc acatcatcac cgccctgcca gaggctaccc acgaggacat cgtgggcgtg     360
ggcaagcagt ggagcggcgc tagggccctg gaggctctgc tgaccgatgc tggcgagctg     420
aggggcccac cgctccagct ggataccggc cagctggtga gatcgccaa gagggcggc      480 gtgaccgcta tggaggctgt gcacgccagc aggaacgctc tgaccggcgc tccactgaac     540 ctgaccccg accaggtggt ggccatcgcg agccacgacg gcggcaagca ggctctcgaa     600
accgtgcaga ggctgctccc ggtgctgtgc caggcccacg gcctcacccc agaccaggtc     660
gtcgcgatcg cctcccacga tggcggcaag caggccctgg agactgtgca gcgcctgctg     720
cccgtcctgt gccaggacca cggcctcacc ccggagcagg tcgtcgctat cgctagcaac     780
ggcggcggca gcaggcgct cgaaaccgtc cagaggctcc tcccagtcct ctgccaggat     840
cacggcctga ccccggatca ggtggtcgcc atcgcttcca caacggcgg caagcaggcg     900 ctggagactg tccagcgcct cctcccagtc ctctgccagg cgcacggcct cacccccgat     960
caggtcgtgg cgatcgcgag caacggcggc ggcaagcagg ctctcgaaac cgtgcagagg    1020
ctgctgccgg tgctctgcca ggctcacggc ctgaccccag accaggtggt ggctatcgcc    1080
tcccacgatg gcggcaagca ggccctggag actgtgcaga ggctcctccc ggtcctgtgc    1140
caggcccacg gcctcacccc cgagcaggtc gtcgcgatcg ctagcaacgg cggcggcaag    1200
caggccctgg agactgtgca gaggctgctc ccagtcctgt gccaggccca cggcctgacc    1260
cccgagcagg tggtcgcgat cgcgagcaac atcggcggca agcaggcgct cgaaaccgtc    1320
cagaggctcc tccccgtgct ctgccaggat acggcctga ccccagagca ggtggtggct    1380
atcgcgagcc acgacggcgg caagcaggct ctcgaaaccg tccagaggct cctcccagtg    1440
ctctgccagg ctcacggcct caccccggac caggtcgtcg ccatcgcttc aacggcggc    1500 ggcaagcagg ctctcgaaac cgtgcagagg ctgctcccgg tgctgtgcca ggcccacggc    1560
ctcaccccag accaggtcgt cgcgatcgcc tcaacatcg gcggcaagca ggccctggag    1620
actgtgcagc gcctgctgcc cgtcctgtgc caggaccacg gcctcacccc ggagcaggtc    1680
gtcgctatcg ctagccacga cggcggcaag caggcgctcg aaaccgtcca gaggctcctc    1740
```

| ccagtcctct gccaggatca cggcctgacc ccggatcagg tggtcgccat cgcttccaac | 1800 |
| aacggcggca agcaggcgct ggagactgtc cagcgcctcc tcccagtcct ctgccaggcg | 1860 |
| cacgcctca cccccgatca ggtcgtggcg atcgcgagca acggcggcgg caagcaggct | 1920 |
| ctcgaaaccg tgcagaggct gctgccggtg ctctgccagg ctcacggcct gaccccagac | 1980 |
| caggtggtgg ctatcgcctc caacaacggc ggcaagcagg ccctggagac tgtgcagagg | 2040 |
| ctcctcccag tcctgtgcca ggcccacggc ctgaccccg agcaggtggt cgcgatcgcg | 2100 |
| agccacgacg gcggcaagca ggcgctcgaa accgtccaga ggctcctccc cgtgctctgc | 2160 |
| caggatcacg gcctcacccc cgaccaggtc gtggctatcg cgtccaacgg cggcaagcag | 2220 |
| gctctcgaga gcatcgtggc ccagctgagc aggccggacc cggccctggc cgccctgacc | 2280 |
| aacgatcacc tggtggctct ggcctgcctg ggcggcaggc cagccatgga cgctgtgaag | 2340 |
| aagggcctgc cgcacgctcc agagctgatc cgcagggtga acaggaggat cggcgagagg | 2400 |
| accagccaca gggtggccct gcagctcgtg aagagcgagc tggaggagaa gaagagcgag | 2460 |
| ctgaggcata aactgaagta cgtgccacac gagtacatcg agctgatcga gatcgccagg | 2520 |
| aacagcaccc aggatcgcat cctggagatg aaggtgatgg agttcttcat gaaagtgtac | 2580 |
| ggctacaggg gcaagcacct gggcggcagc aggaagccag atggcgccat ctacaccgtg | 2640 |
| ggcagcccaa tcgactacgg cgtgatcgtg gataccaagg cttacagcgg cggctacaac | 2700 |
| ctgccgatcg gccaggctga tgagatgcag aggtacgtgg aggagaatca aaccaggaac | 2760 |
| aagcacatca acccaaacga gtggtggaag gtgtacccga gcagcgtgac cgagttcaag | 2820 |
| ttcctgttcg tgagcggcca cttcaagggc aactacaagg ctcagctcac caggctgaac | 2880 |
| cacatcacca actgcaacgg cgccgtgctg agcgtggagg agctgctgat cggcggcgag | 2940 |
| atgatcaagg ctggcaccct gaccctggag gaggtgagga ggaagttcaa caacggcgag | 3000 |
| atcaacttct ga | 3012 |

<210> SEQ ID NO 86
<211> LENGTH: 4032
<212> TYPE: DNA
<213> ORGANISM: Artificial Sequence
<220> FEATURE:
<223> OTHER INFORMATION: Xanthomonas ssp, Zea mays

<400> SEQUENCE: 86

| atggctagct cccccccgaa gaagaagagg aaggtcagct ggaaggatgc tagcggctgg | 60 |
| agcaggatgc acgctgatcc aatcaggccg aggaggccaa gcccagcaag ggagctgctg | 120 |
| ccaggcccac agccagatag ggtgcagcca accgccgata ggggcgtgag cgctccagct | 180 |
| ggcagcccgc tggatggcct gccagctagg aggaccgtga gcaggaccag gctgccgagc | 240 |
| ccaccagctc cgagcccagc cttcagcgct ggcagcttca gcgatctgct gaggccattc | 300 |
| gatccgagcc tgctggatac atcgctgctg gatagcatgc cagctgtggg caccccacac | 360 |
| accgctgctg ctccagctga gtgggatgag atgcagtccg ccctccgcgc cgccgacgac | 420 |
| ccgccgccaa ccgtgagggt ggccgtgacc gctgctaggc cgccaagggc taagccagct | 480 |
| ccaaggagga gggccgctca gccaagcgat gctagccccg ccgcgcaggt cgacctcagg | 540 |
| accctgggct acagccagca gcagcaggag aagatcaagc cgaaggtgag gagcaccgtg | 600 |
| gcccagcacc acgaggctct ggtgggccac ggcttcaccc acgctcacat cgtggccctg | 660 |
| agccagcacc cagctgctct gggcaccgtg gctgtgacct accagcacat catcaccgcc | 720 |
| ctgccagagg ctacccacga ggacatcgtg ggcgtgggca gcagtggag cggcgctagg | 780 |

```
gccctggagg ctctgctgac cgatgctggc gagctgaggg gcccaccgct ccagctggat    840
accggccagc tggtgaagat cgccaagagg ggcggcgtga ccgctatgga ggctgtgcac    900
gccagcagga acgctctgac cggcgctcca ctgaacctga cccccgacca ggtggtggcc    960
atcgcgagca acaacggcgg caagcaggct ctcgaaaccg tgcagaggct gctcccggtg   1020
ctgtgccagg cccacggcct caccccagac caggtcgtcg cgatcgcctc ccacgatggc   1080
ggcaagcagg ccctggagac tgtgcagcgc ctgctgcccg tcctgtgcca ggaccacggc   1140
ctcacccccg gagcaggtcgt cgctatcgct agcaacatcg gcggcaagca ggcgctcgaa   1200
accgtccaga ggctcctccc agtcctctgc caggatcacg gcctgacccc ggatcaggtg   1260
gtcgccatcg cttccaacgg cggcggcaag caggcgctgg agactgtcca gcgcctcctc   1320
ccagtcctct gccaggcgca cggcctcacc cccgatcagg tcgtggcgat cgcgagccac   1380
gacggcggca agcaggctct cgaaaccgtg cagaggctgc tgccggtgct ctgccaggct   1440
cacggcctga ccccagacca ggtggtggct atcgcctccc acgatggcgg caagcaggcc   1500
ctggagactg tgcagaggct cctcccggtc ctgtgccagg cccacggcct caccccgag   1560 caggtcgtcg cgatcgctag caacaacggc ggcaagcagg ccctggagac tgtgcagagg   1620
ctgctcccag tcctgtgcca ggcccacggc ctgaccccg agcaggtggt cgcgatcgcg   1680
agcaacggcg gcggcaagca ggcgctcgaa accgtccaga ggctcctccc cgtgctctgc   1740
caggatcacg gcctgacccc agagcaggtg gtggctatcg cgagcaacaa cggcggcaag   1800
caggctctcg aaaccgtcca gaggctcctc ccagtgctct gccaggctca cggcctcacc   1860
ccggaccagg tcgtcgccat cgcttcccac gatggcggca agcaggctct cgaaaccgtg   1920
cagaggctgc tccgggtgct gtgccaggcc cacggcctca cccagacca ggtcgtcgcg   1980 atcgcctcca acatcggcgg caagcaggcc ctggagactg tgcagcgcct gctgcccgtc   2040
ctgtgccagg accacggcct caccccggag caggtcgtcg ctatcgctag caacaacggc   2100
ggcaagcagg cgctcgaaac cgtccagagg ctcctcccag tcctctgcca ggatcacggc   2160
ctgaccccgg atcaggtggt cgccatcgct tccaacggcg gcggcaagca ggcgctggag   2220
actgtccagc gcctcctccc agtcctctgc caggcgcacg gcctcacccc cgatcaggtc   2280
gtggcgatcg cgagcaacaa cggcggcaag caggctctcg aaaccgtgca gaggctgctg   2340
ccggtgctct gccaggctca cggcctgacc ccagaccagg tggtggctat cgcctcccac   2400
gatggcggca agcaggccct ggagactgtg cagaggctcc tcccggtcct gtgccaggcc   2460
cacggcctca ccccgagca ggtcgtcgcg atcgctagca acatcggcgg caagcaggcc   2520
ctggagactg tgcagaggct gctcccagtc ctgtgccagg cccacggcct gaccccgag   2580 caggtggtcg cgatcgcgag caacaacggc ggcaagcagg cgctcgaaac cgtccagagg   2640
ctcctccccg tgctctgcca ggatcacggc ctcacccccg accaggtcgt ggctatcgcg   2700
tccaacggcg gcaagcaggc tctcgagagc atcgtggccc agctgagcag gccggacccg   2760
gccctggccg ccctgaccaa cgatcacctg gtggctctgg cctgcctggg cggcaggcca   2820 gccatgacg ctgtgaagaa gggcctgccg cacgctccag agctgatccg cagggtgaac   2880
aggaggatcg cgcgagaggac cagccacagg gtggccgact acgctcaggt ggtgagggtg   2940
ctggagttct tccagtgcca cagccacccg gcctacgcct tcgacgaggc tatgacccag   3000
ttcggcatga gcaggaacgg cctggtgcag ctgttcagga gggtgggcgt gaccgagctg   3060
gaggctaggg gcggcaccct gccgccagct agccagaggt gggaccgcat cctccaggcc   3120
```

| | |
|---|---|
| agcggcatga aaagggctaa gccaagcccg accagcgctc agaccccaga tcaggctagc | 3180 |
| ctgcacgctt tcgccgacag cctggagagg gatctggatg ctccgagccc aatgcacgag | 3240 |
| ggcgaccaga ccagggccag cagcaggaag aggagcagga gcgacagggc tgtgaccggc | 3300 |
| ccgagcgccc agcaggctgt ggaggtgagg gtgccagagc agagggatgc cctgcacctg | 3360 |
| ccgctgagct ggagggtgaa gaggccaagg accaggatct ggggcggcct gccagatccg | 3420 |
| ggcaccccaa ccgctgctga tcagctcgtg aagagcgagc tggaggagaa gaagagcgag | 3480 |
| ctgaggcata aactgaagta cgtgccacac gagtacatcg agctgatcga gatcgccagg | 3540 |
| aacagcaccc aggatcgcat cctggagatg aaggtgatgg agttcttcat gaaagtgtac | 3600 |
| ggctacaggg gcaagcacct gggcggcagc aggaagccag atggcgccat ctacaccgtg | 3660 |
| ggcagcccaa tcgactacgg cgtgatcgtg gataccaagg cttacagcgg cggctacaac | 3720 |
| ctgccgatcg gccaggctga tgagatgcag aggtacgtgg aggagaatca aaccaggaac | 3780 |
| aagcacatca acccaaacga gtggtggaag gtgtacccga gcagcgtgac cgagttcaag | 3840 |
| ttcctgttcg tgagcggcca cttcaagggc aactacaagg ctcagctcac caggctgaac | 3900 |
| cacatcacca actgcaacgg cgccgtgctg agcgtggagg agctgctgat cggcggcgag | 3960 |
| atgatcaagg ctggcaccct gaccctggag gaggtgagga ggaagttcaa caacggcgag | 4020 |
| atcaacttct ga | 4032 |

<210> SEQ ID NO 87
<211> LENGTH: 3114
<212> TYPE: DNA
<213> ORGANISM: Artificial Sequence
<220> FEATURE:
<223> OTHER INFORMATION: Xanthomonas ssp, Zea mays

<400> SEQUENCE: 87

```
atggctagct cccccccgaa gaagaagagg aaggtcagct ggaaggatgc tagcggctgg     60
agcaggatgc acgctgatcc atggccaagg aggagggccg ctcagccaag cgatgctagc    120
cccgccgcgc aggtcgacct caggaccctg ggctacagcc agcagcagca ggagaagatc    180
aagccgaagg tgaggagcac cgtggcccag caccacgagg ctctggtggg ccacggcttc    240
acccacgctc acatcgtggc cctgagccag cacccagctg ctctgggcac cgtggctgtg    300
acctaccagc acatcatcac cgccctgcca gaggctaccc acgaggacat cgtgggcgtg    360
ggcaagcagt ggagcggcgc tagggccctg gaggctctgc tgaccgatgc tggcgagctg    420
aggggcccac cgctccagct ggataccggc cagctggtga agatcgccaa gaggggcggc    480
gtgaccgcta tggaggctgt gcacgccagc aggaacgctc tgaccggcgc tccactgaac    540
ctgacccccg accaggtggt ggccatcgcg agcaacaacg gcggcaagca ggctctcgaa    600
accgtgcaga ggctgctccc ggtgctgtgc caggcccacg gcctcacccc agaccaggtc    660
gtcgcgatcg cctcccacga tggcggcaag caggccctgg agactgtgca gcgcctgctg    720
cccgtcctgt gccaggacca cggcctcacc ccggagcagg tcgtcgctat cgctagcaac    780
atcggcggca agcaggcgct cgaaaccgtc cagaggctcc tcccagtcct ctgccaggat    840
cacggcctga ccccggatca ggtggtcgcc atcgcttcca acggcggcgg caagcaggcg    900
ctggagactg tccagcgcct cctcccagtc ctctgccagg cgcacggcct cacccccgat    960
caggtcgtgg cgatcgcgag ccacgacggc ggcaagcagg ctctcgaaac cgtgcagagg   1020
ctgctgccgg tgctctgcca ggctcacggc ctgaccccag accaggtggt ggctatcgcc   1080
tcccacgatg gcggcaagca ggccctggag actgtgcaga ggctcctccc ggtcctgtgc   1140
```

```
caggcccacg gcctcacccc cgagcaggtc gtcgcgatcg ctagcaacaa cggcggcaag    1200
caggccctgg agactgtgca gaggctgctc ccagtcctgt gccaggccca cggcctgacc    1260
cccgagcagg tggtcgcgat cgcgagcaac ggcggcggca agcaggcgct cgaaaccgtc    1320
cagaggctcc tccccgtgct ctgccaggat cacggcctga ccccagagca ggtggtggct    1380
atcgcgagca acaacggcgg caagcaggct ctcgaaaccg tccagaggct cctcccagtg    1440
ctctgccagg ctcacggcct caccccggac caggtcgtcg ccatcgcttc ccacgatggc    1500
ggcaagcagg ctctcgaaac cgtgcagagg ctgctcccgg tgctgtgcca ggcccacggc    1560
ctcaccccag accaggtcgt cgcgatcgcc tccaacatcg gcggcaagca ggccctggag    1620
actgtgcagc gcctgctgcc cgtcctgtgc caggaccacg gcctcacccc ggagcaggtc    1680
gtcgctatcg ctagcaacaa cggcggcaag caggcgctcg aaaccgtcca gaggctcctc    1740
ccagtcctct gccaggatca cggcctgacc ccggatcagg tggtcgccat cgcttccaac    1800
ggcggcggca agcaggcgct ggagactgtc agcgcctcc tcccagtcct ctgccaggcg    1860
cacggcctca ccccgatca ggtcgtggcg atcgcgagca acaacggcgg caagcaggct    1920
ctcgaaaccg tgcagaggct gctgccggtg ctctgccagg ctcacggcct gaccccagac    1980
caggtggtgg ctatcgcctc ccacgatggc ggcaagcagg ccctggagac tgtgcagagg    2040
ctcctcccgg tcctgtgcca ggcccacggc ctcaccccg agcaggtcgt cgcgatcgct    2100
agcaacatcg gcggcaagca ggccctggag actgtgcaga ggctgctccc agtcctgtgc    2160
caggcccacg gcctgacccc cgagcaggtg gtcgcgatcg cgagcaacaa cggcggcaag    2220
caggcgctcg aaaccgtcca gaggctcctc cccgtgctct gccaggatca cggcctcacc    2280
cccgaccagg tcgtggctat cgcgtccaac ggcggcaagc aggctctcga gagcatcgtg    2340
gcccagctga gcaggccgga cccggccctg gccgccctga ccaacgatca cctggtggct    2400
ctggcctgcc tgggcggcag gccagccatg gacgctgtga agaagggcct gccgcacgct    2460
ccagagctga tccgcagggt gaacaggagg atcggcgaga ggaccagcca cagggtggcc    2520
ctgcagctcg tgaagagcga gctggaggag aagaagagcg agctgaggca taaactgaag    2580
tacgtgccac acgagtacat cgagctgatc gagatcgcca ggaacagcac ccaggatcgc    2640
atcctggaga tgaaggtgat ggagttcttc atgaaagtgt acggctacag gggcaagcac    2700
ctgggcggca gcaggaagcc agatggcgcc atctacaccg tgggcagccc aatcgactac    2760
ggcgtgatcg tggataccaa ggcttacagc ggcggctaca acctgccgat cggccaggct    2820
gatgagatgc agaggtacgt ggaggagaat caaaccagga caagcacat caacccaaac    2880 gagtggtgga aggtgtaccc gagcagcgtg accgagttca agttcctgtt cgtgagcggc    2940
cacttcaagg gcaactacaa ggctcagctc accaggctga accacatcac caactgcaac    3000
ggcgccgtgc tgagcgtgga ggagctgctg atcggcggcg agatgatcaa ggctggcacc    3060
ctgaccctgg aggaggtgag gaggaagttc aacaacggcg agatcaactt ctga         3114
```

<210> SEQ ID NO 88
<211> LENGTH: 3075
<212> TYPE: DNA
<213> ORGANISM: Artificial Sequence
<220> FEATURE:
<223> OTHER INFORMATION: Xanthomonas ssp, Zea mays

<400> SEQUENCE: 88

```
atgggaaaac ctattcctaa tcctctgctg ggcctggatt ctaccggagg catggcccct     60
```

| | |
|---|---|
| aagaaaaagc ggaaggtgga cggcggagtg gacctgagaa cactgggata ttctcagcag | 120 |
| cagcaggaga agatcaagcc caaggtgaga tctacagtgg cccagcacca cgaagccctg | 180 |
| gtgggacacg gatttacaca cgcccacatt gtggccctgt ctcagcaccc tgccgccctg | 240 |
| ggaacagtgg ccgtgaaata tcaggatatg attgccgccc tgcctgaggc cacacacgaa | 300 |
| gccattgtgg gagtgggaaa acagtggtct ggagccagag ccctggaagc cctgctgaca | 360 |
| gtggccggag aactgagagg acctcctctg cagctggata caggacagct gctgaagatt | 420 |
| gccaaaggg gcggagtgac cgcggtggaa gccgtgcacg cctggagaaa tgccctgaca | 480 |
| ggagcccctc tgaacctgac ccccgaacag gtggtggcca ttgccagcaa caacggcggc | 540 |
| aagcaggccc tggaaaccgt gcagagactg ctgcccgtgc tgtgccaggc ccatggcctg | 600 |
| acacctgaac aggtggtggc tatcgcctct cacgacggag aaaacaggc tctggaaaca | 660 |
| gtgcagcggc tgctgcctgt gctgtgtcag gctcacggct tgactccaga acaggtggtg | 720 |
| gctattgctt ccaatattgg ggggaaacag gccctggaaa ctgtgcagcg cctgctgcca | 780 |
| gtgctgtgcc aggctcacgg actgaccccc gaacaggtgg tggccattgc cagcaacggc | 840 |
| ggcggcaagc aggccctgga aaccgtgcag agactgctgc ccgtgctgtg ccaggcccat | 900 |
| ggcctgacac ctgaacaggt ggtggctatc gcctctcacg acgaggaaa acaggctctg | 960 |
| gaaacagtgc agcggctgct gcctgtgctg tgtcaggctc acggcttgac tccagaacag | 1020 |
| gtggtggcta ttgcttccca cgacgggggg aaacaggccc tggaaactgt gcagcgcctg | 1080 |
| ctgccagtgc tgtgccaggc tcacgggctg accccgaac aggtggtggc cattgccagc | 1140 |
| aacaacggcg gcaagcaggc cctggaaacc gtgcagagac tgctgcccgt gctgtgccag | 1200 |
| gcccatggcc tgacacctga acaggtggtg gctatcgcct ctaacggcgg aggaaaacag | 1260 |
| gctctggaaa cagtgcagcg gctgctgcct gtgctgtgtc aggctcacgg cttgactcca | 1320 |
| gaacaggtgg tggctattgc ttccaacaac gggggaaac aggccctgga aactgtgcag | 1380 |
| cgcctgctgc cagtgctgtg ccaggctcac ggcctcactc ccgaacaggt ggtggccatt | 1440 |
| gccagccacg acggcggcaa gcaggccctg gaaaccgtgc agagactgct gcccgtgctg | 1500 |
| tgccaggccc atggcctgac acctgaacag gtggtggcta tcgcctctaa tatcggagga | 1560 |
| aaacaggctc tggaaacagt gcagcggctg ctgcctgtgc tgtgtcaggc tcacggcttg | 1620 |
| actccagaac aggtggtggc tattgcttcc aacaacgggg ggaaacaggc cctgaaaact | 1680 |
| gtgcagcgcc tgctgccagt gctgtgccag gctcacggac tgaccccga acaggtggtg | 1740 |
| gccattgcca gcaacggcgg cggcaagcag gccctgaaa ccgtgcagag actgctgccc | 1800 |
| gtgctgtgcc aggcccatgg cctgacacct gaacaggtgg tggctatcgc ctctaacaac | 1860 |
| ggaggaaaac aggctctgga aacagtgcag cggctgctgc ctgtgctgtg tcaggctcac | 1920 |
| ggcttgactc cagaacaggt ggtggctatt gcttcccacg acgggggaa acaggccctg | 1980 |
| gaaactgtgc agcgcctgct gccagtgctg tgccaggctc acgggctgac ccccgaacag | 2040 |
| gtggtggcca ttgccagcaa catcggcggc aagcaggccc tggaaaccgt gcagagactg | 2100 |
| ctgcccgtgc tgtgccaggc ccatggcctg acacctgaac aggtggtggc tatcgcctct | 2160 |
| aacaacggag aaaacaggc tctggaaaca gtgcagcggc tgctgcctgt gctgtgtcag | 2220 |
| gctcacggct tgactccaca gcaggtcgtg gcaattgcta gcaacggcgg cggacggccc | 2280 |
| gccctggaga gcattgtggc ccagctgtct agacctgatc ctgccctggc cgccctgaca | 2340 |
| aatgatcacc tggtggccct ggcctgtctg ggaggcagac ctgccctgga tgccgtgaaa | 2400 |
| aaaggactgc ctcacgcccc tgccctgatt aaaagaacaa atagaagaat ccccgagcgg | 2460 |

| | |
|---|---|
| acctctcaca gagtggccgg atcccagctg gtgaaatctg agctggagga gaagaagtct | 2520 |
| gagctgagac acaagctgaa gtacgtgcct cacgagtaca tcgagctgat cgagatcgcc | 2580 |
| agaaatagca cccaggatag aatcctggag atgaaggtga tggagttctt catgaaagtg | 2640 |
| tacggctaca gaggaaagca tctgggagga agcagaaaac ctgacggagc catttataca | 2700 |
| gtgggcagcc ctatcgatta tggcgtgatc gtggatacaa aggcctacag cggaggctac | 2760 |
| aatctgccta ttggacaggc cgatgagatg cagagatacg tggaggagaa ccaaaccagg | 2820 |
| aacaagcata tcaaccctaa cgagtggtgg aaggtgtacc cttctagcgt gaccgagttc | 2880 |
| aagttcctgt ttgtgagcgg ccacttcaag ggcaattata aggcccagct gaccaggctg | 2940 |
| aaccacatca caaattgtaa tggcgccgtg ctgtctgtgg aggaactgct gattggagga | 3000 |
| gagatgatta aggccggaac actgacactg gaggaggtga agaaagtt caacaacggc | 3060 |
| gagatcaact tctga | 3075 |

<210> SEQ ID NO 89
<211> LENGTH: 3828
<212> TYPE: DNA
<213> ORGANISM: Artificial Sequence
<220> FEATURE:
<223> OTHER INFORMATION: Xanthomonas ssp, Zea mays

<400> SEQUENCE: 89

| | |
|---|---|
| atggctagct ccccccgaa gaagaagagg aaggtcagct ggaaggatgc tagcggctgg | 60 |
| agcaggatgc acgctgatcc aatcaggccg aggaggccaa gcccagcaag ggagctgctg | 120 |
| ccaggcccac agccagatag ggtgcagcca accgccgata ggggcgtgag cgctccagct | 180 |
| ggcagcccgc tggatggcct gccagctagg aggaccgtga caggaccag gctgccgagc | 240 |
| ccaccagctc cgagcccagc cttcagcgct ggcagcttca gcgatctgct gaggccattc | 300 |
| gatccgagcc tgctggatac atcgctgctg gatagcatgc cagctgtggg cacccccacac | 360 |
| accgctgctg ctccagctga gtgggatgag atgcagtccg ccctccgcgc cgccgacgac | 420 |
| ccgccgccaa ccgtgagggt ggccgtgacc gctgctaggc cgccaagggc taagccagct | 480 |
| ccaaggagga gggccgctca gccaagcgat gctagccccg ccgcgcaggt cgacctcagg | 540 |
| accctgggct acagccagca gcagcaggag aagatcaagc cgaaggtgag gagcaccgtg | 600 |
| gcccagcacc acgaggctct ggtgggccac ggcttcaccc acgctcacat cgtggccctg | 660 |
| agccagcacc cagctgctct gggcaccgtg gctgtgacct accagcacat catcaccgcc | 720 |
| ctgccagagg ctacccacga ggacatcgtg ggcgtgggca gcagtggag cggcgctagg | 780 |
| gccctggagg ctctgctgac cgatgctggc gagctgaggg gcccaccgct ccagctggat | 840 |
| accggccagc tggtgaagat cgccaagagg ggcggcgtga ccgctatgga ggctgtgcac | 900 |
| gccagcagga acgctctgac cggcgctcca ctgaacctga cccccgacca ggtggtggcc | 960 |
| atcgcgagcc acgacggcgg caagcaggct ctcgaaaccg tgcagaggct gctcccggtg | 1020 |
| ctgtgccagg cccacggcct caccccagac caggtcgtcg cgatcgcctc ccacgatggc | 1080 |
| ggcaagcagg ccctggagac tgtgcagcgc ctgctgcccg tcctgtgcca ggaccacggc | 1140 |
| ctcacccgg agcaggtcgt cgctatcgct agcaacggcg gcggcaagca ggcgctcgaa | 1200 |
| accgtccaga ggctcctccc agtcctctgc caggatcacg gcctgacccc ggatcaggtg | 1260 |
| gtcgccatcg cttccaacat cggcggcaag caggcgctgg agactgtcca gcgcctcctc | 1320 |
| ccagtcctct gccaggcgca cggcctcacc cccgatcagg tcgtggcgat cgcgagcaac | 1380 |

-continued

| | |
|---|---|
| atcggcggca agcaggctct cgaaaccgtg cagaggctgc tgccggtgct ctgccaggct | 1440 |
| cacggcctga ccccagacca ggtggtggct atcgcctcca acatcggcgg caagcaggcc | 1500 |
| ctggagactg tgcagaggct cctcccagtc ctgtgccagg cccacggcct gaccccgag | 1560 |
| caggtggtcg cgatcgcgag ccacgacggc ggcaagcagg cgctcgaaac cgtccagagg | 1620 |
| ctcctcccg tgctctgcca ggatcacggc ctgaccccag agcaggtggt ggctatcgcg | 1680 |
| agcaacatcg gcggcaagca ggctctcgaa accgtccaga ggctcctccc agtgctctgc | 1740 |
| caggctcacg gcctcacccc ggaccaggtc gtcgccatcg cttccaacat cggcggcaag | 1800 |
| caggctctcg aaaccgtgca gaggctgctc ccggtgctgt gccagcccca cggcctcacc | 1860 |
| ccagaccagg tcgtcgcgat cgcctccaac atcgcggca agcaggccct ggagactgtg | 1920 |
| cagcgcctgc tgcccgtcct gtgccaggac acggcctca ccccgagca ggtcgtcgct | 1980 |
| atcgctagca acaacggcgg caagcaggcg ctcgaaaccg tccagaggct cctcccagtc | 2040 |
| ctctgccagg atcacggcct gaccccggat caggtggtcg ccatcgcttc caacaacggc | 2100 |
| ggcaagcagg cgctggagac tgtccagcgc ctcctcccag tcctctgcca ggcgcacggc | 2160 |
| ctcaccccg atcaggtcgt ggcgatcgcg agcaacatcg gcggcaagca ggctctcgaa | 2220 |
| accgtgcaga ggctgctgcc ggtgctctgc caggctcacg gcctgacccc agaccaggtg | 2280 |
| gtggctatcg cctccaacaa cggcggcaag caggccctgg agactgtgca gaggctcctc | 2340 |
| ccagtcctgt gccaggccca cggcctgacc cccgagcagg tggtcgcgat cgcgagcaac | 2400 |
| aacggcggca agcaggcgct cgaaaccgtc cagaggctcc tccccgtgct ctgccaggat | 2460 |
| cacggcctca ccccgacca ggtcgtggct atcgcgtcca acggcggcaa gcaggctctc | 2520 |
| gagagcatcg tggcccagct gagcaggccg acccggccc tggccgccct gaccaacgat | 2580 |
| cacctggtgg ctctggcctg cctgggcggc aggccagcca tggacgctgt gaagaagggc | 2640 |
| ctgccgcacg ctccagagct gatccgcagg gtgaacagga ggatcggcga gaggaccagc | 2700 |
| cacagggtgg ccgactacgc tcaggtggtg agggtgctgg agttcttcca gtgccacagc | 2760 |
| caccccggcct acgccttcga cgaggctatg acccagttcg gcatgagcag gaacggcctg | 2820 |
| gtgcagctgt tcaggagggt gggcgtgacc gagctggagg ctaggggcgg caccctgccg | 2880 |
| ccagctagcc agaggtggga ccgcatcctc caggccagcg gcatgaaaag ggctaagcca | 2940 |
| agcccgacca cgctcagac ccagatcag gctagcctgc acgctttcgc cgacagcctg | 3000 |
| gagagggatc tggatgctcc gagcccaatg cacgagggcg accagaccag ggccagcagc | 3060 |
| aggaagagga gcaggagcga cagggctgtg accggcccga cgcccagca ggctgtggag | 3120 |
| gtgagggtgc cagagcagag ggatgccctg cacctgccgc tgagctggag ggtgaagagg | 3180 |
| ccaaggacca ggatctgggg cggcctgcca gatccgggca ccccaaccgc tgctgatcag | 3240 |
| ctcgtgaaga gcgagctgga ggagaagaag agcgagctga ggcataaact gaagtacgtg | 3300 |
| ccacacgagt acatcgagct gatcgagatc gccaggaaca gcacccagga tcgcatcctg | 3360 |
| gagatgaagg tgatggagtt cttcatgaaa gtgtacggct acaggggcaa gcacctgggc | 3420 |
| ggcagcagga agccagatgg cgccatctac accgtgggca gcccaatcga ctacggcgtg | 3480 |
| atcgtggata ccaaggctta cagcggcggc tacaacctgc cgatcggcca ggctgatgag | 3540 |
| atgcagaggt acgtggagga gaatcaaacc aggaacaagc acatcaaccc aaacgagtgg | 3600 |
| tggaaggtgt acccgagcag cgtgaccgag ttcaagttcc tgttcgtgag cggccacttc | 3660 |
| aagggcaact acaaggctca gctcaccagg ctgaaccaca tcaccaactg caacggcgcc | 3720 |
| gtgctgagcg tggaggagct gctgatcggc ggcgagatga tcaaggctgg cacccttgacc | 3780 |

```
ctggaggagg tgaggaggaa gttcaacaac ggcgagatca acttctga         3828

<210> SEQ ID NO 90
<211> LENGTH: 2910
<212> TYPE: DNA
<213> ORGANISM: Artificial Sequence
<220> FEATURE:
<223> OTHER INFORMATION: Xanthomonas ssp, Zea mays

<400> SEQUENCE: 90
atggctagct ccccccgaa gaagaagagg aaggtcagct ggaaggatgc tagcggctgg      60
agcaggatgc acgctgatcc atggccaagg aggagggccg ctcagccaag cgatgctagc    120
cccgccgcgc aggtcgacct caggaccctg gctacagcc agcagcagca ggagaagatc     180
aagccgaagg tgaggagcac cgtggcccag caccacgagg ctctggtggg ccacggcttc    240
acccacgctc acatcgtggc cctgagccag cacccagctg ctctgggcac cgtggctgtg    300
acctaccagc acatcatcac cgccctgcca gaggctaccc acgaggacat cgtgggcgtg    360
ggcaagcagt ggagcggcgc tagggccctg gaggctctgc tgaccgatgc tggcgagctg    420
aggggcccac cgctccagct ggataccggc cagctggtga agatcgccaa gaggggcggc    480
gtgaccgcta tggaggctgt gcacgccagc aggaacgctc tgaccggcgc tccactgaac    540
ctgacccccg accaggtggt ggccatcgcg agccacgacg gcggcaagca ggctctcgaa    600
accgtgcaga ggctgctccc ggtgctgtgc caggcccacg gcctcacccc agaccaggtc    660
gtcgcgatcg cctcccacga tggcggcaag caggccctgg agactgtgca gcgcctgctg    720
cccgtcctgt gccaggacca cggcctcacc ccggagcagg tcgtcgctat cgctagcaac    780
ggcggcggca agcaggcgct cgaaaccgtc cagaggctcc tcccagtcct ctgccaggat    840
cacggcctga ccccggatca ggtggtcgcc atcgcttcca acatcggcgg caagcaggcg    900
ctggagactg tccagcgcct cctcccagtc tctgccagg cgcacggcct caccccgat     960
caggtcgtgg cgatcgcgag caacatcggc ggcaagcagg ctctcgaaac cgtgcagagg   1020
ctgctgccgg tgctctgcca ggctcacggc ctgaccccag accaggtggt ggctatcgcc   1080
tccaacatcg gcggcaagca ggccctggag actgtgcaga ggctcctccc agtcctgtgc   1140
caggcccacg gcctgacccc cgagcaggtg gtcgcgatcg cgagccacga cggcggcaag   1200
caggcgctcg aaaccgtcca ggctcctc cccgtgctct gccaggatca cggcctgacc    1260
ccagagcagg tggtggctat cgcgagcaac atcggcggca agcaggctct cgaaaccgtc   1320
cagaggctcc tcccagtgct ctgccaggct cacggcctca ccccggacca ggtcgtcgcc   1380
atcgcttcca acatcggcgg caagcaggct ctcgaaaccg tgcagaggct gctcccggtg   1440
ctgtgccagg cccacggcct caccccagac caggtcgtcg cgatcgcctc caacatcggc   1500
ggcaagcagg ccctggagac tgtgcagcgc ctgctgcccg tcctgtgcca ggaccacggc   1560
ctcaccccgg agcaggtcgt cgctatcgct agcaacaacg gcggcaagca ggcgctcgaa   1620
accgtccaga ggctcctccc agtcctctgc caggatcacg gcctgacccc ggatcaggtg   1680
gtcgccatcg cttccaacaa cggcggcaag caggcgctgg agactgtcca gcgcctcctc   1740
ccagtcctct gccaggcgca cggcctcacc cccgatcagg tcgtggcgat cgcgagcaac   1800
atcggcggca agcaggctct cgaaaccgtg cagaggctgc tgccggtgct ctgccaggct   1860
cacgccctga ccccagacca ggtggtggct atcgcctcca acaacggcgg caagcaggcc   1920
ctggagactg tgcagaggct cctcccagtc ctgtgccagg cccacggcct gacccccgag   1980
```

| | |
|---|---|
| caggtggtcg cgatcgcgag caacaacggc ggcaagcagg cgctcgaaac cgtccagagg | 2040 |
| ctcctccccg tgctctgcca ggatcacggc ctcaccccg accaggtcgt ggctatcgcg | 2100 |
| tccaacggcg gcaagcaggc tctcgagagc atcgtggccc agctgagcag gccggacccg | 2160 |
| gccctggccg ccctgaccaa cgatcacctg gtggctctgg cctgcctggg cggcaggcca | 2220 |
| gccatggacg ctgtgaagaa gggcctgccg cacgctccag agctgatccg cagggtgaac | 2280 |
| aggaggatcg gcgagaggac cagccacagg gtggccctgc agctcgtgaa gagcgagctg | 2340 |
| gaggagaaga agagcgagct gaggcataaa ctgaagtacg tgccacacga gtacatcgag | 2400 |
| ctgatcgaga tcgccaggaa cagcacccag gatcgcatcc tggagatgaa ggtgatggag | 2460 |
| ttcttcatga aagtgtacgg ctacaggggc aagcacctgg gcggcagcag gaagccagat | 2520 |
| ggcgccatct acaccgtggg cagcccaatc gactacggcg tgatcgtgga taccaaggct | 2580 |
| tacagcggcg gctacaacct gccgatcggc caggctgatg agatgcagag gtacgtggag | 2640 |
| gagaatcaaa ccaggaacaa gcacatcaac ccaaacgagt ggtggaaggt gtacccgagc | 2700 |
| agcgtgaccg agttcaagtt cctgttcgtg agcggccact tcaagggcaa ctacaaggct | 2760 |
| cagctcacca ggctgaacca catcaccaac tgcaacggcg ccgtgctgag cgtggaggag | 2820 |
| ctgctgatcg gcggcgagat gatcaaggct ggcaccctga ccctggagga ggtgaggagg | 2880 |
| aagttcaaca acggcgagat caacttctga | 2910 |

<210> SEQ ID NO 91
<211> LENGTH: 3075
<212> TYPE: DNA
<213> ORGANISM: Artificial Sequence
<220> FEATURE:
<223> OTHER INFORMATION: Xanthomonas ssp, Zea mays

<400> SEQUENCE: 91

| | |
|---|---|
| atgggaaaac ctattcctaa tcctctgctg ggcctggatt ctaccggagg catggcccct | 60 |
| aagaaaaagc ggaaggtgga cggcggagtg gacctgagaa cactgggata ttctcagcag | 120 |
| cagcaggaga agatcaagcc caaggtgaga tctacagtgg cccagcacca cgaagccctg | 180 |
| gtgggacacg gatttacaca cgcccacatt gtggccctgt ctcagcaccc tgccgccctg | 240 |
| ggaacagtgg ccgtgaaata tcaggatatg attgccgccc tgcctgaggc cacacacgaa | 300 |
| gccattgtgg gagtgggaaa acagtggtct ggagccagag ccctggaagc cctgctgaca | 360 |
| gtggccggag aactgagagg acctcctctg cagctggata caggacagct gctgaagatt | 420 |
| gccaaagggg gcggagtgac cgcggtggaa gccgtgcacg cctggagaaa tgccctgaca | 480 |
| ggagcccctc tgaacctgac ccccgaacag gtggtggcca ttgccagcca cgacggcggc | 540 |
| aagcaggccc tggaaaccgt gcagagactg ctgcccgtgc tgtgccaggc ccatggcctg | 600 |
| acacctgaac aggtggtggc tatcgcctct cacgacggag aaaacaggc tctggaaaca | 660 |
| gtgcagcggc tgctgcctgt gctgtgtcag gctcacggct tgactccaga acaggtggtg | 720 |
| gctattgctt ccaacggcgg ggggaaacag gccctggaaa ctgtgcagcg cctgctgcca | 780 |
| gtgctgtgcc aggctcacgg actgaccccc gaacaggtgg tggccattgc cagcaacatc | 840 |
| ggcggcaagc aggccctgga aaccgtgcag agactgctgc ccgtgctgtg ccaggcccat | 900 |
| ggcctgacac ctgaacaggt ggtggctatc gcctctaata tcggaggaaa acaggctctg | 960 |
| gaaacagtgc agcggctgct gcctgtgctg tgtcaggctc acggcttgac tccagaacag | 1020 |
| gtggtggcta ttgcttccaa tattggggg aaacaggccc tggaaactgt gcagcgcctg | 1080 |
| ctgccagtgc tgtgccaggc tcacgggctg acccccgaac aggtggtggc cattgccagc | 1140 |

```
cacgacggcg gcaagcaggc cctggaaacc gtgcagagac tgctgcccgt gctgtgccag    1200
gcccatggcc tgacacctga acaggtggtg gctatcgcct ctaatatcgg aggaaaacag    1260
gctctggaaa cagtgcagcg gctgctgcct gtgctgtgtc aggctcacgg cttgactcca    1320
gaacaggtgg tggctattgc ttccaatatt gggggaaac aggccctgga aactgtgcag    1380
cgcctgctgc cagtgctgtg ccaggctcac ggcctcactc ccgaacaggt ggtggccatt    1440
gccagcaaca tcggcggcaa gcaggccctg gaaaccgtgc agagactgct gcccgtgctg    1500
tgccaggccc atggcctgac acctgaacag gtggtggcta tcgcctctaa caacggagga    1560
aaacaggctc tggaaacagt gcagcggctg ctgcctgtgc tgtgtcaggc tcacggcttg    1620
actccagaac aggtggtggc tattgcttcc aacaacgggg ggaaacaggc cctggaaact    1680
gtgcagcgcc tgctgccagt gctgtgccag gctcacggac tgaccccga acaggtggtg    1740 gccattgcca gcaacatcgg cggcaagcag gccctggaaa ccgtgcagag actgctgccc    1800
gtgctgtgcc aggcccatgg cctgacacct gaacaggtgg tggctatcgc ctctaacaac    1860
ggaggaaaac aggctctgga aacagtgcag cggctgctgc ctgtgctgtg tcaggctcac    1920
ggcttgactc cagaacaggt ggtggctatt gcttccaaca cgggggaa acaggccctg    1980 gaaactgtgc agcgcctgct gccagtgctg tgccaggctc acgggctgac ccccgaacag    2040
gtggtggcca ttgccagcaa cggcggcggc aagcaggccc tggaaaccgt gcagagactg    2100
ctgcccgtgc tgtgccaggc catggcctg acacctgaac aggtggtggc tatcgcctct    2160
cacgacggag aaaacaggc tctgaaaaca gtgcagcggc tgctgcctgt gctgtgtcag    2220
gctcacggct tgactccaca gcaggtcgtg gcaattgcta gccacgacgg cggacggccc    2280
gccctggaga gcattgtggc ccagctgtct agacctgatc ctgccctggc cgccctgaca    2340
aatgatcacc tggtggccct ggcctgtctg ggaggcagac ctgccctgga tgccgtgaaa    2400
aaaggactgc ctcacgcccc tgccctgatt aaaagaacaa atagaagaat ccccgagcgg    2460
acctctcaca gagtggccgg atcccagctg gtgaaatctg agctggagga aagaagtct    2520 gagctgagac acaagctgaa gtacgtgcct cacgagtaca tcgagctgat cgagatcgcc    2580
agaaatagca cccaggatag aatcctggag atgaaggtga tggagttctt catgaaagtg    2640
tacggctaca gaggaaagca tctgggagga agcagaaaac ctgacggagc catttataca    2700
gtgggcagcc ctatcgatta tggcgtgatc gtggatacaa aggcctacag cggaggctac    2760
aatctgccta ttggacaggc cgatgagatg cagagatacg tggaggagaa ccaaaccagg    2820
aacaagcata tcaaccctaa cgagtggtgg aaggtgtacc cttctagcgt gaccgagttc    2880
aagttcctgt ttgtgagcgg ccacttcaag ggcaattata aggcccagct gaccaggctg    2940
aaccacatca caattgtaa tggcgccgtg ctgtctgtgg aggaactgct gattggagga    3000
gagatgatta aggccggaac actgacactg gaggaggtga agaaagttc aacaacggc    3060 gagatcaact tctga                                                      3075
```

<210> SEQ ID NO 92
<211> LENGTH: 19
<212> TYPE: DNA
<213> ORGANISM: Zea mays

<400> SEQUENCE: 92
cacacctcgt tgccaaagc                                                    19

<210> SEQ ID NO 93

```
<211> LENGTH: 21
<212> TYPE: DNA
<213> ORGANISM: Zea mays

<400> SEQUENCE: 93
catcgcgtcc taaacaaagg a                                              21

<210> SEQ ID NO 94
<211> LENGTH: 15
<212> TYPE: DNA
<213> ORGANISM: Zea mays

<400> SEQUENCE: 94
cctgtcctgc actgc                                                     15

<210> SEQ ID NO 95
<211> LENGTH: 15
<212> TYPE: DNA
<213> ORGANISM: Zea mays

<400> SEQUENCE: 95
gcagtgcagg acagg                                                     15

<210> SEQ ID NO 96
<211> LENGTH: 22
<212> TYPE: DNA
<213> ORGANISM: Zea mays

<400> SEQUENCE: 96
tgcagtgcag tgcaggacag ga                                             22

<210> SEQ ID NO 97
<211> LENGTH: 23
<212> TYPE: DNA
<213> ORGANISM: Zea mays

<400> SEQUENCE: 97
ctcgttgcca aagctgcatc cgt                                            23

<210> SEQ ID NO 98
<211> LENGTH: 1176
<212> TYPE: DNA
<213> ORGANISM: Artificial Sequence
<220> FEATURE:
<223> OTHER INFORMATION: Escherichia coli

<400> SEQUENCE: 98
atgcaaaaac tcattaactc agtgcaaaac tatgcctggg gcagcaaaac ggcgttgact    60
gaactttatg gtatggaaaa tccgtccagc cagccgatgg ccgagctgtg gatgggcgca   120
catccgaaaa gcagttcacg agtgcagaat gccgccggag atatcgtttc actgcgtgat   180
gtgattgaga gtgataaatc gactctgctc ggagaggccg ttgccaaacg ctttggcgaa   240
ctgcctttcc tgttcaaagt attatgcgca gcacagccac tctccattca ggttcatcca   300
aacaaacaca attctgaaat cggttttgcc aaagaaaatg ccgcaggtat cccgatggat   360
gccgccgagc gtaactataa agatcctaac cacaagccgg agctggtttt tgcgctgacg   420
cctttccttg cgatgaacgc gtttcgtgaa ttttccgaga ttgtctccct actccagccg   480
gtcgcaggtg cacatccggc gattgctcac tttttacaac agcctgatgc cgaacgttta   540
agcgaactgt tcgccagcct gttgaatatg cagggtgaag aaaaatcccg cgcgctggcg   600
attttaaaat cggccctcga tagccagcag ggtgaaccgt ggcaaacgat tcgtttaatt   660
```

```
tctgaatttt acccggaaga cagcggtctg ttctccccgc tattgctgaa tgtggtgaaa    720
ttgaaccctg gcgaagcgat gttcctgttc gctgaaacac cgcacgctta cctgcaaggc    780
gtggcgctgg aagtgatggc aaactccgat aacgtgctgc gtgcgggtct gacgcctaaa    840
tacattgata ttccggaact ggttgccaat gtgaaattcg aagccaaacc ggctaaccag    900
ttgttgaccc agccggtgaa acaaggtgca gaactggact tcccgattcc agtggatgat    960
tttgccttct cgctgcatga ccttagtgat aaagaaacca ccattagcca gcagagtgcc   1020
gccattttgt tctgcgtcga aggcgatgca acgttgtgga aaggttctca gcagttacag   1080
cttaaaccgg gtgaatcagc gtttattgcc gccaacgaat caccggtgac tgtcaaaggc   1140
cacggccgtt tagcgcgtgt ttacaacaag ctgtaa                             1176
```

<210> SEQ ID NO 99
<211> LENGTH: 50
<212> TYPE: DNA
<213> ORGANISM: Artificial Sequence
<220> FEATURE:
<223> OTHER INFORMATION: Escherichia coli

<400> SEQUENCE: 99

```
ttaactcagt gcaaaactat gcctggggca gcaaaacggc gttgactgaa                 50
```

<210> SEQ ID NO 100
<211> LENGTH: 53
<212> TYPE: DNA
<213> ORGANISM: Artificial Sequence
<220> FEATURE:
<223> OTHER INFORMATION: Escherichia coli

<400> SEQUENCE: 100

```
tctccattca ggttcatcca aacaaacaca attctgaaat cggttttgcc aaa             53
```

<210> SEQ ID NO 101
<211> LENGTH: 53
<212> TYPE: DNA
<213> ORGANISM: Artificial Sequence
<220> FEATURE:
<223> OTHER INFORMATION: Escherichia coli

<400> SEQUENCE: 101

```
tgcacatccg gcgattgctc acttttaca acagcctgat gccgaacgtt taa              53
```

<210> SEQ ID NO 102
<211> LENGTH: 18
<212> TYPE: DNA
<213> ORGANISM: Artificial Sequence
<220> FEATURE:
<223> OTHER INFORMATION: Escherichia coli

<400> SEQUENCE: 102

```
ttaactcagt gcaaaact                                                    18
```

<210> SEQ ID NO 103
<211> LENGTH: 18
<212> TYPE: DNA
<213> ORGANISM: Artificial Sequence
<220> FEATURE:
<223> OTHER INFORMATION: Escherichia coli

<400> SEQUENCE: 103

```
ttcagtcaac gccgtttt                                                    18
```

<210> SEQ ID NO 104
<211> LENGTH: 19
<212> TYPE: DNA
<213> ORGANISM: Artificial Sequence
<220> FEATURE:
<223> OTHER INFORMATION: Escherichia coli

<400> SEQUENCE: 104
tctccattca ggttcatcc                                              19

<210> SEQ ID NO 105
<211> LENGTH: 19
<212> TYPE: DNA
<213> ORGANISM: Artificial Sequence
<220> FEATURE:
<223> OTHER INFORMATION: Escherichia coli

<400> SEQUENCE: 105
tttggcaaaa ccgatttca                                              19

<210> SEQ ID NO 106
<211> LENGTH: 19
<212> TYPE: DNA
<213> ORGANISM: Artificial Sequence
<220> FEATURE:
<223> OTHER INFORMATION: Escherichia coli

<400> SEQUENCE: 106
tgcacatccg gcgattgct                                              19

<210> SEQ ID NO 107
<211> LENGTH: 18
<212> TYPE: DNA
<213> ORGANISM: Artificial Sequence
<220> FEATURE:
<223> OTHER INFORMATION: Escherichia coli

<400> SEQUENCE: 107
ttaaacgttc ggcatcag                                               18

<210> SEQ ID NO 108
<211> LENGTH: 1000
<212> TYPE: PRT
<213> ORGANISM: Artificial Sequence
<220> FEATURE:
<223> OTHER INFORMATION: Xanthomonas ssp, Escherichia coli

<400> SEQUENCE: 108

```
Met Glu Gln Lys Leu Ile Ser Glu Glu Asp Leu Val Asp Leu Arg Thr
1               5                   10                  15

Leu Gly Tyr Ser Gln Gln Gln Glu Lys Ile Lys Pro Lys Val Arg
            20                  25                  30

Ser Thr Val Ala Gln His His Glu Ala Leu Val Gly His Gly Phe Thr
        35                  40                  45

His Ala His Ile Val Ala Leu Ser Gln His Pro Ala Ala Leu Gly Thr
    50                  55                  60

Val Ala Val Thr Tyr Gln His Ile Ile Thr Ala Leu Pro Glu Ala Thr
65                  70                  75                  80

His Glu Asp Ile Val Gly Val Gly Lys Gln Trp Ser Gly Ala Arg Ala
                85                  90                  95

Leu Glu Ala Leu Leu Thr Asp Ala Gly Glu Leu Arg Gly Pro Pro Leu
            100                 105                 110
```

```
Gln Leu Asp Thr Gly Gln Leu Val Lys Ile Ala Lys Arg Gly Gly Val
            115                 120                 125

Thr Ala Met Glu Ala Val His Ala Ser Arg Asn Ala Leu Thr Gly Ala
        130                 135                 140

Pro Leu Asn Leu Thr Pro Asp Gln Val Val Ala Ile Ala Ser Asn Gly
145                 150                 155                 160

Gly Gly Lys Gln Ala Leu Glu Thr Val Gln Arg Leu Leu Pro Val Leu
                165                 170                 175

Cys Gln Ala His Gly Leu Thr Pro Asp Gln Val Val Ala Ile Ala Ser
            180                 185                 190

Asn Ile Gly Gly Lys Gln Ala Leu Glu Thr Val Gln Arg Leu Leu Pro
        195                 200                 205

Val Leu Cys Gln Asp His Gly Leu Thr Pro Glu Gln Val Val Ala Ile
    210                 215                 220

Ala Arg Asn Ile Gly Gly Lys Gln Ala Leu Glu Thr Val Gln Arg Leu
225                 230                 235                 240

Leu Pro Val Leu Cys Gln Asp His Gly Leu Thr Pro Asp Gln Val Val
                245                 250                 255

Ala Ile Ala Ser His Asp Gly Gly Lys Gln Ala Leu Glu Thr Val Gln
            260                 265                 270

Arg Leu Leu Pro Val Leu Cys Gln Ala His Gly Leu Thr Pro Asp Gln
        275                 280                 285

Val Val Ala Ile Ala Arg Asn Gly Gly Gly Lys Gln Ala Leu Glu Thr
    290                 295                 300

Val Gln Arg Leu Leu Pro Val Leu Cys Gln Ala His Gly Leu Thr Pro
305                 310                 315                 320

Asp Gln Val Val Ala Ile Ala Ser His Asp Gly Gly Lys Gln Ala Leu
                325                 330                 335

Glu Thr Val Gln Arg Leu Leu Pro Val Leu Cys Gln Ala His Gly Leu
            340                 345                 350

Thr Pro Glu Gln Val Val Ala Ile Ala Arg Asn Ile Gly Gly Lys Gln
        355                 360                 365

Ala Leu Glu Thr Val Gln Arg Leu Leu Pro Val Leu Cys Gln Asp His
    370                 375                 380

Gly Leu Thr Pro Asp Gln Val Val Ala Ile Ala Ser Asn Lys Gly Gly
385                 390                 395                 400

Lys Gln Ala Leu Glu Thr Val Gln Arg Leu Leu Pro Val Leu Cys Gln
                405                 410                 415

Asp His Gly Leu Thr Pro Glu Gln Val Val Ala Ile Ala Ser Asn Gly
            420                 425                 430

Gly Gly Lys Gln Ala Leu Glu Thr Val Gln Arg Leu Leu Pro Val Leu
        435                 440                 445

Cys Gln Ala His Gly Leu Thr Pro Asp Gln Val Val Ala Ile Ala Ser
    450                 455                 460

Asn Lys Gly Gly Lys Gln Ala Leu Glu Thr Val Gln Arg Leu Leu Pro
465                 470                 475                 480

Val Leu Cys Gln Asp His Gly Leu Thr Pro Asp Gln Val Val Ala Ile
                485                 490                 495

Ala Ser His Asp Gly Gly Lys Gln Ala Leu Glu Thr Val Gln Arg Leu
            500                 505                 510

Leu Pro Val Leu Cys Gln Asp His Gly Leu Thr Pro Asp Gln Val Val
        515                 520                 525

Ala Ile Ala Ser Asn Ile Gly Gly Lys Gln Ala Leu Glu Thr Val Gln
```

```
                530             535             540
Arg Leu Leu Pro Val Leu Cys Gln Asp His Gly Leu Thr Pro Asp Gln
545                 550                 555                 560

Val Val Ala Ile Ala Ser Asn Ile Gly Gly Lys Gln Ala Leu Glu Thr
                565                 570                 575

Val Gln Arg Leu Leu Pro Val Leu Cys Gln Ala His Gly Leu Thr Pro
            580                 585                 590

Glu Gln Val Val Ala Ile Ala Arg Asn Ile Gly Gly Lys Gln Ala Leu
        595                 600                 605

Glu Thr Val Gln Arg Leu Leu Pro Val Leu Cys Gln Ala His Gly Leu
    610                 615                 620

Thr Pro Glu Gln Val Val Ala Ile Ala Ser Asn Ile Gly Gly Lys Gln
625                 630                 635                 640

Ala Leu Glu Thr Val Gln Arg Leu Leu Pro Val Leu Cys Gln Ala His
                645                 650                 655

Gly Leu Thr Pro Asp Gln Val Val Ala Ile Ala Arg His Asp Gly Gly
            660                 665                 670

Lys Gln Ala Leu Glu Thr Val Gln Arg Leu Leu Pro Val Leu Cys Gln
        675                 680                 685

Asp His Gly Leu Thr Pro Asp Gln Val Val Ala Ile Ala Ser Asn Gly
    690                 695                 700

Gly Gly Lys Gln Ala Leu Glu Ser Ile Val Ala Gln Leu Ser Arg Pro
705                 710                 715                 720

Asp Pro Ala Leu Ala Ala Leu Thr Asn Asp His Leu Val Ala Leu Ala
                725                 730                 735

Cys Leu Gly Gly Arg Pro Ala Met Asp Ala Val Lys Lys Gly Leu Pro
            740                 745                 750

His Ala Pro Glu Leu Ile Arg Arg Val Asn Arg Arg Ile Gly Glu Arg
        755                 760                 765

Thr Ser His Arg Val Ala Asp Tyr Ala Gln Val Val Arg Val Leu Glu
    770                 775                 780

Phe Phe Gln Cys His Ser His Pro Ala Tyr Ala Phe Asp Glu Ala Met
785                 790                 795                 800

Thr Gln Phe Gly Gln Leu Val Lys Ser Glu Leu Glu Glu Lys Lys Ser
                805                 810                 815

Glu Leu Arg His Lys Leu Lys Tyr Val Pro His Glu Tyr Ile Glu Leu
            820                 825                 830

Ile Glu Ile Ala Arg Asn Ser Thr Gln Asp Arg Ile Leu Glu Met Lys
        835                 840                 845

Val Met Glu Phe Phe Met Lys Val Tyr Gly Tyr Arg Gly Lys His Leu
    850                 855                 860

Gly Gly Ser Arg Lys Pro Asp Gly Ala Ile Tyr Thr Val Gly Ser Pro
865                 870                 875                 880

Ile Asp Tyr Gly Val Ile Val Asp Thr Lys Ala Tyr Ser Gly Gly Tyr
                885                 890                 895

Asn Leu Pro Ile Gly Gln Ala Asp Glu Met Gln Arg Tyr Val Glu Glu
            900                 905                 910

Asn Gln Thr Arg Asn Lys His Ile Asn Pro Asn Glu Trp Trp Lys Val
        915                 920                 925

Tyr Pro Ser Ser Val Thr Glu Phe Lys Phe Leu Phe Val Ser Gly His
    930                 935                 940

Phe Lys Gly Asn Tyr Lys Ala Gln Leu Thr Arg Leu Asn His Ile Thr
945                 950                 955                 960
```

```
Asn Cys Asn Gly Ala Val Leu Ser Val Glu Glu Leu Ile Gly Gly
                965                 970                 975

Glu Met Ile Lys Ala Gly Thr Leu Thr Leu Glu Val Arg Arg Lys
            980                 985                 990

Phe Asn Asn Gly Glu Ile Asn Phe
        995                 1000

<210> SEQ ID NO 109
<211> LENGTH: 1000
<212> TYPE: PRT
<213> ORGANISM: Artificial Sequence
<220> FEATURE:
<223> OTHER INFORMATION: Xanthomonas ssp, Escherichia coli

<400> SEQUENCE: 109

Met Glu Gln Lys Leu Ile Ser Glu Glu Asp Leu Val Asp Leu Arg Thr
1               5                   10                  15

Leu Gly Tyr Ser Gln Gln Gln Glu Lys Ile Lys Pro Lys Val Arg
            20                  25                  30

Ser Thr Val Ala Gln His His Glu Ala Leu Val Gly His Gly Phe Thr
            35                  40                  45

His Ala His Ile Val Ala Leu Ser Gln His Pro Ala Ala Leu Gly Thr
        50                  55                  60

Val Ala Val Thr Tyr Gln His Ile Ile Thr Ala Leu Pro Glu Ala Thr
65                  70                  75                  80

His Glu Asp Ile Val Gly Val Gly Lys Gln Trp Ser Gly Ala Arg Ala
                85                  90                  95

Leu Glu Ala Leu Leu Thr Asp Ala Gly Glu Leu Arg Gly Pro Pro Leu
            100                 105                 110

Gln Leu Asp Thr Gly Gln Leu Val Lys Ile Ala Lys Arg Gly Gly Val
            115                 120                 125

Thr Ala Met Glu Ala Val His Ala Ser Arg Asn Ala Leu Thr Gly Ala
        130                 135                 140

Pro Leu Asn Leu Thr Pro Asp Gln Val Val Ala Ile Ala Ser Asn Gly
145                 150                 155                 160

Gly Gly Lys Gln Ala Leu Glu Thr Val Gln Arg Leu Leu Pro Val Leu
                165                 170                 175

Cys Gln Ala His Gly Leu Thr Pro Asp Gln Val Val Ala Ile Ala Ser
            180                 185                 190

His Asp Gly Gly Lys Gln Ala Leu Glu Thr Val Gln Arg Leu Leu Pro
            195                 200                 205

Val Leu Cys Gln Asp His Gly Leu Thr Pro Glu Gln Val Val Ala Ile
        210                 215                 220

Ala Arg Asn Ile Gly Gly Lys Gln Ala Leu Glu Thr Val Gln Arg Leu
225                 230                 235                 240

Leu Pro Val Leu Cys Gln Asp His Gly Leu Thr Pro Asp Gln Val Val
                245                 250                 255

Ala Ile Ala Ser Asn Lys Gly Gly Lys Gln Ala Leu Glu Thr Val Gln
            260                 265                 270

Arg Leu Leu Pro Val Leu Cys Gln Ala His Gly Leu Thr Pro Asp Gln
            275                 280                 285

Val Val Ala Ile Ala Arg Asn Gly Gly Lys Gln Ala Leu Glu Thr
        290                 295                 300

Val Gln Arg Leu Leu Pro Val Leu Cys Gln Ala His Gly Leu Thr Pro
305                 310                 315                 320
```

-continued

```
Asp Gln Val Val Ala Ile Ala Ser His Asp Gly Gly Lys Gln Ala Leu
                325                 330                 335
Glu Thr Val Gln Arg Leu Leu Pro Val Leu Cys Gln Ala His Gly Leu
            340                 345                 350
Thr Pro Glu Gln Val Val Ala Ile Ala Arg Asn Ile Gly Gly Lys Gln
        355                 360                 365
Ala Leu Glu Thr Val Gln Arg Leu Leu Pro Val Leu Cys Gln Asp His
    370                 375                 380
Gly Leu Thr Pro Asp Gln Val Val Ala Ile Ala Ser Asn Ile Gly Gly
385                 390                 395                 400
Lys Gln Ala Leu Glu Thr Val Gln Arg Leu Leu Pro Val Leu Cys Gln
                405                 410                 415
Asp His Gly Leu Thr Pro Glu Gln Val Val Ala Ile Ala Ser His Asp
            420                 425                 430
Gly Gly Lys Gln Ala Leu Glu Thr Val Gln Arg Leu Leu Pro Val Leu
        435                 440                 445
Cys Gln Ala His Gly Leu Thr Pro Asp Gln Val Val Ala Ile Ala Ser
    450                 455                 460
Asn Lys Gly Gly Lys Gln Ala Leu Glu Thr Val Gln Arg Leu Leu Pro
465                 470                 475                 480
Val Leu Cys Gln Asp His Gly Leu Thr Pro Asp Gln Val Val Ala Ile
                485                 490                 495
Ala Ser His Asp Gly Gly Lys Gln Ala Leu Glu Thr Val Gln Arg Leu
            500                 505                 510
Leu Pro Val Leu Cys Gln Asp His Gly Leu Thr Pro Asp Gln Val Val
        515                 520                 525
Ala Ile Ala Ser His Asp Gly Gly Lys Gln Ala Leu Glu Thr Val Gln
    530                 535                 540
Arg Leu Leu Pro Val Leu Cys Gln Asp His Gly Leu Thr Pro Asp Gln
545                 550                 555                 560
Val Val Ala Ile Ala Ser Asn Lys Gly Gly Lys Gln Ala Leu Glu Thr
                565                 570                 575
Val Gln Arg Leu Leu Pro Val Leu Cys Gln Ala His Gly Leu Thr Pro
            580                 585                 590
Glu Gln Val Val Ala Ile Ala Arg Asn Gly Gly Gly Lys Gln Ala Leu
        595                 600                 605
Glu Thr Val Gln Arg Leu Leu Pro Val Leu Cys Gln Ala His Gly Leu
    610                 615                 620
Thr Pro Glu Gln Val Val Ala Ile Ala Ser Asn Gly Gly Gly Lys Gln
625                 630                 635                 640
Ala Leu Glu Thr Val Gln Arg Leu Leu Pro Val Leu Cys Gln Ala His
                645                 650                 655
Gly Leu Thr Pro Asp Gln Val Val Ala Ile Ala Arg Asn Gly Gly Gly
            660                 665                 670
Lys Gln Ala Leu Glu Thr Val Gln Arg Leu Leu Pro Val Leu Cys Gln
        675                 680                 685
Asp His Gly Leu Thr Pro Asp Gln Val Val Ala Ile Ala Ser Asn Gly
    690                 695                 700
Gly Gly Lys Gln Ala Leu Glu Ser Ile Val Ala Gln Leu Ser Arg Pro
705                 710                 715                 720
Asp Pro Ala Leu Ala Ala Leu Thr Asn Asp His Leu Val Ala Leu Ala
                725                 730                 735
```

```
Cys Leu Gly Gly Arg Pro Ala Met Asp Ala Val Lys Lys Gly Leu Pro
            740                 745                 750

His Ala Pro Glu Leu Ile Arg Arg Val Asn Arg Arg Ile Gly Glu Arg
        755                 760                 765

Thr Ser His Arg Val Ala Asp Tyr Ala Gln Val Arg Val Leu Glu
    770                 775                 780

Phe Phe Gln Cys His Ser His Pro Ala Tyr Ala Phe Asp Glu Ala Met
785                 790                 795                 800

Thr Gln Phe Gly Gln Leu Val Lys Ser Glu Leu Glu Lys Lys Ser
            805                 810                 815

Glu Leu Arg His Lys Leu Lys Tyr Val Pro His Glu Tyr Ile Glu Leu
        820                 825                 830

Ile Glu Ile Ala Arg Asn Ser Thr Gln Asp Arg Ile Leu Glu Met Lys
835                 840                 845

Val Met Glu Phe Phe Met Lys Val Tyr Gly Tyr Arg Gly Lys His Leu
    850                 855                 860

Gly Gly Ser Arg Lys Pro Asp Gly Ala Ile Tyr Thr Val Gly Ser Pro
865                 870                 875                 880

Ile Asp Tyr Gly Val Ile Val Asp Thr Lys Ala Tyr Ser Gly Gly Tyr
            885                 890                 895

Asn Leu Pro Ile Gly Gln Ala Asp Glu Met Gln Arg Tyr Val Glu Glu
        900                 905                 910

Asn Gln Thr Arg Asn Lys His Ile Asn Pro Asn Glu Trp Trp Lys Val
        915                 920                 925

Tyr Pro Ser Ser Val Thr Glu Phe Lys Phe Leu Phe Val Ser Gly His
    930                 935                 940

Phe Lys Gly Asn Tyr Lys Ala Gln Leu Thr Arg Leu Asn His Ile Thr
945                 950                 955                 960

Asn Cys Asn Gly Ala Val Leu Ser Val Glu Glu Leu Leu Ile Gly Gly
            965                 970                 975

Glu Met Ile Lys Ala Gly Thr Leu Thr Leu Glu Glu Val Arg Arg Lys
        980                 985                 990

Phe Asn Asn Gly Glu Ile Asn Phe
        995                 1000

<210> SEQ ID NO 110
<211> LENGTH: 1001
<212> TYPE: PRT
<213> ORGANISM: Artificial Sequence
<220> FEATURE:
<223> OTHER INFORMATION: Xanthomonas ssp, Escherichia coli

<400> SEQUENCE: 110

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95
```

```
Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
            130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                    165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser His Asp Gly
            195                 200                 205

Gly Lys Gln Ala Leu Glu Thr Val Gln Arg Leu Leu Pro Val Leu Cys
210                 215                 220

Gln Ala His Gly Leu Thr Pro Glu Gln Val Val Ala Ile Ala Ser Asn
225                 230                 235                 240

Ile Gly Gly Lys Gln Ala Leu Glu Thr Val Gln Ala Leu Leu Pro Val
                    245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
            275                 280                 285

Pro Val Leu Cys Gln Ala His Gly Leu Thr Pro Glu Gln Val Val Ala
            290                 295                 300

Ile Ala Ser Asn Ile Gly Gly Lys Gln Ala Leu Glu Thr Val Gln Ala
305                 310                 315                 320

Leu Leu Pro Val Leu Cys Gln Ala His Gly Leu Thr Pro Gln Gln Val
                    325                 330                 335

Val Ala Ile Ala Ser Asn Gly Gly Gly Lys Gln Ala Leu Glu Thr Val
            340                 345                 350

Gln Arg Leu Leu Pro Val Leu Cys Gln Ala His Gly Leu Thr Pro Glu
            355                 360                 365

Gln Val Val Ala Ile Ala Ser His Asp Gly Gly Lys Gln Ala Leu Glu
            370                 375                 380

Thr Val Gln Arg Leu Leu Pro Val Leu Cys Gln Ala His Gly Leu Thr
385                 390                 395                 400

Pro Glu Gln Val Val Ala Ile Ala Ser His Asp Gly Gly Lys Gln Ala
                    405                 410                 415

Leu Glu Thr Val Gln Arg Leu Leu Pro Val Leu Cys Gln Ala His Gly
            420                 425                 430

Leu Thr Pro Gln Gln Val Val Ala Ile Ala Ser Asn Asn Gly Gly Lys
            435                 440                 445

Gln Ala Leu Glu Thr Val Gln Arg Leu Leu Pro Val Leu Cys Gln Ala
            450                 455                 460

His Gly Leu Thr Pro Gln Gln Val Val Ala Ile Ala Ser Asn Asn Gly
465                 470                 475                 480

Gly Lys Gln Ala Leu Glu Thr Val Gln Arg Leu Leu Pro Val Leu Cys
                    485                 490                 495

Gln Ala His Gly Leu Thr Pro Glu Gln Val Val Ala Ile Ala Ser His
            500                 505                 510

Asp Gly Gly Lys Gln Ala Leu Glu Thr Val Gln Arg Leu Leu Pro Val
```

```
              515                 520                 525
Leu Cys Gln Ala His Gly Leu Thr Pro Gln Gln Val Ala Ile Ala
530                 535                 540

Ser Asn Asn Gly Gly Lys Gln Ala Leu Glu Thr Val Gln Arg Leu Leu
545                 550                 555                 560

Pro Val Leu Cys Gln Ala His Gly Leu Thr Pro Glu Gln Val Val Ala
                565                 570                 575

Ile Ala Ser Asn Ile Gly Gly Lys Gln Ala Leu Glu Thr Val Gln Ala
                580                 585                 590

Leu Leu Pro Val Leu Cys Gln Ala His Gly Leu Thr Pro Gln Gln Val
                595                 600                 605

Val Ala Ile Ala Ser Asn Gly Gly Lys Gln Ala Leu Glu Thr Val
        610                 615                 620

Gln Arg Leu Leu Pro Val Leu Cys Gln Ala His Gly Leu Thr Pro Gln
625                 630                 635                 640

Gln Val Val Ala Ile Ala Ser Asn Gly Gly Lys Gln Ala Leu Glu
                    645                 650                 655

Thr Val Gln Arg Leu Leu Pro Val Leu Cys Gln Ala His Gly Leu Thr
                660                 665                 670

Pro Gln Gln Val Val Ala Ile Ala Ser Asn Asn Gly Gly Lys Gln Ala
            675                 680                 685

Leu Glu Thr Val Gln Arg Leu Leu Pro Val Leu Cys Gln Ala His Gly
        690                 695                 700

Leu Thr Pro Glu Gln Val Val Ala Ile Ala Ser His Asp Gly Gly Lys
705                 710                 715                 720

Gln Ala Leu Glu Thr Val Gln Arg Leu Leu Pro Val Leu Cys Gln Ala
                    725                 730                 735

His Gly Leu Thr Pro Gln Gln Val Val Ala Ile Ala Ser Asn Gly Gly
                740                 745                 750

Gly Arg Pro Ala Leu Glu Ser Ile Val Ala Gln Leu Ser Arg Pro Asp
            755                 760                 765

Pro Ala Leu Ala Ala Leu Thr Asn Asp His Leu Val Ala Leu Ala Cys
            770                 775                 780

Leu Gly Gly Arg Pro Ala Leu Asp Ala Val Lys Lys Gly Leu Gly Asp
785                 790                 795                 800

Pro Ile Ser Arg Ser Gln Leu Val Lys Ser Glu Leu Glu Glu Lys Lys
                805                 810                 815

Ser Glu Leu Arg His Lys Leu Lys Tyr Val Pro His Glu Tyr Ile Glu
                820                 825                 830

Leu Ile Glu Ile Ala Arg Asn Ser Thr Gln Asp Arg Ile Leu Glu Met
                835                 840                 845

Lys Val Met Glu Phe Phe Met Lys Val Tyr Gly Tyr Arg Gly Lys His
            850                 855                 860

Leu Gly Gly Ser Arg Lys Pro Asp Gly Ala Ile Tyr Thr Val Gly Ser
865                 870                 875                 880

Pro Ile Asp Tyr Gly Val Ile Val Asp Thr Lys Ala Tyr Ser Gly Gly
                885                 890                 895

Tyr Asn Leu Pro Ile Gly Gln Ala Asp Glu Met Gln Arg Tyr Val Glu
            900                 905                 910

Glu Asn Gln Thr Arg Asn Lys His Ile Asn Pro Asn Glu Trp Trp Lys
            915                 920                 925

Val Tyr Pro Ser Ser Val Thr Glu Phe Lys Phe Leu Phe Val Ser Gly
930                 935                 940
```

```
His Phe Lys Gly Asn Tyr Lys Ala Gln Leu Thr Arg Leu Asn His Ile
945                 950                 955                 960

Thr Asn Cys Asn Gly Ala Val Leu Ser Val Glu Glu Leu Leu Ile Gly
                965                 970                 975

Gly Glu Met Ile Lys Ala Gly Thr Leu Thr Leu Glu Glu Val Arg Arg
            980                 985                 990

Lys Phe Asn Asn Gly Glu Ile Asn  Phe
        995                 1000

<210> SEQ ID NO 111
<211> LENGTH: 1007
<212> TYPE: PRT
<213> ORGANISM: Artificial Sequence
<220> FEATURE:
<223> OTHER INFORMATION: Xanthomonas ssp, Escherichia coli

<400> SEQUENCE: 111

Met Gly Asp Pro Lys Lys Arg Lys Val Ile Asp Lys Glu Thr Ala
1               5                   10                  15

Ala Ala Lys Phe Glu Arg Gln His Met Asp Ser Ile Asp Ile Ala Asp
                20                  25                  30

Leu Arg Thr Leu Gly Tyr Ser Gln Gln Gln Glu Lys Ile Lys Pro
            35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125

Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser Asn Gly Gly Gly Lys Gln Ala Leu Glu Thr Val Gln Arg Leu Leu
            180                 185                 190

Pro Val Leu Cys Gln Ala His Gly Leu Thr Pro Glu Gln Val Val Ala
        195                 200                 205

Ile Ala Ser Asn Ile Gly Gly Lys Gln Ala Leu Glu Thr Val Gln Ala
    210                 215                 220

Leu Leu Pro Val Leu Cys Gln Ala His Gly Leu Thr Pro Glu Gln Val
225                 230                 235                 240

Val Ala Ile Ala Ser Asn Ile Gly Gly Lys Gln Ala Leu Glu Thr Val
                245                 250                 255

Gln Ala Leu Leu Pro Val Leu Cys Gln Ala His Gly Leu Thr Pro Glu
            260                 265                 270

Gln Val Val Ala Ile Ala Ser Asn Ile Gly Gly Lys Gln Ala Leu Glu
        275                 280                 285

Thr Val Gln Ala Leu Leu Pro Val Leu Cys Gln Ala His Gly Leu Thr
    290                 295                 300
```

```
Pro Glu Gln Val Val Ala Ile Ala Ser His Asp Gly Gly Lys Gln Ala
305                 310                 315                 320

Leu Glu Thr Val Gln Arg Leu Leu Pro Val Leu Cys Gln Ala His Gly
            325                 330                 335

Leu Thr Pro Gln Gln Val Val Ala Ile Ala Ser Asn Asn Gly Gly Lys
            340                 345                 350

Gln Ala Leu Glu Thr Val Gln Arg Leu Leu Pro Val Leu Cys Gln Ala
            355                 360                 365

His Gly Leu Thr Pro Gln Gln Val Val Ala Ile Ala Ser Asn Gly Gly
370                 375                 380

Gly Lys Gln Ala Leu Glu Thr Val Gln Arg Leu Leu Pro Val Leu Cys
385                 390                 395                 400

Gln Ala His Gly Leu Thr Pro Gln Gln Val Val Ala Ile Ala Ser Asn
            405                 410                 415

Gly Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
            435                 440                 445

Ser His Asp Gly Gly Lys Gln Ala Leu Glu Thr Val Gln Arg Leu Leu
450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
            485                 490                 495

Leu Leu Pro Val Leu Cys Gln Ala His Gly Leu Thr Pro Gln Gln Val
            500                 505                 510

Val Ala Ile Ala Ser Asn Asn Gly Gly Lys Gln Ala Leu Glu Thr Val
            515                 520                 525

Gln Arg Leu Leu Pro Val Leu Cys Gln Ala His Gly Leu Thr Pro Glu
530                 535                 540

Gln Val Val Ala Ile Ala Ser His Asp Gly Gly Lys Gln Ala Leu Glu
545                 550                 555                 560

Thr Val Gln Arg Leu Leu Pro Val Leu Cys Gln Ala His Gly Leu Thr
            565                 570                 575

Pro Glu Gln Val Val Ala Ile Ala Ser Asn Ile Gly Gly Lys Gln Ala
            580                 585                 590

Leu Glu Thr Val Gln Ala Leu Leu Pro Val Leu Cys Gln Ala His Gly
            595                 600                 605

Leu Thr Pro Gln Gln Val Val Ala Ile Ala Ser Asn Gly Gly Gly Lys
            610                 615                 620

Gln Ala Leu Glu Thr Val Gln Arg Leu Leu Pro Val Leu Cys Gln Ala
625                 630                 635                 640

His Gly Leu Thr Pro Glu Gln Val Val Ala Ile Ala Ser His Asp Gly
            645                 650                 655

Gly Lys Gln Ala Leu Glu Thr Val Gln Arg Leu Leu Pro Val Leu Cys
            660                 665                 670

Gln Ala His Gly Leu Thr Pro Glu Gln Val Val Ala Ile Ala Ser Asn
            675                 680                 685

Ile Gly Gly Lys Gln Ala Leu Glu Thr Val Gln Ala Leu Leu Pro Val
            690                 695                 700

Leu Cys Gln Ala His Gly Leu Thr Pro Gln Gln Val Val Ala Ile Ala
705                 710                 715                 720
```

| | | | | | | | | | | | | |
|---|---|---|---|---|---|---|---|---|---|---|---|---|
| Ser | Asn | Asn | Gly | Gly | Lys | Gln | Ala | Leu | Glu | Thr | Val | Gln | Arg | Leu | Leu |
| | | | | 725 | | | | | 730 | | | | | 735 | |
| Pro | Val | Leu | Cys | Gln | Ala | His | Gly | Leu | Thr | Pro | Gln | Val | Val | Ala |
| | | | 740 | | | | | 745 | | | | | 750 | | |
| Ile | Ala | Ser | Asn | Gly | Gly | Gly | Arg | Pro | Ala | Leu | Glu | Ser | Ile | Val | Ala |
| | | | 755 | | | | | 760 | | | | | 765 | | |
| Gln | Leu | Ser | Arg | Pro | Asp | Pro | Ala | Leu | Ala | Ala | Leu | Thr | Asn | Asp | His |
| | 770 | | | | | 775 | | | | | 780 | | | | |
| Leu | Val | Ala | Leu | Ala | Cys | Leu | Gly | Gly | Arg | Pro | Ala | Leu | Asp | Ala | Val |
| 785 | | | | | 790 | | | | | 795 | | | | | 800 |
| Lys | Lys | Gly | Leu | Gly | Asp | Pro | Ile | Ser | Arg | Ser | Gln | Leu | Val | Lys | Ser |
| | | | | 805 | | | | | 810 | | | | | 815 | |
| Glu | Leu | Glu | Glu | Lys | Lys | Ser | Glu | Leu | Arg | His | Lys | Leu | Lys | Tyr | Val |
| | | | 820 | | | | | 825 | | | | | 830 | | |
| Pro | His | Glu | Tyr | Ile | Glu | Leu | Ile | Glu | Ile | Ala | Arg | Asn | Ser | Thr | Gln |
| | | | 835 | | | | | 840 | | | | | 845 | | |
| Asp | Arg | Ile | Leu | Glu | Met | Lys | Val | Met | Glu | Phe | Phe | Met | Lys | Val | Tyr |
| | 850 | | | | | 855 | | | | | 860 | | | | |
| Gly | Tyr | Arg | Gly | Lys | His | Leu | Gly | Gly | Ser | Arg | Lys | Pro | Asp | Gly | Ala |
| 865 | | | | | 870 | | | | | 875 | | | | | 880 |
| Ile | Tyr | Thr | Val | Gly | Ser | Pro | Ile | Asp | Tyr | Gly | Val | Ile | Val | Asp | Thr |
| | | | | 885 | | | | | 890 | | | | | 895 | |
| Lys | Ala | Tyr | Ser | Gly | Gly | Tyr | Asn | Leu | Pro | Ile | Gly | Gln | Ala | Asp | Glu |
| | | | 900 | | | | | 905 | | | | | 910 | | |
| Met | Gln | Arg | Tyr | Val | Glu | Glu | Asn | Gln | Thr | Arg | Asn | Lys | His | Ile | Asn |
| | | | 915 | | | | | 920 | | | | | 925 | | |
| Pro | Asn | Glu | Trp | Trp | Lys | Val | Tyr | Pro | Ser | Ser | Val | Thr | Glu | Phe | Lys |
| | 930 | | | | | 935 | | | | | 940 | | | | |
| Phe | Leu | Phe | Val | Ser | Gly | His | Phe | Lys | Gly | Asn | Tyr | Lys | Ala | Gln | Leu |
| 945 | | | | | 950 | | | | | 955 | | | | | 960 |
| Thr | Arg | Leu | Asn | His | Ile | Thr | Asn | Cys | Asn | Gly | Ala | Val | Leu | Ser | Val |
| | | | | 965 | | | | | 970 | | | | | 975 | |
| Glu | Glu | Leu | Leu | Ile | Gly | Gly | Glu | Met | Ile | Lys | Ala | Gly | Thr | Leu | Thr |
| | | | 980 | | | | | 985 | | | | | 990 | | |
| Leu | Glu | Glu | Val | Arg | Arg | Lys | Phe | Asn | Asn | Gly | Glu | Ile | Asn | Phe |
| | | 995 | | | | | 1000 | | | | | 1005 | | | |

<210> SEQ ID NO 112
<211> LENGTH: 3003
<212> TYPE: DNA
<213> ORGANISM: Artificial Sequence
<220> FEATURE:
<223> OTHER INFORMATION: Xanthomonas ssp, Escherichia coli

<400> SEQUENCE: 112

```
atggagcaga agctgatcag cgaggaggac ctcgtcgacc tcaggaccct gggctacagc      60
cagcagcagc aggagaagat caagccgaag gtgaggagca ccgtggccca gcaccacgag     120
gctctggtgg ccacggcttc acccacgct cacatcgtgg ccctgagcca gcacccagct     180
gctctgggca ccgtggctgt gacctaccag cacatcatca ccgccctgcc agaggctacc     240
cacgaggaca tcgtgggcgt gggcaagcag tggagcggcg ctagggccct ggaggctctg     300
ctgaccgatg ctggcgagct gaggggccca ccgctccagc tggataccgg ccagctggtg     360
aagatcgcca gaggggcgg cgtgaccgct atggaggctg tgcacgccag caggaacgct     420
ctgaccggcg ctccactgaa cctgaccccc gaccaggtgg tggccatcgc gagcaacggc     480
```

-continued

```
ggcggcaagc aggctctcga aaccgtgcag aggctgctcc cggtgctgtg ccaggcccac      540
ggcctcaccc cagaccaggt cgtcgcgatc gcctccaaca tcggcggcaa gcaggccctg      600
gagactgtgc agcgcctgct gcccgtcctg tgccaggacc acggcctcac cccggagcag      660
gtcgtcgcta tcgctagaaa catcggcggc aagcaggcgc tcgaaaccgt ccagaggctc      720
ctcccagtcc tctgccagga tcacggcctg accccggatc aggtggtcgc catcgcttca      780
cacgacggcg gcaagcaggc gctggagact gtccagcgcc tcctcccagt cctctgccag      840
gcgcacggcc tcaccccga tcaggtcgtg gcgatcgcga aaacggcgg cggcaagcag       900 gctctcgaaa ccgtgcagag gctgctgccg gtgctctgcc aggctcacgg cctgaccca      960 gaccaggtgg tggctatcgc ctcccacgac ggcggcaagc aggccctgga gactgtgcag     1020
aggctgctgc cggtcctgtg ccaggcccac ggcctcaccc cgagcaggt cgtcgcgatc     1080 gctagaaaca tcggcggcaa gcaggccctg gagactgtcc agaggctcct cccggtcctg     1140
tgccaggacc acgcctgac cccggaccag gtggtcgcca tcgcctccaa caagggcggc     1200
aagcaggcgc tcgaaaccgt gcagaggctc ctgccggtgc tctgccagga tcacggcctg     1260 acccccagagc aggtggtggc tatcgcgagc aacggcggcg gcaagcaggc tctcgaaacc     1320
gtccagaggc tcctcccagt gctctgccag gctcacggcc tcaccccgga ccaggtcgtc     1380
gccatcgctt caaacaaggg cggcaagcag gccctggaga ctgtgcagag gctgctgccc     1440
gtgctgtgcc aggaccacgg cctgaccca gatcaggtgg tggctatcgc tagccacgac     1500
ggcggcaagc aggcgctgga gactgtccag aggctcctcc cagtcctgtg ccaggatcac     1560
ggcctcaccc cggaccaggt cgtcgccatc gcttcaaaca tcggcggcaa gcaggccctg     1620
gagactgtgc agaggctgct gcccgtgctg tgccaggacc acggcctcac cccggatcag     1680
gtcgtggcca tcgcgtccaa catcggcggc aagcaggcgc tggagactgt ccagaggctg     1740
ctgcccgtcc tgtgccaggc gcacggcctc accccagagc aggtcgtcgc catcgccaga     1800
aacatcggcg gcaagcaggc tctcgaaacc gtgcagaggc tgctgccgt gctctgccag     1860 gcccacggcc tgaccccgga gcaggtggtg gcgatcgcct ccaacatcgg cggcaagcag     1920
gctctcgaaa ccgtgcagag gctcctcccc gtgctctgcc aggctcacgg cctgacccc      1980 gatcaggtgg tcgcgatcgc tagacacgac ggcggcaagc aggccctgga gactgtccag     2040
cgcctgctgc cagtcctgtg ccaggaccac ggcctcaccc cgaccaggt cgtggctatc     2100 gcgtccaacg gcggcggcaa gcaggctctc gagagcatcg tggcccagct gagcaggccg     2160
gacccggccc tggccgccct gaccaacgat cacctggtgg ctctggcctg cctgggcggc     2220
aggccagcca tggacgctgt gaagaagggc ctgccgcacg ctccagagct gatccgcagg     2280
gtgaacagga ggatcggcga gaggaccagc cacagggtgg ccgactacgc tcaggtggtg     2340
agggtgctgg agttcttcca gtgccacagc caccccggcct acgccttcga cgaggctatg     2400
acccagttcg ccagctcgt gaagagcgag ctggaggaga agaagagcga gctgaggcac     2460
aagctgaagt acgtgccaca cgagtacatc gagctgatcg agatcgccag gaacagcacc     2520
caggatcgca tcctggagat gaaggtgatg gagttcttca tgaaggtgta cggctacagg     2580
ggcaagcacc tgggcggcag caggaagcca gatggcgcca tctacaccgt gggcagccca     2640
atcgactacg gcgtgatcgt ggataccaag gcttacagcg gcggctacaa cctgccgatc     2700
ggccaggctg atgagatgca gaggtacgtg gaggagaacc agaccaggaa caagcacatc     2760
aacccaaacg agtggtggaa ggtgtacccg agcagcgtga ccgagttcaa gttcctgttc     2820
```

-continued

| | |
|---|---|
| gtgagcggcc acttcaaggg caactacaag gctcagctca ccaggctgaa ccacatcacc | 2880 |
| aactgcaacg cgccgtgct gagcgtggag gagctgctga tcggcggcga gatgatcaag | 2940 |
| gctggcaccc tgaccctgga ggaggtgagg aggaagttca acaacggcga gatcaacttc | 3000 |
| tga | 3003 |

<210> SEQ ID NO 113
<211> LENGTH: 3003
<212> TYPE: DNA
<213> ORGANISM: Artificial Sequence
<220> FEATURE:
<223> OTHER INFORMATION: Xanthomonas ssp, Escherichia coli

<400> SEQUENCE: 113

| | |
|---|---|
| atggagcaga agctgatcag cgaggaggac ctcgtcgacc tcaggaccct gggctacagc | 60 |
| cagcagcagc aggagaagat caagccgaag gtgaggagca ccgtggccca gcaccacgag | 120 |
| gctctggtgg gccacggctt cacccacgct cacatcgtgg ccctgagcca gcacccagct | 180 |
| gctctgggca ccgtggctgt gacctaccag cacatcatca ccgccctgcc agaggctacc | 240 |
| cacgaggaca tcgtgggcgt gggcaagcag tggagcggcg ctagggccct ggaggctctg | 300 |
| ctgaccgatg ctggcgagct gaggggccca ccgctccagc tggataccgg ccagctggtg | 360 |
| aagatcgcca gaggggcgg cgtgaccgct atggaggctg tgcacgccag caggaacgct | 420 |
| ctgaccggcg ctccactgaa cctgaccccc gaccaggtgg tggccatcgc gagcaacggc | 480 |
| ggcggcaagc aggctctcga accgtgcag aggctgctcc cggtgctgtg ccaggcccac | 540 |
| ggcctcaccc cagaccaggt cgtcgcgatc gcctcccacg acggcggcaa gcaggccctg | 600 |
| gagactgtgc agcgcctgct gcccgtcctg tgccaggacc acggcctcac cccggagcag | 660 |
| gtcgtcgcta tcgctagaaa catcggcggc aagcaggcgc tcgaaaccgt ccagaggctc | 720 |
| ctcccagtcc tctgccagga tcacggcctg accccggatc aggtggtcgc atcgcttca | 780 |
| aacaagggcg gcaagcaggc gctggagact gtccagcgcc tcctcccagt cctctgccag | 840 |
| gcgcacggcc tcaccccga tcaggtcgtg gcgatcgcga aaacggcgg cggcaagcag | 900 |
| gctctcgaaa ccgtgcagag gctgctgccg gtgctctgcc aggctcacgg cctgaccccca | 960 |
| gaccaggtgg tggctatcgc ctcccacgac ggcggcaagc aggccctgga gactgtgcag | 1020 |
| aggctgctgc cggtcctgtg ccaggcccac ggcctcaccc cgagcaggt cgtcgcgatc | 1080 |
| gctagaaaca tcggcggcaa gcaggccctg gagactgtcc agaggctcct cccggtcctg | 1140 |
| tgccaggacc acggcctgac cccggaccag gtggtcgcca tcgcctccaa catcggcggc | 1200 |
| aagcaggcgc tcgaaaccgt gcagaggctc ctgccggtgc tctgccagga tcacggcctg | 1260 |
| accccagagc aggtggtggc tatcgcgagc acgacggcg gcaagcaggc tctcgaaacc | 1320 |
| gtccagaggc tcctcccagt gctctgccag gctcacggcc tcaccccgga ccaggtcgtc | 1380 |
| gccatcgctt caaacaaggg cggcaagcag gccctggaga ctgtgcagag gctgctgccc | 1440 |
| gtgctgtgcc aggaccacgg cctgaccccca gatcaggtgg tggctatcgc tagccacgac | 1500 |
| ggcggcaagc aggcgctgga gactgtccag aggctcctcc cagtcctgtg ccaggatcac | 1560 |
| ggcctcaccc cggaccaggt cgtcgccatc gcttcacacg acggcggcaa gcaggccctg | 1620 |
| gagactgtgc agaggctgct gcccgtgctg tgccaggacc acggcctcac cccggatcag | 1680 |
| gtcgtggcca tcgcgtccaa caagggcggc aagcaggcgc tggagactgt ccagaggctg | 1740 |
| ctgcccgtcc tgtgccaggc cacggcctc accccagagc aggtcgtcgc catcgccaga | 1800 |
| aacggcggcg gcaagcaggc tctcgaaacc gtgcagaggc tgctgccgt gctctgccag | 1860 |

```
gcccacggcc tgaccccgga gcaggtggtg gcgatcgcct ccaacggcgg cggcaagcag    1920
gctctcgaaa ccgtgcagag gctcctcccc gtgctctgcc aggctcacgg cctgaccccc    1980
gatcaggtgg tcgcgatcgc tagaaacggc ggcggcaagc aggccctgga gactgtccag    2040
cgcctgctgc cagtcctgtg ccaggaccac ggcctcaccc cgaccaggt cgtggctatc     2100
gcgtccaacg gcggcggcaa gcaggctctc gagagcatcg tggcccagct gagcaggccg    2160
gacccggccc tggccgccct gaccaacgat cacctggtgg ctctggcctg cctgggcggc    2220
aggccagcca tggacgctgt gaagaagggc ctgccgcacg ctccagagct gatccgcagg    2280
gtgaacagga ggatcggcga gaggaccagc cacagggtgg ccgactacgc tcaggtggtg    2340
agggtgctgg agttcttcca gtgccacagc caccccggcct acgccttcga cgaggctatg    2400
acccagttcg gccagctcgt gaagagcgag ctggaggaga agaagagcga gctgaggcac    2460
aagctgaagt acgtgccaca cgagtacatc gagctgatcg agatcgccag gaacagcacc    2520
caggatcgca tcctggagat gaaggtgatg gagttcttca tgaaggtgta cggctacagg    2580
ggcaagcacc tgggcggcag caggaagcca gatggcgcca tctacaccgt gggcagccca    2640
atcgactacg gcgtgatcgt ggataccaag gcttacagcg gcggctacaa cctgccgatc    2700
ggccaggctg atgagatgca gaggtacgtg gaggagaacc agaccaggaa caagcacatc    2760
aacccaaacg agtggtggaa ggtgtacccg agcagcgtga ccgagttcaa gttcctgttc    2820
gtgagcggcc acttcaaggg caactacaag gctcagctca ccaggctgaa ccacatcacc    2880
aactgcaacg cgccgtgct gagcgtggag gagctgctga tcggcggcga gatgatcaag     2940
gctggcaccc tgaccctgga ggaggtgagg aggaagttca caacggcga gatcaacttc     3000
tga                                                                    3003

<210> SEQ ID NO 114
<211> LENGTH: 3006
<212> TYPE: DNA
<213> ORGANISM: Artificial Sequence
<220> FEATURE:
<223> OTHER INFORMATION: Xanthomonas ssp, Escherichia coli

<400> SEQUENCE: 114
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccccccc agcaggtggt ggccatcgcc agcaataatg gtggcaagca ggcgctggag   540
acggtccagc ggctgttgcc ggtgctgtgc caggcccacg gcttgacccc ggagcaggtg    600
gtggccatcg ccagcacga tggcggcaag caggcgctgg agacggtcca gcggctgttg     660
ccggtgctgt gccaggccca cggcttgacc ccggagcagg tggtggccat cgccagcaat    720
attggtggca gcaggcgct ggagacggtg caggcgctgt tgccggtgct gtgccaggcc     780
cacggcttga ccccggagca ggtggtggcc atcgccagcc acgatggcgg caagcaggcg    840
```

```
ctggagacgg tccagcggct gttgccggtg ctgtgccagg cccacggctt gaccccggag    900
caggtggtgg ccatcgccag caatattggt ggcaagcagg cgctggagac ggtgcaggcg    960
ctgttgccgg tgctgtgcca ggcccacggc ttgacccccc agcaggtggt ggccatcgcc   1020
agcaatggcg gtggcaagca ggcgctggag acggtccagc ggctgttgcc ggtgctgtgc   1080
caggcccacg gcttgacccc ggagcaggtg gtggccatcg ccagccacga tggcggcaag   1140
caggcgctgg agacggtcca gcggctgttg ccggtgctgt gccaggccca cggcttgacc   1200
ccggagcagg tggtggccat cgccagccac gatggcggca agcaggcgct ggagacggtc   1260
cagcggctgt tgccggtgct gtgccaggcc cacggcttga ccccccagca ggtggtggcc   1320
atcgccagca ataatggtgg caagcaggcg ctggagacgg tccagcggct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccgg agcaggtggt ggccatcgcc agccacgatg gcggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagcaat   1740
attggtggca agcaggcgct ggagacggtg caggcgctgt tgccggtgct gtgccaggcc   1800
cacggcttga ccccccagca ggtggtggcc atcgccagca atggcggtgg caagcaggcg   1860
ctggagacgg tccagcggct gttgccggtg ctgtgccagg cccacggctt gaccccccag   1920
caggtggtgg ccatcgccag caatggcggt ggcaagcagg cgctggagac ggtccagcgg   1980
ctgttgccgg tgctgtgcca ggcccacggc ttgacccccc agcaggtggt ggccatcgcc   2040
agcaataatg gtggcaagca ggcgctggag acggtccagc ggctgttgcc ggtgctgtgc   2100
caggcccacg gcttgacccc ggagcaggtg gtggccatcg ccagccacga tggcggcaag   2160
caggcgctgg agacggtcca gcggctgttg ccggtgctgt gccaggccca cggcttgacc   2220
cctcagcagg tggtggccat cgccagcaat ggcggcggca ggccggcgct ggagagcatt   2280
gttgcccagt tatctcgccc tgatccggcg ttggccgcgt tgaccaacga ccacctcgtc   2340
gccttggcct gcctcggcgg gcgtcctgcg ctggatgcag tgaaaaaggg attgggggat   2400
cctatcagcc gttcccagct ggtgaaatct gagctggagg agaagaagtc tgagctgaga   2460
cacaagctga agtacgtgcc tcacgagtac atcgagctga tcgagatcgc cagaaatagc   2520
acccaggata gaatcctgga gatgaaggtg atggagttct tcatgaaagt gtacggctac   2580
agaggaaagc atctgggagg aagcagaaaa cctgacggag ccatttatac agtgggcagc   2640
cctatcgatt atggcgtgat cgtggataca aaggcctaca gcggaggcta caatctgcct   2700
attggacagg ccgatgagat gcagagatac gtggaggaga accaaaccag gaacaagcat   2760
atcaacccta cgagtggtg aaggtgtac ccttctagcg tgaccgagtt caagttcctg   2820
tttgtgagcg ccacttcaa gggcaattat aaggcccagc tgaccaggct gaaccacatc   2880
acaaattgta atggcgccgt gctgtctgtg gaggaactgc tgattggagg agagatgatt   2940
aaggccggaa cactgacact ggaggaggtg agaagaaagt caacaacgg cgagatcaac   3000
ttctga                                                              3006
```

<210> SEQ ID NO 115
<211> LENGTH: 3024
<212> TYPE: DNA
<213> ORGANISM: Artificial Sequence
<220> FEATURE:
<223> OTHER INFORMATION: Xanthomonas ssp, Escherichia coli

<400> SEQUENCE: 115

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gaccccccag caggtggtgg ccatcgccag caatggcggt     540
ggcaagcagg cgctggagac ggtccagcgg ctgttgccgg tgctgtgcca ggcccacggc     600
ttgaccccgg agcaggtggt ggccatcgcc agcaatattg gtggcaagca ggcgctggag     660
acggtgcagg cgctgttgcc ggtgctgtgc caggcccacg gcttgacccc ggagcaggtg     720
gtggccatcg ccagcaatat tggtggcaag caggcgctgg agacggtgca ggcgctgttg     780
ccggtgctgt gccaggccca cggcttgacc ccggagcagg tggtggccat cgccagcaat     840
attggtggca gcaggcgct ggagacggtg caggcgctgt gccggtgct gtgccaggcc     900
cacggcttga ccccggagca ggtggtggcc atcgccagcc acgatggcgg caagcaggcg     960
ctggagacgg tccagcggct gttgccggtg ctgtgccagg cccacggctt gacccccag    1020
caggtggtgg ccatcgccag caataatggt ggcaagcagg cgctggagac ggtccagcgg    1080
ctgttgccgg tgctgtgcca ggcccacggc ttgaccccc agcaggtggt ggccatcgcc    1140
agcaatggcg gtggcaagca ggcgctggag acggtccagc ggctgttgcc ggtgctgtgc    1200
caggcccacg gcttgacccc ccagcaggtg gtggccatcg ccagcaatgg cggtggcaag    1260
caggcgctgg agacggtcca gcggctgttg ccggtgctgt gccaggccca cggcttgacc    1320
ccggagcagg tggtggccat cgccagccac gatggcggca agcaggcgct ggagacggtc    1380
cagcggctgt gccggtgct gtgccaggcc cacggcttga ccccccagca ggtggtggcc    1440
atcgccagca ataatggtgg caagcaggcg ctggagacgg tccagcggct gttgccggtg    1500
ctgtgccagg cccacggctt gacccccag caggtggtgg ccatcgccag caataatggt    1560
ggcaagcagg cgctggagac ggtccagcgg ctgttgccgg tgctgtgcca ggcccacggc    1620
ttgaccccgg agcaggtggt ggccatcgcc agccacgatg gcggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccccagcagg tggtggccat cgccagcaat    1860
ggcggtggca gcaggcgct ggagacggtc cagcggctgt gccggtgct gtgccaggcc    1920
cacggcttga ccccggagca ggtggtggcc atcgccagcc acgatggcgg caagcaggcg    1980
ctggagacgg tccagcggct gttgccggtg ctgtgccagg cccacggctt gaccccggag    2040
caggtggtgg ccatcgccag caatattggt ggcaagcagg cgctggagac ggtgcaggcg    2100
ctgttgccgg tgctgtgcca ggcccacggc ttgaccccc agcaggtggt ggccatcgcc    2160
agcaataatg gtggcaagca ggcgctggag acggtccagc ggctgttgcc ggtgctgtgc    2220
```

```
caggcccacg gcttgacccc tcagcaggtg gtggccatcg ccagcaatgg cggcggcagg    2280
ccggcgctgg agagcattgt tgcccagtta tctcgccctg atccggcgtt ggccgcgttg    2340
accaacgacc acctcgtcgc cttggcctgc ctcggcgggc gtcctgcgct ggatgcagtg    2400
aaaaagggat tggggatcc tatcagccgt tcccagctgg tgaaatctga gctggaggag    2460
aagaagtctg agctgagaca aagctgaag tacgtgcctc acgagtacat cgagctgatc    2520
gagatcgcca gaaatagcac ccaggataga atcctggaga tgaaggtgat ggagttcttc    2580
atgaaagtgt acggctacag aggaaagcat ctgggaggaa gcagaaaacc tgacggagcc    2640
atttatacag tgggcagccc tatcgattat ggcgtgatcg tggatacaaa ggcctacagc    2700
ggaggctaca atctgcctat tggacaggcc gatgagatgc agagatacgt ggaggagaac    2760
caaaccagga caagcatat caaccctaac gagtggtgga aggtgtaccc ttctagcgtg    2820
accgagttca agttcctgtt tgtgagcggc cacttcaagg gcaattataa ggcccagctg    2880
accaggctga accacatcac aaattgtaat ggcgccgtgc tgtctgtgga ggaactgctg    2940
attggaggag agatgattaa ggccggaaca ctgacactgg aggaggtgag aagaaagttc    3000
aacaacggcg agatcaactt ctga                                          3024

<210> SEQ ID NO 116
<211> LENGTH: 53
<212> TYPE: DNA
<213> ORGANISM: Artificial Sequence
<220> FEATURE:
<223> OTHER INFORMATION: Escherichia coli

<400> SEQUENCE: 116
atagagatcc tctagagtcg accatggtga tcactgcagg catgcaagct tgt          53

<210> SEQ ID NO 117
<211> LENGTH: 18
<212> TYPE: DNA
<213> ORGANISM: Artificial Sequence
<220> FEATURE:
<223> OTHER INFORMATION: Escherichia coli

<400> SEQUENCE: 117
atagagatcc tctagagt                                                 18

<210> SEQ ID NO 118
<211> LENGTH: 18
<212> TYPE: DNA
<213> ORGANISM: Artificial Sequence
<220> FEATURE:
<223> OTHER INFORMATION: Escherichia coli

<400> SEQUENCE: 118
acaagcttgc atgcctgc                                                 18

<210> SEQ ID NO 119
<211> LENGTH: 1344
<212> TYPE: PRT
<213> ORGANISM: Artificial Sequence
<220> FEATURE:
<223> OTHER INFORMATION: Xanthomonas ssp, Escherichia coli

<400> SEQUENCE: 119

Met Ala Ser Ser Pro Lys Lys Lys Arg Lys Val Ser Trp Lys Asp
1               5                   10                  15

Ala Ser Gly Trp Ser Arg Met His Ala Asp Pro Ile Arg Pro Arg Arg
            20                  25                  30
```

```
Pro Ser Pro Ala Arg Glu Leu Leu Pro Gly Pro Gln Pro Asp Arg Val
    35                  40                  45

Gln Pro Thr Ala Asp Arg Gly Val Ser Ala Pro Ala Gly Ser Pro Leu
50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Pro Ala Glu Trp
            115                 120                 125

Asp Glu Met Gln Ser Ala Leu Arg Ala Ala Asp Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285

Lys Arg Gly Gly Val Thr Ala Met Glu Ala Val His Ala Ser Arg Asn
    290                 295                 300

Ala Leu Thr Gly Ala Pro Leu Asn Leu Thr Pro Asp Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Ala His Gly Leu Thr Pro Asp Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Asp His Gly Leu Thr Pro Glu
    370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Asp His Gly Leu Thr
                405                 410                 415

Pro Asp Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445
```

-continued

```
Leu Thr Pro Asp Gln Val Val Ala Ile Ala Ser Asn Ile Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Asp Gln Val Val Ala Ile Ala Ser Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
            515                 520                 525

Ile Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Asp His Gly Leu Thr Pro Glu Gln Val Val Ala
            580                 585                 590

Ile Ala Ser His Asp Gly Gly Lys Gln Ala Leu Glu Thr Val Gln Arg
            595                 600                 605

Leu Leu Pro Val Leu Cys Gln Ala His Gly Leu Thr Pro Asp Gln Val
            610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Asp
                645                 650                 655

Gln Val Val Ala Ile Ala Ser Asn Gly Gly Gly Lys Gln Ala Leu Glu
            660                 665                 670

Thr Val Gln Arg Leu Leu Pro Val Leu Cys Gln Asp His Gly Leu Thr
            675                 680                 685

Pro Glu Gln Val Val Ala Ile Ala Ser His Asp Gly Gly Lys Gln Ala
            690                 695                 700

Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Gly Gly Gly Lys
                725                 730                 735

Gln Ala Leu Glu Thr Val Gln Arg Leu Leu Pro Val Leu Cys Gln Ala
            740                 745                 750

His Gly Leu Thr Pro Asp Gln Val Val Ala Ile Ala Ser Asn Ile Gly
            755                 760                 765

Gly Lys Gln Ala Leu Glu Thr Val Gln Arg Leu Leu Pro Val Leu Cys
770                 775                 780

Gln Ala His Gly Leu Thr Pro Asp Gln Val Val Ala Ile Ala Ser Asn
785                 790                 795                 800

Asn Gly Gly Lys Gln Ala Leu Glu Thr Val Gln Arg Leu Leu Pro Val
                805                 810                 815

Leu Cys Gln Ala His Gly Leu Thr Pro Glu Gln Val Val Ala Ile Ala
            820                 825                 830

Ser Asn Ile Gly Gly Lys Gln Ala Leu Glu Thr Val Gln Arg Leu Leu
            835                 840                 845

Pro Val Leu Cys Gln Ala His Gly Leu Thr Pro Glu Gln Val Val Ala
850                 855                 860

Ile Ala Ser Asn Asn Gly Gly Lys Gln Ala Leu Glu Thr Val Gln Arg
```

```
            865                 870                 875                 880
Leu Leu Pro Val Leu Cys Gln Asp His Gly Leu Thr Pro Asp Gln Val
                    885                 890                 895

Val Ala Ile Ala Ser Asn Gly Gly Lys Gln Ala Leu Glu Ser Ile
                900                 905                 910

Val Ala Gln Leu Ser Arg Pro Asp Pro Ala Leu Ala Ala Leu Thr Asn
                915                 920                 925

Asp His Leu Val Ala Leu Ala Cys Leu Gly Gly Arg Pro Ala Met Asp
930                 935                 940

Ala Val Lys Lys Gly Leu Pro His Ala Pro Glu Leu Ile Arg Arg Val
945                 950                 955                 960

Asn Arg Arg Ile Gly Glu Arg Thr Ser His Arg Val Ala Asp Tyr Ala
                965                 970                 975

Gln Val Val Arg Val Leu Glu Phe Phe Gln Cys His Ser His Pro Ala
                980                 985                 990

Tyr Ala Phe Asp Glu Ala Met Thr Gln Phe Gly Met Ser Arg Asn Gly
                995                 1000                1005

Leu Val Gln Leu Phe Arg Arg Val Gly Val Thr Glu Leu Glu Ala
            1010                1015                1020

Arg Gly Gly Thr Leu Pro Pro Ala Ser Gln Arg Trp Asp Arg Ile
            1025                1030                1035

Leu Gln Ala Ser Gly Met Lys Arg Ala Lys Pro Ser Pro Thr Ser
            1040                1045                1050

Ala Gln Thr Pro Asp Gln Ala Ser Leu His Ala Phe Ala Asp Ser
            1055                1060                1065

Leu Glu Arg Asp Leu Asp Ala Pro Ser Pro Met His Glu Gly Asp
            1070                1075                1080

Gln Thr Arg Ala Ser Ser Arg Lys Arg Ser Arg Ser Asp Arg Ala
            1085                1090                1095

Val Thr Gly Pro Ser Ala Gln Gln Ala Val Glu Val Arg Val Pro
            1100                1105                1110

Glu Gln Arg Asp Ala Leu His Leu Pro Leu Ser Trp Arg Val Lys
            1115                1120                1125

Arg Pro Arg Thr Arg Ile Trp Gly Gly Leu Pro Asp Pro Gly Thr
            1130                1135                1140

Pro Thr Ala Ala Asp Gln Leu Val Lys Ser Glu Leu Glu Glu Lys
            1145                1150                1155

Lys Ser Glu Leu Arg His Lys Leu Lys Tyr Val Pro His Glu Tyr
            1160                1165                1170

Ile Glu Leu Ile Glu Ile Ala Arg Asn Ser Thr Gln Asp Arg Ile
            1175                1180                1185

Leu Glu Met Lys Val Met Glu Phe Phe Met Lys Val Tyr Gly Tyr
            1190                1195                1200

Arg Gly Lys His Leu Gly Gly Ser Arg Lys Pro Asp Gly Ala Ile
            1205                1210                1215

Tyr Thr Val Gly Ser Pro Ile Asp Tyr Gly Val Ile Val Asp Thr
            1220                1225                1230

Lys Ala Tyr Ser Gly Gly Tyr Asn Leu Pro Ile Gly Gln Ala Asp
            1235                1240                1245

Glu Met Gln Arg Tyr Val Glu Glu Asn Gln Thr Arg Asn Lys His
            1250                1255                1260

Ile Asn Pro Asn Glu Trp Trp Lys Val Tyr Pro Ser Ser Val Thr
            1265                1270                1275
```

```
Glu Phe Lys Phe Leu Phe Val Ser Gly His Phe Lys Gly Asn Tyr
    1280            1285                1290

Lys Ala Gln Leu Thr Arg Leu Asn His Ile Thr Asn Cys Asn Gly
    1295            1300                1305

Ala Val Leu Ser Val Glu Glu Leu Leu Ile Gly Gly Glu Met Ile
    1310            1315                1320

Lys Ala Gly Thr Leu Thr Leu Glu Glu Val Arg Arg Lys Phe Asn
    1325            1330                1335

Asn Gly Glu Ile Asn Phe
    1340

<210> SEQ ID NO 120
<211> LENGTH: 1344
<212> TYPE: PRT
<213> ORGANISM: Artificial Sequence
<220> FEATURE:
<223> OTHER INFORMATION: Xanthomonas ssp, Escherichia coli

<400> SEQUENCE: 120

Met Ala Ser Ser Pro Pro Lys Lys Arg Lys Val Ser Trp Lys Asp
1               5                   10                  15

Ala Ser Gly Trp Ser Arg Met His Ala Asp Pro Ile Arg Pro Arg Arg
                20                  25                  30

Pro Ser Pro Ala Arg Glu Leu Leu Pro Gly Pro Gln Pro Asp Arg Val
            35                  40                  45

Gln Pro Thr Ala Asp Arg Gly Val Ser Ala Pro Ala Gly Ser Pro Leu
        50                  55                  60

Asp Gly Leu Pro Ala Arg Arg Thr Val Ser Arg Thr Arg Leu Pro Ser
65                  70                  75                  80

Pro Pro Ala Pro Ser Pro Ala Phe Ser Ala Gly Ser Phe Ser Asp Leu
                85                  90                  95

Leu Arg Pro Phe Asp Pro Ser Leu Leu Asp Thr Ser Leu Leu Asp Ser
            100                 105                 110

Met Pro Ala Val Gly Thr Pro His Thr Ala Ala Ala Pro Ala Glu Trp
        115                 120                 125

Asp Glu Met Gln Ser Ala Leu Arg Ala Ala Asp Asp Pro Pro Pro Thr
    130                 135                 140

Val Arg Val Ala Val Thr Ala Ala Arg Pro Pro Arg Ala Lys Pro Ala
145                 150                 155                 160

Pro Arg Arg Arg Ala Ala Gln Pro Ser Asp Ala Ser Pro Ala Ala Gln
                165                 170                 175

Val Asp Leu Arg Thr Leu Gly Tyr Ser Gln Gln Gln Gln Glu Lys Ile
            180                 185                 190

Lys Pro Lys Val Arg Ser Thr Val Ala Gln His His Glu Ala Leu Val
        195                 200                 205

Gly His Gly Phe Thr His Ala His Ile Val Ala Leu Ser Gln His Pro
    210                 215                 220

Ala Ala Leu Gly Thr Val Ala Val Thr Tyr Gln His Ile Ile Thr Ala
225                 230                 235                 240

Leu Pro Glu Ala Thr His Glu Asp Ile Val Gly Val Gly Lys Gln Trp
                245                 250                 255

Ser Gly Ala Arg Ala Leu Glu Ala Leu Leu Thr Asp Ala Gly Glu Leu
            260                 265                 270

Arg Gly Pro Pro Leu Gln Leu Asp Thr Gly Gln Leu Val Lys Ile Ala
        275                 280                 285
```

```
Lys Arg Gly Gly Val Thr Ala Met Glu Ala Val His Ala Ser Arg Asn
290                     295                 300
Ala Leu Thr Gly Ala Pro Leu Asn Leu Thr Pro Asp Gln Val Val Ala
305                 310                 315                 320
Ile Ala Ser Asn Ile Gly Gly Lys Gln Ala Leu Glu Thr Val Gln Arg
            325                 330                 335
Leu Leu Pro Val Leu Cys Gln Ala His Gly Leu Thr Pro Asp Gln Val
                340                 345                 350
Val Ala Ile Ala Ser His Asp Gly Gly Lys Gln Ala Leu Glu Thr Val
            355                 360                 365
Gln Arg Leu Leu Pro Val Leu Cys Gln Asp His Gly Leu Thr Pro Glu
370                 375                 380
Gln Val Val Ala Ile Ala Ser Asn Ile Gly Gly Lys Gln Ala Leu Glu
385                 390                 395                 400
Thr Val Gln Arg Leu Leu Pro Val Leu Cys Gln Asp His Gly Leu Thr
                405                 410                 415
Pro Asp Gln Val Val Ala Ile Ala Ser Asn Ile Gly Gly Lys Gln Ala
                420                 425                 430
Leu Glu Thr Val Gln Arg Leu Leu Pro Val Leu Cys Gln Ala His Gly
            435                 440                 445
Leu Thr Pro Asp Gln Val Val Ala Ile Ala Ser Asn Asn Gly Gly Lys
450                 455                 460
Gln Ala Leu Glu Thr Val Gln Arg Leu Leu Pro Val Leu Cys Gln Ala
465                 470                 475                 480
His Gly Leu Thr Pro Asp Gln Val Val Ala Ile Ala Ser His Asp Gly
                485                 490                 495
Gly Lys Gln Ala Leu Glu Thr Val Gln Arg Leu Leu Pro Val Leu Cys
            500                 505                 510
Gln Ala His Gly Leu Thr Pro Glu Gln Val Val Ala Ile Ala Ser Asn
                515                 520                 525
Gly Gly Gly Lys Gln Ala Leu Glu Thr Val Gln Arg Leu Leu Pro Val
530                 535                 540
Leu Cys Gln Ala His Gly Leu Thr Pro Glu Gln Val Val Ala Ile Ala
545                 550                 555                 560
Ser Asn Gly Gly Gly Lys Gln Ala Leu Glu Thr Val Gln Arg Leu Leu
                565                 570                 575
Pro Val Leu Cys Gln Asp His Gly Leu Thr Pro Glu Gln Val Val Ala
                580                 585                 590
Ile Ala Ser Asn Asn Gly Gly Lys Gln Ala Leu Glu Thr Val Gln Arg
            595                 600                 605
Leu Leu Pro Val Leu Cys Gln Ala His Gly Leu Thr Pro Asp Gln Val
                610                 615                 620
Val Ala Ile Ala Ser His Asp Gly Gly Lys Gln Ala Leu Glu Thr Val
625                 630                 635                 640
Gln Arg Leu Leu Pro Val Leu Cys Gln Ala His Gly Leu Thr Pro Asp
                645                 650                 655
Gln Val Val Ala Ile Ala Ser Asn Ile Gly Gly Lys Gln Ala Leu Glu
                660                 665                 670
Thr Val Gln Arg Leu Leu Pro Val Leu Cys Gln Asp His Gly Leu Thr
            675                 680                 685
Pro Glu Gln Val Val Ala Ile Ala Ser Asn Gly Gly Gly Lys Gln Ala
        690                 695                 700
```

```
Leu Glu Thr Val Gln Arg Leu Leu Pro Val Leu Cys Gln Asp His Gly
705                 710                 715                 720

Leu Thr Pro Asp Gln Val Val Ala Ile Ala Ser Asn Asn Gly Gly Lys
            725                 730                 735

Gln Ala Leu Glu Thr Val Gln Arg Leu Leu Pro Val Leu Cys Gln Ala
            740                 745                 750

His Gly Leu Thr Pro Asp Gln Val Val Ala Ile Ala Ser His Asp Gly
            755                 760                 765

Gly Lys Gln Ala Leu Glu Thr Val Gln Arg Leu Leu Pro Val Leu Cys
770                 775                 780

Gln Ala His Gly Leu Thr Pro Asp Gln Val Val Ala Ile Ala Ser His
785                 790                 795                 800

Asp Gly Gly Lys Gln Ala Leu Glu Thr Val Gln Arg Leu Leu Pro Val
            805                 810                 815

Leu Cys Gln Ala His Gly Leu Thr Pro Glu Gln Val Val Ala Ile Ala
            820                 825                 830

Ser Asn Gly Gly Gly Lys Gln Ala Leu Glu Thr Val Gln Arg Leu Leu
            835                 840                 845

Pro Val Leu Cys Gln Ala His Gly Leu Thr Pro Glu Gln Val Val Ala
850                 855                 860

Ile Ala Ser Asn Asn Gly Gly Lys Gln Ala Leu Glu Thr Val Gln Arg
865                 870                 875                 880

Leu Leu Pro Val Leu Cys Gln Asp His Gly Leu Thr Pro Asp Gln Val
            885                 890                 895

Val Ala Ile Ala Ser His Asp Gly Gly Lys Gln Ala Leu Glu Ser Ile
            900                 905                 910

Val Ala Gln Leu Ser Arg Pro Asp Pro Ala Leu Ala Ala Leu Thr Asn
            915                 920                 925

Asp His Leu Val Ala Leu Ala Cys Leu Gly Gly Arg Pro Ala Met Asp
930                 935                 940

Ala Val Lys Lys Gly Leu Pro His Ala Pro Glu Leu Ile Arg Arg Val
945                 950                 955                 960

Asn Arg Arg Ile Gly Glu Arg Thr Ser His Arg Val Ala Asp Tyr Ala
            965                 970                 975

Gln Val Val Arg Val Leu Glu Phe Phe Gln Cys His Ser His Pro Ala
            980                 985                 990

Tyr Ala Phe Asp Glu Ala Met Thr Gln Phe Gly Met Ser Arg Asn Gly
            995                 1000                1005

Leu Val Gln Leu Phe Arg Arg Val Gly Val Thr Glu Leu Glu Ala
    1010                1015                1020

Arg Gly Gly Thr Leu Pro Pro Ala Ser Gln Arg Trp Asp Arg Ile
    1025                1030                1035

Leu Gln Ala Ser Gly Met Lys Arg Ala Lys Pro Ser Pro Thr Ser
    1040                1045                1050

Ala Gln Thr Pro Asp Gln Ala Ser Leu His Ala Phe Ala Asp Ser
    1055                1060                1065

Leu Glu Arg Asp Leu Asp Ala Pro Ser Pro Met His Glu Gly Asp
    1070                1075                1080

Gln Thr Arg Ala Ser Ser Arg Lys Arg Ser Arg Ser Asp Arg Ala
    1085                1090                1095

Val Thr Gly Pro Ser Ala Gln Gln Ala Val Glu Val Arg Val Pro
    1100                1105                1110

Glu Gln Arg Asp Ala Leu His Leu Pro Leu Ser Trp Arg Val Lys
```

```
                1115                1120                1125

Arg Pro Arg Thr Arg Ile Trp Gly Gly Leu Pro Asp Pro Gly Thr
    1130                1135                1140

Pro Thr Ala Ala Asp Gln Leu Val Lys Ser Glu Leu Glu Glu Lys
    1145                1150                1155

Lys Ser Glu Leu Arg His Lys Leu Lys Tyr Val Pro His Glu Tyr
    1160                1165                1170

Ile Glu Leu Ile Glu Ile Ala Arg Asn Ser Thr Gln Asp Arg Ile
    1175                1180                1185

Leu Glu Met Lys Val Met Glu Phe Phe Met Lys Val Tyr Gly Tyr
    1190                1195                1200

Arg Gly Lys His Leu Gly Gly Ser Arg Lys Pro Asp Gly Ala Ile
    1205                1210                1215

Tyr Thr Val Gly Ser Pro Ile Asp Tyr Gly Val Ile Val Asp Thr
    1220                1225                1230

Lys Ala Tyr Ser Gly Gly Tyr Asn Leu Pro Ile Gly Gln Ala Asp
    1235                1240                1245

Glu Met Gln Arg Tyr Val Glu Glu Asn Gln Thr Arg Asn Lys His
    1250                1255                1260

Ile Asn Pro Asn Glu Trp Trp Lys Val Tyr Pro Ser Ser Val Thr
    1265                1270                1275

Glu Phe Lys Phe Leu Phe Val Ser Gly His Phe Lys Gly Asn Tyr
    1280                1285                1290

Lys Ala Gln Leu Thr Arg Leu Asn His Ile Thr Asn Cys Asn Gly
    1295                1300                1305

Ala Val Leu Ser Val Glu Glu Leu Leu Ile Gly Gly Glu Met Ile
    1310                1315                1320

Lys Ala Gly Thr Leu Thr Leu Glu Glu Val Arg Arg Lys Phe Asn
    1325                1330                1335

Asn Gly Glu Ile Asn Phe
    1340

<210> SEQ ID NO 121
<211> LENGTH: 1038
<212> TYPE: PRT
<213> ORGANISM: Artificial Sequence
<220> FEATURE:
<223> OTHER INFORMATION: Xanthomonas ssp, Escherichia coli

<400> SEQUENCE: 121

Met Ala Ser Ser Pro Pro Lys Lys Lys Arg Lys Val Ser Trp Lys Asp
1               5                   10                  15

Ala Ser Gly Trp Ser Arg Met His Ala Asp Pro Trp Pro Arg Arg Arg
            20                  25                  30

Ala Ala Gln Pro Ser Asp Ala Ser Pro Ala Ala Gln Val Asp Leu Arg
        35                  40                  45

Thr Leu Gly Tyr Ser Gln Gln Gln Gln Glu Lys Ile Lys Pro Lys Val
    50                  55                  60

Arg Ser Thr Val Ala Gln His His Glu Ala Leu Val Gly His Gly Phe
65                  70                  75                  80

Thr His Ala His Ile Val Ala Leu Ser Gln His Pro Ala Ala Leu Gly
                85                  90                  95

Thr Val Ala Val Thr Tyr Gln His Ile Ile Thr Ala Leu Pro Glu Ala
            100                 105                 110

Thr His Glu Asp Ile Val Gly Val Gly Lys Gln Trp Ser Gly Ala Arg
```

```
              115                 120                 125
Ala Leu Glu Ala Leu Leu Thr Asp Ala Gly Glu Leu Arg Gly Pro Pro
        130                 135                 140

Leu Gln Leu Asp Thr Gly Gln Leu Val Lys Ile Ala Lys Arg Gly Gly
145                 150                 155                 160

Val Thr Ala Met Glu Ala Val His Ala Ser Arg Asn Ala Leu Thr Gly
                165                 170                 175

Ala Pro Leu Asn Leu Thr Pro Asp Gln Val Val Ala Ile Ala Ser Asn
                180                 185                 190

Ile Gly Gly Lys Gln Ala Leu Glu Thr Val Gln Arg Leu Leu Pro Val
            195                 200                 205

Leu Cys Gln Ala His Gly Leu Thr Pro Asp Gln Val Val Ala Ile Ala
        210                 215                 220

Ser Asn Gly Gly Gly Lys Gln Ala Leu Glu Thr Val Gln Arg Leu Leu
225                 230                 235                 240

Pro Val Leu Cys Gln Asp His Gly Leu Thr Pro Glu Gln Val Val Ala
                245                 250                 255

Ile Ala Ser Asn Ile Gly Gly Lys Gln Ala Leu Glu Thr Val Gln Arg
                260                 265                 270

Leu Leu Pro Val Leu Cys Gln Asp His Gly Leu Thr Pro Asp Gln Val
            275                 280                 285

Val Ala Ile Ala Ser Asn Asn Gly Gly Lys Gln Ala Leu Glu Thr Val
        290                 295                 300

Gln Arg Leu Leu Pro Val Leu Cys Gln Ala His Gly Leu Thr Pro Asp
305                 310                 315                 320

Gln Val Val Ala Ile Ala Ser Asn Ile Gly Gly Lys Gln Ala Leu Glu
                325                 330                 335

Thr Val Gln Arg Leu Leu Pro Val Leu Cys Gln Ala His Gly Leu Thr
                340                 345                 350

Pro Asp Gln Val Val Ala Ile Ala Ser Asn Asn Gly Gly Lys Gln Ala
            355                 360                 365

Leu Glu Thr Val Gln Arg Leu Leu Pro Val Leu Cys Gln Ala His Gly
        370                 375                 380

Leu Thr Pro Glu Gln Val Val Ala Ile Ala Ser Asn Ile Gly Gly Lys
385                 390                 395                 400

Gln Ala Leu Glu Thr Val Gln Arg Leu Leu Pro Val Leu Cys Gln Ala
                405                 410                 415

His Gly Leu Thr Pro Glu Gln Val Val Ala Ile Ala Ser Asn Gly Gly
                420                 425                 430

Gly Lys Gln Ala Leu Glu Thr Val Gln Arg Leu Leu Pro Val Leu Cys
            435                 440                 445

Gln Asp His Gly Leu Thr Pro Glu Gln Val Val Ala Ile Ala Ser His
        450                 455                 460

Asp Gly Gly Lys Gln Ala Leu Glu Thr Val Gln Arg Leu Leu Pro Val
465                 470                 475                 480

Leu Cys Gln Ala His Gly Leu Thr Pro Asp Gln Val Val Ala Ile Ala
                485                 490                 495

Ser His Asp Gly Gly Lys Gln Ala Leu Glu Thr Val Gln Arg Leu Leu
                500                 505                 510

Pro Val Leu Cys Gln Ala His Gly Leu Thr Pro Asp Gln Val Val Ala
            515                 520                 525

Ile Ala Ser Asn Gly Gly Gly Lys Gln Ala Leu Glu Thr Val Gln Arg
        530                 535                 540
```

```
Leu Leu Pro Val Leu Cys Gln Asp His Gly Leu Thr Pro Glu Gln Val
545                 550                 555                 560

Val Ala Ile Ala Ser His Asp Gly Gly Lys Gln Ala Leu Glu Thr Val
                565                 570                 575

Gln Arg Leu Leu Pro Val Leu Cys Gln Asp His Gly Leu Thr Pro Asp
            580                 585                 590

Gln Val Val Ala Ile Ala Ser Asn Gly Gly Lys Gln Ala Leu Glu
        595                 600                 605

Thr Val Gln Arg Leu Leu Pro Val Leu Cys Gln Ala His Gly Leu Thr
    610                 615                 620

Pro Asp Gln Val Val Ala Ile Ala Ser Asn Ile Gly Gly Lys Gln Ala
625                 630                 635                 640

Leu Glu Thr Val Gln Arg Leu Leu Pro Val Leu Cys Gln Ala His Gly
                645                 650                 655

Leu Thr Pro Asp Gln Val Val Ala Ile Ala Ser Asn Asn Gly Gly Lys
            660                 665                 670

Gln Ala Leu Glu Thr Val Gln Arg Leu Leu Pro Val Leu Cys Gln Ala
        675                 680                 685

His Gly Leu Thr Pro Glu Gln Val Val Ala Ile Ala Ser Asn Ile Gly
    690                 695                 700

Gly Lys Gln Ala Leu Glu Thr Val Gln Arg Leu Leu Pro Val Leu Cys
705                 710                 715                 720

Gln Ala His Gly Leu Thr Pro Glu Gln Val Val Ala Ile Ala Ser Asn
                725                 730                 735

Asn Gly Gly Lys Gln Ala Leu Glu Thr Val Gln Arg Leu Leu Pro Val
            740                 745                 750

Leu Cys Gln Asp His Gly Leu Thr Pro Asp Gln Val Val Ala Ile Ala
        755                 760                 765

Ser Asn Gly Gly Gly Lys Gln Ala Leu Glu Ser Ile Val Ala Gln Leu
    770                 775                 780

Ser Arg Pro Asp Pro Ala Leu Ala Ala Leu Thr Asn Asp His Leu Val
785                 790                 795                 800

Ala Leu Ala Cys Leu Gly Gly Arg Pro Ala Met Asp Ala Val Lys Lys
                805                 810                 815

Gly Leu Pro His Ala Pro Glu Leu Ile Arg Arg Val Asn Arg Arg Ile
            820                 825                 830

Gly Glu Arg Thr Ser His Arg Val Ala Leu Gln Leu Val Lys Ser Glu
        835                 840                 845

Leu Glu Glu Lys Lys Ser Glu Leu Arg His Lys Leu Lys Tyr Val Pro
    850                 855                 860

His Glu Tyr Ile Glu Leu Ile Glu Ile Ala Arg Asn Ser Thr Gln Asp
865                 870                 875                 880

Arg Ile Leu Glu Met Lys Val Met Glu Phe Phe Met Lys Val Tyr Gly
                885                 890                 895

Tyr Arg Gly Lys His Leu Gly Gly Ser Arg Lys Pro Asp Gly Ala Ile
            900                 905                 910

Tyr Thr Val Gly Ser Pro Ile Asp Tyr Gly Val Ile Val Asp Thr Lys
        915                 920                 925

Ala Tyr Ser Gly Gly Tyr Asn Leu Pro Ile Gly Gln Ala Asp Glu Met
    930                 935                 940

Gln Arg Tyr Val Glu Glu Asn Gln Thr Arg Asn Lys His Ile Asn Pro
945                 950                 955                 960
```

-continued

```
Asn Glu Trp Trp Lys Val Tyr Pro Ser Ser Val Thr Glu Phe Lys Phe
            965                 970                 975
Leu Phe Val Ser Gly His Phe Lys Gly Asn Tyr Lys Ala Gln Leu Thr
        980                 985                 990
Arg Leu Asn His Ile Thr Asn Cys Asn Gly Ala Val Leu Ser Val Glu
        995                1000                1005
Glu Leu Leu Ile Gly Gly Glu Met Ile Lys Ala Gly Thr Leu Thr
    1010                1015                1020
Leu Glu Glu Val Arg Arg Lys Phe Asn Asn Gly Glu Ile Asn Phe
    1025                1030                1035

<210> SEQ ID NO 122
<211> LENGTH: 1038
<212> TYPE: PRT
<213> ORGANISM: Artificial Sequence
<220> FEATURE:
<223> OTHER INFORMATION: Xanthomonas ssp, Escherichia coli

<400> SEQUENCE: 122

Met Ala Ser Ser Pro Lys Lys Arg Lys Val Ser Trp Lys Asp
1               5                   10                  15
Ala Ser Gly Trp Ser Arg Met His Ala Asp Pro Trp Pro Arg Arg
            20                  25                  30
Ala Ala Gln Pro Ser Asp Ala Ser Pro Ala Ala Gln Val Asp Leu Arg
        35                  40                  45
Thr Leu Gly Tyr Ser Gln Gln Gln Gln Glu Lys Ile Lys Pro Lys Val
    50                  55                  60
Arg Ser Thr Val Ala Gln His His Glu Ala Leu Val Gly His Gly Phe
65                  70                  75                  80
Thr His Ala His Ile Val Ala Leu Ser Gln His Pro Ala Ala Leu Gly
                85                  90                  95
Thr Val Ala Val Thr Tyr Gln His Ile Ile Thr Ala Leu Pro Glu Ala
            100                 105                 110
Thr His Glu Asp Ile Val Gly Val Gly Lys Gln Trp Ser Gly Ala Arg
        115                 120                 125
Ala Leu Glu Ala Leu Leu Thr Asp Ala Gly Glu Leu Arg Gly Pro Pro
    130                 135                 140
Leu Gln Leu Asp Thr Gly Gln Leu Val Lys Ile Ala Lys Arg Gly Gly
145                 150                 155                 160
Val Thr Ala Met Glu Ala Val His Ala Ser Arg Asn Ala Leu Thr Gly
                165                 170                 175
Ala Pro Leu Asn Leu Thr Pro Asp Gln Val Val Ala Ile Ala Ser Asn
            180                 185                 190
Ile Gly Gly Lys Gln Ala Leu Glu Thr Val Gln Arg Leu Leu Pro Val
        195                 200                 205
Leu Cys Gln Ala His Gly Leu Thr Pro Asp Gln Val Val Ala Ile Ala
    210                 215                 220
Ser His Asp Gly Gly Lys Gln Ala Leu Glu Thr Val Gln Arg Leu Leu
225                 230                 235                 240
Pro Val Leu Cys Gln Asp His Gly Leu Thr Pro Glu Gln Val Val Ala
                245                 250                 255
Ile Ala Ser Asn Ile Gly Gly Lys Gln Ala Leu Glu Thr Val Gln Arg
            260                 265                 270
Leu Leu Pro Val Leu Cys Gln Asp His Gly Leu Thr Pro Asp Gln Val
        275                 280                 285
```

-continued

```
Val Ala Ile Ala Ser Asn Ile Gly Gly Lys Gln Ala Leu Glu Thr Val
    290                 295                 300
Gln Arg Leu Leu Pro Val Leu Cys Gln Ala His Gly Leu Thr Pro Asp
305                 310                 315                 320
Gln Val Val Ala Ile Ala Ser Asn Asn Gly Gly Lys Gln Ala Leu Glu
                325                 330                 335
Thr Val Gln Arg Leu Leu Pro Val Leu Cys Gln Ala His Gly Leu Thr
                    340                 345                 350
Pro Asp Gln Val Val Ala Ile Ala Ser His Asp Gly Gly Lys Gln Ala
                355                 360                 365
Leu Glu Thr Val Gln Arg Leu Leu Pro Val Leu Cys Gln Ala His Gly
370                 375                 380
Leu Thr Pro Glu Gln Val Val Ala Ile Ala Ser Asn Gly Gly Gly Lys
385                 390                 395                 400
Gln Ala Leu Glu Thr Val Gln Arg Leu Leu Pro Val Leu Cys Gln Ala
                405                 410                 415
His Gly Leu Thr Pro Glu Gln Val Val Ala Ile Ala Ser Asn Gly Gly
                420                 425                 430
Gly Lys Gln Ala Leu Glu Thr Val Gln Arg Leu Leu Pro Val Leu Cys
            435                 440                 445
Gln Asp His Gly Leu Thr Pro Glu Gln Val Val Ala Ile Ala Ser Asn
450                 455                 460
Asn Gly Gly Lys Gln Ala Leu Glu Thr Val Gln Arg Leu Leu Pro Val
465                 470                 475                 480
Leu Cys Gln Ala His Gly Leu Thr Pro Asp Gln Val Val Ala Ile Ala
                485                 490                 495
Ser His Asp Gly Gly Lys Gln Ala Leu Glu Thr Val Gln Arg Leu Leu
            500                 505                 510
Pro Val Leu Cys Gln Ala His Gly Leu Thr Pro Asp Gln Val Val Ala
            515                 520                 525
Ile Ala Ser Asn Ile Gly Gly Lys Gln Ala Leu Glu Thr Val Gln Arg
        530                 535                 540
Leu Leu Pro Val Leu Cys Gln Asp His Gly Leu Thr Pro Glu Gln Val
545                 550                 555                 560
Val Ala Ile Ala Ser Asn Gly Gly Gly Lys Gln Ala Leu Glu Thr Val
                565                 570                 575
Gln Arg Leu Leu Pro Val Leu Cys Gln Asp His Gly Leu Thr Pro Asp
            580                 585                 590
Gln Val Val Ala Ile Ala Ser Asn Asn Gly Gly Lys Gln Ala Leu Glu
            595                 600                 605
Thr Val Gln Arg Leu Leu Pro Val Leu Cys Gln Ala His Gly Leu Thr
610                 615                 620
Pro Asp Gln Val Val Ala Ile Ala Ser His Asp Gly Gly Lys Gln Ala
625                 630                 635                 640
Leu Glu Thr Val Gln Arg Leu Leu Pro Val Leu Cys Gln Ala His Gly
                645                 650                 655
Leu Thr Pro Asp Gln Val Val Ala Ile Ala Ser His Asp Gly Gly Lys
                660                 665                 670
Gln Ala Leu Glu Thr Val Gln Arg Leu Leu Pro Val Leu Cys Gln Ala
            675                 680                 685
His Gly Leu Thr Pro Glu Gln Val Val Ala Ile Ala Ser Asn Gly Gly
            690                 695                 700
Gly Lys Gln Ala Leu Glu Thr Val Gln Arg Leu Leu Pro Val Leu Cys
```

Gln Ala His Gly Leu Thr Pro Glu Gln Val Val Ala Ile Ala Ser Asn
705                 710                 715                 720

Asn Gly Gly Lys Gln Ala Leu Glu Thr Val Gln Arg Leu Leu Pro Val
            725                 730                 735

Leu Cys Gln Asp His Gly Leu Thr Pro Asp Gln Val Val Ala Ile Ala
                740                 745                 750

Ser His Asp Gly Gly Lys Gln Ala Leu Glu Ser Ile Val Ala Gln Leu
        755                 760                 765

Ser Arg Pro Asp Pro Ala Leu Ala Ala Leu Thr Asn Asp His Leu Val
770                 775                 780

Ala Leu Ala Cys Leu Gly Gly Arg Pro Ala Met Asp Ala Val Lys Lys
785                 790                 795                 800

Gly Leu Pro His Ala Pro Glu Leu Ile Arg Arg Val Asn Arg Arg Ile
        805                 810                 815

Gly Glu Arg Thr Ser His Arg Val Ala Leu Gln Leu Val Lys Ser Glu
            820                 825                 830

Leu Glu Glu Lys Lys Ser Glu Leu Arg His Lys Leu Lys Tyr Val Pro
                835                 840                 845

His Glu Tyr Ile Glu Leu Ile Glu Ile Ala Arg Asn Ser Thr Gln Asp
850                 855                 860

Arg Ile Leu Glu Met Lys Val Met Glu Phe Phe Met Lys Val Tyr Gly
865                 870                 875                 880

Tyr Arg Gly Lys His Leu Gly Gly Ser Arg Lys Pro Asp Gly Ala Ile
        885                 890                 895

Tyr Thr Val Gly Ser Pro Ile Asp Tyr Gly Val Ile Val Asp Thr Lys
            900                 905                 910

Ala Tyr Ser Gly Gly Tyr Asn Leu Pro Ile Gly Gln Ala Asp Glu Met
                915                 920                 925

Gln Arg Tyr Val Glu Glu Asn Gln Thr Arg Asn Lys His Ile Asn Pro
930                 935                 940

Asn Glu Trp Trp Lys Val Tyr Pro Ser Ser Val Thr Glu Phe Lys Phe
945                 950                 955                 960

Leu Phe Val Ser Gly His Phe Lys Gly Asn Tyr Lys Ala Gln Leu Thr
        965                 970                 975

Arg Leu Asn His Ile Thr Asn Cys Asn Gly Ala Val Leu Ser Val Glu
            980                 985                 990

Glu Leu Leu Ile Gly Gly Glu Met Ile Lys Ala Gly Thr Leu Thr
                995                 1000                1005

Leu Glu Glu Val Arg Arg Lys Phe Asn Asn Gly Glu Ile Asn Phe
    1010                1015                1020

1025                1030                1035

<210> SEQ ID NO 123
<211> LENGTH: 4035
<212> TYPE: DNA
<213> ORGANISM: Artificial Sequence
<220> FEATURE:
<223> OTHER INFORMATION: Xanthomonas ssp, Escherichia coli

<400> SEQUENCE: 123
atggctagct cccccccgaa gaagaagagg aaggtcagct ggaaggatgc tagcggctgg    60
agcaggatgc acgctgatcc aatcaggccg aggaggccaa gcccagcaag ggagctgctg   120
ccaggcccac agccagatag ggtgcagcca accgccgata ggggcgtgag cgctccagct   180
ggcagcccgc tggatggcct gccagctagg aggaccgtga gcaggaccag gctgccgagc   240

-continued

```
ccaccagctc cgagcccagc cttcagcgct ggcagcttca gcgatctgct gaggccattc    300
gatccgagcc tgctggatac atcgctgctg gatagcatgc cagctgtggg caccccacac    360
accgctgctg ctccagctga gtgggatgag atgcagtccg ccctccgcgc cgccgacgac    420
ccgccgccaa ccgtgagggt ggccgtgacc gctgctaggc cgccaagggc taagccagct    480
ccaaggagga gggccgctca gccaagcgat gctagccccg ccgcgcaggt cgacctcagg    540
accctgggct acagccagca gcagcaggag aagatcaagc cgaaggtgag gagcaccgtg    600
gcccagcacc acgaggctct ggtgggccac ggcttcaccc acgctcacat cgtggccctg    660
agccagcacc cagctgctct gggcaccgtg gctgtgacct accagcacat catcaccgcc    720
ctgccagagg ctacccacga ggacatcgtg ggcgtgggca agcagtggag cggcgctagg    780
gccctggagg ctctgctgac cgatgctggc gagctgaggg gccaccgct ccagctggat     840 accggccagc tggtgaagat cgccaagagg ggcggcgtga ccgctatgga ggctgtgcac    900
gccagcagga cgctctgac cggcgctcca ctgaacctga cccccgacca ggtggtggcc     960
atcgcgagca acatcggcgg caagcaggct ctcgaaaccg tgcagaggct gctcccggtg   1020
ctgtgccagg cccacggcct caccccagac caggtcgtcg cgatcgcctc caacggcggc   1080
ggcaagcagg ccctggagac tgtgcagcgc ctgctgcccg tcctgtgcca ggaccacggc   1140
ctcaccccgg agcaggtcgt cgctatcgct agcaacatcg gcggcaagca ggcgctcgaa   1200
accgtccaga ggctcctccc agtcctctgc caggatcacg gcctgacccc ggatcaggtg   1260
gtcgccatcg cttccaacaa cggcggcaag caggcgctgg agactgtcca gcgcctcctc   1320
ccagtcctct gccaggcgca cggcctcacc cccgatcagg tcgtggcgat cgcgagcaac   1380
atcggcggca agcaggctct cgaaaccgtg cagaggctgc tgccggtgct ctgccaggct   1440
cacggcctga ccccagacca ggtggtggct atcgcctcca caacggcggc caagcaggcc   1500
ctggagactg tgcagaggct cctcccggtc ctgtgccagg cccacggcct cacccccgag   1560
caggtcgtcg cgatcgctag caacatcggc ggcaagcagg ccctggagac tgtgcagagg   1620
ctgctcccag tcctgtgcca ggcccacggc ctgaccccg agcaggtggt cgcgatcgcg   1680
agcaacggcg gcggcaagca ggcgctcgaa accgtccaga ggctcctccc cgtgctctgc   1740
caggatcacg gcctgacccc agagcaggtg gtggctatcg cgagccacga cggcggcaag   1800
caggctctcg aaaccgtcca gaggctcctc ccagtgctct gccaggctca cggcctcacc   1860
ccggaccagg tcgtcgccat cgcttcccac gatggcggca agcaggctct cgaaaccgtg   1920
cagaggctgc tccggtgct gtgccaggcc cacggcctca ccccagacca ggtcgtcgcg   1980
atcgcctcca acggcggcgg caagcaggcc ctggagactg tgcagcgcct gctgcccgtc   2040
ctgtgccagg accacggcct caccccgag caggtcgtcg ctatcgctag ccacgacggc   2100
ggcaagcagg cgctcgaaac cgtccagagg ctcctcccag tcctctgcca ggatcacggc   2160 ctgaccccg atcaggtggt cgccatcgct tccaacggcg cggcaagca ggcgctggag    2220 actgtccagc gcctcctccc agtcctctgc caggcgcacg gcctcacccc cgatcaggtc   2280
gtggcgatcg cgagcaacat cggcggcaag caggctctcg aaaccgtgca gaggctgctg   2340
ccggtgctct gccaggctca cggcctgacc ccagaccagg tggtggctat cgcctccaac   2400
aacggcggca agcaggccct ggagactgtg cagaggctcc tcccggtcct gtgccaggcc   2460 cacgcctca ccccgagca ggtcgtcgcg atcgctagca acatcggcgg caagcaggcc    2520
ctggagactg tgcagaggct gctcccagtc ctgtgccagg cccacggcct gaccccgag   2580
```

| | |
|---|---|
| caggtggtcg cgatcgcgag caacaacggc ggcaagcagg cgctcgaaac cgtccagagg | 2640 |
| ctcctcccg tgctctgcca ggatcacggc ctcaccccg accaggtcgt ggctatcgcg | 2700 |
| tccaacggcg gcggcaagca ggctctcgag agcatcgtgg cccagctgag caggccggac | 2760 |
| ccggccctgg ccgccctgac caacgatcac ctggtggctc tggcctgcct gggcggcagg | 2820 |
| ccagccatgg acgctgtgaa gaagggcctg ccgcacgctc cagagctgat ccgcagggtg | 2880 |
| aacaggagga tcggcgagag gaccagccac agggtggccg actacgctca ggtggtgagg | 2940 |
| gtgctggagt tcttccagtg ccacagccac ccggcctacg ccttcgacga ggctatgacc | 3000 |
| cagttcggca tgagcaggaa cggcctggtg cagctgttca ggagggtggg cgtgaccgag | 3060 |
| ctggaggcta ggggcggcac cctgccgcca gctagccaga ggtgggaccg catcctccag | 3120 |
| gccagcggca tgaaaagggc taagccaagc ccgaccagcg ctcagacccc agatcaggct | 3180 |
| agcctgcacg ctttcgccga cagcctggag agggatctgg atgctccgag cccaatgcac | 3240 |
| gagggcgacc agaccagggc cagcagcagg aagaggagca ggagcgacag gctgtgacc | 3300 |
| ggcccgagcg cccagcaggc tgtggaggtg agggtgccag agcagaggga tgccctgcac | 3360 |
| ctgccgctga gctggagggt gaagaggcca aggaccagga tctggggcgg cctgccagat | 3420 |
| ccgggcaccc caaccgctgc tgatcagctc gtgaagagcg agctggagga gaagaagagc | 3480 |
| gagctgaggc ataaactgaa gtacgtgcca cacgagtaca tcgagctgat cgagatcgcc | 3540 |
| aggaacagca cccaggatcg catcctggag atgaaggtga tggagttctt catgaaagtg | 3600 |
| tacggctaca ggggcaagca cctgggcggc agcaggaagc agatggcgc catctacacc | 3660 |
| gtgggcagcc aatcgacta cggcgtgatc gtggatacca aggcttacag cggcggctac | 3720 |
| aacctgccga tcggccaggc tgatgagatg cagaggtacg tggaggagaa tcaaaccagg | 3780 |
| aacaagcaca tcaaccccaaa cgagtggtgg aaggtgtacc cgagcagcgt gaccgagttc | 3840 |
| aagttcctgt tcgtgagcgg ccacttcaag ggcaactaca aggctcagct caccaggctg | 3900 |
| aaccacatca ccaactgcaa cggcgccgtg ctgagcgtgg aggagctgct gatcggcggc | 3960 |
| gagatgatca aggctggcac cctgaccctg gaggaggtga ggaggaagtt caacaacggc | 4020 |
| gagatcaact tctga | 4035 |

<210> SEQ ID NO 124
<211> LENGTH: 4035
<212> TYPE: DNA
<213> ORGANISM: Artificial Sequence
<220> FEATURE:
<223> OTHER INFORMATION: Xanthomonas ssp, Escherichia coli

<400> SEQUENCE: 124

| | |
|---|---|
| atggctagct cccccccgaa gaagaagagg aaggtcagct ggaaggatgc tagcggctgg | 60 |
| agcaggatgc acgctgatcc aatcaggccg aggaggccaa gcccagcaag ggagctgctg | 120 |
| ccaggcccac agccagatag ggtgcagcca accgccgata ggggcgtgag cgctccagct | 180 |
| ggcagcccgc tggatggcct gccagctagg aggaccgtga gcaggaccag gctgccgagc | 240 |
| ccaccagctc cgagcccagc cttcagcgct ggcagcttca gcgatctgct gaggccattc | 300 |
| gatccgagcc tgctggatac atcgctgctg atagcatgc cagctgtggg cacccccacac | 360 |
| accgctgctg ctccagctga gtgggatgag atgcagtccg ccctccgcgc cgccgacgac | 420 |
| ccgccgccaa ccgtgagggt ggccgtgacc gctgctaggc cgccaagggc taagccagct | 480 |
| ccaaggagga gggccgctca gccaagcgat gctagccccg ccgcgcaggt cgacctcagg | 540 |
| accctgggct acagccagca gcagcaggag aagatcaagc cgaaggtgag gagcaccgtg | 600 |

```
gcccagcacc acgaggctct ggtgggccac ggcttcaccc acgctcacat cgtggccctg     660
agccagcacc cagctgctct gggcaccgtg gctgtgacct accagcacat catcaccgcc     720
ctgccagagg ctacccacga ggacatcgtg ggcgtgggca agcagtggag cggcgctagg     780
gccctggagg ctctgctgac cgatgctggc gagctgaggg gccccaccgct ccagctggat    840 accggccagc tggtgaagat cgccaagagg ggcggcgtga ccgctatgga ggctgtgcac     900
gccagcagga acgctctgac cggcgctcca ctgaacctga ccccgacca ggtggtggcc      960 atcgcgagca acatcggcgg caagcaggct ctcgaaaccg tgcagaggct gctcccggtg    1020
ctgtgccagc ccacggcct cacccccgac caggtcgtcg cgatcgcctc ccacgatggc     1080
ggcaagcagg ccctggagac tgtgcagcgc ctgctgcccg tcctgtgcca ggaccacggc    1140
ctcaccccgg agcaggtcgt cgctatcgct agcaacatcg gcggcaagca ggcgctcgaa    1200
accgtccaga ggctcctccc agtcctctgc caggatcacg gcctgacccc ggatcaggtg    1260
gtcgccatcg cttccaacat cggcggcaag caggcgctgg agactgtcca gcgcctcctc    1320
ccagtcctct gccaggcgca cggcctcacc cccgatcagg tcgtggcgat cgcgagcaac    1380
aacggcggca agcaggctct cgaaaccgtg cagaggctgc tgccggtgct gctgccaggct   1440 cacggcctga ccccagacca ggtggtggct atcgcctccc acgatggcgg caagcaggcc    1500
ctggagactg tgcagaggct cctcccggtc tgtgccagg cccacggcct caccccgag     1560 caggtcgtcg cgatcgctag caacggcggc ggcaagcagg ccctggagac tgtgcagagg    1620
ctgctcccag tcctgtgcca ggcccacggc ctgaccccg agcaggtggt cgcgatcgcg    1680
agcaacggcg gcggcaagca ggcgctcgaa accgtccaga ggctcctccc cgtgctctgc    1740
caggatcacg gcctgacccc agagcaggtg gtggctatcg cgagcaacaa cggcggcaag    1800
caggctctcg aaaccgtcca gaggctcctc ccagtgctct gccaggctca cggcctcacc    1860
ccggaccagg tcgtcgccat cgcttccac gatggcggca agcaggctct cgaaaccgtg    1920
cagaggctgc tcccggtgct gtgccaggcc acggcctca ccccagacca ggtcgtcgcg   1980
atcgcctcca acatcggcgg caagcaggcc ctggagactg tgcagcgcct gctgcccgtc    2040
ctgtgccagg accacggcct cacccccgag caggtcgtcg ctatcgctag caacggcggc    2100
ggcaagcagg cgctcgaaac cgtccagagg ctcctcccag tcctctgcca ggatcacggc    2160 ctgacccccgg atcaggtggt cgccatcgct tccaacaacg gcggcaagca ggcgctggag    2220
actgtccagc gcctcctccc agtcctctgc caggcgcacg gcctcacccc cgatcaggtc    2280
gtggcgatcg cgagccacga cggcggcaag caggctctcg aaaccgtgca gaggctgctg    2340
ccggtgctct gccaggctca cggcctgacc ccagaccagg tggtggctat cgcctcccac    2400 gatgcggca agcaggccct ggagactgtg cagaggctcc tccgggtcct gtgccaggcc    2460
cacggcctca ccccgagca ggtcgtcgcg atcgctagca acggcggcgg caagcaggcc    2520
ctggagactg tgcagaggct gctcccagtc ctgtgccagg cccacggcct gaccccgag    2580 caggtggtcg cgatcgcgag caacaacggc ggcaagcagg cgctcgaaac cgtccagagg    2640 ctcctcccg tgctctgcca ggatcacggc ctcaccccg accaggtcgt ggctatcgcg     2700
tcccacgatg gcggcaagca ggctctcgag agcatcgtgg cccagctgag caggccggac    2760
ccggccctgg ccgccctgac caacgatcac ctggtggctc tggcctgcct gggcggcagg    2820
ccagccatgg acgctgtgaa gaagggcctg ccgcacgctc cagagctgat ccgcagggtg    2880
aacaggagga tcggcgagag gaccagccac agggtggccg actacgctca ggtggtgagg    2940
```

```
gtgctggagt tcttccagtg ccacagccac ccggcctacg ccttcgacga ggctatgacc    3000
cagttcggca tgagcaggaa cggcctggtg cagctgttca ggagggtggg cgtgaccgag    3060
ctggaggcta ggggcggcac cctgccgcca gctagccaga ggtgggaccg catcctccag    3120
gccagcggca tgaaaagggc taagccaagc ccgaccagcg ctcagacccc agatcaggct    3180
agcctgcacg ctttcgccga cagcctggag agggatctgg atgctccgag cccaatgcac    3240
gagggcgacc agaccagggc cagcagcagg aagaggagca ggagcgacag ggctgtgacc    3300
ggcccgagcg cccagcaggc tgtggaggtg agggtgccag agcagaggga tgccctgcac    3360
ctgccgctga gctggagggt gaagaggcca aggaccagga tctggggcgg cctgccagat    3420
ccgggcaccc caaccgctgc tgatcagctc gtgaagagcg agctggagga aagaagagc    3480 gagctgaggc ataaactgaa gtacgtgcca cacgagtaca tcgagctgat cgagatcgcc    3540
aggaacagca cccaggatcg catcctggag atgaaggtga tggagttctt catgaaagtg    3600
tacggctaca ggggcaagca cctgggcggc agcaggaagc cagatggcgc catctacacc    3660
gtgggcagcc caatcgacta cggcgtgatc gtggatacca aggcttacag cggcggctac    3720
aacctgccga tcggccaggc tgatgagatg cagaggtacg tggaggagaa tcaaaccagg    3780
aacaagcaca tcaaccccaa cgagtggtgg aaggtgtacc cgagcagcgt gaccgagttc    3840
aagttcctgt tcgtgagcgg ccacttcaag ggcaactaca aggctcagct caccaggctg    3900
aaccacatca ccaactgcaa cggcgccgtg ctgagcgtgg aggagctgct gatcggcggc    3960
gagatgatca aggctggcac cctgacccctg gaggaggtga ggaggaagtt caacaacggc    4020
gagatcaact tctga                                                    4035

<210> SEQ ID NO 125
<211> LENGTH: 3114
<212> TYPE: DNA
<213> ORGANISM: Artificial Sequence
<220> FEATURE:
<223> OTHER INFORMATION: Xanthomonas ssp, Escherichia coli

<400> SEQUENCE: 125
atggctagct cccccccgaa gaagaagagg aaggtcagct ggaaggatgc tagcggctgg      60
agcaggatgc acgctgatcc atggccaagg aggagggccg ctcagccaag cgatgctagc     120
cccgccgcgc aggtcgacct caggaccctg ggctacagcc agcagcagca ggagaagatc     180
aagccgaagg tgaggagcac cgtggcccag caccacgagg ctctggtggg ccacggcttc     240
acccacgctc acatcgtggc cctgagccag cacccagctg ctctgggcac cgtggctgtg     300
acctaccagc acatcatcac cgccctgcca gaggctaccc acgaggacat cgtgggcgtg     360
ggcaagcagt ggagcggcgc tagggccctg gaggctctgc tgaccgatgc tggcgagctg     420
aggggcccac cgctccagct ggataccggc cagctggtga agatcgccaa gaggggcggc     480
gtgaccgcta tggaggctgt gcacgccagc aggaacgctc tgaccggcgc tccactgaac     540 ctgaccccccg accaggtggt ggccatcgcg agcaacatcg gcggcaagca ggctctcgaa     600
accgtgcaga ggctgctccc ggtgctgtgc caggccacg gcctcacccc agaccaggtc     660
gtcgcgatcg cctccaacgg cggcggcaag caggccctgg agactgtgca gcgcctgctg     720
cccgtcctgt gccaggacca cggcctcacc ccggagcagg tcgtcgctat cgctagcaac     780
atcggcggca agcaggcgct cgaaaccgtc cagaggctcc tcccagtcct tgccaggat     840 cacggcctga cccccggatca ggtggtcgcc atcgcttcca caacggcgg caagcaggcg     900 ctggagactg tccagcgcct cctcccagtc ctctgccagg cgcacggcct cacccccgat     960
```

```
caggtcgtgg cgatcgcgag caacatcggc ggcaagcagg ctctcgaaac cgtgcagagg    1020
ctgctgccgg tgctctgcca ggctcacggc ctgaccccag accaggtggt ggctatcgcc    1080
tccaacaacg gcggcaagca ggccctggag actgtgcaga ggctcctccc ggtcctgtgc    1140
caggcccacg gcctcacccc cgagcaggtc gtcgcgatcg ctagcaacat cggcggcaag    1200
caggccctgg agactgtgca gaggctgctc ccagtcctgt gccaggccca cggcctgacc    1260
cccgagcagg tggtcgcgat cgcgagcaac ggcggcggca agcaggcgct cgaaaccgtc    1320
cagaggctcc tccccgtgct ctgccaggat cacggcctga ccccagagca ggtggtggct    1380
atcgcgagcc acgacggcgg caagcaggct ctcgaaaccg tccagaggct cctcccagtg    1440
ctctgccagg ctcacggcct caccccggac caggtcgtcg ccatcgcttc ccacgatggc    1500
ggcaagcagg ctctcgaaac cgtgcagagg ctgctcccgg tgctgtgcca ggcccacggc    1560
ctcaccccag accaggtcgt cgcgatcgcc tccaacggcg gcggcaagca ggccctggag    1620
actgtgcagc gcctgctgcc cgtcctgtgc caggaccacg gcctcacccc ggagcaggtc    1680
gtcgctatcg ctagccacga cggcggcaag caggcgctcg aaaccgtcca gaggctcctc    1740
ccagtcctct gccaggatca cggcctgacc ccggatcagg tggtcgccat cgcttccaac    1800
ggcggcggca agcaggcgct ggagactgtc agcgcctcc tcccagtcct ctgccaggcg    1860 cacgcctca ccccgatca gtcgtggcg atcgcgagca acatcggcgg caagcaggct    1920
ctcgaaaccg tgcagaggct gctgccggtg ctctgccagg ctcacggcct gaccccagac    1980
caggtggtgg ctatcgcctc caacaacggc ggcaagcagg ccctggagac tgtgcagagg    2040
ctcctcccgg tcctgtgcca ggcccacggc ctcaccccgg agcaggtcgt cgcgatcgct    2100
agcaacatcg gcggcaagca ggccctggag actgtgcaga ggctgctccc agtcctgtgc    2160
caggcccacg gcctgacccc cgagcaggtg gtcgcgatcg cgagcaacaa cggcggcaag    2220
caggcgctcg aaaccgtcca gaggctcctc cccgtgctct gccaggatca cggcctcacc    2280
cccgaccagg tcgtggctat cgcgtccaac ggcggcggca agcaggctct cgagagcatc    2340
gtggcccagc tgagcaggcc ggacccggcc ctggccgccc tgaccaacga tcacctggtg    2400
gctctggcct gcctgggcgg caggccagcc atggacgctg tgaagaaggg cctgccgcac    2460
gctccagagc tgatccgcag ggtgaacagg aggatcggcg agaggaccag ccacagggtg    2520
gccctgcagc tcgtgaagag cgagctggag gagaagaaga gcgagctgag gcataaactg    2580
aagtacgtgc acacgagta catcgagctg atcgagatcg ccaggaacag cacccaggat    2640
cgcatcctgg agatgaaggt gatggagttc ttcatgaaag tgtacggcta caggggcaag    2700
cacctgggcg gcagcaggaa gccagatggc gccatctaca ccgtgggcag cccaatcgac    2760 tacgcgtga tcgtggatac caaggcttac agcggcggct acaacctgcc gatcggccag    2820
gctgatgaga tgcagaggta cgtggaggag aatcaaacca ggaacaagca catcaaccca    2880
aacgagtggt ggaaggtgta cccgagcagc gtgaccgagt tcaagttcct gttcgtgagc    2940
ggccacttca agggcaacta caaggctcag ctcaccaggc tgaaccacat caccaactgc    3000
aacggcgccg tgctgagcgt ggaggagctg ctgatcggcg gcgagatgat caaggctggc    3060
accctgaccc tggaggaggt gaggaggaag ttcaacaacg gcgagatcaa cttc         3114
```

<210> SEQ ID NO 126
<211> LENGTH: 3114
<212> TYPE: DNA
<213> ORGANISM: Artificial Sequence
<220> FEATURE:

<223> OTHER INFORMATION: Xanthomonas ssp, Escherichia coli

<400> SEQUENCE: 126

```
atggctagct cccccccgaa gaagaagagg aaggtcagct ggaaggatgc tagcggctgg      60
agcaggatgc acgctgatcc atggccaagg aggagggccg ctcagccaag cgatgctagc     120
cccgccgcgc aggtcgacct caggaccctg gctacagcc agcagcagca ggagaagatc      180
aagccgaagg tgaggagcac cgtggcccag caccacgagg ctctggtggg ccacggcttc     240
acccacgctc acatcgtggc cctgagccag cacccagctg ctctgggcac cgtggctgtg     300
acctaccagc acatcatcac cgccctgcca gaggctaccc acgaggacat cgtgggcgtg     360
ggcaagcagt ggagcggcgc tagggccctg gaggctctgc tgaccgatgc tggcgagctg     420
aggggcccac cgctccagct ggataccggc cagctggtga agatcgccaa gaggggcggc     480
gtgaccgcta tggaggctgt gcacgccagc aggaacgctc tgaccggcgc tccactgaac     540
ctgaccccg accaggtggt ggccatcgcg agcaacatcg gcggcaagca ggctctcgaa      600
accgtgcaga ggctgctccc ggtgctgtgc caggcccacg gctcaccccc agaccaggtc     660
gtcgcgatcg cctcccacga tggcggcaag caggccctgg agactgtgca gcgcctgctg     720
cccgtcctgt gccaggacca cggcctcacc ccggagcagg tcgtcgctat cgctagcaac     780
atcggcggca gcaggcgct cgaaaccgtc cagaggctcc tcccagtcct ctgccaggat      840
cacggcctga ccccggatca ggtggtcgcc atcgcttcca acatcggcgg caagcaggcg     900
ctggagactg tccagcgcct cctcccagtc tctgccagg cgcacggcct cacccccgat      960
caggtcgtgg cgatcgcgag caacaacggc ggcaagcagg ctctcgaaac cgtgcagagg    1020
ctgctgccgg tgctctgcca ggctcacggc ctgaccccag accaggtggt ggctatcgcc    1080
tcccacgatg gcggcaagca ggccctggag actgtgcaga ggctcctccc ggtcctgtgc    1140
caggcccacg gctcaccccc gagcaggtc gtcgcgatcg ctagcaacgg cggcggcaag     1200
caggccctgg agactgtgca gaggctgctc cagtcctgt gccaggccca cggcctgacc     1260
cccgagcagg tggtcgcgat cgcgagcaac ggcggcggca agcaggcgct cgaaaccgtc    1320
cagaggctcc tccccgtgct ctgccaggat cacggcctga ccccagagca ggtggtggct    1380
atcgcgagca acaacggcgg caagcaggct ctcgaaaccg tccagaggct cctcccagtg    1440
ctctgccagg ctcacggcct cacccccgac caggtcgtcg ccatcgcttc ccacgatggc    1500
ggcaagcagg ctctcgaaac cgtgcagagg ctgctcccgg tgctgtgcca ggcccacggc    1560
ctcaccccag accaggtcgt cgcgatcgcc tccaacatcg gcggcaagca ggccctggag    1620
actgtgcagc gcctgctgcc cgtcctgtgc caggaccacg gcctcaccc ggagcaggtc     1680
gtcgctatcg ctagcaacgg cggcggcaag caggcgctcg aaaccgtcca gaggctcctc    1740
ccagtcctct gccaggatca cggcctgacc ccggatcagg tggtcgccat cgcttccaac    1800
aacggcggca gcaggcgct ggagactgtc agcgcctcc tcccagtcct ctgccaggcg      1860
cacggcctca ccccgatca ggtcgtggcg atcgcgagcc acgacggcgg caagcaggct     1920
ctcgaaaccg tgcagaggct gctgccggtg ctctgccagg ctcacggcct gaccccagac    1980
caggtggtgg ctatcgcctc ccacgatggc ggcaagcagg ccctggagac tgtgcagagg    2040
ctcctcccgg tcctgtgcca ggcccacggc ctcaccccg agcaggtcgt cgcgatcgct     2100
agcaacggcg gcggcaagca ggccctggag actgtgcaga ggctgctccc agtcctgtgc    2160
caggcccacg gcctgacccc cgagcaggtg gtcgcgatcg cgagcaacaa cggcggcaag    2220
caggcgctcg aaaccgtcca gaggctcctc cccgtgctct gccaggatca cggcctcacc    2280
```

```
cccgaccagg tcgtggctat cgcgtcccac gatggcggca agcaggctct cgagagcatc      2340
gtggcccagc tgagcaggcc ggacccggcc ctggccgccc tgaccaacga tcacctggtg      2400
gctctggcct gcctgggcgg caggccagcc atggacgctg tgaagaaggg cctgccgcac      2460
gctccagagc tgatccgcag ggtgaacagg aggatcggcg agaggaccag ccacagggtg      2520
gccctgcagc tcgtgaagag cgagctggag gagaagaaga gcgagctgag gcataaactg      2580
aagtacgtgc cacacgagta catcgagctg atcgagatcg ccaggaacag cacccaggat      2640
cgcatcctgg agatgaaggt gatggagttc ttcatgaaag tgtacggcta caggggcaag      2700
cacctgggcg gcagcaggaa gccagatggc gccatctaca ccgtgggcag cccaatcgac      2760
tacggcgtga tcgtggatac caaggcttac agcggcggct acaacctgcc gatcggccag      2820
gctgatgaga tgcagaggta cgtggaggag aatcaaacca ggaacaagca catcaacccca     2880 aacgagtggt ggaaggtgta cccgagcagc gtgaccgagt tcaagttcct gttcgtgagc      2940
ggccacttca agggcaacta caaggctcag ctcaccaggc tgaaccacat caccaactgc      3000
aacggcgccg tgctgagcgt ggaggagctg ctgatcggcg gcgagatgat caaggctggc      3060
accctgaccc tggaggaggt gaggaggaag ttcaacaacg gcgagatcaa cttc            3114
```

<210> SEQ ID NO 127
<211> LENGTH: 20
<212> TYPE: DNA
<213> ORGANISM: Artificial Sequence
<220> FEATURE:
<223> OTHER INFORMATION: Zea mays

<400> SEQUENCE: 127

```
aaccagcgaa ccagcagcgt                                                    20
```

<210> SEQ ID NO 128
<211> LENGTH: 21
<212> TYPE: DNA
<213> ORGANISM: Artificial Sequence
<220> FEATURE:
<223> OTHER INFORMATION: Zea mays

<400> SEQUENCE: 128

```
tttgctacct gcggtaggtg g                                                  21
```

<210> SEQ ID NO 129
<211> LENGTH: 22
<212> TYPE: DNA
<213> ORGANISM: Artificial Sequence
<220> FEATURE:
<223> OTHER INFORMATION: Zea mays

<400> SEQUENCE: 129

```
cggccaattc ctgcattcgt ac                                                 22
```

<210> SEQ ID NO 130
<211> LENGTH: 23
<212> TYPE: DNA
<213> ORGANISM: Artificial Sequence
<220> FEATURE:
<223> OTHER INFORMATION: Zea mays

<400> SEQUENCE: 130

```
gaattgggta ccagcttgca tgc                                                23
```

<210> SEQ ID NO 131

```
<211> LENGTH: 23
<212> TYPE: DNA
<213> ORGANISM: Artificial Sequence
<220> FEATURE:
<223> OTHER INFORMATION: Zea mays

<400> SEQUENCE: 131
gtgccatgta tcggttctag agc                                             23

<210> SEQ ID NO 132
<211> LENGTH: 27
<212> TYPE: DNA
<213> ORGANISM: Artificial Sequence
<220> FEATURE:
<223> OTHER INFORMATION: Zea mays

<400> SEQUENCE: 132
cattaaatta cggacccaaa agcttac                                         27

<210> SEQ ID NO 133
<211> LENGTH: 3494
<212> TYPE: DNA
<213> ORGANISM: Artificial Sequence
<220> FEATURE:
<223> OTHER INFORMATION: Escherichia coli, Zea mays, Agrobacterium
      tumefaciens

<400> SEQUENCE: 133
ctgcagtgca gcgtgacccg gtcgtgcccc tctctagaga taatgagcat tgcatgtcta     60
agttataaaa aattaccaca tattttttt gtcacacttg tttgaagtgc agtttatcta    120
tctttataca tatatttaaa ctttactcta cgaataatat aatctatagt actacaataa    180
tatcagtgtt ttagagaatc atataaatga acagttagac atggtctaaa ggacaattga    240
gtattttgac aacaggactc tacagtttta tctttttagt gtgcatgtgt tctcctttt    300 ttttgcaaat agcttcacct atataatact tcatccattt tattagtaca tccatttagg    360
gtttagggtt aatggttttt atagactaat tttttagta catctatttt attctatttt    420
agcctctaaa ttaagaaaac taaaactcta ttttagtttt tttatttaat aatttagata    480
taaaatagaa taaaataaag tgactaaaaa ttaaacaaat acccctttaag aaattaaaaa   540 aactaaggaa acatttttct tgtttcgagt agataatgcc agcctgttaa acgccgtcga    600
cgagtctaac ggacaccaac cagcgaacca gcagcgtcgc gtcgggccaa gcgaagcaga    660
cggcacggca tctctgtcgc tgcctctgga cccctctcga gagttccgct ccaccgttgg    720
acttgctccg ctgtcggcat ccagaaattg cgtggcggag cggcagacgt gagccggcac    780
ggcaggcggc ctcctcctcc tctcacggca ccggcagcta cggggattc cttcccacc     840 gctccttcgc tttcccttcc tcgccgcg taataaatag acacccctc cacccctct       900 ttccccaacc tcgtgttgtt cggagcgcac acacacacaa ccagatctcc cccaaatcca    960
cccgtcggca cctccgcttc aaggtacgcc gctcgtcctc cccccccccc cctctctacc   1020
ttctctagat cggcgttccg gtccatggtt agggcccggt agttctactt ctgttcatgt   1080
ttgtgttaga tccgtgtttg tgttagatcc gtgctgctag cgttcgtaca cggatgcgac   1140
ctgtacgtca gacacgttct gattgctaac ttgccagtgt ttctctttgg ggaatcctgg   1200
gatggctcta gccgttccgc agacgggatc gatttcatga ttttttttgt ttcgttgcat   1260
agggtttggt ttgcccttt cctttatttc aatatatgcc gtgcacttgt ttgtcgggtc    1320
atcttttcat gcttttttt gtcttggttg tgatgatgtg gtctggttgg gcggtcgttc   1380
```

-continued

```
tagatcggag tagaattctg tttcaaacta cctggtggat ttattaattt tggatctgta    1440
tgtgtgtgcc atacatattc atagttacga attgaagatg atggatggaa atatcgatct    1500
aggataggta tacatgttga tgcgggtttt actgatgcat atacagagat gcttttttgtt  1560
cgcttggttg tgatgatgtg gtgtggttgg gcggtcgttc attcgttcta gatcggagta    1620
gaatactgtt tcaaactacc tggtgtattt attaattttg gaactgtatg tgtgtgtcat    1680
acatcttcat agttacgagt ttaagatgga tggaaatatc gatctaggat aggtatacat    1740
gttgatgtgg gttttactga tgcatataca tgatggcata tgcagcatct attcatatgc    1800
tctaaccttg agtacctatc tattataata aacaagtatg ttttataatt attttgatct    1860
tgatatactt ggatgatggc atatgcagca gctatatgtg gatttttta gccctgcctt    1920
catacgctat ttatttgctt ggtactgttt cttttgtcga tgctcaccct gttgtttggt    1980
gttacttctg cagggatccc cgatcatgca aaaactcatt aactcagtgc aaaactatgc    2040
ctggggcagc aaaacggcgt tgactgaact ttatggtatg gaaaatccgt ccagccagcc    2100
gatggccgag ctgtggatgg gcgcacatcc gaaaagcagt tcacgagtgc agaatgccgc    2160
cggagatatc gtttcactgc gtgatgcgat tgagagtgat aaatcgactc tgctcggaga    2220
ggccgttgcc aaacgctttg gcgaactgcc tttcctgttc aaagtattat gcgcagcaca    2280
gccactctcc attcaggttc atccaaacaa acacaattct gaaatcggtt ttgccaaaga    2340
aaatgccgca ggtatcccga tggatgccgc cgagcgtaac tataaagatc ctaaccacaa    2400
gccggagctg gtttttgcgc tgacgccttt ccttgcgatg aacgcgtttc gtgaatttc    2460
cgagattgtc tccctactcc agccggtcgc aggtgcacat ccggcgattg ctcactttt    2520
acaacagcct gatgccgaac gtttaagcga actgttcgcc agcctgttga atatgcaggg    2580
tgaagaaaaa tcccgcgcgc tggcgatttt aaaatcggcc ctcgatagcc agcatggtga    2640
accgtggcaa acgattcgtt taatttctga attttacccg gaagacagcg gtctgttctc    2700
cccgctattg ctgaatgtgg tgaaattgaa ccctggcgaa gcgatgttcc tgttcgctga    2760
aacaccgcac gcttacctgc aaggcgtggc gctggaagtg atggcaaact ccgataacgt    2820
gctgcgtgcg ggtctgacgc ctaaatacat tgatattccg gaactggttg ccaatgtgaa    2880
attcgaagcc aaaccggcta accagttgtt gacccagccg gtgaaacaag gtgcagaact    2940
ggacttcccg attccagtgg atgattttgc cttctcgctg catgaccta gtgataaaga    3000
aaccaccatt agccagcaga gtgccgccat tttgttctgc gtcgaaggcg atgcaacgtt    3060
gtggaaaggt tctcagcagt tacagcttaa accgggtgaa tcagcgttta ttgccgccaa    3120
cgaatcaccg gtgactgtca aaggccacgg ccgtttagcg cgtgtttaca acaagctgta    3180
agagcttact gaaaaaatta acatctcttg ctaagctggg agctcgatcc gtcgacctgc    3240
agatcgttca acatttggc aataaagttt cttaagattg aatcctgttg ccggtcttgc    3300
gatgattatc atataatttc tgttgaatta cgttaagcat gtaataatta acatgtaatg    3360
catgacgtta tttatgagat gggttttat gattagagtc ccgcaattat acatttaata    3420
cgcgatagaa acaaaatat agcgcgcaaa ctaggataaa ttatcgcgcg cggtgtcatc    3480
tatgttacta gatc                                                     3494
```

<210> SEQ ID NO 134
<211> LENGTH: 8415
<212> TYPE: DNA
<213> ORGANISM: Artificial Sequence
<220> FEATURE:
<223> OTHER INFORMATION: Zea mays, Escherichia coli, Bacillus thuringiensis, Agrobacterium tumefaciens

<400> SEQUENCE: 134

```
gaaggcggga aacgacaatc tgatcatgag cggagaatta agggagtcac gttatgaccc      60
ccgccgatga cgcgggacaa gccgttttac gtttggaact gacagaaccg caacgctgca     120
ggaattggcc gcagcggcca tttaaatcaa ttgggcgcgc cgaattcgag ctcggtacaa     180
gcttgcacat gacaacaatt gtaagaggat ggagaccaca acgatccaac aatacttctg     240
cgacgggctg tgaagtatag agaagttaaa cgcccaaaag ccattgtgtt tggaattttt     300
agttattcta tttttcatga tgtatcttcc tctaacatgc cttaatttgc aaatttggta     360
taactactga ttgaaaatat atgtatgtaa aaaaatacta agcatatttt tgaagctaaa     420
catgatgtta tttaagaaaa tatgttgtta acagaataag attaatatcg aaatggaaac     480
atctgtaaat tagaatcatc ttacaagcta agagatgttc acgctttgag aaacttcttc     540
agatcatgac cgtagaagta gctctccaag actcaacgaa ggctgctgca attccacaaa     600
tgcatgacat gcatccttgt aaccgtcgtc gccgctataa acacggataa ctcaattccc     660
tgctccatca atttagaaat gagcaagcaa gcacccgatc gctcacccca tatgcaccaa     720
tctgactccc aagctctgtt tcgcattagt accgccagca ctccacctat agctaccaat     780
tgagaccttt ccagcctaag cagatcgatt gatcgttaga gtcaaagagt tggtggtacg     840
ggtactttaa ctaccatgga atgatggggc gtgatgtaga gcgaaagcg cctccctacg     900
cggaacaaca ccctcgccat gccgctcgac tacagcctcc tcctcgtcgg cgccacaacg     960
agggagcccg tggtcgcagc caccgaccag catgtctctg tgtcctcgtc cgacctcgac    1020
atgtcatggc aaacagtcgg acgccagcac cagactgacg acatgagtct ctgaagagcc    1080
cgccacctag aaagatccga gccctgctgc tggtagtggt aaccatttc gtcgcgctga    1140
cgcggagagc gagaggccag aaatttatag cgactgacgc tgtggcaggc acgctatcgg    1200
aggttacgac gtggcgggtc actcgacgcg gagttcacag gtcctatcct tgcatcgctc    1260
ggcgcggagt ttacggggac ttatccttac gacgtgctct aaggttgcga taacgggcgg    1320
aggaaggcgt gtggcgtgcg gagacggttt atacacgtag tgtgcgggag tgtgtttcgt    1380
agacgcggga aagcacgacg acttacgaag gttagtggag gaggaggaca cactaaaatc    1440
aggacgcaag aaactcttct attatagtag tagagaagag attataggag tgtgggttga    1500
ttctaaagaa aatcgacgca ggacaaccgt caaaacgggt gctttaatat agtagatata    1560
tatatataga gagagagaga aagtacaaag gatgcatttg tgtctgcata tgatcggagt    1620
attactaacg gccgtcgtaa gaaggtccat catgcgtgga gcgagcccat ttggttggtt    1680
gtcaggccgc agttaaggcc tccatatatg attgtcgtcg ggcccataac agcatctcct    1740
ccaccagttt attgtaagaa taaattaagt agagatattt gtcgtcgggc agaagaaact    1800
tggacaagaa gaagaagcaa gctaggccaa tttcttgccg gcaagaggaa gatagtggcc    1860
tctagtttat atatcggcgt gatgatgatg ctcctagcta gaaatgagag aagaaaaacg    1920
gacgcgtgtt tggtgtgtgt caatggcgtc catccttcca tcagatcaga acgatgaaaa    1980
agtcaagcac ggcatgcata gtatatgtat agcttgtttt agtgtggctt tgctgagacg    2040
aatgaaagca acggcgggca tatttttcag tggctgtagc tttcaggctg aaagagacgt    2100
ggcatgcaat aattcaggga attcgtcagc caattgaggt agctagtcaa cttgtacatt    2160
ggtgcgagca attttccgca ctcaggaggg ctagtttgag agtccaaaaa ctataggaga    2220
ttaaagaggc taaaatcctc tccttatta attttaaata agtagtgtat ttgtattta    2280
```

| | |
|---|---|
| actcctccaa cccttccgat tttatggctc tcaaactagc attcagtcta atgcatgcat | 2340 |
| gcttggctag aggtcgtatg gggttgttaa tagcatagct agctacaagt taaccgggtc | 2400 |
| ttttatattt aataaggaca ggcaaagtat tacttacaaa taaagaataa agctaggacg | 2460 |
| aactgctgga ttattactaa atcgaaatgg acgtaatatt ccaggcaaga ataattgttc | 2520 |
| gatcaggaga caagtggggc attggaccgg ttcttgcaag caagagccta tggcgtggtg | 2580 |
| acacggcgcg ttgcccatac atcatgcctc catcgatgat ccatcctcac ttgctataaa | 2640 |
| aagaggtgtc catggtgctc aagctcagcc aagcaaataa gacgacttgt ttcattgatt | 2700 |
| cttcaagaga tcgagcttct tttgcaccac aaggtcgagg atccaccatg acggccgaca | 2760 |
| acaacaccga ggccctggac agcagcacca ccaaggacgt gatccagaag ggcatcagcg | 2820 |
| tggtgggcga cctgctgggc gtggtgggct tccccttcgg cggcgccctg gtgagcttct | 2880 |
| acaccaactt cctgaacacc atctggccca gcaggaccc ctggaaggcc ttcatggagc | 2940 |
| aggtggaggc cctgatggac cagaagatcg ccgactacgc caagaacaag gcactggccg | 3000 |
| agctacaggg cctccagaac aacgtggagg actatgtgag cgccctgagc agctggcaga | 3060 |
| agaaccccgc tgcaccgttc cgcaaccccc acagccaggg ccgcatccgc gagctgttca | 3120 |
| gccaggccga gagccacttc cgcaacagca tgcccagctt cgccatcagc ggctacgagg | 3180 |
| tgctgttcct gaccacctac gcccaggccg ccaacaccca cctgttcctg ctgaaggacg | 3240 |
| cccaaatcta cggagaggag tggggctacg agaaggagga catcgccgag ttctacaagc | 3300 |
| gccagctgaa gctgacccag gagtacacg accactgcgt gaagtggtac aacgtgggtc | 3360 |
| tagacaagct ccgcggcagc agctacgaga gctgggtgaa cttcaaccgc taccgccgcg | 3420 |
| agatgaccct gaccgtgctg gacctgatcg ccctgttccc cctgtacgac gtgcgcctgt | 3480 |
| accccaagga ggtgaagacc gagctgaccc gcgacgtgct gaccgacccc atcgtgggcg | 3540 |
| tgaacaacct cgcggctac ggcaccacct tcagcaacat cgagaactac atccgcaagc | 3600 |
| cccacctgtt cgactacctg caccgcatcc agttccacac gcgtttccag cccggctact | 3660 |
| acggcaacga cagcttcaac tactggagcg gcaactacgt gagcacccgc cccagcatcg | 3720 |
| gcagcaacga catcatcacc agcccttct acggcaacaa gagcagcgag cccgtgcaga | 3780 |
| accttgagtt caacggcgag aaggtgtacc gcgccgtggc taacaccaac ctggccgtgt | 3840 |
| ggccctctgc agtgtacagc ggcgtgacca aggtggagtt cagccagtac aacgaccaga | 3900 |
| ccgacgaggc cagcacccag acctacgaca gcaagcgcaa cgtgggcgcc gtgagctggg | 3960 |
| acagcatcga ccagctgccc cccgagacca ccgacgagcc cctggagaag ggctacagcc | 4020 |
| accagctgaa ctacgtgatg tgcttcctga tgcagggcag ccgcggcacc atccccgtgc | 4080 |
| tgacctggac ccacaagagc gtcgacttct tcaacatgat cgacagcaag aagatcaccc | 4140 |
| agctgcccct ggtgaaggcc tacaagctcc agagcggcgc cagcgtggtg gcaggccccc | 4200 |
| gcttcaccgg cggcgacatc atccagtgca ccgagaacgg cagcgccgcc accatctacg | 4260 |
| tgaccccga cgtgagctac agccagaagt accgcgcccg catccactac gccagcacca | 4320 |
| gccagatcac cttcacccg agcctggacg ggcccccctt caaccaatac tacttcgaca | 4380 |
| agaccatcaa caagggcgac accctgacct acaacagctt caacctggcc agcttcagca | 4440 |
| cccctttcga gctgagcggc aacaacctcc agatcggcgt gaccggcctg agcgccggcg | 4500 |
| acaaggtgta catcgacaag atcgagttca tccccgtgaa ctagatctga gctctagatc | 4560 |
| cccgaatttc cccgatcgtt caaacatttg gcaataaagt ttcttaagat tgaatcctgt | 4620 |

```
tgccggtctt gcgatgatta tcatataatt tctgttgaat tacgttaagc atgtaataat    4680
taacatgtaa tgcatgacgt tatttatgag atgggttttt atgattagag tcccgcaatt    4740
atacatttaa tacgcgatag aaaacaaaat atagcgcgca aactaggata aattatcgcg    4800
cgcggtgtca tctatgttac tagatcggga attgggtacc agcttgcatg cctgcagtgc    4860
agcgtgaccc ggtcgtgccc ctctctagag ataatgagca ttgcatgtct aagttataaa    4920
aaattaccac atatttttt tgtcacactt gtttgaagtg cagttatct atctttatac      4980 atatatttaa actttactct acgaataata taatctatag tactacaata atatcagtgt    5040
tttagagaat catataaatg aacagttaga catggtctaa aggacaattg agtattttga    5100
caacaggact ctacagtttt atcttttag tgtgcatgtg ttctcctttt tttttgcaaa     5160
tagcttcacc tatataatac ttcatccatt ttattagtac atccatttag ggtttagggt    5220
taatggtttt tatagactaa ttttttagt acatctattt tattctattt tagcctctaa     5280
attaagaaaa ctaaaactct attttagttt tttatttaa taatttagat ataaaataga     5340
ataaaataaa gtgactaaaa attaaacaaa tacccttaaa gaaattaaaa aaactaagga    5400
aacatttttc ttgtttcgag tagataatgc cagcctgtta aacgccgtcg acgagtctaa    5460
cggacaccaa ccagcgaacc agcagcgtcg cgtcgggcca agcgaagcag acggcacggc    5520
atctctgtcg ctgcctctgg accctctcg agagttccgc tccaccgttg gacttgctcc     5580
gctgtcggca tccagaaatt gcgtggcgga gcggcagacg tgagccggca cggcaggcgg    5640
cctcctcctc ctctcacggc accggcagct acggggatt cctttcccac cgctccttcg     5700
ctttcccttc ctcgcccgcc gtaataaata gacaccccct ccacaccctc tttccccaac    5760
ctcgtgttgt tcggagcgca cacacacaca accagatctc ccccaaatcc acccgtcggc    5820
acctccgctt caaggtacgc cgctcgtcct ccccccccc cctctctac cttctctaga      5880 tcggcgttcc ggtccatggt tagggcccgg tagttctact tctgttcatg tttgtgttag    5940
atccgtgttt gtgttagatc cgtgctgcta gcgttcgtac acggatgcga cctgtacgtc    6000
agacacgttc tgattgctaa cttgccagtg tttctctttg gggaatcctg ggatggctct    6060
agccgttccg cagacgggat cgatttcatg attttttttg tttcgttgca tagggtttgg    6120
tttgcccttt tcctttattt caatatatgc cgtgcacttg tttgtcgggt catcttttca    6180 tgctttttt tgtcttggtt gtgatgatgt ggtctggttg ggcggtcgtt ctagatcgga     6240
gtagaattct gtttcaaact acctggtgga tttattaatt ttggatctgt atgtgtgtgc    6300
catacatatt catagttacg aattgaagat gatggatgga aatatcgatc taggataggt    6360
atacatgttg atgcgggttt tactgatgca tatacagaga tgcttttgt tcgcttggtt     6420 gtgatgatgt ggtgtggttg ggcggtcgtt cattcgttct agatcggagt agaatactgt    6480
ttcaaactac ctggtgtatt tattaatttt ggaactgtat gtgtgtgtca tacatcttca    6540
tagttacgag tttaagatgg atggaaatat cgatctagga taggtataca tgttgatgtg    6600
ggttttactg atgcatatac atgatggcat atgcagcatc tattcatatg ctctaacctt    6660
gagtacctat ctattataat aaacaagtat gttttataat tattttgatc ttgatatact    6720
tggatgatgg catatgcagc agctatatgt ggatttttt agccctgcct tcatacgcta     6780
tttatttgct tggtactgtt tcttttgtcg atgctcaccc tgttgtttgg tgttacttct    6840
gcagggatcc ccgatcatgc aaaaactcat taactcagtg caaaactatg cctggggcag    6900
caaaacggcg ttgactgaac tttatggtat ggaaaatccg tccagccagc cgatggccga    6960
gctgtggatg ggcgcacatc cgaaaagcag ttcacgagtg cagaatgccg ccggagatat    7020
```

| | |
|---|---|
| cgtttcactg cgtgatgcga ttgagagtga taaatcgact ctgctcggag aggccgttgc | 7080 |
| caaacgcttt ggcgaactgc ctttcctgtt caaagtatta tgcgcagcac agccactctc | 7140 |
| cattcaggtt catccaaaca aacacaattc tgaaatcggt tttgccaaag aaaatgccgc | 7200 |
| aggtatcccg atggatgccg ccgagcgtaa ctataaagat cctaaccaca gccggagct | 7260 |
| ggttttgcg ctgacgcctt tccttgcgat gaacgcgttt cgtgaatttt ccgagattgt | 7320 |
| ctccctactc cagccggtcg caggtgcaca tccggcgatt gctcactttt tacaacagcc | 7380 |
| tgatgccgaa cgtttaagcg aactgttcgc cagcctgttg aatatgcagg gtgaagaaaa | 7440 |
| atcccgcgcg ctggcgattt taaaatcggc cctcgatagc cagcatggtg aaccgtggca | 7500 |
| aacgattcgt ttaatttctg aattttaccc ggaagacagc ggtctgttct cccgctatt | 7560 |
| gctgaatgtg gtgaaattga accctggcga agcgatgttc ctgttcgctg aaacaccgca | 7620 |
| cgcttacctg caaggcgtgg cgctggaagt gatggcaaac tccgataacg tgctgcgtgc | 7680 |
| gggtctgacg cctaaataca ttgatattcc ggaactggtt gccaatgtga aattcgaagc | 7740 |
| caaaccggct aaccagttgt tgacccagcc ggtgaaacaa ggtgcagaac tggacttccc | 7800 |
| gattccagtg gatgattttg ccttctcgct gcatgacctt agtgataaag aaaccaccat | 7860 |
| tagccagcag agtgccgcca ttttgttctg cgtcgaaggc gatgcaacgt tgtggaaagg | 7920 |
| ttctcagcag ttacagctta aaccgggtga atcagcgttt attgccgcca acgaatcacc | 7980 |
| ggtgactgtc aaaggccacg gccgtttagc gcgtgtttac aacaagctgt aagagcttac | 8040 |
| tgaaaaaatt aacatctctt gctaagctgg gagctcgatc cgtcgacctg cagatcgttc | 8100 |
| aaacatttgg caataaagtt tcttaagatt gaatcctgtt gccggtcttg cgatgattat | 8160 |
| catataattt ctgttgaatt acgttaagca tgtaataatt aacatgtaat gcatgacgtt | 8220 |
| atttatgaga tgggttttta tgattagagt cccgcaatta tacatttaat acgcgataga | 8280 |
| aaacaaaata tagcgcgcaa actaggataa attatcgcgc gcggtgtcat ctatgttact | 8340 |
| agatctgcta gccctgcagg aaatttaccg gtgcccgggc ggccagcatg gccgtatccg | 8400 |
| caatgtgtta ttaag | 8415 |

<210> SEQ ID NO 135
<211> LENGTH: 11632
<212> TYPE: DNA
<213> ORGANISM: Artificial Sequence
<220> FEATURE:
<223> OTHER INFORMATION: Zea mays, Escherichia coli, Bacillus
      thuringiensis, Agrobacterium tumefaciens

<400> SEQUENCE: 135

| | |
|---|---|
| ggttacagcc tgggctgatc tgtggacggt ggaccatgca aggttgtact gggcttgcaa | 60 |
| ggttgtactg ggcctactgg aacagtcata gcccgtgccg tcgtggtgac cgtcgtacgc | 120 |
| ggccgatctg gcagactggg caggtcgctg ctccgtgctg tttgtggatg caatgcaact | 180 |
| atgcaagagt gatcacggaa aacggacgga gcctgtctgt cctgttgcga cgtagtacaa | 240 |
| gcgcctgaac agtgacgcta cgctatgcca cgagcctacg agtggtaggt agtagtacac | 300 |
| tggtcagaat ccagcagtgc acccacgccg ctgctgactt tgctgatgag agggagggt | 360 |
| cgagcgagtc tgtgtgaaac cgtgaacccc gccggggcct tcagtacgta cgataccacg | 420 |
| agcagtagaa aaaacaacgc caagatggca gagtcaacaa ccgatcacag tacgtatcgc | 480 |
| attcacatca agatttttaag aacgacccc ggctggccaa tggcaggcca cttggttgcc | 540 |
| cgtgcccgac agagggacac ggcgccatgc cctccgcgcc gcacggacga ggtgtcgtga | 600 |

```
gaaccggcaa aaaaaaaatc atcgcaagtg cgctgaagtg aagtgccttc ccccgcgttt    660
ccttgcccct ggccggtacc catttggcgc cgattctttt cttgccccc ggccggccgc    720 tcgctcgcct ttggattctt ccaaagccgc tgatgggatg gtggcgaaca cacccaccac    780
ccgtctttgc ccaaagcgac ccggcacagg ccgcgccggc ttcactaacc actagcgctt    840
gtactaataa aatggtttct agcgtttgtt gctctccttt ttcttttttc gccggttctt    900
cggagccgtg tggacactgg acagcgtcca gtccagcagg catagggtgg tctcggcggc    960
ggtcgtccga cgacgatcga tctccatgag attccgcgac aggccaggac ggaaagctgg   1020
gcccttctca ccaattcgcg tcggagccgg aacaagattc cctcccccaa tcatttcgac   1080
gcgccctttc ttcgccaccc ctcgtggccg tgtttcgcgg ccggccctta tctccttccc   1140
gtgacgcgtt cttttgtagc ttagcggccg gcacgttgct aaccaggcta gcttcgttcg   1200
tttttaatct gcctatcgag aagagaagaa aaattcgtcc atggggccac ggcctcttct   1260
gcaggcattt ggcatgtgaa ggaacccgaa ccagtgaatg gagatggacg gatgctgctc   1320
agatacgcag tcaaacctgc cggcgaaatt acggggggag ctggctggct ggctggctgg   1380
acgccagatc acacatggat gacgcggcac ggcagctagc cgagcaggcg ctctgcgcac   1440
gcaattcaac agaaggcggg aaacgacaat ctgatcatga gcggagaatt aagggagtca   1500
cgttatgacc cccgccgatg acgcgggaca agccgtttta cgtttggaac tgacagaacc   1560
gcaacgctgc aggaattggc cgcagcggcc atttaaatca attgggcgcg ccgaattcga   1620
gctcggtaca agcttgcaca tgacaacaat tgtaagagga tggagaccac aacgatccaa   1680
caatacttct gcgacgggct gtgaagtata gagaagttaa acgcccaaaa gccattgtgt   1740
ttggaatttt tagttattct atttttcatg atgtatcttc ctctaacatg ccttaatttg   1800
caaatttggt ataactactg attgaaaata tatgtatgta aaaaaatact aagcatattt   1860
ttgaagctaa acatgatgtt atttaagaaa atatgttgtt aacagaataa gattaatatc   1920
gaaatggaaa catctgtaaa ttagaatcat cttacaagct aagagatgtt cacgctttga   1980
gaaacttctt cagatcatga ccgtagaagt agctctccaa gactcaacga aggctgctgc   2040
aattccacaa atgcatgaca tgcatccttg taaccgtcgt cgccgctata aacacggata   2100
actcaattcc ctgctccatc aatttagaaa tgagcaagca agcacccgat cgctcacccc   2160
atatgcacca atctgactcc caagctctgt ttcgcattag taccgccagc actccaccta   2220
tagctaccaa ttgagacctt tccagcctaa gcagatcgat tgatcgttag agtcaaagag   2280
ttggtggtac gggtacttta actaccatgg aatgatgggg cgtgatgtag agcggaaagc   2340
gcctccctac gcggaacaac accctcgcca tgccgctcga ctacagcctc ctcctcgtcg   2400
gcgccacaac gagggagccc gtggtcgcag ccaccgacca gcatgtctct gtgtcctcgt   2460
ccgacctcga catgtcatgg caaacagtcg gacgccagca ccagactgac gacatgagtc   2520
tctgaagagc ccgccaccta gaaagatccg agccctgctg ctggtagtgg taaccatttt   2580
cgtcgcgctg acgcggagag cgagaggcca gaaatttata gcgactgacg ctgtggcagg   2640
cacgctatcg gaggttacga cgtggcgggt cactcgacgc ggagttcaca ggtcctatcc   2700
ttgcatcgct cggcgcggag tttacgggga cttatcctta cgacgtgctc taaggttgcg   2760
ataacgggcg gaggaaggcg tgtggcgtgc ggagacggtt tatacacgta gtgtgcggga   2820
gtgtgtttcg tagacgcggg aaagcacgac gacttacgaa ggttagtgga ggaggaggac   2880
acactaaaat caggacgcaa gaaactcttc tattatagta gtagagaaga gattatagga   2940
```

```
gtgtgggttg attctaaaga aaatcgacgc aggacaaccg tcaaaacggg tgctttaata    3000
tagtagatat atatatatag agagagagag aaagtacaaa ggatgcattt gtgtctgcat    3060
atgatcggag tattactaac ggccgtcgta agaaggtcca tcatgcgtgg agcgagccca    3120
tttggttggt tgtcaggccg cagttaaggc ctccatatat gattgtcgtc gggcccataa    3180
cagcatctcc tccaccagtt tattgtaaga ataaattaag tagagatatt tgtcgtcggg    3240
cagaagaaac ttggacaaga agaagaagca agctaggcca atttcttgcc ggcaagagga    3300
agatagtggc ctctagttta tatatcggcg tgatgatgat gctcctagct agaaatgaga    3360
gaagaaaaac ggacgcgtgt ttggtgtgtg tcaatggcgt ccatccttcc atcagatcag    3420
aacgatgaaa aagtcaagca cggcatgcat agtatatgta tagcttgttt tagtgtggct    3480
ttgctgagac gaatgaaagc aacggcgggc atattttttca gtggctgtag ctttcaggct    3540
gaaagagacg tggcatgcaa taattcaggg aattcgtcag ccaattgagg tagctagtca    3600
acttgtacat tggtgcgagc aattttccgc actcaggagg gctagtttga gagtccaaaa    3660
actataggag attaaagagg ctaaaatcct ctccttattt aattttaaat aagtagtgta    3720
tttgtatttt aactcctcca acccttccga ttttatggct ctcaaactag cattcagtct    3780
aatgcatgca tgcttggcta gaggtcgtat ggggttgtta atagcatagc tagctacaag    3840
ttaaccgggt ctttatatt taataaggac aggcaaagta ttacttacaa ataaagaata    3900
aagctaggac gaactgctgg attattacta aatcgaaatg gacgtaatat tccaggcaag    3960 ataattgtt cgatcaggag acaagtgggg cattggaccg gttcttgcaa gcaagagcct    4020
atggcgtggt gacacggcgc gttgcccata catcatgcct ccatcgatga tccatcctca    4080
cttgctataa aaagaggtgt ccatggtgct caagctcagc caagcaaata agacgacttg    4140
tttcattgat tcttcaagag atcgagcttc ttttgcacca caaggtcgag gatccaccat    4200
gacggccgac aacaacaccg aggccctgga cagcagcacc accaaggacg tgatccagaa    4260
gggcatcagc gtggtgggcg acctgctggg cgtggtgggc ttccccttcg gcggcgccct    4320
ggtgagcttc tacaccaact tcctgaacac catctggccc agcgaggacc cctggaaggc    4380
cttcatggag caggtggagg ccctgatgga ccagaagatc gccgactacg ccaagaacaa    4440
ggcactggcc gagctacagg gcctccagaa caacgtggag gactatgtga gcgccctgag    4500
cagctggcag aagaacccg ctgcaccgtt ccgcaacccc cacagccagg ccgcatccg    4560 cgagctgttc agccaggccg agagccactt ccgcaacagc atgcccagct cgccatcag    4620 cggctacgag gtgctgttcc tgaccaccta cgcccaggcc gccaacaccc acctgttcct    4680
gctgaaggac gcccaaatct acggagagga gtggggctac gagaaggagg acatcgccga    4740
gttctacaag cgccagctga gctgaccca ggagtacacc gaccactgcg tgaagtggta    4800
caacgtgggt ctagacaagc tccgcggcag cagctacgag agctgggtga acttcaaccg    4860
ctaccgccgc gagatgaccc tgaccgtgct ggacctgatc gccctgttcc ccctgtacga    4920
cgtgcgcctg taccccaagg aggtgaagac cgagctgacc cgcgacgtgc tgaccgaccc    4980
catcgtgggc gtgaacaacc tgcgcggcta cggcaccacc ttcagcaaca tcgagaacta    5040
catccgcaag ccccacctgt tcgactacct gcaccgcatc cagttccaca cgcgtttcca    5100
gcccggctac tacggcaacg acagcttcaa ctactggagc ggcaactacg tgagcacccg    5160
ccccagcatc ggcagcaacg acatcatcac cagcccctc tacggcaaca agagcagcga    5220
gcccgtgcag aaccttgagt tcaacggcga gaaggtgtac cgcgccgtgg ctaacaccaa    5280
cctggccgtg tggcccctctg cagtgtacag cggcgtgacc aaggtggagt tcagccagta    5340
```

```
caacgaccag accgacgagg ccagcaccca gacctacgac agcaagcgca acgtgggcgc    5400
cgtgagctgg gacagcatcg accagctgcc ccccgagacc accgacgagc ccctggagaa    5460
gggctacagc caccagctga actacgtgat gtgcttcctg atgcagggca gccgcggcac    5520
catccccgtg ctgacctgga cccacaagag cgtcgacttc ttcaacatga tcgacagcaa    5580
gaagatcacc cagctgcccc tggtgaaggc ctacaagctc cagagcggcg ccagcgtggt    5640
ggcaggcccc cgcttcaccg gcggcgacat catccagtgc accgagaacg cagcgccgc    5700 caccatctac gtgaccccg acgtgagcta cagccagaag taccgcgccc gcatccacta    5760
cgccagcacc agccagatca ccttcaccct gagcctggac ggggcccct caaccaata    5820 ctacttcgac aagaccatca acaagggcga caccctgacc tacaacagct caacctggc    5880 cagcttcagc acccctttcg agctgagcgg caacaacctc cagatcggcg tgaccggcct    5940
gagcgccggc gacaaggtgt acatcgacaa gatcgagttc atccccgtga actagatctg    6000
agctctagat ccccgaattt ccccgatcgt tcaaacattt ggcaataaag tttcttaaga    6060
ttgaatcctg ttgccggtct tgcgatgatt atcatataat ttctgttgaa ttacgttaag    6120
catgtaataa ttaacatgta atgcatgacg ttatttatga gatgggtttt tatgattaga    6180
gtcccgcaat tatacattta atacgcgata gaaaacaaaa tatagcgcgc aaactaggat    6240
aaattatcgc gcgcggtgtc atctatgtta ctagatcggg aattgggtac cagcttgcat    6300
gcctgcagtg cagcgtgacc cggtcgtgcc cctctctaga gataatgagc attgcatgtc    6360
taagttataa aaaattacca catattttt ttgtcacact tgtttgaagt gcagtttatc    6420
tatctttata catatattta aactttactc tacgaataat ataatctata gtactacaat    6480
aatatcagtg ttttagagaa tcatataaat gaacagttag acatggtcta aaggacaatt    6540
gagtattttg acaacaggac tctacagttt tatcttttta gtgtgcatgt gttctccttt    6600 tttttttgcaa atagcttcac ctatataata cttcatccat tttattagta catccattta    6660
gggtttaggg ttaatggttt ttatagacta atttttttag tacatctatt ttattctatt    6720
ttagcctcta aattaagaaa actaaaactc tattttagtt tttttattta ataatttaga    6780
tataaaatag aataaaataa agtgactaaa aattaaacaa atacccttta agaaattaaa    6840
aaaactaagg aaacatttt cttgtttcga gtagataatg ccagcctgtt aaacgccgtc    6900
gacgagtcta acgacacca accagcgaac cagcagcgtc gcgtcgggcc aagcgaagca    6960
gacggcacgg catctctgtc gctgcctctg gaccctctc gagagttccg ctccaccgtt    7020
ggacttgctc cgctgtcggc atccagaaat tgcgtggcgg agcggcagac gtgagccggc    7080
acggcaggcg gcctcctcct cctctcacgg caccggcagc tacggggat tcctttccca    7140 ccgctccttc gctttccctt cctcgcccgc cgtaataaat agacaccccc tccacaccct    7200
ctttccccaa cctcgtgttg ttcggagcgc acacacacac aaccagatct cccccaaatc    7260
cacccgtcgg cacctccgct tcaaggtacg ccgctcgtcc tccccccccc ccctctctcta    7320 ccttctctag atcggcgttc cggtccatgg ttagggcccg gtagttctac ttctgttcat    7380
gtttgtgtta gatccgtgtt tgtgttagat ccgtgctgct agcgttcgta cacggatgcg    7440
acctgtacgt cagacacgtt ctgattgcta acttgccagt gttctctttt ggggaatcct    7500
gggatggctc tagccgttcc gcagacggga tcgatttcat gattttttt gtttcgttgc    7560 atagggtttg gtttgccctt ttcctttatt tcaatatatg ccgtgcactt gtttgtcggg    7620 tcatctttc atgctttttt ttgtcttggt tgtgatgatg tggtctggtt gggcggtcgt    7680
```

```
tctagatcgg agtagaattc tgtttcaaac tacctggtgg atttattaat tttggatctg    7740
tatgtgtgtg ccatacatat tcatagttac gaattgaaga tgatggatgg aaatatcgat    7800
ctaggatagg tatacatgtt gatgcgggtt ttactgatgc atatacagag atgcttttg     7860 ttcgcttggt tgtgatgatg tggtgtggtt gggcggtcgt tcattcgttc tagatcggag    7920
tagaatactg tttcaaacta cctggtgtat ttattaattt tggaactgta tgtgtgtgtc    7980
atacatcttc atagttacga gtttaagatg gatggaaata tcgatctagg ataggtatac    8040
atgttgatgt gggtttttact gatgcatata catgatggca tatgcagcat ctattcatat   8100
gctctaacct tgagtaccta tctattataa taaacaagta tgttttataa ttattttgat    8160
cttgatatac ttggatgatg gcatatgcag cagctatatg tggattttttt tagccctgcc   8220 ttcatacgct atttatttgc ttggtactgt ttcttttgtc gatgctcacc ctgttgtttg    8280
gtgttacttc tgcagggatc cccgatcatg caaaaactca ttaactcagt gcaaaactat    8340
gcctggggca gcaaaacggc gttgactgaa ctttatggta tggaaaatcc gtccagccag    8400
ccgatggccg agctgtggat gggcgcacat ccgaaaagcg gttcacgagt gcagaatgcc    8460
gccggagata tcgtttcact gcgtgatgcg attgagagtg ataaatcgac tctgctcgga    8520
gaggccgttg ccaaacgctt tggcgaactg cctttcctgt tcaaagtatt atgcgcagca    8580
cagccactct ccattcaggt tcatccaaac aaacacaatt ctgaaatcgg ttttgccaaa    8640
gaaaatgccg caggtatccc gatggatgcc gccgagcgta actataaaga tcctaaccac    8700
aagccggagc tggttttgc gctgacgcct ttccttgcga tgaacgcgtt tcgtgaattt     8760
tccgagattg tctccctact ccagccggtc gcaggtgcac atccggcgat tgctcacttt    8820
ttacaacagc ctgatgccga acgtttaagc gaactgttcg ccagcctgtt gaatatgcag    8880
ggtgaagaaa atcccgcgc gctggcgatt ttaaaatcgg ccctcgatag ccagcatggt     8940
gaaccgtggc aaacgattcg tttaattct gaattttacc cggaagacag cggtctgttc      9000
tccccgctat tgctgaatgt ggtgaaattg aaccctggcg aagcgatgtt cctgttcgct    9060
gaaacaccgc acgcttacct gcaaggcgtg gcgctggaag tgatggcaaa ctccgataac    9120
gtgctgcgtg cgggtctgac gcctaaatac attgatattc cggaactggt tgccaatgtg    9180
aaattcgaag ccaaaccggc taaccagttg ttgacccagc cggtgaaaca aggtgcagaa    9240
ctggacttcc cgattccagt ggatgatttt gccttctcgc tgcatgacct tagtgataaa    9300
gaaaccacca ttagccagca gagtgccgcc attttgttct gcgtcgaagg cgatgcaacg    9360
ttgtggaaag ttctcagca gttacagctt aaaccgggtg aatcagcgtt tattgccgcc    9420
aacgaatcac cggtgactgt caaaggccac ggccgtttag cgcgtgttta caacaagctg    9480
taagagctta ctgaaaaaat taacatctct tgctaagctg ggagctcgat ccgtcgacct    9540
gcagatcgtt caaacatttg gcaataaagt ttcttaagat tgaatcctgt tgccggtctt    9600
gcgatgatta tcatataatt tctgttgaat tacgttaagc atgtaataat taacatgtaa    9660
tgcatgacgt tatttatgag atgggttttt atgattagag tcccgcaatt atacatttaa    9720
tacgcgatag aaaacaaaat atagcgcgca aactaggata aattatcgcg cgcggtgtca    9780
tctatgttac tagatctgct agccctgcag gaaatttacc ggtgcccggg cggccagcat    9840
ggccgtatcc gcaatgtgtt attaagagtt ggtggtacgg gtactttaac taacgaggtg    9900
tgtcgcgcag cgctcctgca cggatgtagc tttggattgc tggataatgt ctcgcgcaag    9960
cgtcgtattt atttatttat ttattacagc ctccaccgcc gtgcgtgctc cgtttcggat   10020
tataataaaa ctaatattaa ataaaaaaat cggattaaag gatgtttccg aaataaagat   10080
```

```
ctccaccaca ggagcgaaag aaaaaaaaag agaaacgggc tatggagaaa tggtgttgcg    10140
agtatacggc ggctccgtcg tcgtcggatc gacatgtaca aagtaggtgc acaaaaggca    10200
aagcaaaatc acctcatcaa agaccaaaag cggagcaaag aatcgatact aaatccacat    10260
gttttttttg ttcctgtcta ctacgtgctg tgcctgtgcg tgaagcacga ttagtacgtg    10320
tactcactct tgtcatattc tttttagtgt cttgtcacta gtcacatgga gtagcaacca    10380
tggctggcga tacccgcgat aaataaaaaa aagagagagg gagtaatata ttagatactc    10440
acccattata aattataaaa tattttagag tttgaatagg tagttcttgt atatttattt    10500
atagaccttc aagtttgtcc gcctctcgag agccgaactt tgttgcccat gcttccccgg    10560
ctcaggtcat gccacctcct tcaccaaggg cacacggaag atctggtgga gcttgtcatc    10620
accccgcgcc cttcaaacat gtgaggatgc gtcgtcgctg gcactagtag cactcattgt    10680
aggcactaca ttgacagttt cctccagata tgtagtgagg aaacacttga caacacgtt     10740 tgggattaca tatgatgttt tgtttgttca tcaatgataa ttccttcttc ttgcttaatg    10800
attggctcta gaaccgatac atggcacatt tcatcaggaa gggcgcatgc acgaaattaa    10860
actgttatcg atgtttcggt ttctaagttg aagaaaacaa tggctaacaa ctagcccatg    10920
tgagcataac gacaaggcct acaaacaaaa cccaagaaat agctaaatca tggtctggat    10980
ccactctgct atgatagatc acctttttcta acatagttca tcctcccatt tgctctcgct    11040
cacctagtgc ctccatcgct gagatcaatg ataagtacca agtgtacgat gaatcccatt    11100
tgtcatgcgt cttgcaagaa tggttggtcc gcttgcagtg ccggtccagc tatggaccca    11160
ggggcctatg tcataactca agcaagacca taccccccata tgctaccaag atgccttta     11220 agaatcctgg taaagaaat cggtggaaga cgactcaacg actatcaggc cccattttt      11280 gggaccatgc tcaaggattt ggcttagca aaagtagata acactatttt ggggagcttg     11340
atctcaagga cacatgaagg aataaagcta ttttagtcaa gacgtcctta aggaacacaa    11400
taagacccta ggtccctaat gactagtgtg ttatatgttt cgagacgctc ctacacctaa    11460
gttcttttag ctatttccat tcacaatgat ggtatatgac ctaggtacca atgccccacg    11520
gagtttctaa cattaagaat gatctaaaac ataaggaccc tagagccagg gcactcctgg    11580
tattaaaaca tttaccagcc cgggccgtcg accacgcgtg ccctatagta ag            11632
```

<210> SEQ ID NO 136  
<211> LENGTH: 1451  
<212> TYPE: DNA  
<213> ORGANISM: Zea mays

<400> SEQUENCE: 136

```
ggttacagcc tgggctgatc tgtggacggt ggaccatgca aggttgtact gggcttgcaa      60
ggttgtactg ggcctactgg aacagtcata gcccgtgccg tcgtggtgac cgtcgtacgc     120
ggccgatctg gcagactggg caggtcgctg ctccgtgctg tttgtggatg caatgcaact    180
atgcaagagt gatcacggaa aacggacgga gcctgtctgt cctgttgcga cgtagtacaa    240
gcgcctgaac agtgacgcta cgctatgcca cgagcctacg agtggtaggt agtagtacac    300
tggtcagaat ccagcagtgc acccacgccg ctgctgactt tgctgatgag agggaggggt    360
cgagcgagtc tgtgtgaaac cgtgaacccc gccggggcct tcagtacgta cgataccacg    420
agcagtagaa aaacaacgc caagatgca gagtcaacaa ccgatcacag tacgtatcgc      480
attcacatca agattttaag aacgaccccc ggctggccaa tggcaggcca cttggttgcc    540
```

```
cgtgcccgac agagggacac ggcgccatgc cctccgcgcc gcacggacga ggtgtcgtga      600
gaaccggcaa aaaaaaaatc atcgcaagtg cgctgaagtg aagtgccttc ccccgcgttt      660
ccttgcccct ggccggtacc catttggcgc cgattctttt cttgccccccc ggccggccgc     720 tcgctcgcct ttggattctt ccaaagccgc tgatgggatg gtggcgaaca cacccaccac     780
ccgtctttgc ccaaagcgac ccggcacagg ccgcgccggc ttcactaacc actagcgctt     840
gtactaataa aatggtttct agcgtttgtt gctctccttt ttcttttttc gccggttctt     900
cggagccgtg tggacactgg acagcgtcca gtccagcagg catagggtgg tctcggcggc     960
ggtcgtccga cgacgatcga tctccatgag attccgcgac aggccaggac ggaaagctgg    1020
gcccttctca ccaattcgcg tcggagccgg aacaagattc cctcccccaa tcatttcgac    1080 gcgcccttc ttcgccaccc ctcgtggccg tgtttcgcgg ccggccctta tctccttccc     1140
gtgacgcgtt cttttgtagc ttagcggccg gcacgttgct aaccaggcta gcttcgttcg    1200 ttttaatct gcctatcgag aagagaagaa aaattcgtcc atggggccac ggcctcttct     1260
gcaggcattt ggcatgtgaa ggaacccgaa ccagtgaatg gagatggacg gatgctgctc    1320
agatacgcag tcaaacctgc cggcgaaatt acggggggag ctggctggct ggctggctgg    1380
acgccagatc acacatggat gacgcggcac ggcagctagc cgagcaggcg ctctgcgcac    1440
gcaattcaac a                                                         1451

<210> SEQ ID NO 137
<211> LENGTH: 1766
<212> TYPE: DNA
<213> ORGANISM: Zea mays

<400> SEQUENCE: 137
agttggtggt acgggtactt taactaacga ggtgtgtcgc gcagcgctcc tgcacggatg       60
tagctttgga ttgctggata atgtctcgcg caagcgtcgt atttatttat ttatttatta      120
cagcctccac cgccgtgcgt gctccgtttc ggattataat aaaactaata ttaaataaaa      180
aaatcggatt aaaggatgtt tccgaaataa agatctccac cacaggagcg aaagaaaaaa      240
aaagagaaac gggctatgga gaaatggtgt tgcgagtata cggcggctcc gtcgtcgtcg      300
gatcgacatg tacaaagtag gtgcacaaaa ggcaaagcaa aatcacctca tcaaagacca      360
aaagcggagc aaagaatcga tactaaatcc acatgttttt tttgttcctg tctactacgt      420
gctgtgcctg tgcgtgaagc acgattagta cgtgtactca ctcttgtcat attcttttta      480
gtgtcttgtc actagtcaca tggagtagca accatggctg gcgataccg cgataaataa       540 aaaaagaga gagggagtaa tatattagat actcacccat tataaattat aaaatatttt       600
agagtttgaa taggtagttc ttgtatattt atttatagac cttcaagttt gtccgcctct      660
cgagagccga actttgttgc ccatgcttcc ccggctcagg tcatgccacc tccttcacca      720
agggcacacg gaagatctgg tggagcttgt catcaccccg cgcccttcaa acatgtgagg      780
atgcgtcgtc gctggcacta gtagcactca ttgtaggcac tacattgaca gtttcctcca     840
gatatgtagt gaggaaacac ttgaacaaca cgtttgggat tacatatgat gttttgtttg      900
ttcatcaatg ataattcctt cttcttgctt aatgattggc tctagaaccg atacatggca      960
catttcatca ggaagggcgc atgcacgaaa ttaaactgtt atcgatgttt cggtttctaa     1020
gttgaagaaa acaatggcta acaactagcc catgtgagca taacgacaag gcctacaaac    1080 aaacccaag aaaatagctaa atcatggtct ggatccactc tgctatgata gatcacctttc   1140 tctaacatag ttcatcctcc catttgctct cgctcaccta gtgcctccat cgctgagatc    1200
```

| | |
|---|---|
| aatgataagt accaagtgta cgatgaatcc catttgtcat gcgtcttgca agaatggttg | 1260 |
| gtccgcttgc agtgccggtc cagctatgga cccaggggcc tatgtcataa ctcaagcaag | 1320 |
| accataccc catatgctac caagatgcct tttaagaatc ctggtaaaag aaatcggtgg | 1380 |
| aagacgactc aacgactatc aggccccatt ttttgggacc atgctcaagg atttggcttt | 1440 |
| agcaaaagta gataacacta ttttggggag cttgatctca aggacacatg aaggaataaa | 1500 |
| gctatttag tcaagacgtc cttaaggaac acaataagac cctaggtccc taatgactag | 1560 |
| tgtgttatat gtttcgagac gctcctacac ctaagttctt ttagctattt ccattcacaa | 1620 |
| tgatggtata tgacctaggt accaatgccc cacggagttt ctaacattaa gaatgatcta | 1680 |
| aaacataagg accctagagc cagggcactc ctggtattaa aacatttacc agcccgggcc | 1740 |
| gtcgaccacg cgtgccctat agtaag | 1766 |

<210> SEQ ID NO 138
<211> LENGTH: 10818
<212> TYPE: DNA
<213> ORGANISM: Zea mays

<400> SEQUENCE: 138

| | |
|---|---|
| ccattaaatc gacgaaagca actagatcct gattttgatt acgattacga ttgacgagta | 60 |
| tggatcatga tttattgca tatttttatga ttttattgca tattttatta ttttattgtc | 120 |
| gatttatgta ctaacttgtt tttgttaaaa taggatgtca agaaaatga agtctttagc | 180 |
| tcgtagtttg cttgggtcga ggaggagctc gaggagcagc tcgaggggtg aggattcagt | 240 |
| ttttcagggc acaggttcta ccatgagcag acggagagcg ctggcagaac atttgcctcc | 300 |
| acaagatgta agttagttgt taaattacat tatttgagtt acttaatatt gtatgatgta | 360 |
| agttatttgt ttcataggat gctgaaattg aggaaccagt ggtagaggat catgcaagag | 420 |
| atgatgttga agatgatggt ggagataatg tgggagatga tgctggagac gacgctggtg | 480 |
| gggattctgg ggctggggat tctggggctg gtggagattc tgcagctggg tctggaactt | 540 |
| ctcgagttaa gagaacgagg aagctgcatt ttgttggacc acctccagag cttccacccg | 600 |
| aatctcgggt tgtaataaag cctagtggaa agtgagtgac atatctttgc ttaaatgtta | 660 |
| ttgaaagtta tgttttaatt tctacattga tttctgtttg caggacttgg atcgacgact | 720 |
| cgttcacagg cacaggacac tacaggcagg tgaacatggt tcttggtaat cttgttcgtc | 780 |
| tgcactggcc tggtcttgtg actttgccta ctggcgagtc tgtccccgcc accacttggg | 840 |
| agcattatcg ctatggtgtc tgtagaacgt ttggcaacac acaggcacta gtttgggatg | 900 |
| cattctgggt atgacttgtt tatactattt tagttattcc atatatgttt gcttttatga | 960 |
| taacactatg gttttgcag aaacggtaca agttgccgga cgatggatca tatgatatga | 1020 |
| acgctcgtta cgtgtttgag tttaacgcga acgatgtcgt tgcagatgca atgtactatg | 1080 |
| cacgaattca ggctataaag gcatggtaca gagcaaatgc tgatgatcga ccgatgccaa | 1140 |
| atacaaaggc cgagtggtca tcaatttact tgacggagga gcaataccta gaggtaaaca | 1200 |
| ggttgttgcc tctcatatcg cacaaagcca tgtatttgct tgctttatttt aaaaattttg | 1260 |
| atgtaggtgt cggtgccgtg gatggccacc cgaccagacg gttatcgggc attgtgcaga | 1320 |
| tggtgggctt cccctgactt tcgtgccatt tccgaaagga acagggggaaa ccgtgggact | 1380 |
| gagtcgttcc acaactacgg cggtgatggt catgtgcgct tggctaagcg aatggtaagt | 1440 |
| cacagtttgt cgtaactttg aatcacatag caaatgtgtc attataactt ttatgtacag | 1500 |

```
gaagtcaaat ccggccgtac gcccacggat gtggaggtgt atatgcaagg gcatagggcc   1560
ataggggttc tgatcctcag aatcctgatg tgttatgcac tcagacggcc accgaccgtc   1620
tagtgagttt ttgatactct attatgtgtg ttgatattgt ttgcaagggc ataggggtta   1680
tgcacttata tttgatattg tttgcctcca ggcttcgtat gggcaggaga tggttcaacg   1740
ccatggggag gagtacgatt ggaggagcca gccaatcgac cctcagacag catatgctag   1800
cgcaggagga caagctcatg gacggtgaga ttatttgatt tggttttcaa aattgtcatc   1860
atatgcttgc gattcaactg agccatgagt tactatacta agtgcatggt tcactcttgt   1920
aggttgggta ttttttgattc tacgattgat tccagagagc tgagacgccg tggacgacaa   1980
tccacatcgt cgtcttcaca gtcgtcccgt tcacgatcag cagcccatga gatagagctt   2040
gcagtgttgc gtcaacaggc agagtaccat caatcagtct tgagggaaca attggagtac   2100
cagaggcaac aatctgaata ccagagacaa caagccgagt accagaagaa gagggacgag   2160
tattatgcaa gcctccaggc ccaaaatcaa gctcttctct cggtaagttg aagtaacatt   2220
ttgtagctta ttttgcaaaa cacttgatgt gtatcttgtt tgttcaacaa tgacttgtat   2280
ataatttgta gcaactagcc caacaagcgg gcgtcccgat gccgacatat gggatgccgc   2340
ctccggactt tgcactgcca atgccaatgt tggcgcctcc acctccacct ccgcctccgc   2400
ctacgtcaca attccctatg gtatgtacac atatgcgtgt gtgacatgtt catagatgtc   2460
ttatgtgttt aaatgaacaa ctgagtggtt actatttcat gtgcttgtgt tatagggatt   2520
tcagacacca cccgcttcag ttgccgcacc tggagatggg tctgggcaag acgacacaac   2580
acattcgtgg gtcaacaacc tattcaacac gcagagtcca gccggaggag gtggctactt   2640
gaaccatcca gacgatggat atgattgatg tgtcgtgatg tttatttatg aaacactttg   2700
caacacttgt ttgtgagaca caatttcagt ttgcaacaac cgtcgaacct atatgttgat   2760
gttaaatttg tgaatgttat tatttatgtg agaatatttg tgattgtgaa tacttattag   2820
aatgtgtata tttgtgattg tgaatgtgaa tgtgtatatg tgcatgaatc tgttttcgtt   2880
ttgtaaatgt cagatttttt aaaaaacaga attttgtgta aattctgtaa tttgttatgt   2940
ccgacggcct agtggtagcc gtcggacata acacatggtt atgtccgacg gcattaacta   3000
ccgtcggaca taagggatgc ttatgtccga cggcctagtg gtagccgtcg gacttaatcc   3060 tgtgggccc acattccgac cggtaaaacg gttgggattt gttatctccg acgggcacac   3120
gcagccgtcg gagatagctt atgtccgacg gctgccgtcg gacattgcac tatttccgac   3180
gagttatctc cgacggctta aagccgtcgg agataaggct ttgccgtcgg aaataatcta   3240
tttccgacgg tttattcctt atgtccgacg gttttggcca tcggacgttt ctccgtttac   3300
tgtagtggaa gggagtgcag tagaagtgca atggcctaat gtccttcacc ataaaaaaaa   3360
caaagttcaa atctttcaga tttatttact cttggagtag catagcatag gtgtacaagg   3420
gaagtgctta taataatggt aacaagatac tcatcctctc atacctgccg tctcactgac   3480
aggaaacggt aggtggcaag ttggtaagct tttcggtttt agccatgtcc gatcccatgt   3540
gtggatcctg tactgtacat cgacatgcga catcttggtt ggcctatctg atctttaatg   3600
tcgccgcgca cagagaggag atccggtctc atgaagtggc tccgcagatt cctcaagggg   3660
ccgaagcccg gcgaaccgag ccgccggcgg ccccaggtgg cggccgggga agaggaggac   3720
gcgctttggc accaacgacc agctagacca aaggtactac tactaccact gtactagtga   3780
ctgagttcct cccttcttct tctacagttc gtctctgtct ctccaaatgg ctctttgatc   3840
tatccaaaca tgccgtttca cagcttcaca tccgattcaa ctcgcatcca ttgcagtgcc   3900
```

```
atcttaaact cttagctccg aaaaaggaag ttgctaaaga ctagtacaat atctttcttc    3960
gctgtttcca gatcgatcca cctaggaacg agaatgagga actagtggac cgtgccattg    4020
ccgagcctct tgcagaggct gtcaaaccgc ccagaggtag taccgtagat ggacgaatcc    4080
agatacacat tccatgtcag catggtataa atttctctga aaccgtttca tccctgcatc    4140
ccgttgctgt aaattgctgc gccagagaaa acccataggg gagaagacag caacgacgac    4200
gaagatctgg caagagccgt acaggacagt ctgaatatga acccttacac gccttacaac    4260
ccctatccac cctctcaggc ccaacctaga gggcacaggt caaccgctat cacaatcacc    4320
atttactggc accctaagat attctctaac gcgccaaagc agctcaatgc cgtcagtgtc    4380
cgtgctgcag ggtatgcgga ggctgcaagc atgagatagg gcgtggccat tacttgagct    4440
gcatgggcat ttactggcac cctcagtgct tccgctgcag gtcctgcggt caccttatcc    4500
gtgagaccga ggtaattaag ctcttgcatt ttctttcacc gtggaagtgt gttacagtgt    4560
taccagagat gagatcatat ccgttattct tttcgtcgtg ccttccagtt caccttgctg    4620
ggtgcggatt cgtaccacaa gctgtgctac aaggagctgc atcatccaaa atgcgacgtc    4680
tgccttcagt ttgtaaggcc tcgtgtcctc ggaaaacctg agcgatctgc actacagact    4740
gataaactgc gtacgcgtta gcatttctac accgtgccgt ctcgtcagtg taatgagagg    4800
ctcattcttt gtagatgtgt ttctgcagat cccaacgaac gggagtggct tgatagagta    4860
cagagcccac ccgttctggg gccagaagta ttgcccttcg catgagcgcg acaggacgcc    4920
acgttgctgc agctgtgaga aaatggaggt acaggtacag atactagata gaaaatgtgg    4980
tcgcagtccg atcactcgtt ttcaaactag gttgtacatt gcctgatcat attcaagggc    5040
atcacttttc ggttgtgatt gtgcagccaa ggaacacgaa gtacatgtcg ctgggagacg    5100
gacgcggcct gtgcatggaa tgcctgggat ctgcagtgat ggacacgagc gagtgccagc    5160
ctctgtacca ttctatcaga gactactacg aggggatgga catgagactg gaccagcaga    5220
tacccgtgct cttggttgag cggcaagcgc tcaacgaagc catggaaggg gagagtaaag    5280
tgagtgtttc ttctggttct gccccttttt tttgtgtgtg tttctgcaaa acgtacagcc    5340
ttcggaaaca ctaacgctga ccgcatctgc gaaatccagg gcccacgcca catgcctgag    5400
actaggggcc tatgtctgtc cgaggagcgg actgtgagca gtgtaagtgt tcaacaactc    5460
aagctgtggc ggttactgct gggatgctta gcccacaatg cgacagtttc tgctcttctg    5520
actgtgtgtt acttctgcag atacttagga ggcccagaat tggtggaaac aaccggttac    5580
tagacatgag aactcggcca cagaagctga ctaggagatg tgaagttact gcaatacttg    5640
tcctgtatgg cctccccagg tctggcaatt ttttttttat ctctggagtc tggaggacat    5700 cactttttg tacctaccgg attcaaatac tgcggttctt ctcacgttct gtgaccggtg    5760
gtgtcgtcgt ttgtgtcaca acgctattgc aggctactga caggttccat cctcgcccat    5820
gagctgatgc acgggtggct gcgtctcaaa ggtacatccg tatatggatg gatggacaaa    5880
acatttcata cacccattta tcatctttat ttatgaattt tcttggaaag ctctaccgga    5940
tcgtactttt cattcaggtt accgaaacct aaacgcggag gtggaagaag gcatatgcca    6000
ggtcatgtct tacttgtggc tggaatcaga gattcttccg tcatcctcga ggcacgcgca    6060
gccttcatca tcctatccag caacatcatc cgagaaaggt ggaatatctc ataccgggaa    6120
gaagctgggc gagttcttca tgcaccagat tgccaatgac acgtcgacgg cctatggtga    6180
cgggttcaga actgcgtacg ctgccgtcaa caagtatggc cttcgccaaa cactgagcca    6240
```

-continued

| | |
|---|---|
| tatacgccta acaggaggtt tccctgtata ataagagtga aaaaaacata aaatgtccat | 6300 |
| gcatgatcat atcgatatca aaaggttata tacatattgg gatgaagttg gctatggaac | 6360 |
| actggatgca tagtgattca atttcggtga cctttgagtt ttcaaagagg taatgtcgga | 6420 |
| gtaaatcaga aagtaaaccc gtataaagca tggttgagac gattgtttac tctatagtga | 6480 |
| tgcatgctac atgcatggcc aagaagagag caacgggcca taggaccatc gttattaccc | 6540 |
| atcgttgtta atcaaattta gggctagata aatagtaaac catctatagg aacatccaga | 6600 |
| gtcaatctac tctatgtatc ataccgacca ggggcggatc taggtaaaat aaccattgat | 6660 |
| gtcatctcca ttaaattata gtatcatcaa cctatttaag tgctaacaat catacatttt | 6720 |
| aatgaagatt attaaaatcc attggtgtca catgacacca caaaaatggc ctagatccgc | 6780 |
| ccctgatacc gacaaaccta gaaaaatttg taactgagaa ctgatgacca tacacatgaa | 6840 |
| catgaattag gactttcaaa gagtccaatc aaagtaaaca attagactaa gcatgtaaga | 6900 |
| tagggtgcca gatgttgtat caggcttttg agcacatgtg caacttgtat gtcgtggaac | 6960 |
| gtgacaaccg gtcaaggaat gcgcatgtga cggtgtaaaa tcaatataac aacatgaaga | 7020 |
| acaatcataa gtataggttg aaactacaca tgataactag tatatctttc taacaacaat | 7080 |
| gattagtaca atatgtaccg tggtaaagtg gtgacaccat tagagatcgc attagaacgg | 7140 |
| catggcgctt actttaaaaa atgttagaga agcggttatg gtcaaacaga atattatgtg | 7200 |
| aatatgcggg aagatgaaca aatctataac acagaaacga aggaaccaaa taggatcagc | 7260 |
| ggagagtaca gtgccaacgc gcgacgaaac gaggaagcca gaaaggcacc gccgcatgcc | 7320 |
| cgcaccgcgt gactgtcgaa ggcggccgtg agcgctccga catcgaagga gtttatttca | 7380 |
| aaaatgggac gaccaacatt gcgcttttca catttgtttc ctaacgttgc actcttcac | 7440 |
| atatggcacc gagacacgca atcttgttga caccgctcgt agtccggtcc gggcagtgag | 7500 |
| gtcttacctg tcgtggtttc agaaaccggg gataataaga tttgtgttcg gtaaggacgc | 7560 |
| agcgcggact cactctgaat ggtcagagga ctcaatgatg gatctgagac aaggggttat | 7620 |
| actggtttag gcttgcgccc tagtccaatg ttgatcatag tattgcttag agcgtgttac | 7680 |
| agttgagtgc tcgtatctag aagatgggg ttgtcttgct cttttatagc tcaaggatag | 7740 |
| atcttacaat gagacttgta ttctgttggg gtcgagctca gcttcctact tctgggtgac | 7800 |
| gtagctcctc cggtatcgtc tgctgggtcg tgcgccatcg tatccctggt atggcgtcgc | 7860 |
| gtcttatccg ttcgccgtat gagttcttgt agctattctg atgcaaacgt agtggtgcct | 7920 |
| ggtgggtctc gcagagtcgg tttgtggtga ggtttagggg cgtctttagt acaacttcat | 7980 |
| cttccatcat tccctatgcg tcaccttcca gcatgcgtag gcgtacgctt cgtacagcgt | 8040 |
| attaccgcgt cccttctgga cttctggtat gtaggtcact gtagagaccc aatgctgggt | 8100 |
| tgattggtcc caccggtcag cgaggatgct ctctagaatg tatctggcgt cgtgattggc | 8160 |
| agaggccttc ggtactgctc ccatggttca gacgtggctt ggtggtgatc tgtctcatcg | 8220 |
| tgctgacgtg acttgatagt actaggtcgg ctccttacctc ctatagatgt gctcgctaga | 8280 |
| aagtccattg tcatcttgct gggttgctcg gcatgtaggt tgatcggtaa atccgcctcg | 8340 |
| tcgagttgct cgataatgtt gctcggcggg cgggtatgta ggtagtccga cctcaccggg | 8400 |
| ttgttcggca atcccgcctc gccgagttgc tcggtgaacg ggttggtcgg cagccccacc | 8460 |
| tcgccaggtt gtttggcaca cgtgttggtc tgttggtggg tcgtcgagag ccctttggg | 8520 |
| cttttttggg caccccggttt ctggtacccc acaatacccg agctagagtt ccacatttgc | 8580 |
| ccctaccttc cttcccggct ccggcgacaa gcccaggatc ctggtgtaat ggggcgagga | 8640 |

```
gaagcagttc ttgacggagg agaccagctc catgatcccc aacaaaatga aggagacaac    8700
cgaggcctac ctcggcgtca ccatcaataa cactgttgtc accgtcccag tctatttcaa    8760
tgagtcccag cgccagacta ccaaaaacgt cgccgtcatc tccggccttc accgtcatgc    8820
gcatcatcaa cgagcccacc actgtcgcca tcacctacgg gctcgacaag aaatcgagca    8880
gcaacaacga gaataatgtc gtcatcttcg acctcgacgg cggtaccttt gacgtcgcgc    8940
tccggcggct aaggaccgca ctgccgacga gggcatgagt ggcgccgaga tggaagagaa    9000
gaggagcaca aatggcggtc gtcggcaaag acaaagagaa ctcgagcgtg agtggaggaa    9060
ggggcaaatg tgtaactcca gcttggatat gactccactg accagattac gagcgacatc    9120
aactagattg tgtgtctcag tggctcagtg ccatttttg aggtttgggt gccaatattt    9180
tttcgtagtg gaaggcaccg cgcccatcgg gttttgggag ccaaacgcca aacccgctcg    9240
cctcatattc cgcaacgtac agcggtttca tgggctggtt gaaggcccgg ccgcaaacc    9300 aaccgagtcg ggccgacgcc ctgggagatc cgcacggctg gtctggccca agcaacctgg    9360
tgggttggtg ccaggttaca gcctgggctg atctgtggac ggtggaccat gcaaggttgt    9420
actgggcttg caaggttgta ctgggcctac tggaacagtc atagcccgtg ccgtcgtggt    9480
gaccgtcgta cgcggccgat ctggcagact gggcaggtcg ctgctccgtg ctgtttgtgg    9540
atgcaatgca actatgcaag agtgatcacg gaaaacggac ggagcctgtc tgtcctgttg    9600
cgacgtagta caagcgcctg aacagtgacg ctacgctatg ccacgagcct acgagtggta    9660
ggtagtagta cactggtcag aatccagcag tgcacccacg ccgctgctga ctttgctgat    9720
gagagggagg ggtcgagcga gtctgtgtga accgtgaac cccgccgggg ccttcagtac    9780
gtacgatacc acgagcagta gaaaaaacaa cgccaagatg gcagagtcaa caaccgatca    9840
cagtacgtat cgcattcaca tcaagatttt aagaacgacc cccggctggc caatggcagg    9900
ccacttggtt gcccgtgccc gacagaggga cacggcgcca tgccctccgc gccgcacgga    9960
cgaggtgtcg tgagaaccgg caaaaaaaaa aatcatcgca agtgcgctga agtgaagtgc   10020 cttccccgc gtttccttgc ccctggccgg tacccatttg cgccgattc ttttcttgcc   10080 ccccggccgg ccgctcgctc gcctttggat tcttccaaag ccgctgatgg gatggtggcg   10140
aacacaccca ccaccgtct ttgcccaaag cgacccggca caggccgcgc cggcttcact   10200
aaccactagc gcttgtacta ataaaatggt ttctagcgtt tgttgctctc cttttctttt   10260
tttcgccggt tcttcggagc cgtgtggaca ctggacagcg tccagtccag caggcatagg   10320
gtggtctcgg cggcggtcgt ccgacgacga tcgatctcca tgagattccg cgacaggcca   10380
ggacggaaag ctgggcccttctcaccaatt cgcgtcggag ccggaacaag attccctccc   10440
ccaatcattt cgacgcgccc tttcttcgcc acccctcgtg gccgtgttc gcggccggcc   10500 cttatctcct tcccgtgacg cgttcttttg tagcttagcg gccggcacgt tgctaaccag   10560
gctagcttcg ttcgttttta atctgcctat cgagaagaga agaaaaattc gtccatgggg   10620
ccacggcctc ttctgcaggc atttggcatg tgaaggaacc cgaaccagtg aatggagatg   10680
gacggatgct gctcagatac gcagtcaaac ctgccggcga aattacgggg ggagctggct   10740
ggctggctgc ctgacgcca gatcacacat ggatgacgcg gcacggcagc tagccgagca   10800
ggcgctctgc gcacgcaa                                                10818

<210> SEQ ID NO 139
<211> LENGTH: 6300
<212> TYPE: DNA
```

<213> ORGANISM: Zea mays

<400> SEQUENCE: 139

```
gcactgcact gcactgcacg gatgcagctt tggcaacgag gtgtgtcgcg cagcgctcct      60
gcacggatgt agctttggat tgctggataa tgtctcgcgc aagcgtcgta tttatttatt     120
tatttattac agcctccacc gccgtgcgtg ctccgtttcg gattataata aaactaatat     180
taaataaaaa aatcggatta aaggatgttt ccgaaataaa gatctccacc acaggagcga     240
aagaaaaaa aagagaaacg ggctatggag aaatggtgtt gcgagtatac ggcggctccg     300
tcgtcgtcgg atcgacatgt acaaagtagg tgcacaaaag gcaaagcaaa atcacctcat     360
caaagaccaa agcggagca aagaatcgat actaaatcca catgttttt ttgttcctgt     420
ctactacgtg ctgtgcctgt gcgtgaagca cgattagtac gtgtactcac tcttgtcata     480
ttcttttag tgtcttgtca ctagtcacat ggagtagcaa ccatggctgg cgatacccgc     540
gataaataaa aaaagagag agggagtaat atattagata ctcacccatt ataaattata     600
aaatatttta gagtttgaat aggtagttct tgtatattta tttatagacc ttcaagtttg     660
tccgcctctc gagagccgaa ctttgttgcc catgcttccc cggctcaggt catgccacct     720
ccttcaccaa gggcacacgg aagatctggt ggagcttgtc atcaccccgc gcccttcaaa     780
catgtgagga tgcgtcgtcg ctggcactag tagcactcat tgtaggcact acattgacag     840
tttcctccag atatgtagtg aggaaacact tgaacaacac gtttgggatt acatatgatg     900
ttttgtttgt tcatcaatga taattccttc ttcttgctta atgattggct ctagaaccga     960
tacatggcac atttcatcag gaagggcgca tgcacgaaat taaactgtta tcgatgtttc    1020
ggtttctaag ttgaagaaaa caatggctaa caactagccc atgtgagcat aacgacaagg    1080
cctacaaaca aaacccaaga aatagctaaa tcatggtctg gatccactct gctatgatag    1140
atcaccttt ctaacatagt tcatcctccc atttgctctc gctcacctag tgcctccatc    1200
gctgagatca atgataagta ccaagtgtac gatgaatccc atttgtcatg cgtcttgcaa    1260
gaatggttgg tccgcttgca gtgccggtcc agctatggac ccaggggcct atgtcataac    1320
tcaagcaaga ccataccccc atatgctacc aagatgcctt ttaagaatcc tggtaaaaga    1380
aatcggtgga agacgactca acgactatca ggccccattt ttggaccat gctcaagga    1440
tttggcttta gcaaaagtag ataacactat tttggggagc ttgatctcaa ggacacatga    1500
aggaataaag ctattttagt caagacgtcc ttaaggaaca caataagacc ctaggtccct    1560
aatgactagt gtgttatatg tttcgagacg ctcctacacc taagttcttt tagctatttc    1620
cattcacaat gatggtatat gacctaggta ccaatgcccc acggagtttc taacattaag    1680
aatgatctaa aacataagga ccctagagcc agggcactcc tggtattaaa acatttaaac    1740
cctattgcct tagtgctgat ttttgttttt tgtttgtagg aggagaaacg agcacttgtt    1800
gcctctcgcg acaatcttga taggctgtac cgtgatgcca gtaactcctt gaccatccta    1860
gagaggagcc accgcttcac catgtctgac ctagatcatc accaccatga gctgcaggcg    1920
tctcaagatg aagtcttgca acttggacga ttgttgtcga ctaaggattc caccatcaag    1980
gatctgcgct tctaaaaagc tcgtcccgca ggagctagag gcggcccagc ttgctattaa    2040
gactctaaag gacaactgca ccgtcctgaa gacccagcgc gataaagcta tggataaagt    2100
tgttcgcgct ggacggatcc tgatgaggag gcacggcgtt gtggtgcctg acgatattgt    2160
tgtcgatgtc aaggccgcgc ctgatgctac aagtcgtccc tcttttctg ttgctcctgc    2220
gaaggatacc gtctgcaagg atgtttcgat gcagtgatgt cctgtaaaac actttactta    2280
```

```
ttgagttagt atctccttgg aggatggatg taatatggat tcaatgtgca tgcgacaatt    2340
gtgttagaac tcgaatattc tacgaacagg gtgccggaaa acggccctag cactggcaag    2400
taagatgttc tcttttcctg aagtgttttc aattttagcc ggttgttatg ctattagggt    2460
atagtggtca ccctaaacag cgcaaatgca agtataccgc gttggcttaa ggtgtgttcc    2520
gacttaagtc agttgccttg ctggtagggc atagtggtca ccctgagtaa agtaagtcag    2580
agtatattgc accgacctaa gtcgattgca ctactagcag ggtatagtga tcaccctaag    2640
tcaagtaagc atgagcatat cgcaccgact taggtcatca ccgacttaag ccgattgttc    2700
tgttagcagg gtataatggt caccctaagt cagataagca tgagcatgtc acaccggctt    2760
aagtcgttgc cgacttaagc cgattgctcc gtcagcaggg tatagtggtc accctaataa    2820
gtcaggtaag catgagcata tcgcactggc ttaagtcgtt gccgacttaa gccgattgct    2880
ccgtcagtag ggtatagtgg tcaccctaag tcaagtaagc gtgagcatgt cgcactggct    2940
taagtcgatt gctccgtcag cagggtataa tggtcacttt aagtcaagta agtgtgagca    3000
tgtcgcacca gcttaagtca tcgccgactt aagctgattg ctccattagc agggtatagt    3060
ggtcacccta agtaggtaa tcgtgctgat ttcaagtcta gcccaatcaa agtcagttgt    3120
aagtcaagag tatgaatgcc tttggagaat gaaaacttta ttgatgatga aattctcgga    3180
tttacagagt acaatgttcc ttcaagaatt ttgaggcctt gctaaggata gaattttctg    3240
aggtgttcta tgttccatga gttcccttct gtgccgtcca tttgagtaag ccggtatggt    3300
cccggccgag tgaccgcctc taatatgatg aacgatcctt cccacagtgg tgatagcttg    3360
tgccgccctt cccccgttag aattcggcga aggaccaagt ctcccactgc aaaggatcgg    3420
tgccgcatag ctttatcatg gtagcacctc aaggtctgct ggtacctagc cgactgaatt    3480
actgtgttca atagttcttc ttccagtaca tcaatatctt ccagtctggt cgcttctgct    3540
tcagctatgc tttcgaaagt taatcttggt gccctgaaga ttaggtcagc gggcagcact    3600
gcctctaacc cataaaccat gaaaaacggg gtatttctat gcagagctcg actgggttga    3660
gttctcaggc tctagaccac gtatggcagc tctctgatcc attttcctgc aagcttttca    3720
ctcttgtcaa atattttctt cctgagtgct tctagtatca ttccgttggt tctttctacc    3780
tggccattgg ctcttgggtg tgctactgat gcatacttaa cctggaagct ccgttgctcg    3840
cagaaatcga gttcagagct ggtgaagttg atcccagat cggtgatgat gttgtttggt    3900
atcccaaacc tgaatattat gtcttgtata aactccacca ctttggctga ggtcaaggaa    3960
gcaattggct tgtactttat ccattttgtg aatttgttaa tggcaaccag tacatgagta    4020
tagcctccct gagccttctt aaaaggtccg atcatgtcca gcccacagca tgcgaacggc    4080
catgttacag gaatggtctg cagctgctgc gcgggtaagt gttgttgctt tgataggaat    4140
tggcatgctt cacacttctg gactaactcg gcaacatcgt tctttattgt tggccaatag    4200
aaaccggatc taaaagcctt cccgaccaga gtccttgacg ctgcatgtat tccacactgc    4260
ccggcgtgga tttcatccaa caattgtttc tcggtagtcg agtgaataca tttcatgagg    4320
actcttgctg cacctctcct gtacagtaag ccccatatga tggtgtagtg ggccaactgc    4380
ctcgcgatgc attccactgc agccttgtca tctggctctt cttcattttt atatacctga    4440
tgataggctc tctccagtcg ttggggtccg actctggttg gctcaaggta ttgcacactt    4500
ccacctgatc caagatgatg cttggttgtg atatttcttg gacgaagatc ccaggtggag    4560
cctgggcccg actggatccc agcttcgaca acgcgtctgc tgctgcgttg cggtctcgtt    4620
```

```
ccacatgatg gaactctaat ccttcaaatt tgtcctctag ttttcgcaca accgcgcagt    4680
atttgcccat ggagtcagtc gagcagtcct agtctttgct tatctggatt atgaccacta    4740
gcgaatcacc ataccatc agtttcttga tgccgagtga tacaacaatg cttaaaccat      4800
ggatcagttc ttcatacttt gctgcattat ttgacgctgg aaatagtagc tggagtgcat    4860
aattgtgttg ctcacctcca ggagcaataa agagaatccc tgcacccgct ccctatagtt    4920
tcaacgagcc atcaaagtac attttccaca cctcgataac ctctgggcta tctgggacct    4980
gatgttcagt ccactctgat acgaagtcaa ccagcgcctg agtcttgatt gccgtgcggg    5040
gccagaactc tatgttgtga gctccaagct cacacgccca cttggcgatc cttccaatag    5100
cttctttgtt gtggagaatg tccctattg ggaatcctat gaccactatg actttgtggt     5160
cgtcaaagta gtgtcggagt ttgcgtgcgg ttagaagtac tgcatacaac aacttctgta    5220
cttgaggata ccttatcttt gagggcccga ggacttcact gatgaagtag actggatgtt    5280
gcaccgggta cacatgtcct tcctccaccc gcttgactac taacgtggtg cttaccacgt    5340
gagtcgtgct ggagatgtat aacatcaaat cttccaccaa ctgattcagc gtagctcgtc    5400
gtggcggctt gagcactggt ggtgtagtca aaaaatttta gttcctctag agcttcctgc    5460
gcctctgtgg tccactgaaa cttgtccacc tttttgagca atttgtagaa ggccatgcct    5520 tgctcccta gtcttgatat gaacctgctc agggctgcca tgcatccagt aagcctctgt     5580
acctttttct atgatcgcaa cacttccatt ctcatgatgg ccttgacctt ttccgggtta    5640
gcttcaatcc cttggtgact gacaatgaat ctgagtaact tccctgcctg tactctgaaa    5700 acacacttt ctgggttgag cttccaccgg taatgcctca ggctattgaa gactagctgc     5760
aaatcttcaa tgaagttttc tgttttgatc accacatcat caacataggc ttccacccgc    5820
ttgccccagt ggtcggctaa gcatgtctga atggctctct ggtaagttgc tcccgtgttc    5880
ttgaggtcga atgacatgaa ggtgtaatag aaagctccaa atggggtgat gaaagcattc    5940
ttctcctcat cttctttttgc taagcagata tgatggtatc tagaatagca gtctaggaag    6000
gacaacatag aacagccagc ggtcgaatca accacctgat ctattctagg gagcccgaag    6060
ggatctttgg tgtctcagac ctgggggacc ctcaaccaaa tcgacaagtg aattttgtgt    6120
cgcgtgtccc tgcccagatg gattagtgca agatgaaaca caagaggagg ggtgaggttt    6180
atattatctt gcaccagggt gcttgcagta ggggatacaa tctttgcgag agagggaacg    6240
gatcccaggt ctcttgagag atctagtgtt gtgaagggga gttcgatgtt tgagcaagcc    6300

<210> SEQ ID NO 140
<211> LENGTH: 90
<212> TYPE: DNA
<213> ORGANISM: Zea mays

<400> SEQUENCE: 140
cgctgcgcga cacacctcgt tgccaaagct gcatccgtgc agtgcagtgc agtgcaggac     60
aggacctcct ttgtttagga cgcgatgctg                                     90
```

METHODS AND COMPOSITIONS FOR IDENTIFYING AND ENRICHING FOR CELLS COMPRISING SITE SPECIFIC GENOMIC MODIFICATIONS

RELATED APPLICATIONS

This application claims the benefit of provisional application 62/096,442 filed Dec. 23, 2014 and incorporated by reference in its entirety herein.

SEQUENCE LISTING

A substitute Sequence Listing in ASCII text format, submitted under 37 C.F.R. § 1.821, entitled "80484_ST25v2.txt", 409 kilobytes in size, generated on May 16, 2016 and filed via EFS-Web is provided in lieu of a paper copy. This Sequence Listing is hereby incorporated by reference into the specification for its disclosures.

FIELD OF THE INVENTION

The present invention relates to methods and compositions for modifying a target site in the genome of a plant cell. Such modifications include transgene integration and mutations. The present invention further relates to methods and compositions for identifying and enriching for a cell with one or more transgenes integrated at a target site within the genome of the cell, as well as for identifying and enriching for a cell comprising a mutation introduced at a target site within the genome of the cell without integration into the genome of a heterologous nucleotide sequence encoding a nuclease for site specific cleavage at the target site within the genome.

BACKGROUND OF THE INVENTION

Recent advances in the field of targeted modifications of a genome have made is so that routine targeted modifications may soon be possible. Significant advances have been made in the last few years towards the development of methods and compositions to target and cleave genomic DNA by site specific nucleases (e.g., Zinc Finger Nucleases (ZFNs), Meganucleases, Transcription Activator-Like Effector Nucelases (TALENS) and Clustered Regularly Interspaced Short Palindromic Repeats/CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide, such as a transgene, within a predetermined genomic locus. This predetermined genomic locus is not obvious. Many sites in the genome are non-ideal for, for example, transgene insertion, due to highly repetitive nucleotide sequence, methylation, and other characteristics that result in a very high or very low level of recombination or poor expression of genes on introduced transgenes. Therefore, there is a need in the art to identify ideal target sites within a genome for targeted modifications, such as transgene insertion.

Once a target site has been used for targeted modification, there is a need to determine if the desired targeted modification was successfully created. Existing methods of screening for targeted genomic modifications in cells are primarily based on polymerase chain reaction (PCR) protocols, nucleic acid sequencing and Southern analysis. In the case of PCR amplification, the screening process of handling the complexity of gene insertion or modification at a specific site is inefficient due to the complexity of PCR primer settings and inherent ambiguity of PCR amplification due to the resulting complexity of genome rearrangement and genome ploidy. Some of the problems with PCR include: 1) no clear distinction between one copy and two copy insertions due to ploidy of the genome; 2) a requirement for complex primer design and large sets of primer combinations to deal with the complexity of gene insertion or modification at the specific site(s); and 3) low throughput of gel electrophoresis and ambiguity of amplification bands. Although subsequent sequencing can help in identifying the characteristics of PCR amplification products, there are problems with large scale sequencing efforts and interpretation of results for large sample numbers. Further gene segregation analysis is required to isolate homozygous progeny for further screening. These steps require large scale operations for screening of commercial crops in order to capture less than 2% of potential candidates and the inventory scale of plants in greenhouses require commercial scales of space and operational costs until the plant growth stage is mature enough to carry out Southern analyses.

The present invention addresses these shortcomings in the art by providing an ideal target site for a *maize* genome. The present invention also provides a more strategic and efficient approach to identify and enrich for cells with a targeted genomic insertion or a targeted genomic mutation, which reduces the number of candidate plants with high accuracy at the very early stages of the screening process, avoiding a large scale sequencing effort and reducing greenhouse operational costs for plant maintenance.

SUMMARY OF THE INVENTION

In one aspect, the present invention provides a method of integrating a transgene into a genomic nuclease cleavage site in a *maize* genome, comprising introducing into a *maize* cell: a) a first nucleic acid molecule comprising at least about 100 contiguous nucleotides, wherein said contiguous nucleotides have at least about 90% identity with a target site in the nucleotide sequence of SEQ ID NO:1 or the nucleotide sequence of SEQ ID NO:2, and further comprising a transgene; and b) a second nucleic acid molecule comprising a nucleotide sequence encoding a nuclease for site-directed cleavage at a genomic nuclease cleavage site adjacent to the nucleotide sequence of SEQ ID NO:1 or the nucleotide sequence of SEQ ID NO:2 that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the *maize* genome. The present invention also provides a method of producing a *maize* plant, plant part, or progeny thereof comprising a transgene integrated into a genomic nuclease cleavage site in the *maize* genome, comprising regenerating a *maize* plant from the *maize* cell produced by the method described above. The present invention further provides a *maize* plant, plant part, or progeny thereof comprising a transgene integrated into a genomic nuclease cleavage site in the *maize* genome, produced by the method described.

In a further aspect, the present invention provides a method of enriching for a cell comprising a transgene inserted into a nuclease cleavage site in a genome of the cell, comprising: a) introducing into a plurality of cells: i) a first nucleic acid molecule comprising at least 100 contiguous nucleotides, wherein the at least 100 contiguous nucleotides have at least 90% identity with a target site in the genome of the cell, and further comprising a transgene; and ii) a second nucleic acid molecule encoding a nuclease for site-directed cleavage at a nuclease cleavage site in the genome of the cell adjacent to the nucleotide sequence in the genome of the cell that corresponds to the at least 100 contiguous nucleotides of (a), under conditions wherein expression of the second nucleic acid molecule can occur to produce the nuclease and the nuclease can cleave at the nuclease cleavage site in the genome of the cell and integrate the transgene into the nuclease cleavage site in the genome of the cell; b) culturing the cells of (a) to produce a cell line or tissue; c) extracting a genomic DNA sample from the cell line or tissue of (b); d) performing real-time quantitative polymerase chain reaction (qPCR) assays T and G on the sample of (c), wherein the assays T and G respectively comprise the following probes: i) a first probe comprising a nucleotide sequence that is complementary to a nucleotide sequence of the target site, at least five base pairs away from the nuclease cleavage site for carrying out assay T, and ii) a second probe comprising a nucleotide sequence that is complementary to a nucleotide sequence of the transgene for carrying out assay G; e) obtaining a DNA copy number of the target site from the results of assay T and a DNA copy number of the transgene from the results of assay G; and f) enriching for a cell line or tissue that has reduced copy number in assay T relative to a reference and a copy number greater than zero for assay G, thereby enriching for the cell comprising the transgene inserted into the nuclease cleavage site in the genome of the cell.

Furthermore, the present invention provides a method of identifying a cell comprising a transgene inserted into a nuclease cleavage site in a genome of the cell, comprising: a) introducing into a plurality of cells: i) a first nucleic acid molecule comprising at least 100 contiguous nucleotides having at least 90% identity with a target site in the genome of the cell, and further comprising a transgene; and ii) a second nucleic acid molecule encoding a nuclease for site-directed cleavage at a nuclease cleavage site in the genome of the cell adjacent to the nucleotide sequence in the genome corresponding to the at least 100 contiguous nucleotides of (a), under conditions wherein expression of the second nucleic acid molecule can occur to produce the nuclease and the nuclease can cleave at the nuclease cleavage site in the genome of the cell and integrate the transgene into the nuclease cleavage site in the genome of the cell; b) culturing the cells of (a) to produce a cell line or tissue; c) extracting a genomic DNA sample from the cell line or tissue of (b); d) performing real-time quantitative polymerase chain reaction (qPCR) assays T and G on the sample of (c), wherein the assays T and G respectively comprise the following probes: i) a first probe comprising a nucleotide sequence that is complementary to a nucleotide sequence of the target site, at least five base pairs away from the nuclease cleavage site for carrying out assay T, and ii) a second probe comprising a nucleotide sequence that is complementary to a nucleotide sequence of the transgene for carrying out assay G; e) obtaining a DNA copy number of the target site from the results of assay T and a DNA copy number of the transgene from the results of assay G; and f) identifying a cell line or tissue that has reduced copy number in assay T relative to a reference and a copy number greater than zero for assay G, thereby identifying the cell comprising the transgene inserted into the nuclease cleavage site in the genome of the cell. The present invention also provides for a cell line or tissue that is enriched for or identified by the described methods, and further provides for a plant, plant part, or progeny thereof derived from the cell line or tissue.

In further aspects of this invention, a method is provided of enriching for a cell comprising a mutation introduced into a nuclease cleavage site in a genome of the cell and lacking integration of a heterologous nucleotide sequence encoding a nuclease for site-directed cleavage of a nucleotide sequence at the nuclease cleavage site into the genome of the cell, comprising: a) introducing a nucleic acid molecule comprising a heterologous sequence encoding a nuclease for site-directed cleavage of the nucleotide sequence at the nuclease cleavage site in the genome of the cell into a plurality of cells under conditions wherein expression of the nucleic acid molecule can occur to produce the nuclease and the nuclease can cleave the nucleotide sequence at the nuclease cleavage site in the genome of the cell, thereby introducing a mutation at the nuclease cleavage site in the genome of the cell without integration of the heterologous nucleotide sequence encoding the nuclease into the genome of the cell; b) culturing the plurality of cells of (a) to produce a cell line or tissue; c) extracting a genomic DNA sample from the cell line or tissue of (b); d) performing real-time quantitative polymerase chain reaction (qPCR) assays 1 and 2 on the sample of (c), wherein the assays respectively comprise the following probes: i) a first probe comprising a nucleotide sequence that is complementary to the nucleotide sequence comprising the nuclease cleavage site to carry out assay 1, and ii) a second probe comprising a nucleotide sequence that is complementary to the heterologous nucleotide sequence encoding the nuclease to carry out assay 2; e) obtaining a DNA copy number of the nuclease cleavage site from the results of assay 1 and a DNA copy number of the heterologous nucleotide sequence encoding the nuclease from the results of assay 2; and f) enriching for a cell line or tissue that has a reduced copy number for assay 1 relative to a reference and a copy number equal to zero for assay 2, thereby enriching for the cell comprising the mutation introduced into the nuclease cleavage site in the genome of the cell and lacking integration of the heterologous nucleotide sequence encoding the nuclease into the genome of the cell.

Also provided as an aspect of this invention is a method of identifying a cell comprising a mutation introduced into a nuclease cleavage site in a genome of the cell and lacking integration of a heterologous nucleotide sequence encoding a nuclease for site-directed cleavage of a nucleotide sequence at the nuclease cleavage site into the genome of the cell, comprising: a) introducing a nucleic acid molecule comprising a heterologous sequence encoding a nuclease for site-directed cleavage of the nucleotide sequence at the nuclease cleavage site in the genome of the cell into a plurality of cells under conditions wherein expression of the nucleic acid molecule can occur to produce the nuclease and the nuclease can cleave the nucleotide sequence at the nuclease cleavage site in the genome of the cell, thereby introducing a mutation at the nuclease cleavage site in the genome of the cell without integration of the heterologous nucleotide sequence encoding the nuclease into the genome of the cell; b) culturing the plurality of cells of (a) to produce a cell line or tissue; c) extracting a genomic DNA sample from the cell line or tissue of (b); d) performing real-time quantitative polymerase chain reaction (qPCR) assays 1 and 2 on the sample of (c), wherein the assays respectively comprise the following probes: i) a first probe comprising a nucleotide sequence that is complementary to the nucleotide sequence comprising the nuclease cleavage site to carry out assay 1, and ii) a second probe comprising a nucleotide sequence that is complementary to the heterologous nucleotide sequence encoding the nuclease to carry out assay 2; e) obtaining a DNA copy number of the nuclease cleavage site from the results of assay 1 and a DNA copy number of the heterologous nucleotide sequence encoding the nuclease from the results of assay 2; and f) identifying a cell line or tissue that has a reduced copy number for assay 1 relative to a reference and a copy number equal to zero for assay 2, thereby identifying the cell comprising the mutation introduced into the nuclease cleavage site in the genome of the cell and lacking integration of the heterologous nucleotide sequence encoding the nuclease into the genome of the cell. The present invention also provides for a cell line or tissue that is enriched for or identified by the described methods, and further provides for a plant, plant part, or progeny thereof derived from the cell line or tissue.

In additional aspects, the present invention provides a method of producing a plant, plant part, or progeny thereof comprising a mutation introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). The present invention further provides the plant, plant part, or progeny thereof produced by the method described.

The present invention also provides a method for modifying a target site in the genome of a plant cell, comprising: a) introducing into the plant cell a first nucleic acid comprising at least 100 contiguous nucleotides, wherein the at least 100 contiguous nucleotides have at least 90% identity with a target site in the genome of the cell, and further comprising a transgene; and b) a second nucleic acid molecule encoding nuclease for site-directed cleavage at a nuclease cleavage site in the genome of the cell adjacent to the nucleotide sequence in the genome of the cell that corresponds to the at least 100 contiguous nucleotides of (a), wherein the nuclease is a modified Cas9 nuclease comprising SEQ ID NO: 30, under conditions wherein expression of the second nucleic acid molecule can occur to produce the nuclease and the nuclease can cleave at the nuclease cleavage site in the genome of the cell and modify the target site in the genome of the plant cell.

The present invention also provides a method of producing a *maize* plant, plant part, or progeny thereof comprising a modification at a target site in the genome of the plant cell, comprising: a) introducing into the plant cell a first nucleic acid comprising at least 100 contiguous nucleotides, wherein the at least 100 contiguous nucleotides have at least 90% identity with a target site in the genome of the cell, and further comprising a transgene; b) a second nucleic acid molecule encoding nuclease for site-directed cleavage at a nuclease cleavage site in the genome of the cell adjacent to the nucleotide sequence in the genome of the cell that corresponds to the at least 100 contiguous nucleotides of (a), wherein the nuclease is a modified Cas9 nuclease comprising SEQ ID NO: 30, under conditions wherein expression of the second nucleic acid molecule can occur to produce the nuclease and the nuclease can cleave at the nuclease cleavage site in the genome of the cell and modify the target site in the genome of the plant cell; and c) regenerating a plant, plant part, or progeny thereof from the plant cell of (a). The present invention further provides the plant, plant part, or progeny thereof produced by the method described.

The present invention also provides a method of integrating a transgene into a genomic nuclease cleavage site in an event MIR604 transgenic *maize* genome, comprising introducing into an event MIR604 *maize* cell: a) a first nucleic acid molecule comprising at least 100 contiguous nucleotides, wherein said at least 100 contiguous nucleotides have at least 90% identity with a target site in a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, and further comprising a transgene; and b) a second nucleic acid molecule comprising a nucleotide sequence encoding a nuclease for site-directed cleavage at a genomic nuclease cleavage site adjacent to a nucleotide sequence with at least 90% identity to a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, that corresponds to the at least 100 contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the *maize* genome. The present invention further provides a method of producing a *maize* plant, plant part, or progeny thereof comprising a transgene integrated into a genomic nuclease cleavage site in an event MIR604 *maize* genome, comprising regenerating a *maize* plant from the *maize* cell produced by the method described. The present invention further provides a *maize* plant, plant part, or progeny thereof comprising a transgene integrated into a genomic nuclease cleavage site in the event MIR604 *maize* genome, produced by the method described.

along with single TALEN vector (F1, cTNmir604Fw1-01 or R2, cTNmir604Rv2-01) or a pair of TALEN genes (FR1, cTNmir604Fw1-01 and cTNmir604Rv1-01) under the control of *maize* ubiquitin promoter (prZmUbi1-10) or without TALEN (ctl, blank control). cTNmir604Rv2-01 does not recognize MIR604FR1 sequence and results in background level of GUS activity (R2, negative control).

Figure 5:
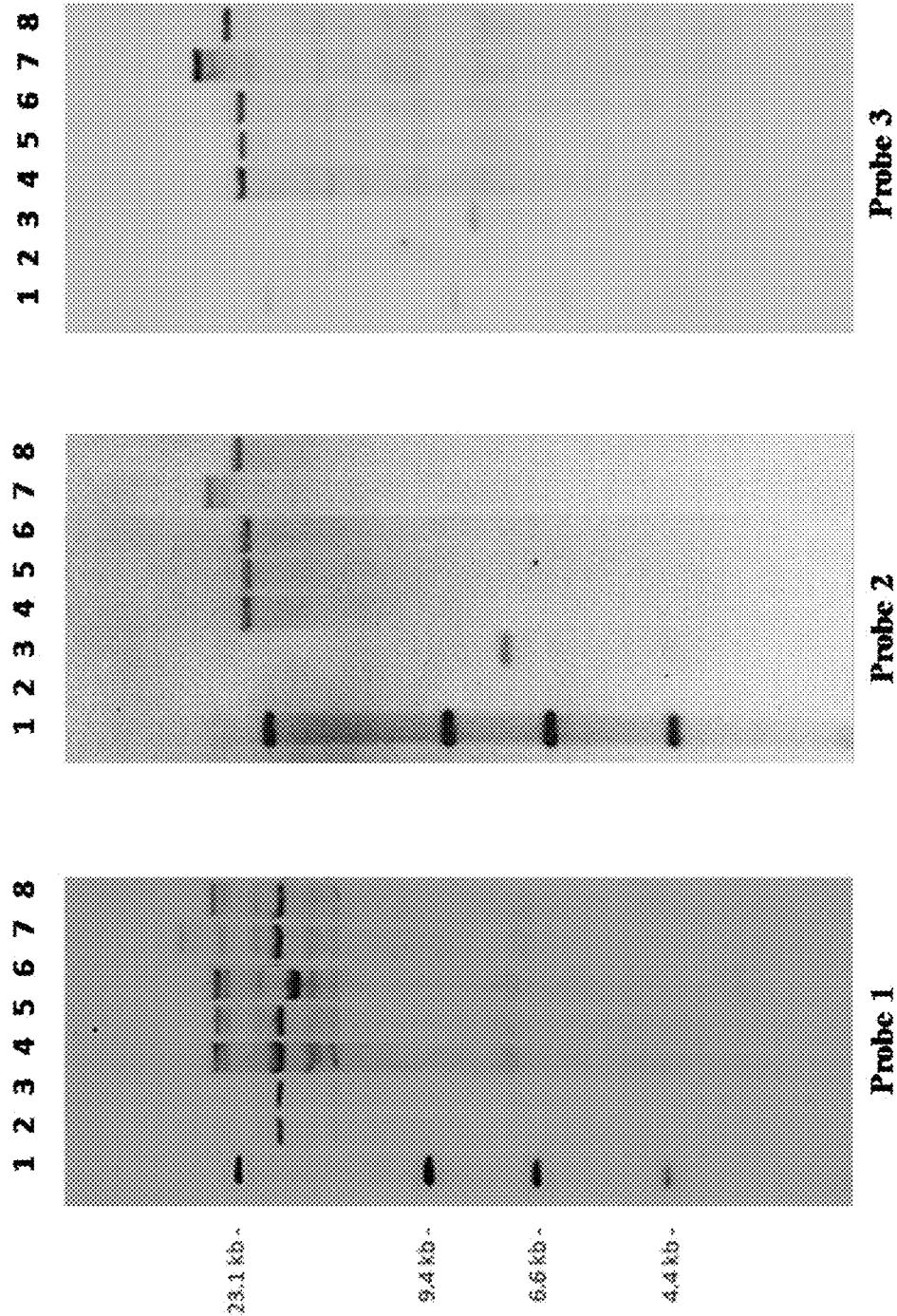

FIG. 5. DNA blot analysis of targeted insertion events at the safe harbor locus #1 (MIR604 insertion site). DNA Probe 1: against flanking native genomic sequences; Probe 2: probe against prCMP; Probe 3: Probe against cPMI (See FIG. 2 for probe locations in the schematic map). Lane 1: DIG-labeled markers; Lane 2: Wild type *maize* transformation line NP2222; Lane 3: NP2222 spiked with 21942; digested with HindIII (releasing a 8553 by fragment); Lane 4: MZET134207E056A; Lane 5: MZET134300A679A; Lane 6: MZET134505A104A; Lane 7: MZET141322A015A; Lane 8: MZET141322B143A; All *maize* genomic DNAs in lane 2 to 8 were digested with Bsu36I restriction enzyme. Note: Probe 1 also hybridizes weakly to homologous sequences in other parts of the genome. WT safe harbor locus has the dominant 17.5 Kb band, whereas targeted insertion events have the fragment size increased to 28 Kb. For probe 2 and 3, the 28 Kb Bsu36I bands contain targeted insertion of donor DNA sequences through homologous recombination. In lane 7, the event likely contains an insertion of the rearranged donor DNA molecule.

Figure 6:
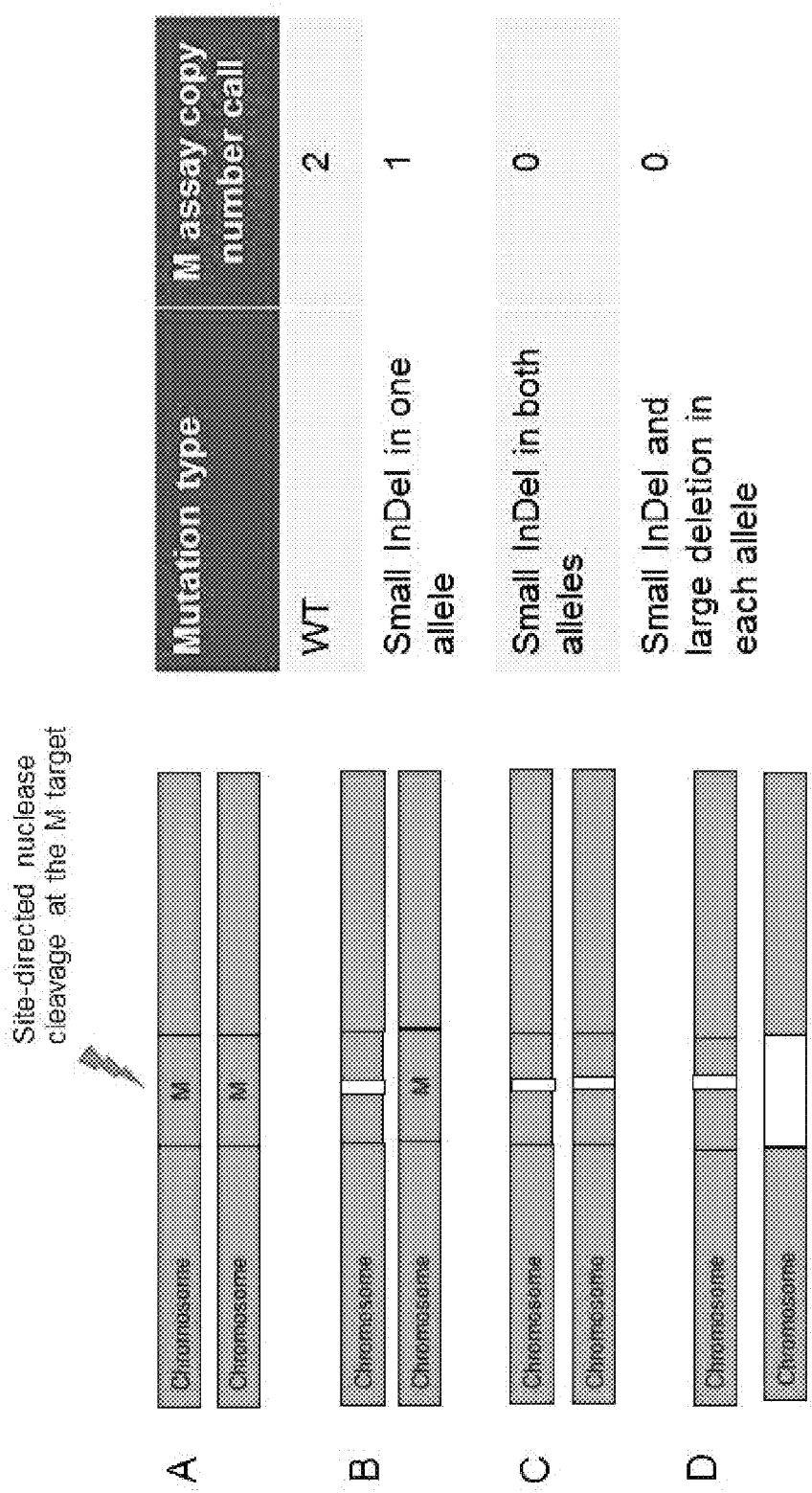

FIG. 6. Schematic diagram showing reduction of target sequence copy number in a plant with a mutation in the target sequence (M) generated by cleavage with a site-directed nuclease.

FIG. 7. Schematic representation of Taqman assay probe design for a target sequence in the MIR604 insertion site (SEQ ID NO: 140) and interpretation of Taqman assay results in regard to targeted mutation.

Figure 8A:
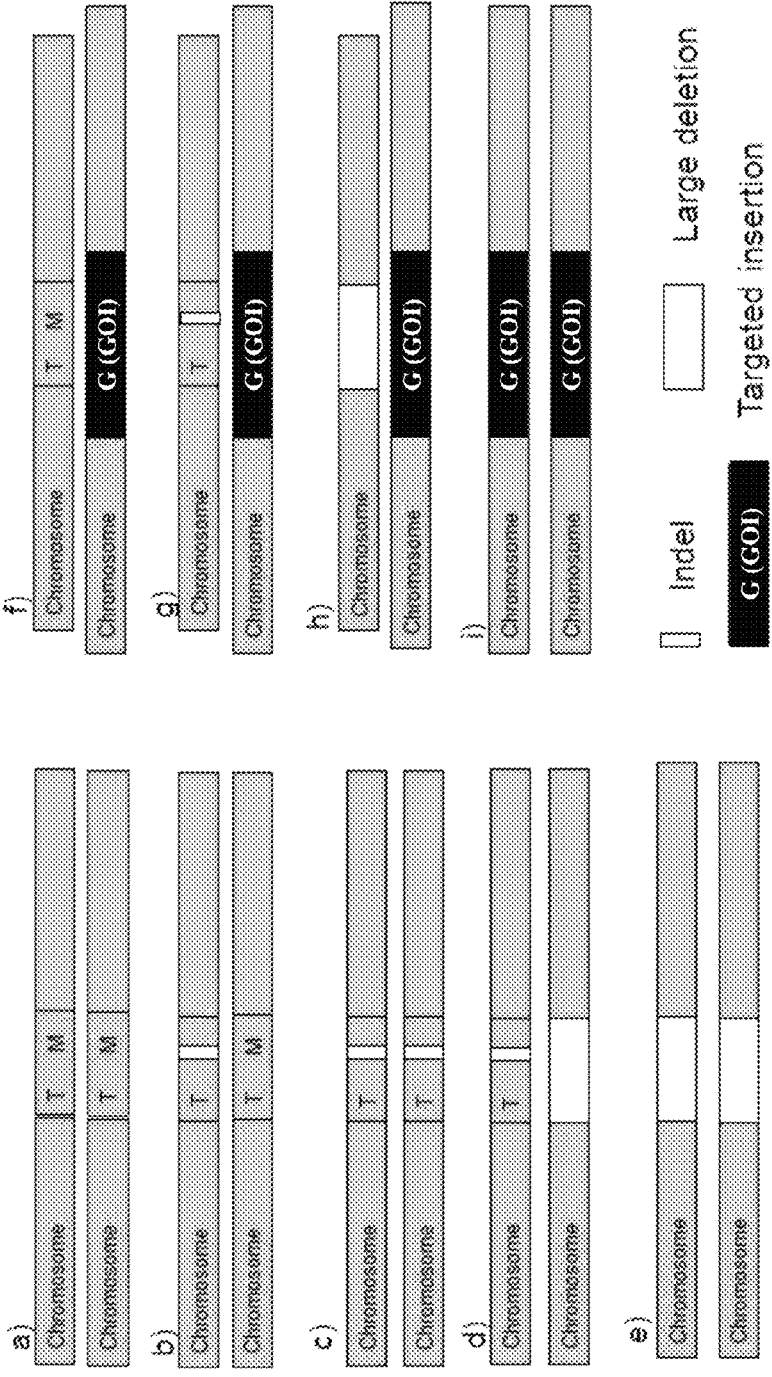

FIGS. 8A-B. Strategies to enrich for potential targeted insertion events based on copy number reduction of target sequences. (A) Schematic representation of potential types of mutations and targeted insertion as a result of targeted nuclease cleavage at the target locus in a targeted insertion experiment. M is the site-directed nuclease cleavage site; T is a sequence located away from M by at least 5 nucleotides in the region of the target locus and it should be as far away as possible from M but within the region replaced by targeted insertion. However, T can sit within the same amplicon as assay for M. G is an assay target for transgenic sequences (gene of interest (GOI)). (B) Copy number call of different assays in plants with different kinds of mutations or insertions in the target site as shown in (A) using real-time qPCR assays.

Figure 9:
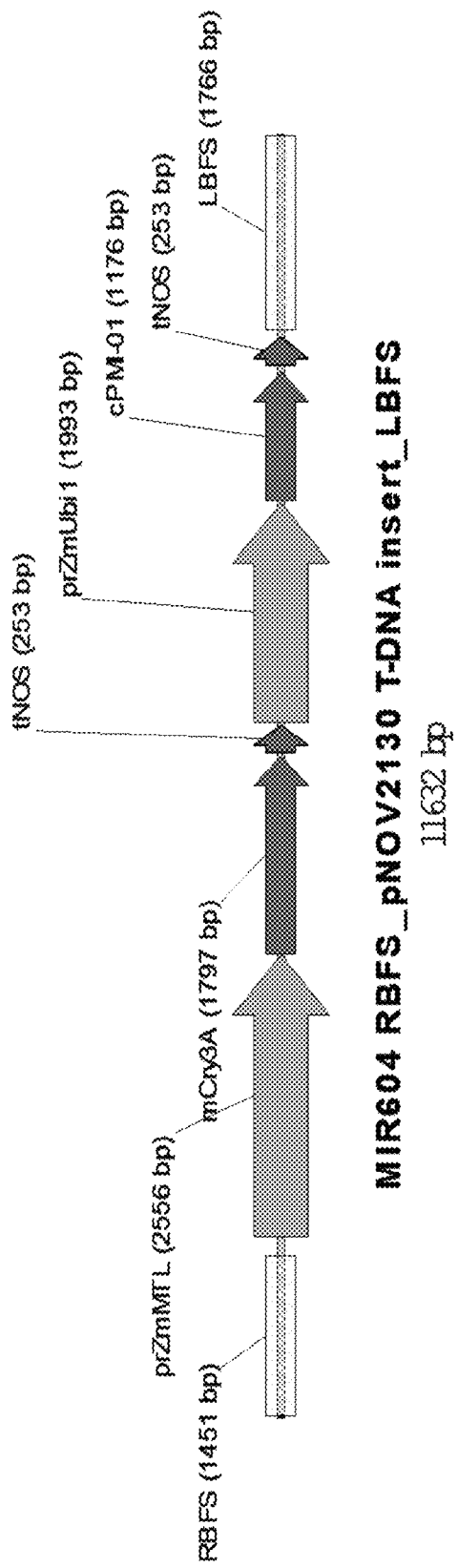

FIG. 9. Schematic drawing of MIR604 transgenic event T-DNA insertions and flanking regions. MIR604 RB FS: *maize* genomic region flanking the T-DNA right border; MIR604 LB FS: *maize* genomic region flanking the T-DNA left border; prUbi1: *maize* ubiquitin-1 promoter; cPMI-01: PMI coding sequence; tNOS: Nopaline synthase terminator; mCry3A: synthetic form of Cry3A gene sequence (mCry3A) from *Bacillus thuringiensis*. (U.S. Pat. No. 7,897,748)

Figure 10:
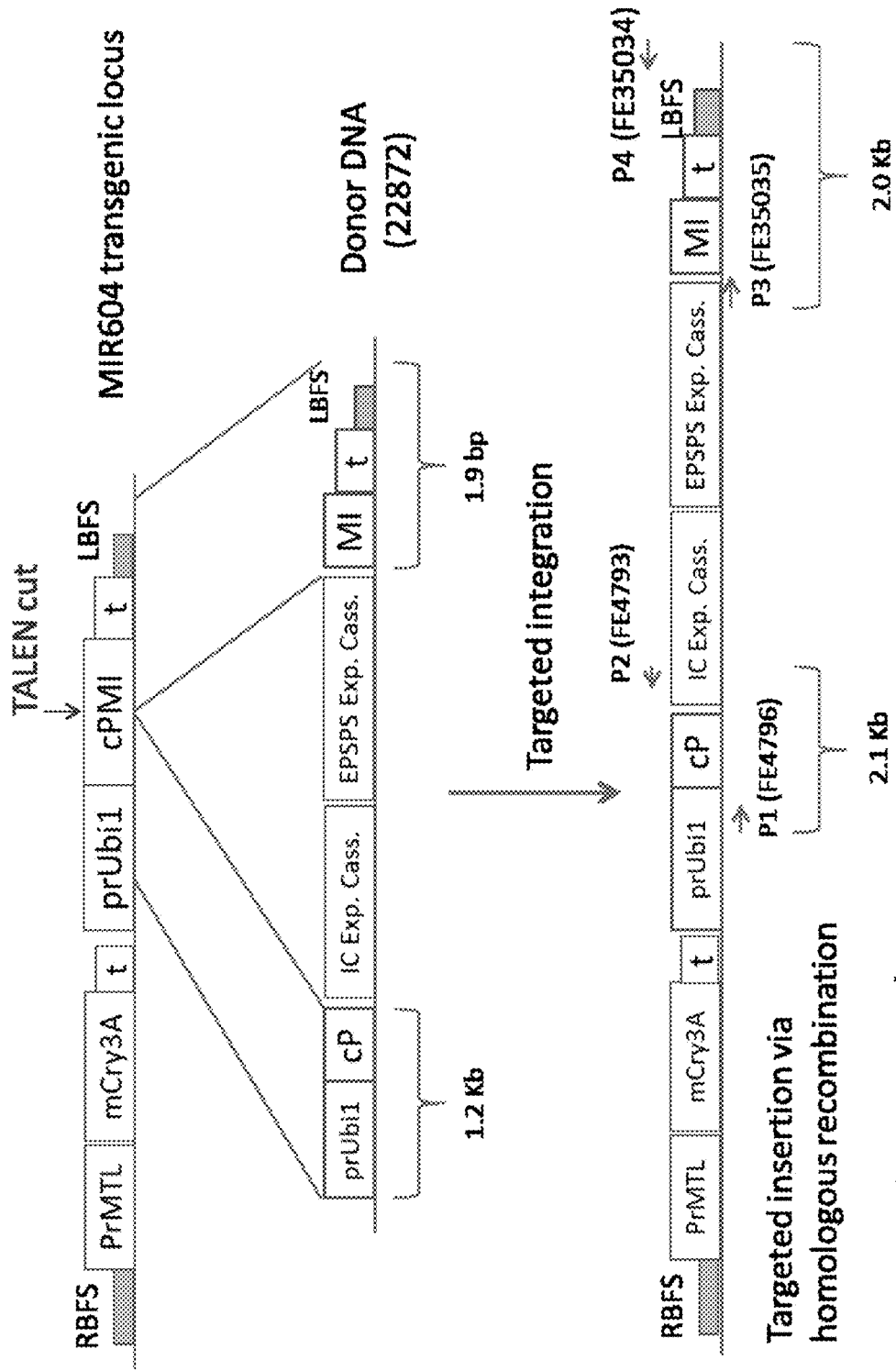

FIG. 10. Targeted insertion of an insecticidal gene (IC) expression cassette (Exp. Cass.) and an expression cassette comprising the selectable marker ZmEPSPS (EPSPS Exp. Cass.) from donor vector 22872 the into MIR604 transgene locus (FIG. 9) mediated by TALENs expressed from vector 22840. A pair of TALENs is expressed from 22840 and cleaves the cPMI target sequence. t: tNOS-05; LBFS: *maize* genomic sequences flanking the T-DNA Left Border; RBFS: *maize* genomic sequences flanking the T-DNA Right Border; P1(FE4796): SEQ ID NO: 127; P2 (FE4793): SEQ ID NO: 128; P3 (FE35035): SEQ ID NO: 132; P4 (FE35034): SEQ ID NO: 131.

Figure 11:
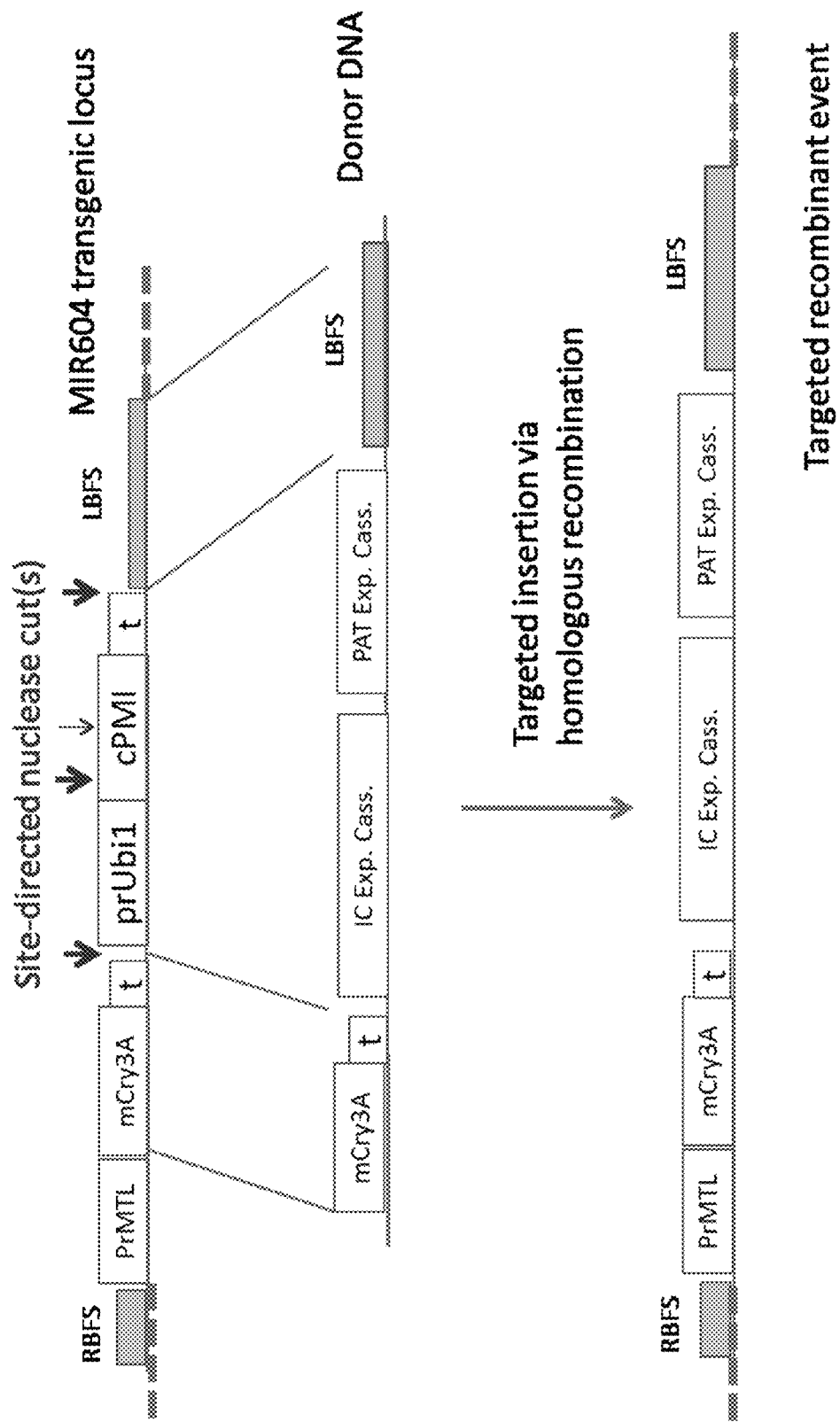

FIG. 11. Targeted insertion of transgene expression cassettes into MIR604 transgene locus (FIG. 9) mediated by site-directed nuclease to replace the whole PMI marker gene cassette.

Figure 12:
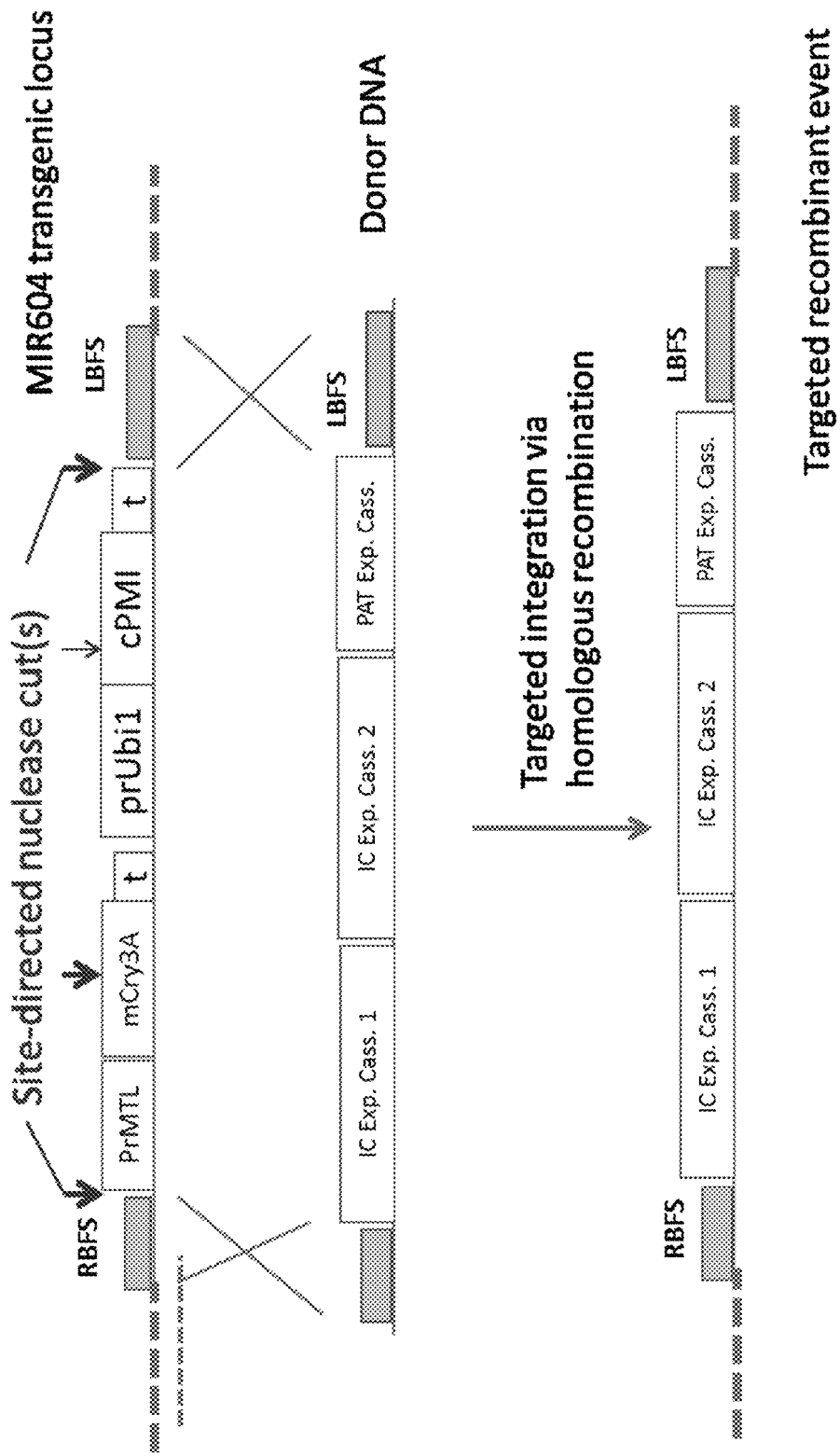

FIG. 12. Targeted insertion of the donor transgene expression cassettes into MIR604 transgene locus (FIG. 9) mediated by site-directed nuclease to replace the whole MIR604 T-DNA insert.

BRIEF DESCRIPTION OF THE SEQUENCES IN THE SEQUENCE LISTING

SEQ ID NO: 1 is a nucleotide sequence of the MIR604 insertion site sequence from *maize* line A188. This the MIR604 insertion site without an event MIR604 transgene.

SEQ ID NO: 2 is *maize* elite line NP2222 genomic sequences corresponding to the A188 MIR604 insertion site and its flanking sequences.

SEQ ID NO: 3-27 are nucleotide sequences that are potential target sequences for Cas9-mediated cleavage proximal to the MIR604 insertion site.

SEQ ID NO: 28 is a *maize* genomic target sequence, MIR604FR2.

SEQ ID NO: 29 is a nucleotide sequence encoding a Type II Cas9 gene from *Streptococcus pyogenes* SF370 optimized with *maize*-preferred codons.

SEQ ID NO: 30 is an amino acid sequence comprising a modified Cas9 protein.

SEQ ID NO: 31-34 are nucleotide sequences that can be used to guide Cas9 cleavage of the MIR604 insertion site.

SEQ ID NO: 35 is a nucleotide sequence encoding tracRNA scaffold and PolIII termination sequences.

SEQ ID NO: 36 is a nucleotide sequence encoding a single guide RNA (sgRNA).

SEQ ID NO: 37 is a nucleotide sequence comprising an expression cassette comprising prOsU3 and coding sequences for the sgRNA of SEQ ID NO: 36.

SEQ ID NO: 38 is a nucleotide sequence comprising xJHAX-03.

SEQ ID NO: 39 is a nucleotide sequence comprising xJHAX-04.

SEQ ID NO: 40-65 are nucleotide sequences selected as TALEN target sequences based on NP2222 genomic sequences (SEQ ID NO: 2).

SEQ ID NO: 66 is a nucleotide sequence comprising the TALEN target sequence MIR604FR1.

SEQ ID NO: 67 is a nucleotide sequence comprising the TALEN target sequence MIR604FR2.

SEQ ID NO: 68 is an amino acid sequence of the artificial nuclease cTNmir604Fw1-01 which recognizes target sequence SEQ ID NO: 42.

SEQ ID NO: 69 is an amino acid sequence of the artificial nuclease cTNmir604Fw1-02 which recognizes target sequence SEQ ID NO: 42.

SEQ ID NO: 70 is an amino acid sequence of the artificial nuclease cTNmirFw1-03 which recognizes target sequence SEQ ID NO: 42.

SEQ ID NO: 71 is an amino acid sequence of the artificial nuclease cTNmir604Rv1-01 which recognizes target sequence SEQ ID NO: 43.

SEQ ID NO: 72 is an amino acid sequence of the artificial nuclease cTNmir604Rv1-02 which recognizes target sequence SEQ ID NO: 43.

SEQ ID NO: 73 is an amino acid sequence of the artificial nuclease cTNmir604Rv1-03 which recognizes target sequence SEQ ID NO: 43.

SEQ ID NO: 74 is an amino acid sequence of the artificial nuclease cTNmir604Fw2-01 which recognizes target sequence SEQ ID NO: 53.

SEQ ID NO: 75 is an amino acid sequence of the artificial nuclease cTNmir604Fw2-02 which recognizes target sequence SEQ ID NO: 53.

SEQ ID NO: 76 is an amino acid sequence of the artificial nuclease cTNmir604Fw2-03 which recognizes target sequence SEQ ID NO: 53.

SEQ ID NO: 77 is an amino acid sequence of the artificial nuclease cTNmire604RV2-01 which recognizes target sequence SEQ ID NO: 54.

SEQ ID NO: 78 is an amino acid sequence of the artificial nuclease cTNmir604RV2-02 which recognizes target sequence SEQ ID NO: 54.

SEQ ID NO: 79 is an amino acid sequence of the artificial nuclease cTNmir604Rv2-03 which recognizes target sequence SEQ ID NO: 54.

SEQ ID NO: 80 is an amino acid sequence of the artificial nuclease cTNmir604Fw2-05 which recognizes target sequence SEQ ID NO: 53.

SEQ ID NO: 81 is an amino acid sequence of the artificial nuclease cTNmir604Rv2-04 which recognizes target sequence SEQ ID NO: 65.

SEQ ID NO: 82 is a nucleotide sequence encoding for the full length artificial nuclease molecule cTNmir604Fw1-01 (SEQ ID NO:68).

SEQ ID NO: 83 is a nucleotide sequence encoding for the truncated artificial nuclease molecule cTNmir604Fw1-03 (SEQ ID NO:70).

SEQ ID NO: 84 is a nucleotide sequence encoding for the full length artificial nuclease molecule cTNmir604Rv1-01 (SEQ ID NO:71).

SEQ ID NO: 85 is a nucleotide sequence encoding for the truncated artificial nuclease molecule cTNmir604Rv1-03 (Seq. ID No.72).

SEQ ID NO: 86 is a nucleotide sequence encoding for the full length artificial nuclease molecule cTNmir604Fw2-01 (SEQ ID NO:72).

SEQ ID NO: 87 is a nucleotide sequence encoding for the truncated artificial nuclease molecule cTNmir604Fw2-03 (SEQ ID NO:73).

SEQ ID NO: 88 is a nucleotide sequence encoding for the truncated artificial nuclease molecule cTNmir604Fw2-05 (SEQ ID NO:80).

SEQ ID NO: 89 is a nucleotide sequence encoding for the full length artificial nuclease molecule cTNmir604Rv2-01 (SEQ ID NO:77).

SEQ ID NO: 90 is a nucleotide sequence encoding for the truncated artificial nuclease molecule cTNmir604Rv2-03 (SEQ ID NO:79).

SEQ ID NO: 91 is a nucleotide sequence encoding for the truncated artificial nuclease molecule cTNmir604Rv2-04 (SEQ ID NO.81).

SEQ ID NO: 92-97 are nucleotide sequences useful for using qPCR for the detection of mutations within the SEQ ID NO: 67 target sequence.

SEQ ID NO: 98 is a nucleotide sequence comprising a gene encoding phosphomannose isomerase (cPMI-01).

SEQ ID NO: 99-101 are nucleotide sequences comprising PMI target sequences for genomic modification meditated by TALENs SEQ ID NO: 102-107 are nucleotide sequences comprising TALEN sequence targets within SEQ ID NO: 98.

SEQ ID NO: 108 is an amino acid sequence of the artificial nuclease protein TLN_PMIFW1a which recognizes SEQ ID NO: 102

SEQ ID NO: 109 is an amino acid sequence of the artificial nuclease protein TLN_PMIRV1a which recognizes SEQ ID NO: 103.

SEQ ID NO: 110 is an amino acid sequence of the artificial nuclease protein TLN_PMIFW3 which recognizes SEQ ID NO: 106

SEQ ID NO: 111 is an amino acid sequence of the artificial nuclease protein TLN_PMIRV3 which recognizes SEQ ID NO: 107.

SEQ ID NO: 112 is a nucleotide sequence which encodes for the artificial nuclease protein TLN_PMIFW1a.

SEQ ID NO: 113 is a nucleotide sequence which encodes for the artificial nuclease protein TLN_PMIRV1a.

SEQ ID NO: 114 is a nucleotide sequence which encodes for the artificial nuclease protein TLN_PMIFW3.

SEQ ID NO: 115 is a nucleotide sequence which encodes for the artificial nuclease protein TLN_PMIRV3.

SEQ ID NO: 116-118 are nucleotide sequences comprising the artificial nuclease target sequences.

SEQ ID NO: 119 is an amino acid sequence of the artificial nuclease protein TLN_rPMIFW1-01 which recognizes SEQ ID NO: 117.

SEQ ID NO: 120 is an amino acid sequence of the artificial nuclease protein TLN_rPMIRv1-01 which recognizes SEQ ID NO: 118.

SEQ ID NO: 121 is an amino acid sequence of the artificial nuclease protein TLN_rPMIFw1-02 which recognizes SEQ ID NO: 117.

SEQ ID NO: 122 is an amino acid sequence of the artificial nuclease protein TLN_rPMIRv1-02 which recognizes SEQ ID NO: 118.

SEQ ID NO: 123 is a nucleotide sequence encoding the artificial nuclease protein TLN_rPMIFW1-01.

SEQ ID NO: 124 is a nucleotide sequence encoding the artificial nuclease protein TLN_rPMIRv1-01.

SEQ ID NO: 125 is a nucleotide sequence encoding the artificial nuclease protein TLN_rPMIFW1-02.

SEQ ID NO: 126 is a nucleotide sequence encoding the artificial nuclease protein TLN_rPMIRv1-02.

SEQ ID NO: 127-132 are nucleotide sequences useful for the detection of targeted integration.

SEQ ID NO: 133 is a nucleotide sequence of the PMI expression cassette (prZmUbi1-cPMI-tNOS) present in the T-DNA insert of event MIR604 transgenic plants (FIG. 9).

SEQ ID NO: 134 is a nucleotide sequence of the T-DNA insert present in event MIR604 and of the right and left border regions (FIG. 9).

SEQ ID NO: 135 is a nucleotide sequence of event MIR604 transgene locus including the whole T-DNA insert and the flanking genomic DNA regions, including RBFS and LBFS (FIG. 9).

SEQ ID NO: 136 is a nucleotide sequence of the B73 *maize* genomic region proximal to the MIR604 T-DNA insertion right border (RB) region (RBFS in FIG. 9).

SEQ ID NO: 137 is a nucleotide sequence of the B73 *maize* genomic region proximal to the MIR604 T-DNA insertion left border (LB) region (LBFS in FIG. 9).

SEQ ID NO: 138 is a nucleotide sequence of the elite *maize* line NP2222 genomic sequence corresponding to the B73 MIR604 insertion site locus sequences proximal to the RB region including the RBFS (FIG. 9).

SEQ ID NO: 139 is a nucleotide sequence of the elite maize line NP2222 genomic sequence corresponding to the B73 MIR604 T-DNA insertion site locus sequences proximal to the LB region including the LBFS (FIG. 9).

SEQ ID NO: 140 is a nucleotide sequence of the MIR604 insertion site in a maize genome (FIG. 7).

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., *Glossary of Genetics: Classical and Molecular*, 5$^{th}$ edition, Springer-Verlag: New York, 1994.

"Accuracy" of an amplification method such as a polymerase chain reaction (PCR) method (e.g., TaqMan) means the closeness of agreement between a test result and an accepted reference value.

As used herein, the term "amplified" means the construction of multiple copies of a nucleic acid molecule or multiple copies complementary to the nucleic acid molecule using at least one of the nucleic acid molecules as a template. See, e.g., Diagnostic Molecular Microbiology: Principles and Applications, D. H. Persing et al., Ed., American Society for Microbiology, Wash., D.C. (1993). The product of amplification is termed an amplicon.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

The "coefficient of linearity ($R^2$)" is the correlation coefficient of a standard curve obtained by linear regression analysis.

"Dynamic range" as used herein means the range of DNA concentrations over which the method of the invention performs in a linear manner with an acceptable level of accuracy and precision.

"Detection kit" as used herein refers to a kit used to detect target DNA from the events of interest in a sample comprising nucleic acid probes and primers of the present invention, which will be processed specifically under optimum conditions to a target DNA sequence, and other materials necessary to enable nucleic acid hybridization and/or amplification methods.

As used herein the term transgenic "event" refers to a recombinant plant produced by transformation and regeneration of a single plant cell with heterologous DNA, for example, an expression cassette that includes one or more genes of interest (e.g., transgenes). The term "event" refers to the original transformant and/or progeny of the transformant that include the heterologous DNA. The term "event" also refers to progeny produced by a sexual outcross between the transformant and another line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event MIR604," "MIR604" or "MIR604 event" as used herein, means the original MIR604 transformant and/or progeny of the MIR604 transformant (U.S. Pat. Nos. 7,361, 813, 7,897,748, 8,354,519, and 8,884,102, incorporated by references herein).

The insertion site of event MIR604 has many characteristics which make it a good candidate for a target site for genomic modifications. Such characteristics include that the site does not interrupt native genes, the site is not in a highly repetitive region of nucleotide sequence, the nucleotide sequence of the site is not significantly repeated elsewhere in the *maize* genome, and transgenes introduced at this site are known to have good expression levels, both in the initially transformed plant, in other *maize* varieties into which event MIR604 has been introduced, and in the progeny of event MIR604 plants, for multiple generations. Additionally, the success of event MIR604 as a commercial product and in a successful commercial-level breeding program, where event MIR604 is introduced into at least dozens of *maize* varieties and has shown excellent expression of the transgenes in multiple environmental conditions, indicates that the event MIR604 insertion site is a good candidate for targeted insertion.

"Expression cassette" as used herein means a nucleic acid molecule capable of directing expression of a particular nucleotide sequence in an appropriate host cell, comprising a promoter operably linked to the nucleotide sequence of interest, typically a coding region, which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

"Genotype" as used herein is the genetic material inherited from parent plants not all of which is necessarily expressed in the descendant plants. By way of example, the MIR604 genotype refers to the heterologous genetic material transformed into the genome of a plant as well as the genetic material flanking the inserted sequence.

As used herein, "heterologous" refers to a nucleic acid molecule or nucleotide sequence not naturally associated with a host cell into which it is introduced, that either originates from another species or is from the same species or organism but is modified from either its original form or the form primarily expressed in the cell, including non-naturally occurring multiple copies of a naturally occurring nucleic acid sequence. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., present in a different copy number, and/or under the control of different regulatory sequences than that found in the native state of the nucleic acid molecule. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

A "homologous" nucleic acid sequence is a nucleic acid sequence naturally associated with a host cell into which it is introduced. A homologous nucleic acid sequence can also be a nucleic acid sequence that is naturally associated with other nucleic acid sequences that may be present, e.g., in a nucleic acid construct. As one nonlimiting example, a promoter may be present in a nucleic acid construct in combination with one or more regulatory elements and/or coding sequences that naturally occur in association with that particular promoter, i.e., they are homologous to the promoter.

"Operably-linked" refers to the association of nucleic acid sequences on a single nucleic acid sequence so that the function of one affects the function of the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences in sense or antisense orientation can be operably-linked to regulatory sequences.

"Primers" as used herein are isolated nucleic acids that are annealed to a complementary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other nucleic-acid amplification methods.

A "probe" is an isolated nucleic acid molecule that is complementary to a portion of a target nucleic acid molecule and is typically used to detect and/or quantify the target nucleic acid molecule. Thus, in some embodiments, a probe can be an isolated nucleic acid molecule to which is attached a detectable moiety or reporter molecule, such as a radioactive isotope, ligand, chemiluminescenc agent, fluorescence agent or enzyme. Probes according to the present invention can include not only deoxyribonucleic or ribonucleic acids but also polyamides and other probe materials that bind specifically to a target nucleic acid sequence and can be used to detect the presence of and/or quantify the amount of, that target nucleic acid sequence.

A TaqMan probe is designed such that it anneals within a DNA region amplified by a specific set of primers. As the Taq polymerase extends the primer and synthesizes the nascent strand from a single-strand template from 3' to 5' of the complementary strand, the 5' to 3' exonuclease of the polymerase extends the nascent strand through the probe and consequently degrades the probe that has annealed to the template. Degradation of the probe releases the fluorophore from it and breaks the close proximity to the quencher, thus relieving the quenching effect and allowing fluorescence of the fluorophore. Hence, fluorescence detected in the quantitative PCR thermal cycler is directly proportional to the fluorophore released and the amount of DNA template present in the PCR.

Primers and probes are generally between 5 and 100 nucleotides or more in length. In some embodiments, primers and probes can be at least 20 nucleotides or more in length, or at least 25 nucleotides or more, or at least 30 nucleotides or more in length. Such primers and probes hybridize specifically to a target sequence under optimum hybridization conditions as are known in the art. Primers and probes according to the present invention may have complete sequence complementarity with the target sequence, although probes differing from the target sequence and which retain the ability to hybridize to target sequences may be designed by conventional methods according to the invention.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

The polymerase chain reaction (PCR) is a technique for "amplifying" a particular piece of DNA. In order to perform PCR, at least a portion of the nucleotide sequence of the DNA molecule to be replicated must be known. In general, primers or short oligonucleotides are used that are complementary (e.g., substantially complementary or fully complementary) to the nucleotide sequence at the 3' end of each strand of the DNA to be amplified (known sequence). The DNA sample is heated to separate its strands and is mixed with the primers. The primers hybridize to their complementary sequences in the DNA sample. Synthesis begins (5' to 3' direction) using the original DNA strand as the template. The reaction mixture must contain all four deoxynucleotide triphosphates (dATP, dCTP, dGTP, dTTP) and a DNA polymerase. Polymerization continues until each newly-synthesized strand has proceeded far enough to contain the sequence recognized by the other primer. Once this occurs, two DNA molecules are created that are identical to the original molecule. These two molecules are heated to separate their strands and the process is repeated. Each cycle doubles the number of DNA molecules. Using automated equipment, each cycle of replication can be completed in less than 5 minutes. After 30 cycles, what began as a single molecule of DNA has been amplified into more than a billion copies ($2^{30}=1.02\times10^9$).

The oligonucleotides of an oligonucleotide primer pair are complementary to DNA sequences located on opposite DNA strands and flanking the region to be amplified. The annealed primers hybridize to the newly synthesized DNA strands. The first amplification cycle will result in two new DNA strands whose 5' end is fixed by the position of the oligonucleotide primer but whose 3' end is variable ('ragged' 3' ends). The two new strands can serve in turn as templates for synthesis of complementary strands of the desired length (the 5' ends are defined by the primer and the 3' ends are fixed because synthesis cannot proceed past the terminus of the opposing primer). After a few cycles, the desired fixed length product begins to predominate.

A quantitative polymerase chain reaction (qPCR), also referred to as real-time polymerase chain reaction, monitors the accumulation of a DNA product from a PCR reaction in real time. qPCR is a laboratory technique of molecular biology based on the polymerase chain reaction (PCR), which is used to amplify and simultaneously quantify a targeted DNA molecule. Even one copy of a specific sequence can be amplified and detected in PCR. The PCR reaction generates copies of a DNA template exponentially. This results in a quantitative relationship between the amount of starting target sequence and amount of PCR product accumulated at any particular cycle. Due to inhibitors of the polymerase reaction found with the template, reagent limitation or accumulation of pyrophosphate molecules, the PCR reaction eventually ceases to generate template at an exponential rate (i.e., the plateau phase), making the end point quantitation of PCR products unreliable. Therefore, duplicate reactions may generate variable amounts of PCR product. Only during the exponential phase of the PCR reaction is it possible to extrapolate back in order to determine the starting quantity of template sequence. The measurement of PCR products as they accumulate (i.e., real-time quantitative PCR) allows quantitation in the exponential phase of the reaction and therefore removes the variability associated with conventional PCR. In a real time PCR assay, a positive reaction is detected by accumulation of a fluorescent signal. For one or more specific sequences in a DNA sample, quantitative PCR enables both detection and quantification. The quantity can be either an absolute number of copies or a relative amount when normalized to DNA input or additional normalizing genes. Since the first documentation of real-time PCR, it has been used for an increasing and diverse number of applications including mRNA expression studies, DNA copy number measurements in genomic or viral DNAs, allelic discrimination assays, expression analysis of specific splice variants of genes and gene expression in paraffin-embedded tissues and laser captured micro-dissected cells.

As used herein, the phrase "Ct value" refers to "threshold cycle," which is defined as the "fractional cycle number at which the amount of amplified target reaches a fixed threshold." In some embodiments, it represents an intersection between an amplification curve and a threshold line. The amplification curve is typically in an "S" shape indicating the change of relative fluorescence of each reaction (Y-axis) at a given cycle (X-axis), which in some embodiments is recorded during PCR by a real-time PCR instrument. The threshold line is in some embodiments the level of detection at which a reaction reaches a fluorescence intensity above background. See Livak & Schmittgen (2001) 25 *Methods* 402-408. It is a relative measure of the concentration of the target in the PCR. Generally, good Ct values for quantitative assays such as qPCR are in some embodiments in the range of 10-40 for a given reference gene. Ct levels are inversely proportional to the amount of target nucleic acid in the sample (i.e., the lower the Ct level the greater the amount of detectable target nucleic acid in the sample). Additionally, good Ct values for quantitative assays such as qPCR show a linear response range with proportional dilutions of target gDNA.

In some embodiments, qPCR is performed under conditions wherein the Ct value can be collected in real-time for quantitative analysis. For example, in a typical qPCR experiment, DNA amplification is monitored at each cycle of PCR during the extension stage. The amount of fluorescence generally increases above the background when DNA is in the log linear phase of amplification. In some embodiments, the Ct value is collected at this time point.

The term "transformation" as used herein refers to the transfer of a nucleic acid molecule into the genome of a host cell, resulting in genetically stable inheritance. In some embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or any combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation-sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hagen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "nucleotide sequence" "nucleic acid," "nucleic acid sequence," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid molecule refers to a chain of nucleotides without regard to length of the chain. The nucleotides contain a sugar, phosphate and a base which is either a purine or pyrimidine. A nucleic acid molecule can be double-stranded or single-stranded. Where single-stranded, the nucleic acid molecule can be a sense strand or an antisense strand. A nucleic acid molecule can be synthesized using oligonucleotide analogs or derivatives (e.g., inosine or phosphorothioate nucleotides). Such oligonucleotides can be used, for example, to prepare nucleic acid molecules that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. Unless otherwise indicated, a particular nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid molecule is used interchangeably with gene, cDNA, and mRNA encoded by a gene.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, at least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant parasite, reducing the growth of a nematode plant parasite, reducing cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. U.S.A.* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. U.S.A.* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism. A "homologous" nucleotide sequence is a nucleotide sequence naturally associated with a host cell into which it is introduced.

By the term "express" or "expression" of a polynucleotide coding sequence, it is meant that the sequence is transcribed, and optionally translated.

"Nucleotide sequence of interest" refers to any nucleotide sequence which, when introduced into a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "nucleotide sequence of interest" may also be one that is transferred to plants for the production of commercially valuable enzymes or metabolites in the plant.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter in operative association with a nucleotide sequence encoding miR396c would be capable of effecting the expression of that miR396c nucleotide sequence.

The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

"Transient transformation" in the context of a polynucleotide means that a polynucleotide is introduced into the cell and does not integrate into the genome of the cell.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "promoter" includes "promoter regulatory sequences."

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Gene" refers to a nucleic acid fragment that expresses mRNA, functional RNA, or specific protein, including regulatory sequences. The term "native gene" refers to a gene as found in nature. The term "chimeric gene" refers to any gene that contains 1) DNA sequences, including regulatory and coding sequences that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a nucleic acid molecule that has been introduced into the genome by transformation and is stably maintained. A transgene may comprise at least one expression cassette, typically comprises at least two expression cassettes, and may comprise ten or more expression cassettes. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

Accordingly, in one embodiment, the present invention provides a method of integrating a transgene into a genomic nuclease cleavage site in a *maize* genome, comprising introducing into a *maize* cell: a) a first nucleic acid molecule comprising at least 80, at least 90, at least 100, at least 110, at least 120, at least 130, at least 140, or at least 150 contiguous nucleotides, wherein said contiguous nucleotides have at least 80%, at least 85%, at least 90%, at least 93%, at least 95%, at least 96%, at least 97%, at least 98%, at least 99%, or 100% identity with a target site in the nucleotide sequence of SEQ ID NO:1 or the nucleotide sequence of SEQ ID NO:2, and further comprising a transgene; and b) a second nucleic acid molecule comprising a nucleotide sequence encoding a nuclease for site-directed cleavage at a genomic nuclease cleavage site adjacent to the nucleotide sequence of SEQ ID NO:1 or the nucleotide sequence of SEQ ID NO:2 that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the *maize* genome.

As used herein, a "target site" means a region of nucleotides in the genome that is the selected or preferred site for insertion of a nucleotide sequence (e.g., one or more transgenes, expression cassettes, or nucleotide sequences of interest) into the genome as well as a selected or preferred site for introducing a mutation (e.g., a substitution and/or a deletion, and/or an insertion such as an INDEL) into the genome. In some embodiments, a target site can comprise a nuclease cleavage site, also referred to as a genomic nuclease cleavage site. A nonlimiting example of a target site of this invention is the chromosome interval on chromosome 1 defined by and including base pair (bp) position 38,860,000 to base pair (bp) position 39,105,000 as defined by *Maize* B73 RefGen_V2 available in the *Maize* Genome Database.

As used herein, the terms "adjacent" or "adjacent to" with regard to one or more nucleotide sequences of this invention means immediately next to (e.g., with no intervening sequence) or separated by from about 1 base to about 10,000 bases (e.g., 1, 2, 3, 4, 5, 6, 7, 8, 9, 10, 15, 20, 30, 40, 50, 100, 200, 500, 1000, 2000, 3000, 4000, 5000, 6000, 7000, 8000, 9000, or 10,000 bases), including any values included within this range but not explicitly recited herein.

A "nuclease cleavage site" or "genomic nuclease cleavage site" is a region of nucleotides that comprise a nuclease cleavage sequence that is recognized by a specific nuclease, which acts to cleave the nucleotide sequence of the genomic DNA in one or both strands. Such cleavage by the nuclease enzyme initiates DNA repair mechanisms within the cell, which establishes an environment for homologous recombination to occur. In the methods herein wherein the first nucleic acid molecule comprises, for example, at least about 100 contiguous nucleotides having, for example, at least 90% identity with a target site in the genome of the cell, the first nucleic acid molecule is integrated into the genome of the cell via homologous recombination, thereby integrating the one or more transgenes into the genome of the cell.

In some embodiments of the above method, the first nucleic acid molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or 20,000 nucleotides, including any value within this range not explicitly recited herein.

In some embodiments of the above method, the nucleotide sequence comprising the genomic nuclease cleavage site in the *maize* genome can be the nucleotide sequence of SEQ ID NO:1, SEQ ID NO:2, SEQ ID NO:3, SEQ ID NO:28, SEQ ID NO:66, or SEQ ID NO:67.

In some embodiments of the above method, the genomic nuclease cleavage site is located within a chromosome interval on chromosome 1 defined by and including base pair (bp) position 38,860,000 to base pair (bp) position 39,015,000 as defined by *Maize* B73 RefGen_V2, available in the *Maize* Genome Database.

In some embodiments of the method above, the nuclease has cleavage specificity for a nuclease cleavage site in the nucleotide sequence selected from the group consisting of SEQ ID NO:1 (HiII-MIR604), SEQ ID NO:2 (AX-MIR604), SEQ ID NO:3, SEQ ID NO:28, SEQ ID NO:66, SEQ ID NO:67 and any combination thereof.

In some embodiments, the first nucleic acid molecule and the second nucleic acid molecule can be introduced into the *maize* cell by biolistic nucleic acid delivery, via an *Agrobacterium*, by co-transformation, and/or with a T-DNA vector in any combination and/or order.

In some embodiments, the first nucleic acid molecule and the second nucleic acid molecule can be present on a single nucleic acid construct and in some embodiments, the first nucleic acid molecule and the second nucleic acid molecule can be present on separate nucleic acid constructs.

In some embodiments, the first nucleic acid molecule and/or the second nucleic acid molecule can be transiently expressed in the *maize* cell.

In some embodiments, the first nucleic acid molecule and/or the second nucleic acid molecule can be stably integrated into the *maize* genome in the *maize* cell.

The present invention further provides a method of producing a *maize* plant, plant part, or progeny thereof comprising a transgene integrated into the genomic nuclease cleavage site in the *maize* genome, comprising regenerating a *maize* plant from the *maize* cell produced by the method described herein. Accordingly, the present invention provides a *maize* plant, plant part, or progeny thereof comprising the transgene integrated into the genomic nuclease cleavage site in the *maize* genome, produced by the method of this invention.

The present invention is based in some embodiments on the unexpected discovery and development of rapid (e.g., high throughput) methods to identify and enrich for cells that comprise one or more transgenes integrated into the genome at a target site that employ selective combinations of quantitative polymerase chain reaction (qPCR) assays.

The present invention further provides a method of identifying a cell and/or enriching for a cell comprising a transgene inserted into a nuclease cleavage site in a genome of the cell, comprising: a) introducing into a plurality of cells: i) a first nucleic acid molecule comprising at least 80, at least 90, at least 100, at least 110, at least 120, at least 130, at least 140, or at least 150 contiguous nucleotides—wherein the contiguous nucleotides have at least 80%, at least 85%, at least 90%, at least 93%, at least 95%, at least 96%, at least 97%, at least 98%, at least 99%, or 100% identity with a target site in the genome of the cell, and further comprising a transgene; and ii) a second nucleic acid molecule encoding a nuclease for site-directed cleavage at a nuclease cleavage site in the genome of the cell adjacent to the nucleotide sequence in the genome of the cell that corresponds to the contiguous nucleotides of (i), under conditions wherein expression of the second nucleic acid molecule can occur to produce the nuclease and the nuclease can cleave at the nuclease cleavage site in the genome of the cell and integrate the transgene into the nuclease cleavage site in the genome of the cell; b) culturing the cells of (a) to produce at least one cell line or tissue; c) extracting a genomic DNA sample from each of the cell lines or tissues of (b); d) performing real-time quantitative polymerase chain reaction (qPCR) assays T and G on the samples of (c), wherein the assays T and G respectively comprise the following probes: i) a first probe comprising a nucleotide sequence that is complementary to a nucleotide sequence of the target site, at least one, at least two, at least three, at least four, at least five, at least six, at least seven, at least eight, at least nine, at least ten, at least twelve, or at least fifteen base pairs away from the nuclease cleavage site for carrying out assay T, and ii) a second probe comprising a nucleotide sequence that is complementary to a nucleotide sequence of the transgene for carrying out assay G; e) obtaining a DNA copy number of the target site from the results of assay T and a DNA copy number of the transgene from the results of assay G; and f) identifying and/or enriching for a cell line or tissue that has reduced copy number in assay T relative to a reference and a copy number greater than zero for assay G, thereby identifying and/or enriching for the cell comprising the transgene inserted into the nuclease cleavage site in the genome of the cell.

In the methods described above directed to identifying and/or enriching for cells that comprise one or more transgenes inserted into a nuclease cleavage site in a genome of the cell, the qPCR assays can be performed in a high-throughput format as is well known in the art, such that a large volume of samples can be assayed rapidly and simultaneously. Such rapid and efficient screening allows for the identification and enrichment for the small percentage of cells (e.g., around 2%) among the plurality of cells employed in these methods, which would typically be a large volume of cells.

In the methods described above, the first probe (for carrying out assay T) can comprise, consist essentially of or consist of a nucleotide sequence that is complementary (e.g., at least about 90%, 95%, 98%, 99% or 100% complementary) to nucleotide sequence at least five (e.g., 4, 5, 6, 7, 8, 9, 10, 11, 12, 13, 14, 15, 16, 17, 18, 19, 20) base pairs away from the nuclease cleavage site and the second probe (for carrying out assay G) can comprise a nucleotide sequence that is complementary (e.g., at least about 90%, 95%, 98%, 99% or 100% complementary) to at least one of the one or more transgenes.

In some embodiments of the enriching and identifying methods described above, in addition to the step of identifying and/or enriching for a cell line or tissue that has reduced copy number in assay T relative to a reference and a copy number greater than zero (e.g., a copy number of about one, a copy number of about 2, or a copy number of about 3) for assay G, the methods in some embodiments can further comprise the step of discarding a cell line or tissue that has no change in the DNA copy number of assay T in comparison with a reference, and in some embodiments, can further comprise the step of discarding a cell line or tissue that has a copy number of zero (e.g., a copy number of less than one) for assay G.

As used herein, being "positive" or a positive result for an assay (e.g., assay G) means that the copy number is greater than zero and being "negative" for an assay (e.g., assay G) means that the copy number is zero or less than one.

As also used herein, a "reference" is a genome that has a fixed gene copy number. In some embodiments, the reference can be a "wild type" genome (e.g., a genome of a cell that has not had the first and second nucleic acid molecules of this invention introduced into it according to the methods of this invention)

In particular embodiments of the invention, the first and second probes are fluorescence probes and in some embodiments, the first and second probes are Taqman probes.

In some embodiments of the invention, the qPCR assays are performed in the same mixture and in some embodiments, the qPCR assays are performed in different mixtures, in any combination.

In embodiments in which the plant is a *maize* plant, the nuclease cleavage site is a *maize* MIR604 transgene insertion site, namely a nucleotide sequence with at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2.

In some embodiments of the methods described herein, the nuclease can be a non-engineered nuclease (e.g., a nuclease in its "native" form or "wild type" form without modifications). In some embodiments, the nuclease can be an engineered nuclease with programmable cleavage target specificity. Non-limiting examples of a nuclease of this invention include CRISPR gRNA-Cas9 nuclease, zinc finger nuclease, engineered meganuclease and/or TAL effector nuclease, singly or in any combination.

The present invention also provides a cell line or tissue that is identified and/or enriched by the methods described herein, wherein the cell line or tissue is derived from a plant or a plant part. In some embodiments, the cell line or tissue is derived from a monocot plant or monocot plant part. In some embodiments, the cell line or tissue is derived from a dicot plant or plant part. In some embodiments, the cell line or tissue is derived from a cereal plant or cereal plant part. In further embodiments, the cell line or tissue is derived from a *maize* plant or *maize* plant part. Other nonlimiting examples of a plant of this invention include rice, sugarcane, barley, sugarbeet, potato, tobacco, soybean, tomato, wheat and sunflower.

Further provided herein is a cell line or tissue that is identified and/or enriched by the methods described herein, wherein the cell line or tissue is derived from a eukaryotic organism.

In some embodiments of the enriching and identifying methods described above, in addition to the step of identifying and/or enriching for a cell line or tissue that has reduced copy number in assay T relative to a reference and is positive for assay G, the methods in some embodiments can further comprise the step of discarding a cell line or tissue that has no change in the DNA copy number of assay T in comparison with a reference, and in some embodiments, can further comprise the step of discarding a cell line or tissue that is negative for assay G.

As used herein, being "positive" for an assay (e.g., assay G) means that the copy number is greater than zero and being "negative" for an assay (e.g., assay G) means that the copy number is equal to zero.

As also used herein, a "reference" is a genome or other nucleic acid molecule that has a fixed gene copy number. In some embodiments, the reference can be a "wild type" genome (e.g., a genome of a cell that has not had the first and second nucleic acid molecules of this invention introduced into it according to the methods of this invention)

In particular embodiments of the invention, the first and second probes are fluorescence probes and in some embodiments the first and second probes are Taqman probes.

In some embodiments of the invention, the qPCR assays are performed in the same mixture and in some embodiments, the qPCR assays are performed in different mixtures, in any combination.

In embodiments in which the plant produced is a *maize* plant, the nuclease cleavage site is a *maize* MIR604 transgene insertion site, namely a nucleotide sequence with at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2

Further provided herein is a method of identifying a cell and/or for enriching for a cell comprising a mutation introduced into a nuclease cleavage site in a genome of the cell and lacking integration of a heterologous nucleotide sequence encoding a nuclease for site-directed cleavage of a nucleotide sequence at the nuclease cleavage site into the genome of the cell, comprising: a) introducing a nucleic acid molecule comprising a heterologous sequence encoding a nuclease for site-directed cleavage of the nucleotide sequence at the nuclease cleavage site in the genome of the cell into a plurality of cells under conditions wherein expression of the nucleic acid molecule can occur to produce the nuclease and the nuclease can cleave the nucleotide sequence at the nuclease cleavage site in the genome of the cell, thereby introducing a mutation at the nuclease cleavage site in the genome of the cell without integration of the heterologous nucleotide sequence encoding the nuclease into the genome of the cell; b) culturing the plurality of cells of (a) to produce at least one cell line or tissue; c) extracting a genomic DNA sample from each of the cell lines or tissues of (b); d) performing real-time quantitative polymerase chain reaction (qPCR) assays 1 and 2 on the samples of (c), wherein the assays respectively comprise the following probes: i) a first probe comprising a nucleotide sequence that is complementary to the nucleotide sequence comprising the nuclease cleavage site to carry out assay 1, and ii) a second probe comprising a nucleotide sequence that is complementary to the heterologous nucleotide sequence encoding the nuclease to carry out assay 2; e) obtaining a DNA copy number of the nuclease cleavage site from the results of assay 1 and a DNA copy number of the heterologous nucleotide sequence encoding the nuclease from the results of assay 2; and f) identifying and/or enriching for a cell line or tissue that has a reduced copy number for assay 1 relative to a reference and a copy number equal to zero for assay 2, thereby identifying and/or enriching for the cell comprising the mutation introduced into the nuclease cleavage site in the genome of the cell and lacking integration of the heterologous nucleotide sequence encoding the nuclease into the genome of the cell.

In some embodiments of the methods described herein, the cell line or tissue may be derived from a plant or plant part, for example a plant derived from tissue culture or germinated seeds. In some embodiments the plant can be a monocot and in some embodiments, the plant can be a dicot. In some embodiments, the plant can be a cereal. In particular embodiments, the plant can be a *maize* plant. Other nonlimiting examples of a plant of this invention include rice, sugarcane, barley, sugarbeet, potato, tobacco, soybean, tomato, wheat and sunflower. In some embodiments, the cell line or tissue that is identified and/or enriched by the methods described herein is derived from a eukaryotic organism.

In some embodiments of the enriching and identifying methods described above, in addition to the step of identifying and/or enriching for a cell line or tissue that has a reduced copy number in assay 1 relative to a reference and a copy number equal to zero (e.g., is less than one) for assay 2, the methods in some embodiments can further comprise the step of discarding a cell line or tissue that has no change in the DNA copy number of assay 1 relative to a reference, and in some embodiments, can further comprise the step of discarding a cell line or tissue that has a copy number greater than zero (e.g., a copy number of about 1, a copy number of about 2, or a copy number of about 3) for assay 2.

As used herein, being "positive" or a positive result for an assay (e.g., assay 2) means that the copy number is greater than zero (e.g., a copy number of about 1, a copy number of about 2, or a copy number of about 3) and being "negative" for an assay (e.g., assay 2) means that the copy number is equal to zero (e.g., is less than one).

As also used herein, a "reference" is a genome or other nucleic acid molecule that has a fixed gene copy number. In some embodiments, the reference can be a "wild type" genome (e.g., a genome of a cell that has not had the first and second nucleic acid molecules of this invention introduced into it according to the methods of this invention).

In particular embodiments of the invention, the first and second probes are fluorescence probes and in some embodiments, the first and second probes are Taqman probes.

In some embodiments of the invention, the qPCR assays are performed in the same mixture and in some embodiments, the qPCR assays are performed in different mixtures, in any combination.

In some embodiments of the methods described herein, the tissue can be a plant derived from tissue culture or germinated seeds. In some embodiments the plant can be a monocot and in some embodiments, the plant can be a dicot. In particular embodiments, the plant can be a *maize* plant. Other nonlimiting examples of a plant of this invention include rice, sugarcane, barley, sugarbeet, potato, tobacco, soybean, tomato, wheat and sunflower.

In some embodiments of the methods described herein, the nuclease can be a non-engineered nuclease (e.g., a nuclease in its "native" form or "wild type" form without modifications). In some embodiments, the nuclease can be an engineered nuclease with programmable cleavage target specificity. Non-limiting examples of a nuclease of this invention include CRISPR gRNA-Cas9 nuclease (for example, a Cas9 nuclease comprising SEQ ID NO: 30) zinc finger nuclease, engineered meganuclease and/or TAL effector nuclease, singly or in any combination.

In embodiments in which the plant is a *maize* plant, the nuclease cleavage site is a *maize* MIR604 transgene insertion site, namely a nucleotide sequence with at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2

The present invention additionally provides a kit of reagents and instructions for carrying out the methods and assay of this invention. In some embodiments, a kit or a package comprising the compositions, formulations and/or agents for carrying out the methods of the present invention is provided. For example, a kit may include means for obtaining a cell or tissue, as well as means for obtaining a nucleic acid sample. The kit may also contain reagents for carrying out the steps of the methods of this invention. Such reagents can include site-specific probes and/or primers that facilitate isolation and biochemical characterization of nucleic acid molecules of this invention. The kit can contain one or more separate containers.

Although the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container. For example, wherein the components of the kit are in lyophilized form, the kit may optionally contain a sterile and physiologically acceptable reconstitution medium such as water, saline, buffered saline, and the like.

In some embodiments, the containers of the kit can include at least one vial, test tube, flask, bottle, syringe or other containers, into which the compositions/formulations of the present invention, and any other desired agent, may be placed and suitably aliquoted.

In additional embodiments, the present invention provides a method of producing a plant, plant part, or progeny thereof comprising a mutation introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). In another embodiment, the present invention provides for the plant cell produced by the method described above. In a further embodiment, the present invention provides for a plant or plant part regenerated or derived from the plant cell produced by the method described above.

In some embodiments of the method described above, the plant is a monocot. In other embodiments, the plant is a dicot. In some embodiments, the plant is a cereal. In further embodiments the plant is *maize*. Other nonlimiting examples of a plant of this invention include rice, sugarcane, barley, sugarbeet, potato, tobacco, soybean, tomato, wheat and sunflower.

In some embodiments of the methods described above, the mutation comprises at least one nucleotide substitution, the deletion of at least one nucleotide, or a combination of substitution, deletion, and/or insertion, such as for example an INDEL.

In some embodiments of the methods described above, the nucleic acid molecule is biolistic nucleic acid delivery, *Agrobacterium*-mediated transformation, or any method of plant transformation known in the art.

In some embodiments of the methods described above, the nuclease for site-directed cleavage is a non-engineered nuclease. In some embodiments, the nuclease is an engineered nuclease with programmable cleavage target specificity. In some embodiments, the nuclease is a Cas9. In some embodiments, the nuclease is a Cas9 comprising SEQ ID NO: 30.

The present invention additionally provides a method of producing a plant, plant part, or progeny thereof comprising a transgene introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). In another embodiment, the present invention provides for the plant cell produced by the method described above. In a further embodiment, the present invention provides for a plant or plant part regenerated or derived from the plant cell produced by the method described above.

In some embodiments of the method described above, the transgene may comprise at least one, at least two, at least three, at least four, at least five, at least six, at least seven, at least eight, at least nine, at least ten, or ten or more expression cassettes.

In some embodiments of the method described above, the nuclease cleavage site is or is adjacent to a nucleotide sequence that has at least 80%, at least 85%, at least 90%, at least 93%, at least 95%, at least 96%, at least 97%, at least 98%, at least 99%, or 100% identity to the nucleotide sequence of SEQ ID NO:1 or SEQ ID NO:2.

In some embodiments of the methods described above, the plant is a monocot. In other embodiments, the plant is a dicot. In some embodiments, the plant is a cereal. In further embodiments the plant is *maize*. Other nonlimiting examples of a plant of this invention include rice, sugarcane, barley, sugarbeet, potato, tobacco, soybean, tomato, wheat and sunflower.

In some embodiments of the methods described above, the first nucleic acid molecule and the second nucleic acid molecule are introduced at the same time, for example by co-transformation, biolistic nucleic acid delivery, or *Agrobacterium*-mediated transformation. In some embodiments, the first nucleic acid molecule and the second nucleic acid molecule are separate molecules. In some embodiments, a single nucleic acid molecule or construct comprises the first nucleic acid molecule and the second nucleic acid molecule described above.

In some embodiments of the methods described above, the nuclease for site-directed cleavage is a non-engineered nuclease. In some embodiments, the nuclease is an engineered nuclease with programmable cleavage target specificity. In some embodiments, the nuclease is a Cas9. In some embodiments, the nuclease is a Cas9 comprising SEQ ID NO: 30.

The present invention additionally provides a method for modifying a target site in the genome of a plant cell, comprising: a) introducing into the plant cell a first nucleic acid comprising at least 100 contiguous nucleotides, wherein the at least 100 contiguous nucleotides have at least 90% identity with a target site in the genome of the cell, and further comprising a transgene; and b) a second nucleic acid molecule encoding nuclease for site-directed cleavage at a nuclease cleavage site in the genome of the cell adjacent to the nucleotide sequence in the genome of the cell that corresponds to the at least 100 contiguous nucleotides of (a), wherein the nuclease is a modified Cas9 nuclease comprising SEQ ID NO: 30, under conditions wherein expression of the second nucleic acid molecule can occur to produce the nuclease and the nuclease can cleave at the nuclease cleavage site in the genome of the cell and modify the target site in the genome of the plant cell. In another embodiment, the present invention provides for the plant cell produced by the method described above. In a further embodiment, the present invention provides for a plant or plant part regenerated or derived from the plant cell produced by the method described above.

In some embodiments of the method described above, the plant is a monocot. In other embodiments, the plant is a dicot. In some embodiments, the plant is a cereal. In further embodiments the plant is *maize*. In some embodiments, the *maize* is transgenic. In further embodiments, the transgenic *maize* is event MIR604. Other nonlimiting examples of a plant of this invention include rice, sugarcane, barley, sugarbeet, potato, tobacco, soybean, tomato, wheat and sunflower.

In some embodiments of the methods described above, the modification of the target site comprises at least one nucleotide substitution, the deletion of at least one nucleotide, or a combination of substitution, deletion, and/or insertion, such as for example an INDEL. In other embodiments, the modification of the target site is an insertion, such as a transgene insertion.

In some embodiments of the methods described above, the nucleic acid molecule is biolistic nucleic acid delivery, *Agrobacterium*-mediated transformation, or any method of plant transformation known in the art.

The present invention additionally provides a method of integrating a transgene into a genomic nuclease cleavage site in an event MIR604 transgenic *maize* genome, comprising introducing into an event MIR604 *maize* cell: a) a first nucleic acid molecule comprising at least 100 contiguous nucleotides, wherein said at least 100 contiguous nucleotides have at least 90% identity with a target site in a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, and further comprising a transgene; and b) a second nucleic acid molecule comprising a nucleotide sequence encoding a nuclease for site-directed cleavage at a genomic nuclease cleavage site adjacent to a nucleotide sequence with at least 90% identity to a nucleotide sequence selected from the group comprising SEQ ID NO:133, SEQ ID NO: 134, SEQ ID NO: 135, SEQ ID NO: 136, SEQ ID NO: 137, SEQ ID NO: 138, and SEQ ID NO: 139, that corresponds to the at least 100 contiguous nucleotides of (a), under conditions wherein expression of the second nucleic acid molecule can occur to produce the nuclease and the nuclease can cleave the nucleotide sequence at the genomic nuclease cleavage site, whereby the transgene is integrated at the genomic nuclease target cleavage site in the *maize* genome.

The present invention further provides a method of producing a *maize* plant, plant part, or progeny thereof comprising a transgene integrated into a genomic nuclease cleavage site in an event MIR604 *maize* genome, comprising regenerating a *maize* plant from the *maize* cell produced by the method described in the proceeding paragraph. The present invention further provides a *maize* plant, plant part, or progeny thereof comprising a transgene integrated into a genomic nuclease cleavage site in an event MIR604 *maize* genome, produced by the method described above.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1. Regions Around the MIR604 Transgene Insertion Site as a Potential Safe Harbor The following artificially defined criteria are used to identify potential *maize* genomic safe harbor regions that are suitable for targeted transgene integration and stable expression: (1) Regions that contain mostly unique sequences so it is suitable for performing targeted integration mediated by homologous recombination; (2) Regions that are not part of a known functional gene including those encoding for miRNAs; Ideally, these regions should be at least 2 Kb upstream of any known open reading frame or 1 Kb downstream from the 3'-untranslated region (3'-UTR) of a gene; thus integration of transgene will not interrupt any endogenous gene sequences or affect function of neighboring endogenous genes; (3) Regions that are not close to heterochromatic regions with highly repetitive sequences such as pericentromeric regions that may result in unstable expression of transgenes or potential silencing of inserted transgenes; (4) Regions that do not contain known cis-acting elements such as enhancers or repressors so that transgene expression pattern and level is altered unexpectedly when inserted. (5) Regions that have empirical data showing good transgene expression.

Several candidate regions are identified using the above criteria in the *maize* genome, for example, in chromosome 1 between position 38,555,000 and 38,605,000, between position 38,640,000 and 38,715,000, and between position 38,860,000 and 39,015,000 (*Maize* B73 RefGen_V2). Since commercial transgenic events usually have good transgene expression, insertion sites of commercial events are also examined for their potential to serve as candidate safe harbors. However, almost all of them fail to meet the above criteria except for the root-worm resistance trait event MIR604. Interestingly, the transgene insert in MIR604 happens to be located at Chromosome 1 between position 39,014,056 and 39,014,148 close to the end of position 39,015,000. Regions flanking the MIR604 insertion site is unique in that it is the only one out of the many examined to meet all of the safe harbor criteria. Since MIR604 event has been on market for several years, the region around the insertion site is an ideal candidate as safe harbor for insertion of additional transgenes. However, it is shown before that transgene inserted into the previously generated transgene loci may also lead to expression variation (Day et al. "Transgene integration into the same chromosome location can produce alleles that express at a predictable level or alleles that are differentially silenced *Genes and Develop.* 14:2869-2880 (2000)). It is important to verify the hypothesis that the MIR604 insertion site region is a good safe harbor for expression of new transgene alleles at the same locus created via site-directed transformation using different site-directed nucleases and delivery approaches.

Example 2. Cloning of the Genomic Sequences Flanking the MIR604 Insertion Site in HiII The MIR604 transgenic event was generated from binary vector pNOV2130 using *Agrobacterium*-mediated transformation of A188 *maize* immature embryos using mannose as selection. *Maize* varieties containing MIR604 transgene are widely grown in the United States. MIR604 event contains single copy insertion of pNOV2130 T-DNA in the *maize* genome. The sequences of MIR604 insertion site and its flanking regions are described in U.S. Pat. No. 8,354,519, incorporated in its entirety herein, and are as in SEQ ID NO: 1.

Example 3. Cloning of Chromosomal Sequences Corresponding to the Safe Harbor Locus 1 (MIR604 Insertion Site) Sequences from a Transformable Elite *Maize* Variety NP2222

The original MIR604 insertion site sequences (SEQ ID. NO:1) were derived from non-elite transformation variety A188. It is desirable to insert the transgene directly into an elite transformation variety. However, the sequences from the elite transformation target variety might be different than from A188 and thus will not be recognized by site-directed nucleases designed using the A188 genomic sequences. To obtain genomic sequences corresponding to the MIR604 insertion site flanking regions in the elite *maize* transformation variety NP2222 (U.S. Pat. No. 9,133,474, incorporated by reference herein), PCR primers were designed based on A188 MIR604 insertion site flanking sequences and used to amplify corresponding regions from NP2222. Amplified sequences were sequenced and assembled into a contig which was used for assembly of Hi-Seq whole genome deep sequencing reads around the insertion site. Finally, the NP2222 genomic sequences, named AX_MIR604, which corresponds to the A188 MIR604 insertion site were obtained and are as in SEQ ID NO:2. Sequence comparison shows that there are significant differences in the genomic sequences between NP2222 and A188, including many InDels (insertions/deletions) and nucleotide substitutions.

Example 4. Targeted Insertion of Transgenes at the MIR604 Insertion Site Safe Harbor Mediated by Programmable CRISPR-Cas9 Nuclease Example 4.1. Introduction to CRISPR-Cas9 Nucleases for Mediating Targeted Insertion Targeted insertion of transgenic sequences for replacing short stretches of DNA sequences (allele replacement) or inserting large DNA fragments (transgene insertion) can be mediated by DNA breaks introduced by CRISPR-Cas9 nucleases via homologous recombination (Shan et al., *Nature Biotechnology* 31:686-688 (2013); Wang et al., *Cell* 153:910-918 (2013); Yang et al., *Cell* 154:1370-1379 (2013); Puchta and Fauser, *Plant Journal* 78:727-741 (2014); Chen and Gao, *Plant Cell Rep.* 33:575-583 (2014)). In this example, CRISPR-Cas9 nucleases are used to mediate the insertion of large DNA molecules into the desired chromosomal safe harbor target in corn plants. The MIR604 event insertion site in NP2222 corn line was chosen as the tentative transgene expression safe harbor for studying Cas9/gRNA-mediated transgene insertion.

Example 4.2. Candidate Safe Harbor (MIR604) Target Sequence Selection

The putative safe harbor regions at and surrounding the MIR604 insertion site are scanned for potential Cas9 cleavage sites by using the rule of 5'-G/A-(N)$_{18-20}$-NGG-3' in both strands so that the target template sequences A(N)$_{18-20}$ and G(N)$_{18-20}$ preceding the 5'-NGG-3' sequence motif can be conveniently placed under the control of a DNA PolIII promoter such as rice prOsU3 and prOsU6, respectively. Many sequences can be identified as potential Cas9-gRNA cleavage targets around the MIR604 insertion site. For example, the following potential target sequences were identified for Cas9-mediated cleavage: 5'-AGTGC AGTGC AGTGC AGGAC AGG-3' (SEQ ID. NO:3), 5'-ACTAA TCGTG CTTCA CGCAC AGG-3'(SEQ ID. NO:4), 5'-AGGCA CAGCA CGTAG TAGAC AGG-3'(SEQ ID. NO:5); 5'-ACATG TCGAT CCGAC GACGA CGG-3'(SEQ ID. NO:6), 5'-AGTTT TATTA TAATC CGAA ACGG-3'(SEQ ID. NO:7), 5'-AATCC GAAAC GGAGC ACGCA CGG-3' (SEQ ID. NO:8), 5'-AAACG GAGCA CGCAC GGCGG TGG-3'(SEQ ID. NO:9), 5'-GGAGC ACGCA CGGCG GTGG AGG-3'(SEQ ID. NO:10), 5'-ATCCA AAGCT ACATC CGTGC AGG-3'(SEQ ID. NO:11), 5'-GTGCA GTGCA GTGCA GTGC AGG-3'(SEQ ID. NO:12), 5'-GGACA GGACC TCCTT TGTTT AGG-3'(SEQ ID. NO:13), 5'-GCGTG CGCAG AGCGC CTGCT CGG-3'(SEQ ID. NO:14), 5'-GCGTC ATCCA TGTGT TC TGG-3'(SEQ ID. NO:15), 5'-GTCCA TCTCC ATTCA CTGGT T CGG-3'(SEQ ID. NO:16), 5'-AATGC CTGCA GAAGA GGCCG TGG-3'(SEQ ID. NO:17). Similarly, target sequences from the other strand were also identified, for example: 5'-GCGGC CGGCA CGTTG CTAAC C AGG-3'(SEQ ID. NO:18), 5'-AGAGA AGAAA AATTC GTCCA TGG-3'(SEQ ID. NO:19), 5'-GGCCT CTTCT GCAGG CATT TGG-3'(SEQ ID. NO:20), 5'-AAGGA ACCCG AACCA GTGAA TGG-3'(SEQ ID. NO:21), 5'-ATCGG TCCTAA ACAAA GG AGG-3'(SEQ ID. NO:22), 5'-GGATG CAGCT TTGGC AACG AGG-3'(SEQ ID. NO:23), 5'-GTCGC GCAGC GCTCC TGCA CGG-3'(SEQ ID. NO:24), 5'-GCTCC TGCAC GGATG TAGCT T TGG-3'(SEQ ID. NO:25), 5'-GGATG TAGCT TTGGA TTGC TGG-3'(SEQ ID. NO:26), 5'-AAATA AAAAA ATCGG ATTAA AGG-3'(SEQ ID. NO:27).

One of the above listed sequences, 5'-AGTGC AGTGC AGTGC AGGAC AGG-3'(SEQ ID NO:3), which is located very close to the MIR604 insert site, was chosen as a target sequence for testing Cas9-gRNA mediated transgene insertion. Sequences (20 bp) preceding the Cas9 recognition PAM motif (5'-NGG-3'), 5'-AGTGC AGTGC AGTGC AGGAC-3' (SEQ ID NO:28, aka. xMIR604FR2) were used to construct sgRNA expression vector using the rice PolIII promoter prOsU3 in the example below.

Example 4.3. CRISPR-Cas9 and Guide RNA Design and Expression Vectors

Example 4.3.1. Optimization of Cas9 for Expression in *Maize* Cells

In order to achieve good expression in *maize* cells, Type II Cas9 gene from *Streptococcus pyogenes* SF370 was optimized with *maize*-preferred codons (cBCas9Nu-01, SEQ ID NO:29). A nuclear localization signal was also incorporated into the C-terminus of Cas9 to improve its targeting to nucleus (Cas9Nuc, SEQ ID NO:30). To express the modified Cas9 protein (Cas9Nuc) in *maize* cells, the *maize*-optimized Cas9 gene (cBCas9Nu-01, SEQ ID NO:29) was placed under the control of *maize* ubiquitin-1 promoter (prUbi1-10) followed by a terminator sequence (tNOS).

Example 4.3.2. Guide RNAs (gRNAs) for Mediating the MIR604 Insertion Site Safe Harbor Modification: gRNA Design and its Expression For targeted cleavage of the safe harbor #1 (MIR604 insertion site) target sequence (5'-AGTGC AGTGC AGTGC AGGAC AGG-3', SEQ ID NO:3), crRNAs of at least 17 nucleotides (nt) long were designed against the *maize* genomic target sequence (5'-AGTGC AGTGC AGTGC AGGAC-3', SEQ ID NO:28,) preceding the 5'-NGG-3' for Cas9-mediated target recognition. For example, crRNAs of 17-nt (5'-GC AGTGC AGTGC AGGAC-3', SEQ ID NO:31), 18-nt (5'-TGC AGTGC AGTGC AGGAC-3', SEQ ID NO:32), 19-nt (5'-GTGC AGTGC AGTGC AGGAC-3', SEQ ID NO:33), 20-nt (5'-AGTGC AGTGC AGTGC AGGAC-3', SEQ ID NO:28) or 21-nt (5'-C AGTGC AGTGC AGTGC AGGAC-3', SEQ ID NO:34) can be used to guide Cas9 cleavage of the safe harbor #1(MIR604 insertion site). The target crRNA is co-delivered with tracRNA and Cas9 protein or mRNA to mediate target site cleavage. Preferably, the crRNA molecule is fused with tracRNA molecule covalently into a single guide RNA (sgRNA). sgRNAs can be synthesized chemically or produced by in vitro transcription. In vitro produced sgRNAs can be used directly for physical delivery such as biolistic bombardment with Cas9 RNA or protein to mediate target cleavage and homology-directed target modification if repair donor oligonucleotide is co-delivered. More preferably, sgRNA is produced in planta from a DNA expression cassette comprising a RNA polymerase III (PolIII) promoter, for example the rice U3 or U6 promoters (prOsU3 and prOsU6). For prOsU3, the transcriptional start site begins with nucleotide A, whereas for prOsU6, the transcriptional start site begins with nucleotide G (Shan et al., (2013) *Nature Biotechnology* 31: 686-688; Xie and Yang, (2013) *Molecular Plant* 6:1975-1983). For example, to produce sgRNA targeting the safe harbor #1(MIR604 insertion site) sequence (5'-AGTGC AGTGC AGTGC AGGAC AGG-3', SEQ ID NO:3), 19-nt DNA oligonucleotides (5'-GTGC AGTGC AGTGC AGGAC-3', SEQ ID NO:33) or 20-nt oligonucleotides (5'-AGTGC AGTGC AGTGC AGGAC-3', SEQ ID NO:28) were fused to the DNA sequences encoding tracRNA scaffold and PolIII termination sequences (5'-GTTTT AGAGC TAGAA ATAGC AAGTT AAAAT AAGGC TAGTC CGTTA TCAAC TTGAA AAAGT GGCAC CGAGT CGGTG CTTTT TTTTT-3', SEQ ID NO:35) (Mali et al. (2013). Science 339:823-826) to form coding sequence for a single guide RNA (sgRNA) named rBsgRNA-01 (Seq. ID. NO:36) which was placed under the control of rice polymerase III promoter U3 (prOsU3) or U6 (prOsU6). For this example, the expression cassette comprised prOsU3 and coding sequences for the sgRNA rBsgRNA-01, comprising the 20-nt xMIR604FR2 (SEQ ID NO:28) target RNA fused with tracRNA (SEQ ID NO:37). The expression cassette comprising prOsU3 promoter and rBsgRNA-01 sgRNA was cloned into a biolistic transformation vector along with the Cas9 expression cassette. This biolistic transformation vector is referred to as 22169.

Example 4.4. Generation of Targeted Insertion Events at the MIR604 Insertion Site Safe Harbor

Figure 1:
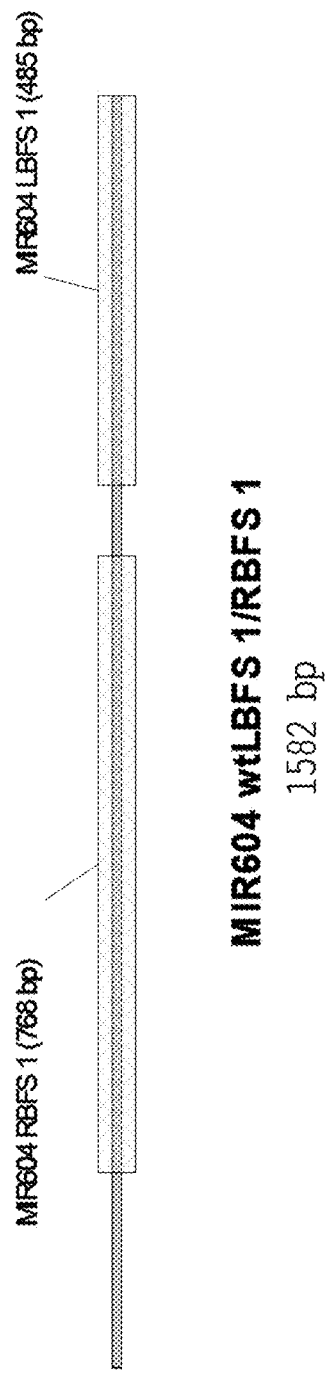
FIG. 1. Schematic diagram showing MIR604 insertion site flanking sequences. 88 base pairs of sequences between MIR604RBFS1 and MIR604LBFS1 are deleted in MIR604 event during T-DNA integration. This MIR604 insertion site does not contain the event MIR604 transgene.
Figure 2:
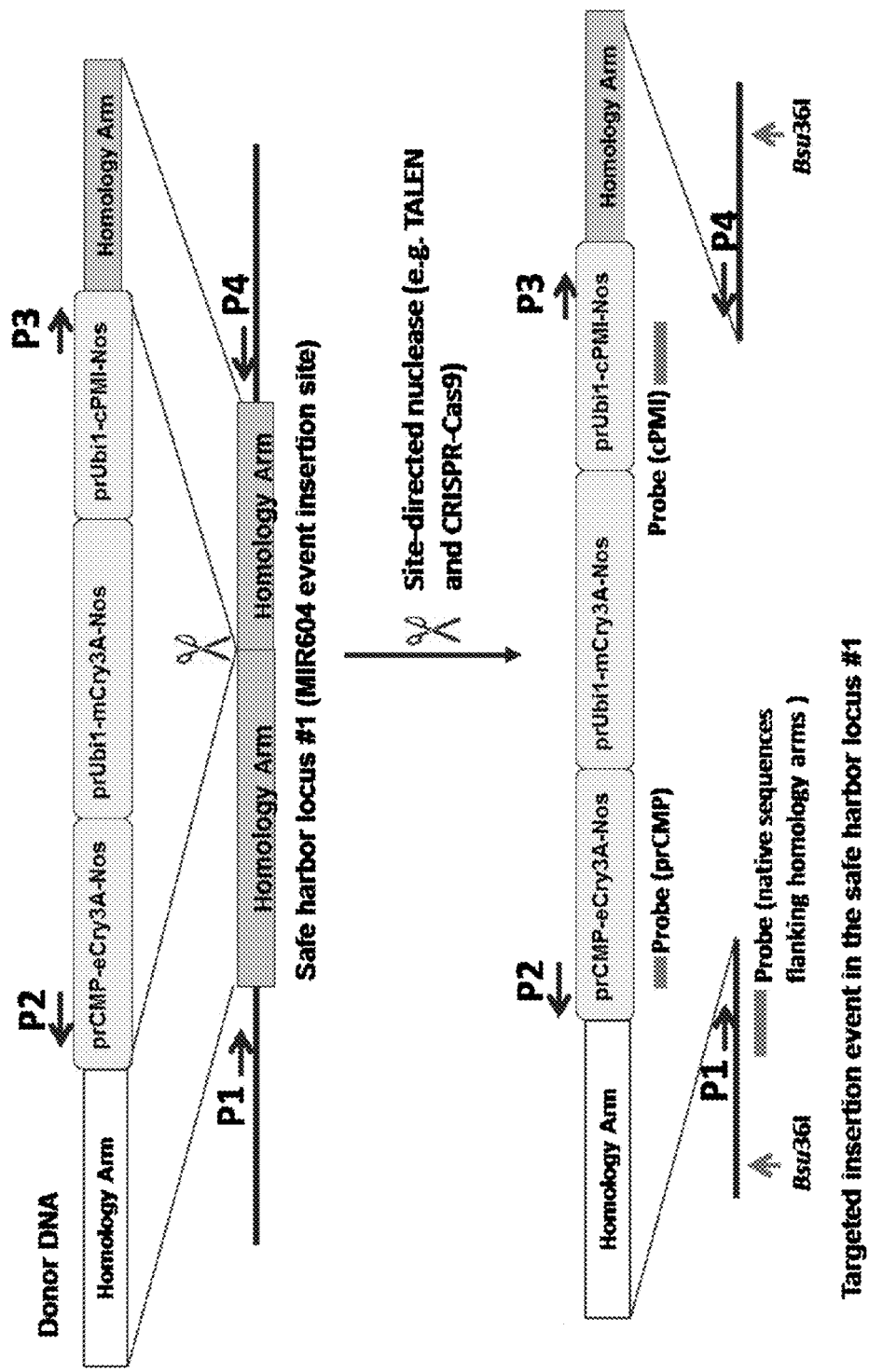
FIG. 2. Schematic representation of targeted insertion into MIR604 insertion site safe harbour locus and PCR reactions to identify potential targeted integration events with two primer pairs: P1 (FE4706)/P2 (FE4705) and P3 (FE4708)/P4 (FE4707). P1 (FE4706) and P4 (FE4707) only binds to chromosomal regions outside the homology arms present in the donor and target region, whereas P2 (FE4705) and P3 (FE4708) only binds to donor molecules. Primer pair P1(FE4706) and P2 (FE4705) produces a fragment of 2.87 Kbp and primer pair P3(FE4708)/P4(FE4707) amplifies a fragment of 2.0 Kbp only if targeted insertion is present at the safe harbor locus #1 (MIR604 insertion site). The approximate position of Bsu36I restriction sites and probes used in Southern DNA blot analysis (FIG. 5) are indicated in the targeted insertion event.

Example 4.4.1. Construction Donor Vector for Targeted Insertion Via Homologous Recombination A gene targeting donor vector (referred to as 21942) was constructed by inserting expression cassettes for 2 insect control genes (eCry3.1Ab and mCry3A) and the PMI selectable marker gene between two homology arms (xJHAX-03, SEQ ID NO:38 and xJHAX-04, SEQ ID NO:39). From the 5' end, the donor nucleic acid sequence comprises xJHAX-03 operably linked to an eCry3.1Ab expression cassette, which is operably linked to a mCry3A expression cassette, which is operably linked to a cPMI expression cassette, which is operably linked to xJHAX-04 (FIG. 2). The two homology arms (xJHAX-03 and xJHAX-04) have sequences identical to part of the safe harbor #1 (MIR604 insertion site) sequences (SEQ ID NO:2) and are for guiding the targeted insertion of the donor sequences to the Cas9 cleavage site at the target locus using homologous recombination (FIG. 2).

Figure 3:
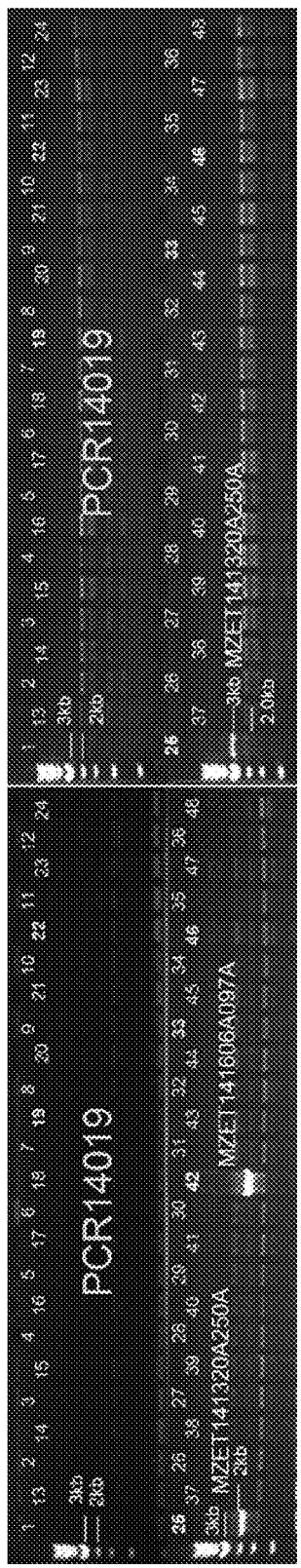
FIG. 3. An example of PCR screening assay as outlined in FIG. 2. In the left panel, PCR is done with P3(FE4708)/and P4(FE4707) which amplifies a fragment of 2.0 Kbp from 2 events (lane 25, MZET141320A250A and lane 42, event MZET141606A097A). In the right panel, PCR is done with pair P1 (FE4706) and P2 (FE4705) produces a fragment of 2.87 Kbp from only 1 event (lane 25, MZET141320A250A).

Example 4.4.2. Generation of Targeted Insertion Events at the MIR604 Insertion Site Safe Harbor with Biolistic Bombardment For target gene sequence modification mediated by homology-directed repair, a donor DNA molecule needs to be co-delivered with Cas9 and sgRNA. To generate potential events carrying targeted insertion events at the safe harbor locus #1, plasmid DNA of a vector (22169) carrying an expression cassette for Cas9Nuc and sgRNA was mixed with a fragment of vector 21942 comprising the donor nucleic acid sequence (FIG. 2), which comprises the expression cassettes and homology arms described in example 4.4.1. The DNA (Cas9Nuc and sgRNA vector with donor nucleic acid sequence) was then precipitated onto gold particles and used to bombard immature *maize* embryos (line NP2222). Methods for *maize* immature embryo bombardment, callus induction tissue regeneration and rooting methods have been described previously (Wright et al., *Plant Cell Reports* 20:429-436 (2001)). Briefly, immature embryos were isolated from harvested immature ears at about 9-11 days after pollination and pre-cultured for 1 to 3 days on osmoticum media. Pre-cultured embryos were then bombarded with the DNA described above using BioRad PDS-1000 Biolistic particle delivery system. Bombarded embryos were then incubated in callus induction media and then moved onto mannose selection media. Mannose resistant calli were transferred to regeneration media to induce shoot formation. Shoots were then sub-cultured onto rooting media. Samples were then harvested from rooted plants for Taqman assays to detect mutations in the target site to enrich for potential targeted insertion events (described herein) and junction PCRs were performed to identify potential plants containing the targeted insertion (FIG. 2 and FIG. 3). Identified putative targeted insertion events were further characterized by more detailed PCR, sequencing and Southern analysis for confirmation (FIG. 5). Table 1 shows an experiment (MZET134300) that resulted in the recovery of a targeted insertion event MZET134300A679A. In this experiment, more than 80% of transgenic events positive for donor nucleic acid expression cassettes (384 out of 473 events) contain modifications at the target site sequence xMIR604FR2 (SEQ ID NO:28). PCR reactions were performed on a subset of events and identified one clean targeted insertion event through double crossover homologous recombination at both homology arms. Additional DNA sequencing and Southern blot analysis confirmed that the event was a clean targeted insertion event, meaning that this event comprises a single copy of the donor nucleic acid sequence described in example 4.4.1, specifically the eCry3.1Ab, mCry3A, and PMI expression cassettes, is backbone free, shows evidence of a double-crossover homologous recombination event, and has no integration of the vector DNA comprising the nuclease. This Example shows that the MIR604 insertion site is a good target site for targeted insertion.

In addition, we assayed for the presence of mutations in regenerated plants that escaped the mannose selection process or transformation escapes that do not contain donor nucleic acid sequence expression cassettes. As expected, out of 471 escapes, only 2 plants are positive for the Cas9Nuc nuclease expression vector and both of these 2 plants have biallelic mutations in the genomic target (Table 2). Surprisingly, a high percentage of escape plants (23.9%, 112 out of 469 plants) negative for any transgene (donor nucleic acid sequence expression cassettes or Cas9Nuc expression vector) have mutations at the safe harbor locus #1 (MIR604 insertion site) target sequence xMIR604FR2 (SEQ ID NO:28). 37 of these 112 events have biallelic mutations, i.e., both copies of the xMIR604FR2 sequence (SEQ ID NO:28) in the *maize* genome are mutated. The remaining 75 events have mutation in one of the copies of the sequence. This surprising result indicates that transient expression of Cas9 nuclease and sgRNA in the *maize* cells is sufficient for generating mutations at the chromosome targets. Also, selection is optional to obtain mutant plants. If sufficient number of regenerated plants is screened, targeted mutants can be easily identified through transient delivery and expression of Cas9Nuc protein and gRNA or gRNAs in plant cells.

TABLE 2

Breakdown of different types of events in regenerated plants with gRNA-Cas9 mediated targeted mutagenesis at the safe harbor locus #1(MIR604 insertion site) target sequence xMIR604FR2 (SEQ ID NO: 28)

| Experiment MZET13430 | Number | Percentage |
|---|---|---|
| Total immature embryo targets | 3620 | |
| Total regenerated plants | 944 | |
| Donor nucleic acid (PMI) positive plants (Transformants) | 473 | 13.1%[1] |
| Events with no target site modification | 89 | |
| Events with target site modification | 384 | 81.2% |
| Events with monoallelic modification | 20 | |

TABLE 1

Targeting experiments in corn with sgRNA-Cas9 nuclease at the safe harbor locus #1(MIR604 insertion site) target sequence xMIR604FR2 (SEQ ID NO: 28)

| Experiment ID | DNA used for bombardment | No. of embryos | Total transgenic events | Events with target site mutation | Events with potential targeted insertion | Events with confirmed clean targeted insertion |
|---|---|---|---|---|---|---|
| MZET134300 | 22169, 21942 (1:1, 8 × 10^10 molecules of each) | 3620 | 473 | 384 | 29 | 1 |

To determine the efficiency of sgRNA-Cas9 mediated genome modification, we assayed for the presence of mutations in all 473 transgenic plants described in Table 1, using high throughput Taqman assays as described in the subsequent Examples. Since the transformation is done through co-delivery of repair donor and Cas9 nuclease constructs, we expect to see donor nucleic acid sequence in transgenic plants that do not contain the Cas9Nuc expression vector. Indeed, out of the 473 PMI-positive plants for donor nucleic acid sequence, 301 of them (63.6%) have and 172 of them (36.4%) do not have co-integrated Cas9 nuclease expression vector, respectively (Table 2). 83 plants (17.5%) without a co-integrated Cas9Nuc nuclease expression vector (22169) have their target site (xMIR604FR2, SEQ ID NO:28) modified either in one allele (7 plants) or both alleles (76 plants) of the *maize* genome (Table 2).

TABLE 2-continued

Breakdown of different types of events in regenerated plants with gRNA-Cas9 mediated targeted mutagenesis at the safe harbor locus #1(MIR604 insertion site) target sequence xMIR604FR2 (SEQ ID NO: 28)

| Experiment MZET13430 | Number | Percentage |
|---|---|---|
| Monoallelic modification with co-integration of Cas9 vector | 13 | |
| Monoallelic modification without co-integration of Cas9 vector | 7 | |
| Events with biallelic modification | 364 | |
| Biallelic modification with co-integration of Cas9 vector | 288 | |
| Biallelic modification without co-integration of Cas9 vector | 76 | |

TABLE 2-continued

Breakdown of different types of events in regenerated plants with gRNA-Cas9 mediated targeted mutagenesis at the safe harbor locus #1(MIR604 insertion site) target sequence xMIR604FR2 (SEQ ID NO: 28)

| Experiment MZET13430 | Number | Percentage |
| --- | --- | --- |
| Donor nucleic acid (PMI) negative plants (Escapes) | 471 | 13.0%[2] |
| Events with no target site modification | 357 | 75.8% |
| Events with target site modification | 114 | 24.2% |
| Events with monoallelic modification | 75 | 15.9% |
| Monoallelic modification with co-integration of Cas9 vector (22169) | 0 | |
| Monoallelic modification without co-integration of Cas9 vector (22169) | 75 | 15.9% |
| Events with biallelic modification | 39 | 8.3% |
| Biallelic modification with co-integration of Cas9 vector (22169) | 2 | |
| Biallelic modification without co-integration of Cas9 vector (22169) | 37 | 7.9% |
| Total number of events with mutations at the target site | 498 | 52.7% |

[1]Transformation frequency is 13.1%
[2]Escape frequency is 13.0%

Example 4.4.3. Generation of Targeted Insertion Events at the MIR604 Insertion Site Safe Harbor with *Agrobacterium*-Mediated Transformation Targeted insertion of transgenes into the safe harbor locus can also be generated with DNA donor and expression vectors for Cas9 nuclease and sgRNA delivered via *Agrobacterium*. *Agrobacterium*-mediated transformation methods have been described elsewhere (Ishida et al., *Nat. Biotechnol.* 14:745-750 (1996)). Briefly, binary vectors for delivering donor DNA and expression cassettes of Cas9 and sgRNA are constructed. Donor DNA may be introduced in the same binary vector as expression cassettes of Cas9 and sgRNA, or may be introduced into separate T-DNA in the same binary vector, or may be introduced into separate binary vectors which can be transformed into the same *Agrobacterium* strain or separate *Agrobacterium* strains and delivered together through co-transformation. To construct a binary vector for *Agrobacterium*-mediated delivery of Cas9 and sgRNA, a DNA fragment containing the Cas9 and sgRNA expression cassettes is inserted into binary vector backbone to form pB-Cas9-U3-xMIR604FR2.

Similarly, a binary donor vector is constructed by inserting a nucleic acid fragment containing homology arms (xJHAX-03 and xJHAX-04), an eCry3.1Ab expression cassette, a mCry3A expression cassette, and a PMI marker expression cassettes into a binary vector. Both binary vectors are introduced into *Agrobacterium* strain LBA4404 containing a helper plasmid through electroporation. *Agrobacterium* strains containing these binary vectors are mixed and then used to co-infect *maize* immature embryos. Infected embryos are co-cultivated with *Agrobacterium* cells for 2-4 days and then used to induce calli. Calli are selected with mannose-containing media and mannose-resistant calli are regenerated into plantlets using a method similar to Negrotto et al. *Plant Cell Rep.* 19:798-803 (2000). Samples are taken from rooted plantlets for qPCR Taqman assays to enrich for potential targeted insertion events as described in the subsequent Examples and then junction PCR analyses are carried out to identify targeted insertion events as shown in FIG. 2 and FIG. 3. Identified putative targeted insertion events are further characterized in detail by Southern analysis and sequencing of PCR products.

Example 5. Targeted Insertion of Transgene Sequences to the MIR604 Insertion Site Safe Harbor Mediated by TALE Nucleases (TALENs)

Example 5.1. Selection of TALEN Recognition Target Against AX-MIR604 Sequences

Target sequences were selected from the AX MIR604 (SEQ ID NO:2) for TALEN design. Table 3 lists the selected sequences, their names and identifier numbers.

TABLE 3

Selected TALEN target sequences based on NP2222 genomic sequences (SEQ ID NO: 2)

| TALEN target name | Sequence (5' to 3') | Length | Sequence identifier |
| --- | --- | --- | --- |
| MIR604A1FW1 | TTGCT ACTCC ATGTG ACT | 18 | SEQ ID NO: 40 |
| MIR604A1RV1 | TTGTC ATATT CTTTT T | 16 | SEQ ID NO: 41 |
| MIR604A2FW1; aka. mir604Fw1 | TACAC GTACT AATCG TGCT | 19 | SEQ ID NO: 42 |
| MIR604A2RV1; aka. mir604Rv1 | TCCTG TCTAC TACGT GCT | 18 | SEQ ID NO: 43 |
| MIR604A2RV2 | TTGTT CCTGT CTACT ACGT | 19 | SEQ ID NO: 44 |
| MIR604A3FW1 | TTGGT CTTTG ATGAG GTGAT | 20 | SEQ ID NO: 45 |
| MIR604A3RV1 | TCGAC ATGTA CAAAG TAGGT | 20 | SEQ ID NO: 46 |
| MIR604A4FW1 | TTCGG AAACA TCCTT TAAT | 19 | SEQ ID NO: 47 |
| MIR604A4RV1 | TTATA ATAAA ACTAA TATT | 19 | SEQ ID NO: 48 |
| MIR604A5FW1 | TAATA AATAA ATAAA TAAAT | 20 | SEQ ID NO: 49 |
| MIR604A5RV1 | TTGGA TTGCT GGATA ATGT | 19 | SEQ ID NO: 50 |
| MIR604A6FW1 | TCGTT GCCAA AGCTG CAT | 18 | SEQ ID NO: 51 |

TABLE 3-continued

Selected TALEN target sequences based on NP2222 genomic sequences (SEQ ID NO: 2)

| TALEN target name | Sequence (5' to 3') | Length | Sequence identifier |
|---|---|---|---|
| MIR604A6RV1 | TCCTG TCCTG CACTG CACT | 19 | SEQ ID NO: 52 |
| MIR604A7FW1; aka. mir604Fw2 | TGCAT CCGTG CAGTG CAGT | 19 | SEQ ID NO: 53 |
| MIR604A7RV1; aka. mir604Rv2 | TCCTA AACAA AGGAG GT | 17 | SEQ ID NO: 54 |
| MIR604A8FW1 | TAGGA CGCGA TGCTG CT | 17 | SEQ ID NO: 55 |
| MIR604A8RV1 | TGCGC ACGCA AGTGT CGT | 18 | SEQ ID NO: 56 |
| MIR604A9FW1 | TCCAT CTCCA TTCAC TGGT | 19 | SEQ ID NO: 57 |
| MIR604A9RV1 | TTCTG CAGGC ATTTG GCAT | 19 | SEQ ID NO: 58 |
| MIR604A10FW1 | TTTTC TTCTC TTCTC GAT | 18 | SEQ ID NO: 59 |
| MIR604A10RV1 | TAACC AGGCT AGCTT CGTT | 19 | SEQ ID NO: 60 |
| MIR604A11FW1 | TAAGC TACAA AAGAA CGC | 18 | SEQ ID NO: 61 |
| MIR604A11RV1 | TGTTT CGCGG CCGGC CCT | 18 | SEQ ID NO: 62 |
| MIR604A12FW1 | TTTCC GTCCT GGCCT GTC | 18 | SEQ ID NO: 63 |
| MIR604A12RV1 | TCGTC CGACG ACGAT CGAT | 19 | SEQ ID NO: 64 |
| MIR604Rv2-LT | TCCTA AACAA AGGAG GTCC | 19 | SEQ ID NO: 65 |

Example 5.2. Design of TALEN Fusion Nucleases Against Selected the MIR604 Insertion Site Safe Harbor Sequences DNA binding specificity of TALENs is designed against the target sequences in Table 3. As an example, here is the design of two pairs of heterodimeric TALENs to cleave target sequences MIR604AXA2 (aka. MIR604FR1, SEQ ID NO:66, 5'-TACAC GTACT AATCG TGCTT CACGC ACAGG CACAG CACGT AGTAG ACAGG A-3') and MIR604AXA7 (aka. MIR604FR2, SEQ ID NO:67, 5'-TG-CAT CCGTG CAGTG CAGTG CAGTG CAGGA CAGGA CCTCC TTTGT TTAGG A-3'). Individual TALEN monomers recognizing 2 targets, MIR604A2FW1(aka. mir604Fw1, 5'-TACAC GTACT AATCG TGCT-3', SEQ ID NO:42) and MIR604A2RV1 (aka. mir604Rv1, 5'-TCCTG TCTAC TACGT GCT-3', SEQ ID NO:43) within the MIR604AXA2 sequence, were assembled individually. For TALEN against MIR604A2FW1 (aka. mir604Fw1, 5'-TACAC GTACT AATCG TGCT-3', SEQ ID NO:42), the specificity determining di-residues within the RVD (Repeat-Variable Di-residue) repeats are as the following,

| | RVD position | | | | | | | | | | | | | | | | | | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 |
| RVD residue | N/A | NI | HD | NI | HD | NN | NG | NI | HD | NG | NI | NI | NG | HD | NN | NG | NN | HD | NG |
| Target nucleotide | T | A | C | A | C | G | T | A | C | T | A | A | T | C | G | T | G | C | T |

For TALEN against MIR604A2RV1 (aka. mir604Rv1, 5'-TCCTG TCTAC TACGT GCT-3', SEQ ID NO:43), the specificity determining di-residues within the DVR repeats are as the following,

| | RVD position | | | | | | | | | | | | | | | | | | |
|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 |
| RVD residue | N/A | HD | HD | NG | NN | NG | HD | NG | NI | HD | NG | NI | HD | NN | NG | NN | HD | NG |
| Target nucleotide | T | C | C | T | G | T | C | T | A | C | T | A | C | G | T | G | C | T |

We constructed three versions of each TALEN containing the RVDs recognizing mir604Fw1 (SEQ ID NO:42), a first full-length version that keeps most of the TAL effector protein sequences such as the N-terminal T3 SS and the NLSs after the RVD repeat region (cTNmir604Fw1-01, SEQ ID NO:68), a second shorter version that has removed the N-terminal T3SS (cTNmir604Fw1-02, SEQ ID NO:69), and a third short version with deletions in the N-terminal T3SS and also NLSs after the RVD repeat region (cTNmir604Fw1-03, SEQ ID NO:70). Similarly, we constructed three versions of each TALEN containing the RVDs recognizing mir604Rv1 (SEQ ID NO:43), a first full-length version that keeps most of the TAL effector protein sequences such as the N-terminal T3SS and the NLSs after the RVD repeat region (cTNmir604Rv1-01, SEQ ID NO:71), a second shorter version that has removed the N-terminal T3SS (cTNmir604Rv1-02, SEQ ID NO:72), and a third short version with deletions in the N-terminal T3SS and also NLSs after the DVR repeat region (cTNmir604Rv1-03, SEQ ID NO:73). The amino acid sequences of these engineered nucleases are shown in SEQ ID NO:68 (cTNmir604Fw1-01), SEQ ID NO:69 (cTNmir604Fw1-02), SEQ ID NO:70 (cTNmir604Fw1-03), SEQ ID NO:71 (cTNmir604Rv1-01), SEQ ID NO:72 (cTNmir604Rv1-02) and SEQ ID NO:73 (cTNmir604Rv1-03).

Individual TALEN monomers recognizing another 2 target sequences, MIR604A7FW1 (aka. mir604Fw2, 5'-TGCAT CCGTG CAGTG CAGT-3', SEQ ID. NO:53) and MIR604A7RV1 (aka. mir604Rv2, 5'-TCCTA AACAA AGGAG GT-3', SEQ ID NO:54) within the MIR604AXA7 (aka. mir604FR2, SEQ ID. NO:67) sequence, were also assembled individually. For TALENs against MIR604A7FW1 (aka. mir604Fw2, 5'-TGCAT CCGTG CAGTG CAGT-3', SEQ ID NO:53), the specificity determining di-residues within the RVD repeats are as the following, as the N-terminal T3SS and the NLSs after the RVD repeat region, a second shorter version (cTNmir604Fw2-02, SEQ ID NO.75) that has removed the N-terminal T3SS, and a third short version (cTNmir604Fw2-03, SEQ ID NO.76) that has deletions in the N-terminal T3SS and also NLSs after the RVD repeat region. Similarly, we constructed three versions of each TALEN containing the RVDs recognizing MIR604Rv2 (SEQ ID NO:50), a first full-length version (cTNmir604Rv2-01, SEQ ID NO.77) that keeps most of the TAL effector protein sequences such as the N-terminal T3SS and the NLSs after the RVD repeat region, a second shorter version (cTNmir604Rv2-02, SEQ ID NO.78) that has removed the N-terminal T3SS, and a third short version (cTNmir604Rv2-03, SEQ ID NO.79) with deletions in the N-terminal T3SS and also NLSs after the RVD repeat region.

For MIR604AXA7 (aka. mir604FR2, SEQ ID NO:67) sequence cleavage, another pair of TALENS were assembled that have slightly different amino acid sequences and recognition specificity: cTNmir604Fw2-05 (SEQ ID NO.80) containing the RVDs recognizing mir604Fw2 (SEQ ID NO:53) and cTNmir604Rv2-04 (SEQ ID NO.81) containing the RVDs recognizing MIR604Rv2-LT (SEQ ID NO:65, 5'-TCCTA AACAA AGGAG GTCC-3'), respectively. The amino acid sequences of these engineered nucleases are in SEQ ID NO.74 (cTNmir604Fw2-01), SEQ ID NO.75 (cTNmir604Fw2-02), SEQ ID NO.76 (cTNmir604Fw2-03), SEQ ID NO.77 (cTNmir604Rv2-01), SEQ ID NO.78 (cTNmir604Rv2-02), SEQ ID NO.79 (cTNmir604Rv2-03), SEQ ID NO.80 (cTNmir604Fw2-05) and SEQ ID NO.81 (cTNmir604Rv2-04).

Example 5.3. Assembly of TALEN Against AX-MIR604 Insertion Locus Sequences

Artificial TALE fusion nuclease protein sequences (SEQ ID NO:68 to SEQ ID NO.81) were back-translated into

| | RVD position | | | | | | | | | | | | | | | | | | |
|---|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 | 17 | 18 |
| RVD residue | N/A | NN | HD | NI | NG | HD | HD | NN | NG | NN | HD | NI | NN | NG | NN | HD | NI | NN | NG |
| Target nucleotide | T | G | C | A | T | C | C | G | T | G | C | A | G | T | G | C | A | G | T |

For TALENs against MIR604A7RV1 (aka. mir604Rv2, 5'-TCCTA AACAA AGGAG GT-3', SEQ ID NO:54), the specificity determining di-residues within the DVR repeats are as the following, DNA coding sequences using plant-preferred codons for maximizing expression in corn and other monocot plants. Some of examples are shown here. For example, SEQ ID NO:82 is the DNA coding sequence for cTNmir604Fw1-01

| | RVD position | | | | | | | | | | | | | | | | |
|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | 16 |
| RVD residue | N/A | HD | HD | NG | NI | NI | NI | HD | NI | NI | NI | NN | NN | NI | NN | NN | NG |
| Target nucleotide | T | C | C | T | A | A | A | C | A | A | A | G | G | A | G | G | T |

We constructed three versions of each TALEN containing the RVDs recognizing mir604Fw2 (SEQ ID NO:53), a first full-length version (cTNmir604Fw2-01, SEQ ID NO.74) that keeps most of the TAL effector protein sequences such protein sequence (SEQ ID NO:68) and SEQ ID NO:84 is the DNA coding sequence for cTNmir604Rv1-01 protein sequence (SEQ ID NO:71). Artificial fusion nuclease DNA sequences were then assembled from library of fragments containing different RVD repeats, promoter and terminator to form TALEN expression cassettes directly after Type IIs enzyme digestion and ligation as described (Cermak et al., *Nucleic Acid Research* 39(12):e82 (2011); Zhang et al., *Nature Biotech* 29:149-154 (2011)). For example, the assembled reporter construct MIRA2R1FLA-GUUS contains the assembled TALEN sequence TLNMIR604A2RV1 (SEQ ID NO:84) encoding cTNmir604Rv1-01 (SEQ ID NO:71) under the control of *maize* ubiquitin promoter (prZmUbi1-10) and also has a nonfunctional GUS recombination assay substrate cassette containing a direct repeat of GUS fragment and an inverted repeat of the 18 bp TALEN recognition sequence MIR604A2RV1 (aka. mir604Rv1, 5'-TCCTG TCTAC TACGT GCT-3', SEQ ID NO:43). Similarly, expression constructs containing other assembled TALENs are assembled in similar fashion. In many cases, expression cassettes for a pair of TALENs, e.g., cTNmir604Fw1-01 (SEQ ID NO:68) and cTNmir604Rv1-01 (SEQ ID NO:71) which recognize and cleave a target sequence MIR604AXA2

(aka. MIR604FR1, 5'-<u>TACAC GTACT AATCG TGCT</u> T CACGC ACAGG CAC <u>AG CACGT AGTAG ACAGG A</u>-3', SEQ ID NO: 66, only the upper strand is shown), are placed in the same transformation vector in order to coordinate their simultaneous expression in the target tissue during transformation.

Example 5.4. Transient Assay for TALEN Activity Against AX_MIR604 DNA Sequences

Figure 4:
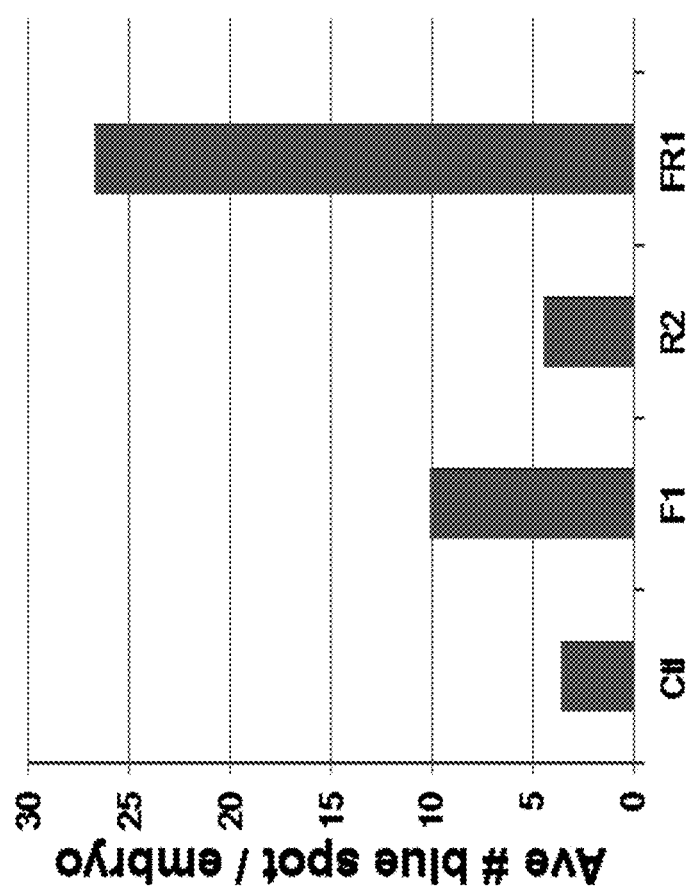
FIG. 4. Number of GUS spots in *maize* immature embryos bombarded with vectors containing GUUS repeat intramolecular recombination substrate with MIR604FR1 target sequence (5'-<u>TACAC GTACT AATCG TGCTT</u> CACGC ACAGG CAC<u>AG CACGT AGTAG ACAGG A</u>-3', SEQ ID NO: 66)

Assembled construct MIRA2R1FLA-GUUS containing the assembled TALEN sequence (SEQ ID NO:84) encoding for cTNmir604Rv1-01 (SEQ ID NO:71) under the control of *maize* ubiquitin promoter (prZmUbi1-10) and the nonfunctional GUS recombination assay substrate cassette were bombarded into immature *maize* embryos. The direct repeat of GUS fragment also contains an inverted repeat of the cTNmir604Rv1-01 TALEN recognition sequence mir604Rv1 (5'-TCCTG TCTAC TACGT GCT-3', SEQ ID. NO:43). Similarly, expression constructs containing DNA sequences encoding for cTNmir604Fw1-01, cTNmir604Fw1-02, cTNmir604Fw1-03, cTNmir604Rv1-02, cTNmir604Rv1-03, or the corresponding pairs of them were bombarded into *maize* embryos along with their target substrate(s). In many cases, expression cassettes for a pair of TALENs recognizing and cleaving a target sequence, e.g., cTNmir604Fw1-01 and cTNmir604Rv1-01 for MIR604AXA2 (aka. mir604FR1, SEQ ID NO:66), were placed in the same transformation vector in order to coordinate their simultaneous expression in the target tissue. 1 to 4 days after bombardment, transformed *maize* embryos were placed in X-Gluc solution overnight to detect GUS activity histochemically. GUS activity is only visible when the GUUS repeat undergoes intramolecular recombination. Co-expression of a pair of TALENs (cTNmir604Fw1-01 and cTNmir604Rv1-01) recognizing MIR604FR1 (SEQ ID NO:66) target greatly increases the number of blue spots (FIG. 4, treatment FR1), suggesting the target sequence is cleaved by the pair of heterodimeric TALENs to increase the frequency of homologous recombination.

Example 5.5. *Maize* Chromosomal Locus Containing the Target Recognition Sites is Cleaved at High Frequency by Artificial TALENs To test cleavage of chromosomal target sequence mir604FR2 (SEQ ID NO:67) by TALENs expressed in *maize* cells, two different pairs of TALENs were used. The first pair of TALENs were in a single expression vector (21321) comprising nucleic acid sequences encoding for the expression of cTNmir604Fw2-03 and cTNmir604Rv2-03, and the second pair of TALENs were in a single expression vector (21998) comprising nucleic acid sequences encoding for the expression of cTNmir604Fw2-05 and cTNmir604Rv2-04. The expression vectors (21321 and 21998) were each co-delivered by biolistic transformation into *maize* embryos along with the donor vector 21942 described in Example 4.4.1. Transformed embryos were selected on mannose to recover stable transgenic plants. Stable transgenic plants were analyzed for the presence of mutations in the target region using qPCR Taqman assay and/or sequencing of PCR products. Results in Table 4 show that for both pairs of TALENs for target site MIR604FR2

(5'-<u>TGCAT CCGTG CAGTG CAGTG</u> CAGTG CAGGA CAGGA CCTCC TTTGT TTAGG A- 3', SEQ ID NO: 67)

resulted in high percentage of mutation in stable transformants when TALEN expression vectors are delivered into plant cells with biolistic method. Both the full length and truncated version of TALENs can mediate targeted mutagenesis at the target loci efficiently.

Interestingly, we also detected mutations of MIR604 insertion site locus mir604FR2 target site (5'-<u>TGCAT CCGTG CAGTG CAGTG</u> CAGTG CAGGA CAGGA CCTCC TTTGT TTAGG A- 3', SEQ ID NO: 67)

in many regenerated mannose selection escape plants. For example, in co-transformation experiments with vector TALEN vector 21321 and donor 21942 (Table 4), 14 of the plants generated, namely MZET130501B017A, MZET130501B038A, MZET130501B027A, MZET130501B031A, MZET130501A012A, MZET130501B041A, MZET130501B096A, MZET130402A030A, MZET130501B044A, MZET130501B057A, MZET130501B084A, MZET130501B130A, MZET130501B045A, MZET130704C003A, contained a mutation in the mir604FR2 target sequence, but they did not harbor any detectable transgenes from either donor or TALEN expression vectors and thus were escapes of mannose selection. In these escape plants, about 5% of them have mutations in the mir604FR2 target site and some of them have both alleles of the mir604FR2 target sequences mutated. Therefore, it is a viable approach to recover plants with mutations in target sites by transiently delivering TALENs and then regenerating untransformed plants directly without selection. Mutant plants can be identified by screening population of regenerants with proper assays such as PCR.

To test cleavage of chromosomal target locus by TALENs expressed in maize cells delivered by Agrobacterium, 4 different binary vectors (21631, 21632, 21633 and 21634) containing expression cassettes of different pairs of TALENs were constructed. All four binary vectors comprise the donor nucleic acid sequence comprising expression cassettes for eCry3.1Ab, mCry3A, and PMI. 21631 and 21633 additionally comprise nucleic acid sequences encoding for the expression of cTNmir604Fw1-01 and cTNmir604Rv1-01; 21632 and 21634 additionally comprise nucleic acid sequences encoding for the expression of cTNmir604Fw2-01 and cTNmir604Rv2-01. 21631 and 21632 have the TALEN expression cassettes and the gene targeting donor in one T-DNA, while 21633 and 21634 have these in two separate T-DNAs. Expression of the pair of TALENs in 21631 and 21633 is expected to result in cleavage of the chromosomal target sequence MIR604AXA2

(aka. MIR604FR1, 5'-<u>TACAC GTACT AATCG TGCTT</u> CACGC ACAGG CAC<u>AG CACGT AGTAG ACAGG A</u>-3', SEQ ID NO: 66)

in the maize genome. Similarly, expression of the pair of TALENs in 21632 and 21634 should result in cleavage of the chromosomal target sequence MIR604AXA7 (aka. MIR604FR2, (aka. MIR604FR2, 5'-<u>TGCAT CCGTG CAGTG CAGTG</u> CAGTG CAGGA CAGG<u>A CCTCC TTTGT TTAGG A</u>-3', SEQ ID NO: 67)

in the maize genome. These vectors transformed into maize embryos by Agrobacterium-mediated transformation method. Stable transgenic plants were analyzed for the presence of mutations in the target region using Taqman assay and/or sequencing of PCR products. Results in Table 4 show that for both pairs of TALENs for target site MIR604FR1 (SEQ ID NO:66) and MIR604FR2 (SEQ ID NO:67) resulted in high percentage of mutation in stable transformants when delivered via Agrobacterium-mediated transformation (Table 4).

TABLE 4

High rate of mutagenesis of mir604FR1 (SEQ ID NO: 66) and mir604FR2 (SEQ ID NO: 67) target sequences at the native chromosomal MIR604 insertion site locus in stable transformants derived from co-transformation of a TALEN expression vector and a donor vector containing PMI selectable marker gene

| Target locus | Delivery method | Nuclease vector | Donor | No. of experiments | Total explants | No. of stable events | No. of events with target site mutation | Mutation frequency (% transformants) |
|---|---|---|---|---|---|---|---|---|
| MIR604 insertion site FR2 target | Biolistic | 21321 | 21942 | 7 | 6279 | 132 | 46 | 34.8% |
| MIR604 insertion site FR2 target | Biolistic | 21998 | 21942 | 2 | 7845 | 519 | 148 | 28.5% |
| MIR604 insertion site FR1 target | Agrobacterium | 21631 | 21631 | 3 | 4521 | 492 | 134 | 27.2% |
| MIR604 insertion site FR1 target | Agrobacterium | 21633 | 21633 | 3 | 5305 | 1024 | 218 | 21.3% |
| MIR604 insertion site FR2 target | Agrobacterium | 21632 | 21632 | 3 | 4633 | 673 | 316 | 47.0% |
| MIR604 insertion site FR2 target | Agrobacterium | 21634 | 21634 | 2 | 5764 | 990 | 247 | 24.9% |

Example 5.6. Targeted Insertion of Transgenic Sequences into NP2222 Chromosomal Locus Corresponding to the MIR604 Insertion Site Mediated by Assembled TALENs Cultured immature embryos Maize elite inbred line NP2222 were co-transformed with the targeting donor vector 21942 and TALEN expression vector 21321 or 21998 using particle bombardment (Table 4 and Table 5). Targeting donor vector 21942 contains trait gene expression cassettes flanked by regions of homology (xJHAX-03 and xJHAX-04) flanking the TALEN cleavage site (SEQ ID NO:67) at the MIR604 insertion site. Table 5 shows the analysis results for potential targeted insertion at the MIR604FR2 cleavage site (SEQ ID NO:67). Four events showing PCR products as expected for double-stranded homologous recombination are obtained out of 519 PMI positive stable events (Table 5). Of these, a single event was identified as a clean event, meaning that it comprises a single copy of the donor nucleic acid sequence described in example 4.4.1, specifically the eCry3.1Ab, mCry3A, and PMI expression cassettes, is backbone free, shows evidence of a double-crossover homologous recombination event, and has no integration of the vector DNA comprising the nuclease.

TABLE 5

Targeted insertion of mCry3A, eCry3.1Ab, and PMI expression cassettes into native safe harbor locus (native MIR604 insertion site locus) mediated by cleavage of FR2 sequence by TALEN

| Delivery method | Nuclease vector | Donor | Number of Expts | Total explants | Total positive events | Targeted events | Intact Low Copy events |
|---|---|---|---|---|---|---|---|
| Biolistic | 21998: | 21942 | 2 | 7845 | 519 | 4 | 1 |

In the above experiments, transformation was done using particle bombardment of cultured immature embryos. However, immature embryos or calli derived from cultured embryos can also be used as targets. Transformation can also be done using an *Agrobacterium*-mediated gene delivery method as shown in Table 4 using target tissues such as immature embryos, cultured embryos or calli derived from cultured embryos. For example, *Agrobacterium*-mediated transformation and recovery of events as result of targeted insertion mediated by TALEN to target site can be done using mannose selection in a fashion as described in the art (U.S. Pat. No. 7,935,862, for example), where, for example, NP2222 immature embryos are used as transformation targets.

Example 6. Targeted Insertion of Transgenes at the Safe Harbor (MIR604 Insertion Site) Mediated by Engineered Meganucleases Example 6.1. *Maize* Chromosomal Target Sequence Selection for Design of Engineered Meganucleases Targeted insertion of transgenic sequences for replacing short stretch of DNA sequences (allele replacement) or inserting large DNA fragment (transgene insertion) can also be mediated by homologous recombination using DNA breaks introduced by engineered meganucleases (Puchta and Fauser, *Plant Journal* 78:727-741 (2014); Chen and Gao, *Plant Cell Rep.* 33:575-583 (2014)). The present example shows if breaks induced by engineered meganucleases can be used to mediate the insertion of large DNA molecules into the desired chromosomal safe harbor target in corn plants. To compare its effectiveness against TALEN and CRISPR-Cas9, the safe harbor locus #1 (MIR604 event insertion site) was chosen as the transgene insertion site. Therefore, although not to be limited by methodology, the present application teaches transgene insertion mediated by 3 nucleases platforms, namely TALEN, meganuclease and sgRNA-Cas9. Maize safe harbor locus #1 (aka. MIR604 event insertion site) sequences (SEQ ID NO: 1 or SEQ ID NO: 2) were scanned for optimal targets for designing engineered meganucleases using technologies in the art, e.g., by using rational protein design methodology to design engineered meganucleases with altered cleavage specificity based on LAGLIDADG family meganuclease I-CreI (U.S. Pat. No. 8,021,867). The rationally designed engineered I-CreI meganuclease variants that cleave the target sequence at high efficiency and with minimal off target cleavage are selected to mediate targeted insertion of transgenes at the safe harbor locus. DNA sequences encoding novel meganuclease variants are placed under the control of *maize* ubiquitin-1 promoter (prUbi1-10) followed by the NOS terminator and the expression cassette is sub-cloned into a biolistic transformation vector backbone.

To test the in planta activity of engineered I-CreI meganuclease variant in cleaving *maize* chromosomal target sequence and its ability to mediate targeted insertion through homologous recombination, meganuclease expression vector is co-bombarded with targeting donor vector 21942 into immature *maize* embryos. Briefly, plasmid DNA vector carrying expression cassette for the engineered meganuclease is mixed with a fragment of vector 21942 which encodes the donor nucleic acid sequence and precipitated onto gold particles. The donor nucleic acid sequence of vector 21942 contains regions from xJHAX-03 to xJHAX-04, including PMI marker gene and two gene cassettes as described in Example 4.4.1. Immature embryos are isolated from harvested immature ears at about 9-11 days after pollination and pre-cultured for 1 to 3 days on osmoticum media. Pre-cultured embryos are then bombarded with gold particles with co-precipitated DNA vectors (21942 fragment and the meganuclease expression plasmid) using BioRad PDS-1000 Biolistic particle delivery system. Methods for *maize* immature embryo bombardment, callus induction tissue regeneration and rooting methods are known in the art (for example, Wright et al. 2001, *Plant Cell Reports* 20:429-436 (2001)). Bombarded embryos are then incubated in callus induction media and then moved onto mannose selection media. Mannose resistant calli are transferred to regeneration media to induce shoot formation. Shoots are then sub-cultured onto rooting media. Samples are then harvested from rooted plants for PCR and Taqman assays to identify potential plants containing the targeted insertion. Identified putative targeted insertion events are further characterized by more detailed PCR, sequencing and Southern analysis for confirmation. In addition to the stably transformed events, we also assay for the presence of mutations in regenerated plants that escaped the mannose selection, i.e., transformation escapes that do not contain any transgene from the targeted insertion donor or the meganuclease vector. Escape plants that are negative for any transgene but have mutations at the safe harbor locus #1(MIR604 insertion site) target sequence are identified. Transient expression of the meganuclease in the *maize* cells is sufficient for generating mutations at the chromosome targets. Also, selection is optional to obtain mutant plants. If a sufficient number of regenerated plants is screened, targeted mutants can be easily identified through transient delivery and expression of meganuclease in plant cells.

Example 6.2. Generation of Targeted Insertion Events at the MIR604 Insertion Site Safe Harbor Locus Mediated by Engineered Meganucleases The two homology arms, namely xJHAX-03 (SEQ ID NO: 38) and xJHAX-04 (SEQ ID NO: 39), of donor vector 21942 have sequences identical to the safe harbor #1 (MIR604 insertion site SEQ ID NO: 1 and SEQ ID NO: 2) and are used to guide targeted insertion of donor vector sequences to the cleavage site of engineered meganuclease at the target locus using homologous recombination. PCR reactions are also performed in a subset of events that are likely to targeted insertion based on Taqman analysis. Events identified to have a targeted insertion at the target locus using PCR primer pairs spanning the recombination junctions are analyzed by detailed DNA sequencing and Southern blot analysis to confirm that targeted insertion has happened.

Example 6.3. Generation of Targeted Insertion Events at the Safe Harbor Locus #1 (MIR604 Insertion Site) with *Agrobacterium*-Mediated Transformation Mediated by Engineered Meganucleases Targeted insertion of transgenes into the safe harbor locus can also be generated with DNA donor and expression vectors for meganuclease delivered via *Agrobacterium*. *Agrobacterium*-mediated transformation methods are well-known in the art (for example, Ishida et al., *Nat. Biotechnol.* 14:745-750 (1996)). Meganuclease expression cassette and donor DNA can be placed either into separate binary vectors or in the same binary vector and then co-transformed in plant cells. Donor DNA and meganuclease can be co-delivered by using separate binary vectors. Binary vector 22445 is constructed by inserting the donor nucleic acid sequence from vector 21942 (namely, the three expression cassettes operably linked to xJHAX-03 (SEQ ID NO: 38) and xJHAX-04 (SEQ ID NO: 39), as described in Example 4.4.1), into a binary vector useful for *Agrobacterium*-mediated transformation. A binary vector is also constructed for co-delivery of both the donor nucleic acid sequence and the meganuclease expression cassette from a single binary vector, where the donor nucleic acid sequence and the meganuclease expression cassette are each operably linked to right and left border sequences, so that they comprise two separate T-DNA's in a single binary vector. These binary vectors are transformed into *Agrobacterium* strain LBA4404 (pVGW7) via electroporation and then used for transformation of *maize* immature embryos. For *Agrobacterium*-mediated transformation, the *Agrobacterium* strain comprising the binary vector comprising 2 T-DNA's is used to infect *maize* immature embryos. Alternatively, *Agrobacterium* strains containing two binary vectors are mixed and then used to co-infect *maize* immature embryos. Infected embryos are co-cultivated with *Agrobacterium* cells for 2-4 days and then used to induce calli. Calli are selected with mannose-containing media and mannose-resistant calli are regenerated into plantlets. Samples are taken from rooted plantlets for Taqman and PCR analysis for identifying targeted insertion events as described above for biolistic transformation. PCR reactions are also performed in a subset of events that are likely to have targeted insertion based on Taqman analysis. Events identified to have targeted insertion at the target locus using PCR primer pairs spanning the recombination junctions are analyzed by detailed DNA sequencing and Southern blot analysis to confirm that targeted insertion has occurred.

Example 7. Molecular Characterization of Targeted Insertion of Transgenic Sequences into Genomic AX_MIR604 Locus Targeted insertion events identified by PCR assays were further characterized by more detailed sequencing and Southern blot analysis for confirmation. For example, events positive for junction PCRs (FIG. 2 and FIG. 3) as expected from homologous recombination occurring at one or both homologous arms were obtained from screening PMI positive stable events (as shown in Table 1 and Table 5). Detailed overlapping PCR analyses were done using primers spanning targeted insertion junctions comprising the AX MIR604 (SEQ ID NO:2) flanking genomic regions (xJHAX-03 and xJHAX-04) and part of the transformation donor vector. Presence of positive PCR signal suggests that site-directed nucleases indeed mediate targeted insertion into the MIR604 safe harbor locus (SEQ ID NO:2) at the DNA cleavage site of MIR604FR2

(5'-<u>TGCAT CCGTG CAGTG CAGTG</u> CAGTG CAGGA CAGG<u>A

CCTCC TTTGT TTAGG A</u>- 3', SEQ ID NO: 67)

Detailed Southern blot analysis showed that indeed insertion of gene stacks happened at the MIR604 insertion site safe harbor target locus through double crossover homologous recombination as shown by the presence of expected size (FIG. 5, lanes 4, 5, 6 and 8). Lanes 4, 5, 6 and 8 have a ~28 Kb band as expected for double recombination product of donor vector with ~18 Kb chromosomal target fragment. Another event from the same experiment in lane 7 (FIG. 5) has a copy of insertion that is probably from a single crossover recombination and has additional rearrangements since the size of the recombinant band is much larger than expected size of ~28 Kb.

Example 8. Gene Expression and Insect Resistance of Transgenic Events Obtained by Targeted Insertion Technologies Targeted insertion events (MZET130403A067A, MZET134406B450A, MZET134504B010A, MZET134505A104A, MZET134711A236A, MZET140508A344A, MZET140807A856A, MZET140913A741A, MZET140913A594A, MZET130403A067A, MZET131500A128A) are evaluated for transgene expression by qPCR and ELISA assays. As a control, random integration events derived from donor vector (21942 or 22445) are also assayed for trait gene expression. Expression level is also compared with a *maize* line (AX5707DW) with the introgressed MIR604 locus. Since the inserted transgene contains Western corn rootworm resistance genes mCry3Aa and eCry3.1Ab, transgenic events and their progeny are evaluated in respect to the performance of insect resistance by growing them in pots infected by corn rootworm.

Example 9. High Throughput Assay for Identifying Plants with Targeted Mutations at Desirable Sequences Currently, targeted mutants are identified using one of the following methods. The first method is PCR amplification of the target region followed by restriction enzyme digestion and gel electrophoresis if the mutated sequence contains a restriction site (Lloyd et al. 2005, *Proc. Natl. Acad. Sci. U.S.A.* 102:2232-37 (2005); Zhang et al, *Proc. Natl. Acad. Sci. U.S.A.* 107:12028-33 (2010)). This method is simple, but requires the presence of a suitable restriction site and thus cannot be used for most targets. A second method is PCR amplification of the target region followed by Sanger sequencing or deep sequencing (Gross et al., *Hum. Genet.* 105:72-78 (1999). Shukla et al., *Nature* 459:437-41 (2009); Townsend et al., *Nature* 459:442-45 (2009)). A sequencing approach is definitive and sensitive, but takes a longer time and throughput can be limited by capacity. A third approach is PCR amplification of the target region followed by denaturation, annealing and capillary electrophoresis (Li-Sucholeik et al., *Electrophoresis* 20:1224-1232 (1999); Larsen et al., *Hum. Mutat.* 13:318-327 (1999)) or denaturing high-performance liquid chromatography to detect base pair changes by heteroduplex analysis (McCallum et al., *Nature Biotechnology* 18:455-457). These methods are limited by throughput and the identified mutations need to be further verified by sequencing. A fourth method is PCR amplification of the target region followed by denaturation, heteroduplex formation/strand annealing, digestion with mismatch-specific nuclease (such as CEL1 and T7 endonuclease) and gel electrophoresis (Oleykowski et al., *Nucleic Acids Res.* 26:597-4602 (1998); Colbert et al., *Plant Physiol.* 126:480-484 (2001); Lombardo et al., *Nat. Biotechnol.* 25:1298-306 (2007)), for example using the commercially available Surveyer™ nuclease assay kit (Transgenomic, Gaithersburg, Md., U.S.A.; Qiu et al., *BioTechniques* 36:702-707 (2004)). However, the gel-based assays are not as sensitive as high-throughput DNA sequencing and can only detect mutation with frequency of 1% or more. Therefore, there is still a need for a simple and high throughput method for identifying induced mutations of target sequences. Additionally, all of the above approaches of identifying a potential mutant in a target site are based on the presence of a new signal in a qualitative fashion, either a new band in a gel or a new peak in a chromatogram that is different from the wild type reference sequence.

We developed an alternative approach of identifying potential mutations. The method measures the reduction of the wild type target site sequence in cells or tissues that have been treated with a site-directed nuclease in a quantitative fashion in comparison with a reference sample as shown in FIG. 6. In a DNA sample isolated from wild type (WT) tissues, there is no reduction of the target sequence DNA copy number. Typically, the copy number call in WT tissue is 2 copies for a single copy gene in a diploid organism. For example, ADH gene in WT *maize* has 2 copies. If one of the copies is mutated, only one copy of the wild type (WT) target site sequence remains. If both copies of the target sequences are mutated, the copy number of the M target sequence becomes zero (FIG. 6). Thus, by performing quantitative polymerase reaction assays to measure changes in the target sequence copy number, it is possible to detect if there is a mutation present in the DNA samples by comparing the result with that of a reference sample such as WT tissue. This quantitative approach significantly differs from previously known methods.

Target gene copy number can be assayed by several quantitative polymerase reaction (qPCR) techniques. Generally, qPCR is performed in such a way in that the amplified DNA is detected and measured quantitatively as the reaction progresses, or in "real time". Therefore, qPCR is also referred to as real-time PCR. There are several potential approaches for the real-time detection of products in qPCR: (1) Measurement of PCR product with non-specific fluorescent dyes (such as SYBR® Green) that intercalate with any double-stranded DNA; this detection method is suitable when a single amplicon is being studied, as the dye will intercalate into any double-stranded DNA generated. (2) Measurement of PCR product based on target sequence-specific binding of oligonucleotide probes covalently labeled with a fluorescent reporter tag, such as in TagMan® probes, Molecular Beacons™, or Scorpion primers. The oligonucleotide itself has no significant fluorescence, but it fluoresces either when annealed to the template (as in Molecular Beacons™) or when the dye is clipped from the oligonucleotide during extension (as in TagMan® probes). The advantage of fluorescent probes is that they can be used in multiplex assays for detection of several target sequences in the same reaction. With TagMan® probes, a target sequence-specific oligonucleotide probe is constructed with a fluorescent reporter at one end and a fluorescence quencher at the opposite end. The close proximity of the reporter to the quencher prevents detection of its fluorescence. The fluorescent oligonucleotide probe is broken down by the 5'- to 3'-exonuclease activity of the Taq polymerase so the fluorescent tag is no longer in proximity with the quencher and thus allows unquenched emission of fluorescence, which can be detected after excitation with a laser (Groves, *J Biomol. Tech.* 10:11-16 (1999)). An increase in the number of copies of PCR product at each PCR cycle results in a proportional increase in fluorescence due to the breakdown of the probe and release of the reporter.

As an example, we have designed a Taqman® probe-based method to specifically detect targeted mutation at the *maize* genomic MIR604 insertion site sequence that contains the cleavage site of CRISPR-Cas9 nuclease gRNA targeting SEQ ID NO:3 (5'-AGTGC AGTGC AGTGC AGGAC AGG-3') and the pair of TALENs (cTNmir604Fw2-01/cTNmir604Rv2-01) cleaving target sequence (SEQ ID NO:67, 5'-TGCAT CCGTG CAGTG CAGTG CAGTG CAGGA CAGGA CCTCC TTTGT TTAGG A-3'). As shown in FIG. 7, a real-time qPCR Taqman assay for detecting mutations within SEQ ID NO:67 target sequence consists of two primers, a FW primer, 5'-CACAC CTCGT TGCCA AAGC-3' (SEQ ID NO:92) and a RV primer, 5'-CATCG CGTCC TAAAC AAAGG A-3' (SEQ ID NO:93), and a fluorescently labeled Taqman® probe (5'-CCTGT CCTGC ACTGC-3', SEQ ID NO:94) which hybridizes to the nuclease cleavage target site sequence (5'-GCAGT GCAGG ACAGG-3', SEQ ID NO:95, the target site M as shown in FIG. 6).

Example 10. Generation of Plants with Targeted Mutations at Desirable Sequences without Transgene Insertion Using the target specific assay as outlined above and in FIG. 6 and FIG. 7 and qPCR Taqman assays for other target sequences, *maize* plants regenerated from immature embryos treated with engineered TALE nucleases or gRNA-Cas9 as described previously in Example 4 and Example 5 were assayed for copy number of different target sequences. Table 6 shows the results.

Fluorescently labeled MGB Tagman® probe comprising of sequence 5'-CCTGT CCTGC ACTGC-3' (SEQ ID NO.94) for assay 4 (Mir604 JHAX Fw2/Rv2_MGB) is for detecting the copy number of intact nuclease cleavage site sequence (5'-GCAGT GCAGG ACAGG-3', SEQ ID NO:95)

corresponding to the target sequence M in FIG. 6. A "low" copy number call has 1 copy. A "med" copy number call has 2 copies. A "high" copy number call has 3 or more copies. In WT *maize* plants and regenerated plants with no target site mutation, the copy number call with Assay 4 (the last column in Table 6, Mir604 JHAXFw2/Rv2_MGB) is "Med" (2 copies). In this set of 20 plants, 11 plants (55%) have no mutation at the genomic target sequence (SEQ ID NO:95, 5'-GCAGT GCAGG ACAGG-3'), but 6 plants (30%) have mutations in one copy of the target sequences (Low copy call), and 3 plants (15%) have both copies of the target sequences are mutated (copy call is 0). Since the qPCR assays can be multiplexed, several other assays for detecting transgene sequences are performed at the same time. In this set of plants, 7 of the 20 plants contain detectable transgene insertions (positive for Assays 1 to 3). Of the 9 plants with target sequence mutations, 5 (MZET130501B027A, MZET130501B031A, MZET130501B038A, MZET130501B044A and MZET130501B045A) of them do not contain any detectable transgene insertions, including 1 plant (MZET130501B027A) that has both copies of the target sequence mutated (biallelic or homozygous mutations). This experiment clearly demonstrated that targeted mutations at desirable sequences can be efficiently generated without transgene insertion by transiently expressing a site-directed nuclease. Additionally, the mutants can be efficiently identified using high throughput real-time qPCR assays containing at least one assay probe hybridizing to the nuclease cleavage site.

locus, we developed a high throughput approach of enriching for potential mutations. The method involves the use of one assay (Assay T in FIG. 8A) to identify a plant that has a reduction in the copy number of the target sequence (Target T). The fluorescent probe for assay target T is located away from the fluorescent probe of assay target M (FIG. 8A) which detects the copy number of the site-directed nuclease cleavage site M (also in FIG. 6) by at least 5 nucleotides in the region of the target locus. It should be noted that assay T probe can sit within the same amplicon as assay M probe. However, it should be as far away from M as possible as long as it is still within the region replaced by targeted insertion of transgenic sequences (as shown in FIG. 8A, region containing gene of interest (GOI). Since targeted insertion usually replaces certain sequences at the target locus other than the nuclease cleavage site (M), whereas non-targeted events that are mostly likely modified at the nuclease cleavage site by NHEJ usually would have smaller target site deletions. If a plant has reduced copy number at the nuclease cleavage site (Target M), but not having a reduced copy number call (i.e., wild type) at target region further away (Target T), this plant is very likely to have only small deletion and no targeted insertion at the target locus (Event types a, b and c in FIG. 8A and FIG. 8B) and can be discarded irrespective of the Target M or Target G copy number call. Events can be further enriched by looking at the Assay G results. Any plants negative for GOI (Assay G), i.e., event types d and e in FIG. 8A without transgene can be

TABLE 6

Copy number determination of target sequence (SEQ ID NO: 67)in regenerated maize plants from a Biolistic transformation experiment using qPCR Taqman assays

| Plant ID | Construct ID | Assay 1[1]: cTNmir604Fw2-03 | Assay 2[2]: cPMI-09 | Assay 3[3]: mCry3A | Assay 4[4]: Mir604 JHAX Fw2/Rv2_MGB |
|---|---|---|---|---|---|
| MZET130501B026A | 21321 21942 | 0 | 0 | 0 | Med |
| MZET130501B027A | 21321 21942 | 0 | 0 | 0 | 0 |
| MZET130501B028A | 21321 21942 | 0 | High | High | Low |
| MZET130501B029A | 21321 21942 | 0 | 0 | 0 | Med |
| MZET130501B030A | 21321 21942 | 0 | 0 | 0 | Med |
| MZET130501B031A | 21321 21942 | 0 | 0 | 0 | Low |
| MZET130501B032A | 21321 21942 | 0 | Low | Low | 0 |
| MZET130501B033A | 21321 21942 | 0 | High | High | 0 |
| MZET130501B034A | 21321 21942 | 0 | Low | Low | Med |
| MZET130501B035A | 21321 21942 | 0 | 0 | 0 | Med |
| MZET130501B036A | 21321 21942 | 0 | 0 | 0 | Med |
| MZET130501B037A | 21321 21942 | 0 | 0 | 0 | Med |
| MZET130501B038A | 21321 21942 | 0 | 0 | 0 | Low |
| MZET130501B039A | 21321 21942 | 0 | Low | Low | Med |
| MZET130501B040A | 21321 21942 | Low | High | 0 | Med |
| MZET130501B041A | 21321 21942 | 0 | 0 | 0 | Med |
| MZET130501B042A | 21321 21942 | 0 | High | High | Low |
| MZET130501B043A | 21321 21942 | 0 | 0 | 0 | Med |
| MZET130501B044A | 21321 21942 | 0 | 0 | 0 | Low |
| MZET130501B045A | 21321 21942 | 0 | 0 | 0 | Low |

[1]Assay 1 (cTNmir604Fw2-03) is for detecting insertion of site-directed TALE nuclease expression vector (21321)
[2]Assay 2 for detecting inserted selectable marker gene cPMI-09 present in the donor vector (21942)
[3]Assay 3 for detecting inserted insect control gene mCry3A present in the donor vector (21942)
[4]Assay 4 (Mir604 JHAX Fw2/Rv2_MGB)is for detecting the copy number of intact target sequence (5'-GCAGT GCAGG ACAGG-3', SEQ ID NO: 95) that is hybridizing to Taqman probe comprising of sequences 5'-CCTGT CCTGC ACTGC-3', (SEQ ID NO: 94)

Example 11. High Throughput Assays and Strategies for Enriching Plants with Potential Targeted Insertion at Desirable Genomic Loci For identifying potential transgenic events containing targeted insertion at the MIR604 insertion site safe harbor further discarded. The rest of the plants, i.e., event types from d to i in FIG. 8B with positive GOI signal are chosen as candidate plants with potential targeted insertion at the target locus and these events are characterized further by PCR reactions specific for recombination junctions as shown in FIG. 2.

Example 12. Use of High Throughput qPCR Assays for Enrichment of Candidate Transgenic Events with Targeted Insertion at the Genomic Safe Harbor Locus MIR604 Insertion Site Results of copy number call of different target sequences were obtained using target-specific Assay 1 (Table 7, corresponding to assay T in FIG. 8), Assay 2 for nuclease cleavage site (Table 7, corresponding to target M in FIG. 8) and other transgene sequences (Assays 3 to 7 in Table 7, corresponding to assay G in FIG. 8) from *maize* plants regenerated from immature embryos treated with engineered TALEN as described previously in Example 5.

Table 7 shows assay results of some representative *maize* plants obtained from targeting experiments with co-delivery of the TALE nuclease expression vector 21321 and donor vector 21942. In this experiment, Assay 1 which is corresponding to the assay T of FIG. 8 has a Taqman probe sequence of 5'-CTCGT TGCCA AAGCT GCATC CGT-3' (SEQ ID NO:97) which is located 18 bases away from the nuclease cleavage site (SEQ ID NO: 67, 5'-<u>TGCAT CCGTG CAGTG CAGTG</u> CAGTG CA/GGA CAG<u>GA CCTCC TTTGT TTAGG A</u>-3', where "/" indicates potential cleavage position)

All plants that have "Med" copy number call for target (Assay 1) can be discarded irrespective of other assay results since there is no homologous recombination-mediated replacement of the target sequences (SEQ ID NO:67). In some events (MZET130501A012A and MZET130501B033A) Assay 1 has higher copy number call than Assay 2, it means that the deletion around the nuclease cleavage site is relatively small at the target region. By using results from other assays (Assay 3 to Assay 7), further enrichment can be obtained by discarding plants that do not have genes of interest (GOI). If high quality targeted insertion events are desired, any plants positive for nuclease expression vector (Assay 6), and/or vector backbone (Assay 7), and having more than one copy of the donor vector (Assay 3 to 5) can be discarded. By using this enrichment method, only a subset of the total transgenic plants from a targeted insertion experiment will need to be analyzed further by other assays such as junction PCR (FIG. 2 and FIG. 3) and DNA blot analysis (FIG. 5) to identify truly targeted insertion events. For example, events MZET131500A118A and MZET131500A128A (FIG. 5) were identified by following the above enrichment process from a set of 334 plants in targeted insertion experiment MZET131500A.

TABLE 7

Taqman assays of transgenic events and use of assay results to enrich for potential targeted insertion events from regenerated maize plants derived from a Biolistic transformation experiment using qPCR Taqman assays.

| Plant ID | Assay 1 MIR604Fw2/ Rv2 insertion site | Assay 2 Mir604JHAXFw2/ Rv2_MGB | Assay 3 prCMP-04 | Assay 4 cPMI-09 | Assay 5 cWrangr-01 | Assay 6 cTNmir604Fw2-03 | Assay 7 xprLacZ-01-01 | Note |
|---|---|---|---|---|---|---|---|---|
| MZET130402A039A | Med | Med | 0 | 0 | 0 | 0 | 0 | Discard#* |
| MZET130402A040A | 0 | 0 | High | Med | High | 0 | 0 | Keep& |
| MZET130402A055A | Med | Med | Low | Low | Low | Low | 0 | Discard# |
| MZET130402A056A | Med | Med | 0 | 0 | 0 | 0 | 0 | Discard#* |
| MZET130501A012A | Low | 0 | 0 | 0 | 0 | 0 | 0 | Discard* |
| MZET130501A013A | Med | Med | 0 | 0 | 0 | 0 | 0 | Discard#* |
| MZET130501B031A | Low | Low | 0 | 0 | 0 | 0 | 0 | Discard* |
| MZET130501B032A | 0 | 0 | Low | Low | Low | 0 | 0 | Keep& |
| MZET130501B033A | Low | 0 | High | High | High | 0 | 0 | Keep& |
| MZET130501B034A | Med | Med | Low | Low | Low | 0 | 0 | Discard#* |
| MZET130501B050A | Low | Low | Low | Low | Med | 0 | 0 | Keep& |
| MZET130501B061A | Med | Med | 0 | 0 | 0 | 0 | 0 | Discard#* |
| MZET130501B062A | 0 | 0 | Low | Low | Med | 0 | 0 | Keep& |
| MZET130501B063A | Med | Med | 0 | 0 | 0 | 0 | 0 | Discard* |
| MZET130501B064A | 0 | 0 | Low | Low | Low | 0 | 0 | Keep& |
| MZET130501B065A | Med | Med | Low | Low | Low | 0 | 0 | Discard# |
| MZET130501B066A | Med | Med | 0 | 0 | 0 | 0 | 0 | Discard# |
| MZET130501B135A | 0 | 0 | Low | Low | Med | Low | 0 | Keep& |
| MZET130501B136A | Med | Med | 0 | 0 | 0 | 0 | 0 | Discard* |
| MZET130704B006A | Med | Med | 0 | 0 | 0 | 0 | 0 | Discard* |
| MZET130704B007A | 0 | 0 | High | High | High | 0 | 0 | Keep& |
| MZET130704B008A | 0 | 0 | Low | Low | Low | 0 | 0 | Keep& |
| MZET130704B009A | Med | Med | 0 | Med | Med | 0 | 0 | Discard#* |
| MZET130704B030A | 0 | 0 | 0 | Low | Low | 0 | 0 | Discard* |
| MZET130704B031A | Med | Med | 0 | 0 | 0 | 0 | 0 | Discard# |
| MZET130704B032A | Med | Med | 0 | 0 | 0 | 0 | 0 | Discard# |
| MZET130704B033A | 0 | 0 | Low | Low | Low | 0 | 0 | Keep& |
| MZET130704B036A | Med | Med | 0 | Low | 0 | 0 | 0 | Discard# |
| Assay purpose | Target region status | Nuclease cleavage site | Donor vector GOI cassette 1 | Donor vector GOI cassette 2 | Donor vector GOI cassette 3 | Nuclease expression vector | Vector backbone | |

For no target change;
*For no (intact) GOI insertion;
&For further junction PCR assays to identify targeted insertion events

Example 13. Targeted Gene Stacking and Replacement of Transgene Sequences at the MIR604 Transgene Locus

Example 13.1. T-DNA Insert Sequences of *Maize* Commercial Event MIR604

*Maize* event MIR604 contains a single copy insertion of pNOV2130 T-DNA in a *maize* genome. The T-DNA insertion and its flanking genomic sequences were cloned and shown FIG. 9. The PMI marker gene sequence (cPMI-01, Seq. ID No. 98) is present in the transgene T-DNA insert located next to the flanking *maize* genomic region MIR604LBFS1.

Example 13.2. Selection of TALEN Target Site Sequences in MIR604 Event Transgene Locus In order to stack additional trait gene cassettes to the MIR604 transgene locus, we concentrated our effort on the unique regions of the transgene. The PMI gene (cPMI-01, SEQ ID No. 98) is a desirable target since it is a selectable marker gene and is no longer needed after transgenic plant generation is completed. A new selectable marker gene cassette can be used to replace the PMI cassette using MIR604_RBFS1 or the mCry3A gene expression cassette and MIR604_LBFS1 as regions of homology. We have chosen 3 target sequences (Seq. ID No. 99 to 101) in the PMI gene to design and assemble TALENs for demonstrating feasibility of gene insertion into the MIR604 transgenic locus. PMI_Target_Sequence #1 contains the following sequences, 5'-TTAAC TCAGT GCAAA ACTAT GCCTG GGGCA GCAAA ACGGC GTTGA CTGAA-3' (SEQ ID No.99), PMI_Target_Sequence #2 has the following sequences, 5'-TCTCC ATTCA GGTTC ATCCA AACAA ACACA ATTCT GAAAT CGGTT TTGCC AAA-3', SEQ ID No. 100) and PMI_Target_Sequence #3 contains the following sequences, 5'-TGCAC ATCCG GCGAT TGCTC ACTTT TTACA ACAGC CTGAT GCCGA ACGTT TAA-3' (SEQ ID No. 101).

Example 13.3. Design and Assembly of TALEN Fusion Nuclease Genes Against the PMI Gene Sequences TALENs were designed for targeted cleavage of PMI transgene at sequence targets #1 and #3 (SEQ ID No. 99 and 101). For example, a pair of TALENs for cleaving PMI target sequence #1 (SEQ ID No. 99) were designed for TsPMIFW1 (5'-TTA ACT CAG TGC AAA ACT-3', SEQ ID No.102) and TsPMIRV1 (5'-TTC ACT CAA CGC CGT TTT-3', SEQ ID No.103). TALEN molecule TLN_PMIFW1a (SEQ ID No. 108) was designed to bind the TsPMIFW1 sequence target (5'-TTA ACT CAG TGC AAA ACT-3', SEQ ID No. 102) and TALEN molecule TLN_PMIRV1a (5'-TTC AGT CAA CGC CGT TTT-3', SEQ ID No.109) was designed to recognize TsPMIRV1 sequence target (SEQ ID No. 103). Similarly, another pair of TALENs was designed against TsPMIFW3 (5'-TGC ACA TCC GGC GAT TGC T-3', SEQ ID No.106) and TsPMIRV3 (5'-TTA AAC GTT CGG CAT CAG-3', SEQ ID No.107) for cleavage of PMI Target Sequence #3 (SEQ ID No. 101). TALEN molecule TLN_PMIFW3 (SEQ ID No.110) was designed to bind the TsPMIFW3 sequence (5'-TGC ACA TCC GGC GAT TGC T-3', SEQ ID No. 106) and TALEN molecule TLN_PMIRV3 (SEQ ID No.111) was designed to bind the TsPMIRV3 sequence (5'-TTA AAC GTT CGG CAT CAG-3', SEQ ID No. 107). The protein coding sequences of designed TALEN proteins TLN_PMIFW1a (SEQ ID No. 108), TLN_PMIRV1a (SEQ ID No. 109), TLN_PMIFW3 (SEQ ID No.110) and TLN_PMIRV3 (SEQ ID No.111) were back-translated into DNA sequences. DNA molecules encoding these TALENs were assembled as described in previous examples. The TALEN gene DNA sequences cTNPMIFW1a (SEQ ID No. 112), cTNPMIRV1a (SEQ ID No. 113), cTNPMIFW3-02 (SEQ ID No. 114) and cTNPMIRV3-02 (SEQ ID No.115) encode TLN_PMIFW1a (SEQ ID No.108), TLN_PMIRV1a (SEQ ID No. 109), TLN_PMIFW3 (SEQ ID No.110) and TLN_PMIRV3 (SEQ ID No.111), respectively.

Example 13.4. TALEN Expression Vector and Targeting Donor Vector Construction DNA sequences, cTNPMIFW3-02 (SEQ ID No. 114) and cTNPMIRV3-02 (SEQ ID No. 115) were introduced into expression cassettes, each driven by a constitutive promoter. The two TALEN gene expression cassettes were then introduced into a binary vector backbone to form binary vector 22840. Donor vector 22842 comprises the donor nucleic acid sequence, which comprises an insecticidal gene expression cassette and a glyphosate tolerance gene cassette between two homology sequences (xMIR604-01 and xMIR604-02). The glyphosate tolerance gene cassette comprises the gene ZmEPSPS, whose presence can be used to identify a successful insertion of the donor nucleic acid sequence. The two homology sequences (xMIR604-01 and xMIR604-02) are identical to sequences flanking the TALEN target sequence, i.e. PMI Target Sequence #3 (SEQ ID No. 101). Targeted insertion of donor sequences from vector 22872 via homologous recombination into the MIR604 transgenic locus mediated by TALEN cleavage is illustrated in FIG. 10.

Example 13.5. Stacking of Additional Trait Genes into a Transgenic Locus of a Commercial Event (MIR604) and Inactivation of an Unneeded Transgene

*Maize* MIR604 event is widely cultivated for controlling Western corn rootworm (WCR) (Que et al., 2010, *GM Crops.* 1, 220-229). MIR604 transgene contains a PMI selectable marker gene for the generation of the transgenic event (FIG. 9). PMI gene doesn't offer any agronomic benefit and is no longer needed after event generation. However, it can be used as a landing pad for insertion of other trait gene cassettes into the MIR604 locus. To demonstrate such utility, MIR604 transgene locus was introgressed into an elite corn transformation line (NP2222) to form a new transgene receptor line NP2222DW. Line NP2222DW was used as transformation host for generation of targeted insertion events through site-directed nuclease mediated insertion into the PMI gene via homologous recombination. Immature embryos derived from selfed or sib-crossed NP2222DW plants were co-infected with recA-minus *Agrobacterium* strain LBA4404 (carrying helper plasmid pVGW7) containing binary vector 22840 (comprising TALEN expression cassettes) or 22872 (comprising donor nucleic acid sequence, which comprises two expression cassettes). Generation of transgenic events from infected immature embryos was as described except glyphosate was used as selection (Negrotto et al. (2000), *Plant Cell Rep.* 19, 798-803). Calli derived from infected immature embryos were selected on 2 mM of glyphosate. Plants were regenerated on media containing 0.2 mM glyphosate. Glyphosate selected plants were sampled determining for transgene copy number and target site cleavage with Taqman assays.

Plants with target sequence cleavage were further analyzed by PCR for targeted integration with primers spanning across recombination junctions (FIG. 10). For example, for amplification of recombination junction involving xMIR604-02, the primer pair (P1/P2), FE4796 (SEQ ID NO: 127)/FE4793 (SEQ ID NO: 128) was used and the reaction would produce a PCR product of 2.13 Kb if recombination occurred. Another primer pair, FE35036 (SEQ ID NO: 129')/FE35037 (SEQ ID NO: 130) with a product of 2.5 kb was also used for identification of potential targeted recombinants involving homology region of xMIR604-02. For amplification of recombination junction involving xMIR604-01, a pair of primers (P3/P4), FE35034 (SEQ ID NO: 131)/FE35035 (SEQ ID NO: 132) was used and the PCR reaction is expected to produce a product of 2 Kb if there is homologous recombination. Table 8 shows several experiments of targeted insertion that targeted events were recovered using glyphosate selection ("ZmEPSPS positive events"). These experiments demonstrated DNA sequences containing additional trait genes can be efficiently inserted into the existing commercial event MIR604 locus through homologous recombination mediated by TALEN. It should be pointed out that other site-directed nucleases including engineered meganuclease, zinc finger nuclease or CRISPR-Cas9 can be used to substitute for TALEN in the above mentioned vector 22840 for cleaving the PMI gene sequences to mediate targeted insertion. Similarly, other methods of gene delivery including biolistic particle bombardment, whisker-mediated transformation, electroporation and PEG-mediated protoplast transformation can be used to introduce the site-directed nuclease expression vector and donor DNA molecules.

of targeted insertion events through site-directed nuclease mediated insertion into the MIR604 locus via homologous recombination. For replacing only the PMI cassette, the mCry3A gene and the LBFS region were used as homology sequences in the donor vector (FIG. 11). The same TALEN expression vector (22840) can be delivered into the NP2222DW *maize* cells along with the donor containing an insecticidal (IC) expression cassette and a selectable marker (such as PMI, ZmEPSPS, or PAT) expression cassettes (FIG. 11). Furthermore, one or more site-directed nucleases can be used to introduce chromosomal breaks in the PMI cassette sequences. For example, two or more single-guide RNAs (sgRNAs) can be used in conjunction with the Cas9 protein to cleave PMI cassette sequence simultaneously to remove the whole PMI expression cassette (FIG. 11). Immature embryos are placed on callus induction media and then calli are selected on bialaphos-containing media. Generation of transgenic events from infected immature embryos, is, for example, as described above for mannose or glyphosate, where bialaphos may also be used as selection agent. Selected plants are sampled for transgene copy number and target site cleavage with Taqman assays. Plants with target sequence cleavage are further analyzed by PCR for targeted integration with primers spanning across the recombination junctions (FIG. 11).

For replacing the whole MIR604 T-DNA insert, both RBFS and LBFS are inserted into the donor molecule to serve as homology sequences to mediate insertion of novel trait gene cassettes (for example, insecticidal (IC) gene expression cassettes 1, 2, and a selectable marker (PAT, for example) expression cassette as the third cassette via homologous recombination (FIG. 12). Immature embryos isolated from selfed or sib-crossed NP2222DW ears are co-infected with recA-minus *Agrobacterium* strain

TABLE 8

Targeted insertion of expression cassettes flanked by homologous sequences in donor vector 22872 into MIR604 transgenic locus mediated by TALEN expressed from vector 22840 delivered by Agrobacterium infection

| Experiment | Target Sequence | Nuclease vector ID | Donor vector ID | Total explants | ZmEPSPS positive events | Events with cPMI-01 target site mutations* | No. of targeted events** |
|---|---|---|---|---|---|---|---|
| MZET144515 | cPMI-01 | 22840 | 22872 | 1682 | 53 | 10 | 2 |
| MZET151723 | cPMI-01 | 22840 | 22872 | 2676 | 252 | ND | 9 |
| MZET151818 | cPMI-01 | 22840 | 22872 | 4500 | 307 | ND | 4 |
| MZET152212 | cPMI-01 | 22840 | 22872 | 3680 | 628 | 236 | 8 |
| MZET152311 | cPMI-01 | 22840 | 22872 | 4150 | 808 | 277 | 12 |

*Based on target sequence (cPMI-01) copy number call as determined by qPCR Taqman assay.
**As identified by PCR reactions with primers spanning across recombination junctions (FIG. 10)

Example 13.6. Stacking of Additional Trait Genes into MIR604 Transgenic Locus by Replacing the PMI Gene Cassette or the Whole Transgene The genomic region harboring MIR604 transgene is a preferred location for trait gene expression. In addition to inserting additional transgenes into the PMI gene, the whole MIR604 transgene locus can be used as a landing pad for insertion of other trait gene cassettes by replacing part of the transgene sequences or the whole T-DNA insert. Similar to targeted insertion into PMI gene above (Example 13.5), line NP2222DW was used as transformation host for generation LBA4404 (carrying helper plasmid pVGW7) containing binary vector 22840 and the donor DNA vector comprising IC expression cassettes 1, 2, and the PAT expression cassette. Similarly, more than one site-directed nuclease can be used simultaneously to cleave more than one MIR604 transgene sequence. For example, two or more single-guide RNAs (sgRNAs) can be used in conjunction with the Cas9 protein to cleave T-DNA sequence within the MIR604 transgene (for example, LB- and RB-proximal sequences and/or PMI and mCry3A cassettes) simultaneously to remove at least one expression cassette of the MIR604 T-DNA insert (FIG. 12). Infected immature embryos are placed on callus induction media and then calli are selected on bialaphos-containing media. Generation of transgenic events from infected immature embryos, is, for example, as described above for mannose or glyphosate, where bialaphos may also be used as selection agent. Selected plants are sampled for transgene copy number and target site cleavage with Taqman assays. Plants with target sequence cleavage are further analyzed by PCR for targeted integration with primers spanning across the recombination junctions (FIG. 12). It should be obvious to those skilled in the art that other methods of gene delivery including biolistic particle bombardment, whisker-mediated transformation, electroporation and PEG-mediated protoplast transformation can be used to introduce site-directed nuclease expression vector and donor DNA molecules.

Example 14. Targeted Gene Stacking and Replacement of Transgenic Loci Containing a Nonfunctional Selectable Marker Gene

Example 14.1. Design and Assembly of TALENs for Making Chromosomal Breaks in Transgenic Loci Containing a Nonfunctional Selectable Marker Gene It is known in the art that transgene sequences can be inserted into transgenic *maize* and rice loci containing a truncated non-functional selectable marker gene PMI, by using *Agrobacterium*-mediated transformation and taking advantage of dsDNA breaks created by expression of native meganuclease I-CeuI (U.S. Pat. No. 7,935,862, incorporated by reference herein). However, targeted insertion mediated by native meganucleases is limited by the fact that a previously engineered nuclease cleavage site has to be inserted first in the transgene locus. Here, we want to test if novel designer site-directed nucleases such as TALEN can be designed against randomly chosen sequences within the existing transgenic locus to mediate targeted insertion of additional transgene sequences, to overcome this limitation. To achieve this, two pairs of TALENs were designed against a randomly selected target sequence (5'-<u>ATAGA GATCC TCTAG AGTCG ACCAT GGTGA TC</u>ACT GCAGG CATGC AAGCT TGT -3', SEQ ID. No. 116, only the upper strand is shown)

within the transgene locus of pNOV5025 transgenic events. Two sequences within this stretch of DNA were chosen as TALEN binding sites, 5'-ATAGA GATCC TCTAG AGT-3' (aka. rPMIFw1, SEQ ID No. 117, only the upper strand is shown) and 5'-ACAAG CTTGC ATGCC TGC-3' (aka. rPMIRv1, SEQ ID No. 118, only the lower strand is shown). One pair of TALENs consists of one full-length TALEN (cTNrPMIFw1-01, SEQ ID No. 119) designed against target sequence rPMIFw15'-ATAGA GATCC TCTAG AGT-3' (SEQ. ID. No.117) and another full-length TALEN (cTNrP-MIRv1-01, SEQ ID No. 120) designed against target sequence rPMIRv1 5'-ACAAG CTTGC ATGCC TGC-3' (SEQ ID No.118). The second pair of TALENs consists of one truncated TALEN (cTNrPMIFw1-02, SEQ. ID. No. 121) designed against target sequence rPMIFw1, 5'-ATAGA GATCC TCTAG AGT-3' (SEQ. ID. No. 117) and another truncated TALEN (cTNrPMIRv1-02, SEQ. ID. No. 122) designed against target sequence rPMIRv1, 5'-ACAAG CTTGC ATGCC TGC-3' (SEQ ID No.118).

Example 14.2. Expression and Transformation Vectors of TALENs for Truncated PMI Target Locus Sequences Artificial fusion nuclease DNA sequences were then assembled from library of fragments containing different RVD repeats, promoter and terminator to form TALEN expression cassettes directly after Type IIs enzyme digestion and ligation as described (Cermak et al, 2011, Nucleic Acid Research 39(12):e82; Zhang et al., 2011, Nature Biotech 29:149-154). Several expression vectors (21438, 21792 and 21793) for TALENs against truncated PMI target sequences were made. Vector 21438 comprises expression cassettes for TALENs cTNrPMIFw1-01 and cTNrPMIRv1-01. Vector 21792 comprises expression cassettes for TALENS cTNrP-MIRv1-01 and cTNrPMIFw1-01. Vector 21793 comprises expression cassettes for TALENs cTNrPMIRv1-02 and cTNrPMIFw1-02. Initially, an existing targeting donor vector pNOV5045 (U.S. Pat. No. 7,935,862) was used for testing targeted insertion. Later, additional targeting donor vectors 21779 and 22173 were also constructed and used for targeted insertion experiments (Table 9). Donor vectors pNOV5025, 21779, and 22713 contain the complementing 5'-region of the PMIintron cassette for restoring the PMI function and also other sequences of interest and regions of homology. Upon cleavage of the chromosomal target sequences by TALENs, donor vector sequence can be integrated into the target site via homologous recombination.

Example 14.3. Targeted Insertion of Transgenes into Transgenic Loci Containing a Nonfunctional Truncated PMI Gene Mediated by TALEN Selectable transgenic loci were generated from target vector pNOV5025 (described in U.S. Pat. No. 7,935,862) using *Agrobacterium*-mediated transformation in *maize* line NP2222 as described using PPO as selectable marker. To test the effect of TALEN-mediated targeted insertion into these pNOV5025 loci, a donor vector (pNOV5045, 21779 or 22173) was co-delivered into immature *maize* embryo tissues along with a TALEN expression vector (21438, 21792 or 21793). After gene delivery and tissue recovery, transformed target tissues were placed on culture media containing mannose selection agent to recover events with targeted insertion, i.e. cells with reconstituted functional PMI gene as described (U.S. Pat. No. 7,935,862). Targeted insertion events through homologous recombination should be resistant to mannose. To differentiate truly targeted events from selection escapes, tissues (callus or leaf) from putative mannose resistant events were first analyzed by PCR using primers spanning a targeted insertion junction. The presence of a positive PCR signal suggests TALEN-mediated targeted insertion into the pNOV5025 transgenic loci. Positive events are further analyzed by Southern blot analysis method to confirm that these events have truly targeted insertion as described (U.S. Pat. No. 7,935,862). Table 9 shows the results of several targeted insertion experiments. The results demonstrate that useful trait genes can be inserted reproducibly into predetermined transgene loci by reconstituting a selectable marker gene at a useful frequency using different TALEN expression vectors and targeting donors. Both the full length and truncated version of TALENs can mediate targeted insertion at the transgenic loci.

TABLE 9

Targeted insertion experiments of pNOV5025 transgenic target loci with different donor vectors mediated by TALEN expression

| Target locus | Nuclease vector | Donor | # Experiments | Total explants | Targeted events | Intact LC events |
|---|---|---|---|---|---|---|
| pNOV5025 transgenic loci with truncated PMI, F1 embryos | 21438: FL TALEN | pNOV5045: GUS + tPMI | 8 | 6536 | 0 | 0 |
| pNOV5025 transgenic lines with truncated PMI, F2 embryos | 21438: FL TALEN | 21779: tPMI | 7 | 11521 | 4 | 4 |
| pNOV5025 transgenic lines with truncated PMI, F2 embryos | 21792: FL TALEN | 21779: tPMI | 3 | 8590 | 1 | 1 |
| pNOV5025 transgenic lines with truncated PMI, F2 embryos | 21793; dNC TALEN | 21779: tPMI | 5 | 10180 | 1 | 1 |

Although the foregoing invention has been described in some detail by way of illustration and example for purposes of clarity of understanding, it will be apparent that certain changes and modifications may be practiced with the scope of the present invention.

What is claimed is:

1. A method of integrating a transgene into a genomic nuclease cleavage site in a maize genome, comprising introducing into a maize cell:
   a) a first nucleic acid molecule comprising a genomic target site, wherein the nucleic acid molecule comprises at least 100 contiguous nucleotides with at least 90% identity to at least 100 contiguous nucleotides of SEQ ID NO:2, and further comprising a transgene; and
   b) a second nucleic acid molecule comprising a nucleotide sequence encoding a nuclease for site-directed cleavage at a genomic nuclease cleavage site,
   under conditions wherein expression of the second nucleic acid molecule can occur to produce the nuclease and the nuclease can cleave the nucleotide sequence at the genomic nuclease cleavage site, whereby the transgene is integrated at the genomic nuclease cleavage site in the maize genome.

2. The method of claim 1, wherein the genomic nuclease cleavage site is located within a chromosome interval on chromosome 1 defined by and including base pair (bp) position 38,860,000 to base pair (bp) position 39,015,000 as defined by Maize B73 RefGen_V2.

3. The method of claim 1, wherein the first nucleic acid molecule and the second nucleic acid molecule are introduced into the maize cell by biolistic nucleic acid delivery.

4. The method of claim 1, wherein the first nucleic acid molecule and the second nucleic acid molecule are introduced into the maize cell via an *Agrobacterium*.

5. The method of claim 1, wherein the first nucleic acid molecule and the second nucleic acid molecule are present on a single nucleic acid construct.

6. The method of claim 1, wherein the first nucleic acid molecule and the second nucleic acid molecule are present on separate nucleic acid constructs.

7. The method of claim 1, wherein the first nucleic acid molecule and/or the second nucleic acid molecule are transiently expressed in the maize cell.

8. A method of producing a maize plant or plant part, or progeny thereof, comprising a transgene integrated into a genomic nuclease cleavage site in the maize genome, comprising regenerating a maize plant from the maize cell produced by the method of claim 1.

9. The method of claim 1, wherein the genomic nuclease cleavage site is located within a maize chromosome that comprises at least 100 contiguous nucleotides with at least 90% identity to SEQ ID NO: 2.

10. The method of claim 1, wherein the genomic nuclease cleavage site comprises SEQ ID NO: 3-28, SEQ ID NO: 31-34, SEQ ID NO: 40-67, or a complement thereof.

11. The method of claim 1, wherein the first nucleic acid molecule comprises SEQ ID NO: 38, SEQ ID NO: 39, or a complement thereof.

* * * * *